United States Patent
Pflumm et al.

(10) Patent No.: US 9,537,105 B2
(45) Date of Patent: *Jan. 3, 2017

(54) MATERIALS FOR ORGANIC ELECTROLUMINESCENT DEVICES

(71) Applicant: Merck Patent GmbH, Darmstadt (DE)

(72) Inventors: Christof Pflumm, Darmstadt (DE);
Arne Buesing, Frankfurt am Main (DE); Amir Hossain Parham, Frankfurt am Main (DE); Teresa Mujica-Fernaud, Darmstadt (DE); Holger Heil, Frankfurt am Main (DE); Philipp Stoessel, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/800,828

(22) Filed: Jul. 16, 2015

(65) Prior Publication Data
US 2015/0318478 A1   Nov. 5, 2015

Related U.S. Application Data

(63) Continuation of application No. 13/322,614, filed as application No. PCT/EP2010/002683 on May 3, 2010, now Pat. No. 9,126,970.

(51) Int. Cl.
*H01L 51/54* (2006.01)
*C09K 11/06* (2006.01)
(Continued)

(52) U.S. Cl.
CPC ........... *H01L 51/006* (2013.01); *C07D 209/70* (2013.01); *C07D 209/82* (2013.01); *C07D 307/78* (2013.01); *C07D 333/52* (2013.01); *C07D 401/14* (2013.01); *C07D 403/04* (2013.01); *C07D 403/10* (2013.01); *C07D 403/14* (2013.01); *C07D 407/10* (2013.01); *C07D 409/10* (2013.01); *C07D 413/04* (2013.01); *C07D 413/10* (2013.01); *C07D 417/10* (2013.01); *C07D 471/04* (2013.01); *C07D 487/04* (2013.01); *C07D 493/04* (2013.01); *C07D 498/04* (2013.01); *C07D 513/04* (2013.01); *C07F 9/65683* (2013.01); *C07F 9/65685* (2013.01); *C07F 9/65848* (2013.01); *C07F 15/0033* (2013.01); *C07F 15/0086* (2013.01); *C09B 15/00* (2013.01); *C09B 17/00* (2013.01); *C09B 19/00* (2013.01); *C09B 57/00* (2013.01); *C09K 11/025* (2013.01); *C09K 11/06* (2013.01);
(Continued)

(58) Field of Classification Search
None
See application file for complete search history.

(56) References Cited

U.S. PATENT DOCUMENTS 7,993,760 B2   8/2011   Komori et al.
8,318,323 B2   11/2012   Kato et al.
(Continued)

FOREIGN PATENT DOCUMENTS

CN   101139319 A   3/2008
EP   0603696 A1   6/1994
(Continued)

OTHER PUBLICATIONS

Bradley, W., et al., "Chemistry of Idanthrone. Part I. The Mode of Formation of Indanthrone from 2-Aminoanthraquinone and Potassium Hydroxide," Journal of the Chemical Society, 1951, pp. 2129-2146.

(Continued)

*Primary Examiner* — Andrew K Bohaty
(74) *Attorney, Agent, or Firm* — Drinker Biddle & Reath LLP

(57) ABSTRACT

The present invention describes indenocarbazole derivatives having electron- and hole-transporting properties, in particular for use in the emission and/or charge-transport layer of electroluminescent devices or as matrix material. The invention furthermore relates to a process for the preparation of the compounds according to the invention and to electronic devices comprising same.

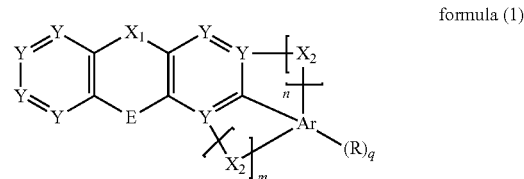

formula (1)

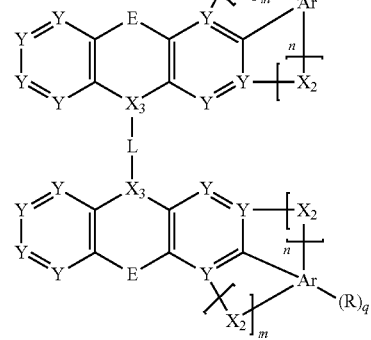

formula (1')

10 Claims, No Drawings

(51) Int. Cl.

| | | |
|---|---|---|
| H01L 51/00 | (2006.01) | |
| C07D 209/70 | (2006.01) | |
| C07D 401/14 | (2006.01) | |
| C07D 493/04 | (2006.01) | |
| C09K 11/02 | (2006.01) | |
| H01L 51/50 | (2006.01) | |
| C07D 209/82 | (2006.01) | |
| C07D 307/78 | (2006.01) | |
| C07D 333/52 | (2006.01) | |
| C07D 403/04 | (2006.01) | |
| C07D 403/10 | (2006.01) | |
| C07D 403/14 | (2006.01) | |
| C07D 407/10 | (2006.01) | |
| C07D 409/10 | (2006.01) | |
| C07D 413/04 | (2006.01) | |
| C07D 413/10 | (2006.01) | |
| C07D 417/10 | (2006.01) | |
| C07D 471/04 | (2006.01) | |
| C07D 487/04 | (2006.01) | |
| C07D 498/04 | (2006.01) | |
| C07D 513/04 | (2006.01) | |
| C07F 9/6568 | (2006.01) | |
| C07F 9/6584 | (2006.01) | |
| C07F 15/00 | (2006.01) | |
| C09B 15/00 | (2006.01) | |
| C09B 17/00 | (2006.01) | |
| C09B 19/00 | (2006.01) | |
| C09B 57/00 | (2006.01) | |
| H05B 33/10 | (2006.01) | |

(52) U.S. Cl.
CPC ...... *H01L 51/0061* (2013.01); *H01L 51/0067* (2013.01); *H01L 51/0071* (2013.01); *H01L 51/0072* (2013.01); *H01L 51/5012* (2013.01); *H01L 51/5056* (2013.01); *H01L 51/5072* (2013.01); *H05B 33/10* (2013.01); *C09K 2211/1007* (2013.01); *C09K 2211/1011* (2013.01); *C09K 2211/1014* (2013.01); *C09K 2211/1029* (2013.01); *C09K 2211/1033* (2013.01); *C09K 2211/1037* (2013.01); *C09K 2211/1044* (2013.01); *C09K 2211/1059* (2013.01); *C09K 2211/1088* (2013.01); *C09K 2211/1092* (2013.01); *H01L 51/001* (2013.01); *H01L 51/5016* (2013.01); *H01L 51/5048* (2013.01); *H01L 51/5096* (2013.01); *H01L 2251/308* (2013.01); *H01L 2251/5384* (2013.01); *Y02E 10/549* (2013.01)

(56) References Cited

U.S. PATENT DOCUMENTS

| 9,126,970 | B2* | 9/2015 | Pflumm | C07D 209/82 |
|---|---|---|---|---|
| 2003/0134147 | A1* | 7/2003 | Burn | C07C 211/54 |
| | | | | 428/690 |
| 2004/0076853 | A1 | 4/2004 | Jarikov | |
| 2006/0063033 | A1 | 3/2006 | Sohn et al. | |
| 2006/0255332 | A1 | 11/2006 | Becker et al. | |
| 2008/0093980 | A1 | 4/2008 | Stoessel et al. | |
| 2008/0124455 | A1* | 5/2008 | Shin | C07D 209/80 |
| | | | | 427/66 |
| 2008/0220285 | A1 | 9/2008 | Vestweber et al. | |
| 2009/0066225 | A1 | 3/2009 | Kimura et al. | |
| 2009/0096356 | A1 | 4/2009 | Murase et al. | |
| 2009/0295276 | A1 | 12/2009 | Asari et al. | |
| 2009/0302742 | A1 | 12/2009 | Komori et al. | |
| 2009/0302743 | A1* | 12/2009 | Kato | H01L 51/0073 |
| | | | | 313/504 |
| 2009/0309488 | A1* | 12/2009 | Kato | C07D 487/04 |
| | | | | 313/504 |
| 2010/0187977 | A1 | 7/2010 | Kai et al. | |
| 2011/0284827 | A1 | 11/2011 | Morishita et al. | |
| 2012/0018717 | A1 | 1/2012 | Kim et al. | |
| 2012/0091438 | A1 | 4/2012 | Yabunouchi et al. | |
| 2012/0104940 | A1 | 5/2012 | Shin et al. | |

FOREIGN PATENT DOCUMENTS

| EP | 0938787 | A2 | 4/1999 |
|---|---|---|---|
| EP | 1860097 | A1 | 11/2007 |
| EP | 1956022 | A1 | 8/2008 |
| JP | 11154594 | A | 6/1999 |
| JP | 2003-261473 | A | 9/2003 |
| JP | 2006135146 | A | 5/2006 |
| JP | 2008506657 | A | 3/2008 |
| JP | 2008148533 | A | 6/2008 |
| JP | 2009/009965 | A | 1/2009 |
| JP | 2010045281 | A | 2/2010 |
| JP | 2012520872 | A | 9/2012 |
| JP | 2012521418 | A | 9/2012 |
| JP | 2012522040 | A | 9/2012 |
| JP | 5238025 | B2 | 7/2013 |
| JP | 5343089 | B2 | 11/2013 |
| JP | 5438757 | B2 | 3/2014 |
| KR | 20100105099 | A | 9/2010 |
| KR | 20100108701 | A | 10/2010 |
| KR | 20100108903 | A | 10/2010 |
| TW | 200734340 | | 9/2007 |
| WO | WO-2005/003253 | A2 | 1/2005 |
| WO | WO-2006/122630 | A1 | 11/2006 |
| WO | WO-2007063754 | A1 | 6/2007 |
| WO | WO 2007063796 | A1 | 6/2007 |
| WO | WO-2008022633 | A2 | 2/2008 |
| WO | WO-2008/056746 | A1 | 5/2008 |
| WO | WO-2009/148602 | | 12/2009 |
| WO | WO-2010107244 | A2 | 9/2010 |
| WO | WO-2010114021 | A2 | 10/2010 |
| WO | WO-2010114243 | A2 | 10/2010 |
| WO | WO-2012107244 | A1 | 8/2012 |

OTHER PUBLICATIONS

Hu, N., et al., "5, 11-Dihydro-5, 11-di-naphthylindolo[3,2-*b*]carbazole: Atropisomerism in a Novel Hole-Transport Molecule for Organic Light-Emitting Diodes," J. Am. Chem. Soc., 1999, vol. 121, pp. 5097-5098.

Kehrmann, F., et al., "Zur Constitution der Fluorindine III," Chimische Berichte, 1896, vol. 29, pp. 1246-1254, (Document is not in the English language but can be found in the International Search Report filed with this application).

Klimenko, L.S., et al., "Photocyclization of 2-azido-1-(4-*tert*-butylphenoxy)-9, 10-anthraquinone in the presence of substituted phenols," Russian Chemical Bulletin, International Edition, Jun. 2007, vol. 56, No. 6, pp. 1130-1134.

Klimenko, L.S., et al., "Solid-state photochemical reactions of 1-aryloxy(1-arylthio)-9, 10-anthraqunone derivatives," Mendeleev Commun., 2006, vol. 16, No. 4, pp. 224-225.

Ott, R., et al., "Phenazine, 3. Mitt.: N-(o-Aminophenyl)-benzo[alpha]phenazine-5-amin, das vermeintliche 'Dihyronaphthodiphenazine' Kehrmanns, und sein Derivate," Monatshefte für Chemie, 1976, vol. 107, pp. 879-888. (Document is not in the English language but can be found in the International Search Report filed with this application).

Wen-Yong, L., et al., "Kinked Star-Shaped Fluorene/Triazatruxene Co-oligomer Hybrids with Enhanced Functional Properties for High-Performance, Solution-Processed, Blue Organic Light-Emitting Diodes," Adv. Funct. Mater., 2008, vol. 18, pp. 265-276.

Royer et al., "Synthesis of pentacyclic hereoaromatic systems related to indolocarbazole alkaloids", Database Accession No. 128: 308641 CA, dated Jun. 16, 1998.

English Translation of Japanese Office Action Application No. 2012-512225, mailed Jun. 10, 2014.

(56) References Cited

OTHER PUBLICATIONS

English Translation of the Taiwanese Office Action regarding Application No. 099116847 dated Jul. 29, 2014.
Xia, Binbin, et al., "Quantitative structure-activity relationship studies of a series of non-benzodiazepine structural ligands binding to benzodiazepine receptor"; European Journal of Medicine Chemistry, 43 (2008) 1489-1498.
Rong, Liangoe, et al., "Efficient Synthesis of Polysubstituted Pyridine under Solvent-free Conditions without Using Any Catalysts", Synthetic Communications, 2008, vol. 38:1808-1814.
Janosik, Tomasz, et al., "Reastions of 1,3"-biindolyl: Synthesis of Indolo [=3,2-a] carbazoles", Tetrahedron 55 (1999), 2371-2380.
Taiwanese Applicaiton I378099.
Chatterjea, J.N., "Synthesis of 2-Azafluorenones & Related Compounds", Journal of Scientific & Industrial Research, vol. 14B, 1995.
Winter, Andreas, "Unusual Terpyridines as Ligands for Novel Light-Emitting Iridium (III) Complexes: Synthesis and Characterization". Aust. J. Chem. 2006, 59, 773-782.
Janosik et al., "Reaction of 2,3'-biindolyl: Synthesis of Indolo[3,2-a]carbazoles" Tetrahedron, 55, 2372-2380, 1999.
Machine translation of JP11-154594, Jun. 8, 1999.
Ahmed eta l. J. Chem. Soc. Perkin Trans. 1, 1973, pp. 1099-1103 year of publication 1973.

* cited by examiner

US 9,537,105 B2

MATERIALS FOR ORGANIC ELECTROLUMINESCENT DEVICES

RELATED APPLICATIONS

This application is a continuation application of application Ser. No, 13/322,614, filed Nov. 28, 2011 which is incorporated by reference in its entirety. Application Ser. No. 13/322,614 is a national stage application (under 35 U.S.C. §371) of PCT/IEP2010/002683, filed May 3, 2010, which claims benefit of German Application No, 10 2009 023 155.2, filed May 29, 2009.

The present invention describes indenocarbazole derivatives having electron- and hole-transporting properties, in particular for use in the emission and/or charge-transport layer of electroluminescent devices or as matrix material. The invention furthermore relates to a process for the preparation of the compounds according to the invention and to electronic devices comprising same.

The general structure of organic electroluminescent devices is described, for example, in U.S. Pat. Nos. 4,539,507, 5,151,629, EP 0676461 and WO 98/27136. However, these devices are still in need of improvement:

1. The efficiency in the case of fluorescent and also phosphorescent OLEDs should be improved.
2. The operating lifetime is frequently still comparatively short, in particular in the case of blue emission, so that there is a further need for improvement here.
3. The operating voltage, both in the case of fluorescent and phosphorescent OLEDs, should be reduced, which results in an improvement in the power efficiency. This is of major importance, in particular, for mobile applications.
4. In hole-transport materials in accordance with the prior art, the voltage is dependent on the layer thickness of the hole-transport layer. In practice, a thicker hole-transport layer would frequently be desirable in order to improve the optical coupling-out and the production yield. However, this frequently cannot be achieved with materials in accordance with the prior art owing to the associated increase in voltage. There therefore continues to be a need for improvement here.

In particular also in the case of phosphorescent electroluminescent devices, improvements to the above-mentioned properties are still desirable. In particular, there is a need for improvement in matrix materials for phosphorescent emitters which simultaneously result in good efficiency, a long lifetime and a low operating voltage. The properties of the matrix materials, in particular, are frequently limiting for the lifetime and efficiency of the organic electroluminescent device.

In accordance with the prior art, carbazole derivatives, for example bis(carbazolyl)biphenyl, are frequently used as matrix materials for phosphorescent emitters. There is still a need for improvement here, in particular with respect to the lifetime and the glass-transition temperature of the materials.

Furthermore, ketones (WO 2004/093207), phosphine oxides and sulfones (WO 2005/003253) are used as matrix materials for phosphorescent emitters. In particular with ketones, low operating voltages and long lifetimes are achieved. There is nevertheless still a need for improvement here, in particular with respect to the efficiency and the compatibility with metal complexes which contain ketoketonate ligands, for example acetylacetonate.

Furthermore, metal complexes, for example BAlq$_3$ or bis[2-(2-benzothiazolyl)phenolate]zinc(II), are used as matrix materials for phosphorescent emitters. There is still a need for improvement here, in particular with respect to the operating voltage and the chemical stability. Purely organic compounds are frequently more stable than these metal complexes. Thus, some of these metal complexes are sensitive to hydrolysis, which makes handling of the complexes more difficult.

In particular, there is still a need for improvement in the case of matrix materials for phosphorescent emitters which simultaneously result in high efficiencies, long lifetimes and low operating voltages and which are also compatible with phosphorescent emitters which carry ketoketonate ligands.

Improvements in the properties are likewise also still desirable in the case of electron-transport materials since it is also precisely the properties of the electron-transport material that exert a significant influence on the above-mentioned properties of the organic electroluminescent device. In particular, there is a need for improvement in the case of electron-transport materials which simultaneously result in good efficiency, a long lifetime and a low operating voltage. It is also precisely the properties of the electron-transport material that are frequently limiting for the lifetime, the efficiency and the operating voltage of the organic electroluminescent device.

It would be desirable here to have available electron-transport materials which result in better electron injection into the emitting layer, since an electron-richer emission layer results in better efficiency. In addition, better injection enables the operating voltage to be reduced. Further improvements to the electron-transport material are therefore necessary for this purpose.

Electroluminescent devices which use AlQ$_3$ as electron conductor have already been known for a long time and were described as long ago as 1993 in U.S. Pat. No. 4,539,507. AlQ$_3$ has since then frequently been used as electron-transport material, but has a number of disadvantages: it cannot be vapour-deposited without a residue since it partially decomposes at the sublimation temperature, which represents a major problem, in particular, for production plants. This has the consequence that the vapour-deposition sources constantly have to be cleaned or exchanged. Furthermore, decomposition products of AlQ$_3$ enter the OLED, where they contribute to a shortened lifetime and reduced quantum and power efficiency. AlQ$_3$ additionally has low electron mobility, which results in high voltages and thus lower power efficiency. In order to avoid short circuits in the display, it is desired to increase the layer thickness; this is not possible with AlQ$_3$ owing to the low charge-carrier mobility and the resultant increase in voltage. The charge-carrier mobility of other electron conductors (U.S. Pat. No. 4,539,507) is likewise too low in order to build up thicker layers therewith, with the lifetime of the OLED being even worse than on use of AlQ$_3$. The inherent colour (yellow in the solid) of AlQ$_3$, which can result in colour shifts due to re-absorption and weak re-emission, particularly in the case of blue OLEDs, also proves to be unfavourable. Blue OLEDs can only be produced here with considerable efficiency and colour location deficiencies.

Thus, there continues to be a demand for electron-transport materials which result in good efficiencies and at the same time in long lifetimes in organic electroluminescent devices.

Owing to good hole mobility, indenofluorenamines are used as charge-transport materials and -injection materials. EP 1860097, WO 2006/100896, DE 102006025846, WO 2006/122630 and WO 2008/006449 disclose indenofluorenediamines for use in electronic devices. Good lifetimes are quoted therein on use as hole-transport material, but there is still a need to reduce the operating voltage in order to achieve better power efficiencies, especially in the case of blue emission.

The object of the present invention thus consists in the provision of such compounds.

Surprisingly, it has been found that electroluminescent devices which comprise indenocarbazole derivatives and related compounds of the following formula (1) have significant improvements over the prior art, in particular on use as matrix materials for phosphorescent dopants, but also, depending on the substitution, on use as electron-transport or hole-transport compounds.

To this end, the invention provides a compound of the general formula (1) or formula (1'):

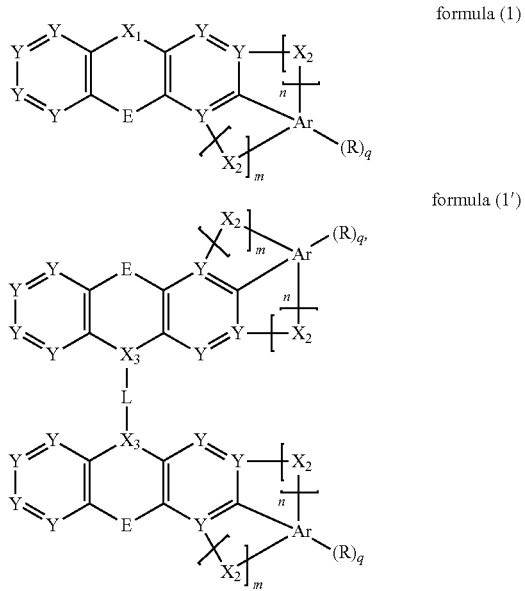

formula (1)

formula (1')

where the following applies to the symbols and indices used

Y is C if a group $X_2$ is bonded to the group Y, or is on each occurrence, identically or differently, CR or N if no group $X_2$ is bonded to the group Y;

E is on each occurrence, identically or differently, a covalent single bond or a divalent bridge selected from $N(R^1)$, $B(R^1)$, $C(R^1)_2$, O, $Si(R^1)_2$, $C=NR^1$, $C=C(R^1)_2$, S, S=O, $SO_2$, $P(R^1)$ and $P(=O)R^1$;

$X_1$ is on each occurrence, identically or differently, a divalent bridge selected from $N(R^1)$, $B(R^1)$, O, $C(R^1)_2$, $Si(R^1)_2$, $C=NR^1$, $C=C(R^1)_2$, S, S=O, $SO_2$, $P(R^1)$ and $P(=O)R^1$;

$X_2$ is on each occurrence, identically or differently, a divalent bridge selected from $N(R^1)$, $B(R^1)$, $C(R^1)_2$, $Si(R^1)_2$, C=O, $C=NR^1$, $C=C(R^1)_2$, S, S=O, $SO_2$, $CR^1-CR^1$, $P(R^1)$ and $P(=O)R^1$;

$X_3$ is on each occurrence, identically or differently, a divalent bridge selected from N, B, $C(R^1)$, $Si(R^1)$, P and P(=O);

L is a divalent aromatic or heteroaromatic ring system having 5 to 40 aromatic ring atoms, which may be substituted by one or more radicals $R^1$;

Ar is on each occurrence, identically or differently, an aromatic or heteroaromatic ring system, preferably an aryl or heteroaryl group having 5 to 40 ring atoms, which may be substituted by one or more radicals $R^1$;

n, m are, identically or differently on each occurrence, 0 or 1, with the proviso that n+m=1 or 2;

q is 1, 2, 3, 4, 5 or 6;

R is on each occurrence, identically or differently, H, D, F, Cl, Br, I, $N(Ar)_2$, C(=O)Ar, $P(=O)Ar_2$, S(=O)Ar, $S(=O)_2Ar$, $CR^2=CR^2Ar$, CN, $NO_2$, $Si(R^2)_3$, $B(OR^2)_2$, $OSO_2R^2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$, where one or more non-adjacent $CH_2$ groups may be replaced by $R^2C=CR^2$, C≡C, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aryl or heteroaryl group having 5 to 40 ring atoms, which may in each case be substituted by one or more radicals $R^2$, or an aromatic or heteroaromatic ring system having 5 to 60 aromatic ring atoms, which may in each case be substituted by one or more radicals $R^2$, or an aryloxy or heteroaryloxy group having 5 to 40 aromatic ring atoms, which may be substituted by one or more radicals $R^2$, or an aralkyl or heteroaralkyl group having 5 to 40 aromatic ring atoms, which may be substituted by one or more radicals $R^2$, or a combination of these systems; two or more substituents R here, together with the atoms to which they are bonded, may also form a mono- or polycyclic aliphatic or aromatic ring system with one another or, if they are bonded to Ar, with Ar;

$R^1$ is on each occurrence, identically or differently, H, D, F, Cl, Br, I, CN, $NO_2$, $CF_3$, $B(OR^2)_2$, $Si(R^2)_3$, a straight-chain alkyl, alkoxy or thioalkoxy group having 1 to 40 C atoms or a branched or cyclic alkyl, alkoxy or thioalkoxy group having 3 to 40C atoms, or an alkenyl or alkynyl group having 2 to 40 C atoms, each of which may be substituted by one or more radicals $R^2$, where one or more non-adjacent $CH_2$ groups may be replaced by $-R^2C=CR^2-$, $-C=C-$, $Si(R^2)_2$, $Ge(R^2)_2$, $Sn(R^2)_2$, C=O, C=S, C=Se, $C=NR^2$, $-O-$, $-S-$, $-COO-$ or $-CONR^2-$ and where one or more H atoms may be replaced by F, Cl, Br, I, CN or $NO_2$, or arylamines, or substituted or unsubstituted carbazoles, which may in each case be substituted by one or more radicals $R^2$, or an aryl or heteroaryl group having 5 to 40 ring atoms, which may be substituted by one or more aromatic, heteroaromatic or non-aromatic radicals $R^2$, or an aromatic or heteroaromatic ring system having 5 to 60 aromatic ring atoms, which may be substituted by one or more non-aromatic radicals $R^2$, or an aryloxy or heteroaryloxy group having 5 to 40 aromatic ring atoms, which may be substituted by one or more radicals $R^2$, or an aralkyl or heteroaralkyl group having 5 to 40 aromatic ring atoms, which may be substituted by one or more radicals $R^2$, or a combination of these systems; two or more substituents $R^1$ here may also form a mono- or polycyclic aliphatic or aromatic ring system with one another, together with the atoms to which they are bonded;

$R^2$ is on each occurrence, identically or differently, H, D or an aliphatic hydrocarbon radical having 1 to 20 C atoms or an aryl or heteroaryl group having 5 to 40 ring atoms, or a combination of these groups;

structures in which $X_1=X_2=N(R^1)$ and at the same time E stands for a single covalent bond and Y stands for CR or C are excluded here; the following compound is furthermore excluded from the invention:

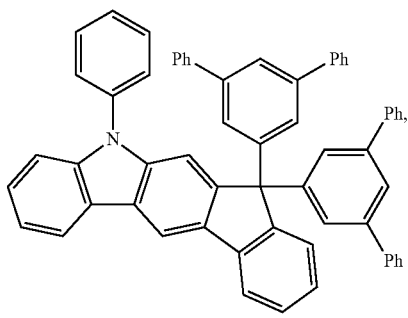

Ph = phenyl

The following compounds are furthermore preferably excluded from the invention:

For the purposes of the present invention, an alkyl group having 1 to 40 C atoms, in which, in addition, individual H atoms or $CH_2$ groups may be substituted by $-R^2C=CR^2-$, $-C\equiv C-$, $Si(R^2)_2$, $Ge(R^2)_2$, $Sn(R^2)_2$, $C=O$, $C=S$, $C=Se$, $C=NR^2$, $-O-$, $-S-$, $-COO-$ or $-CONR^2-$, is preferably taken to mean the radicals methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl and 2,2,2-trifluoroethyl. For the purposes of this invention, an alkenyl group is taken to mean, in particular, ethenyl, propenyl, butenyl, pentenyl, cyclopentenyl, hexenyl, cyclohexenyl, heptenyl, cycloheptenyl, octenyl and cyclooctenyl. For the purposes of this invention, an alkynyl group is taken to mean, in particular, ethynyl, propynyl, butynyl, pentynyl, hexynyl or octynyl. A $C_1$- to $C_{40}$-alkoxy group is preferably

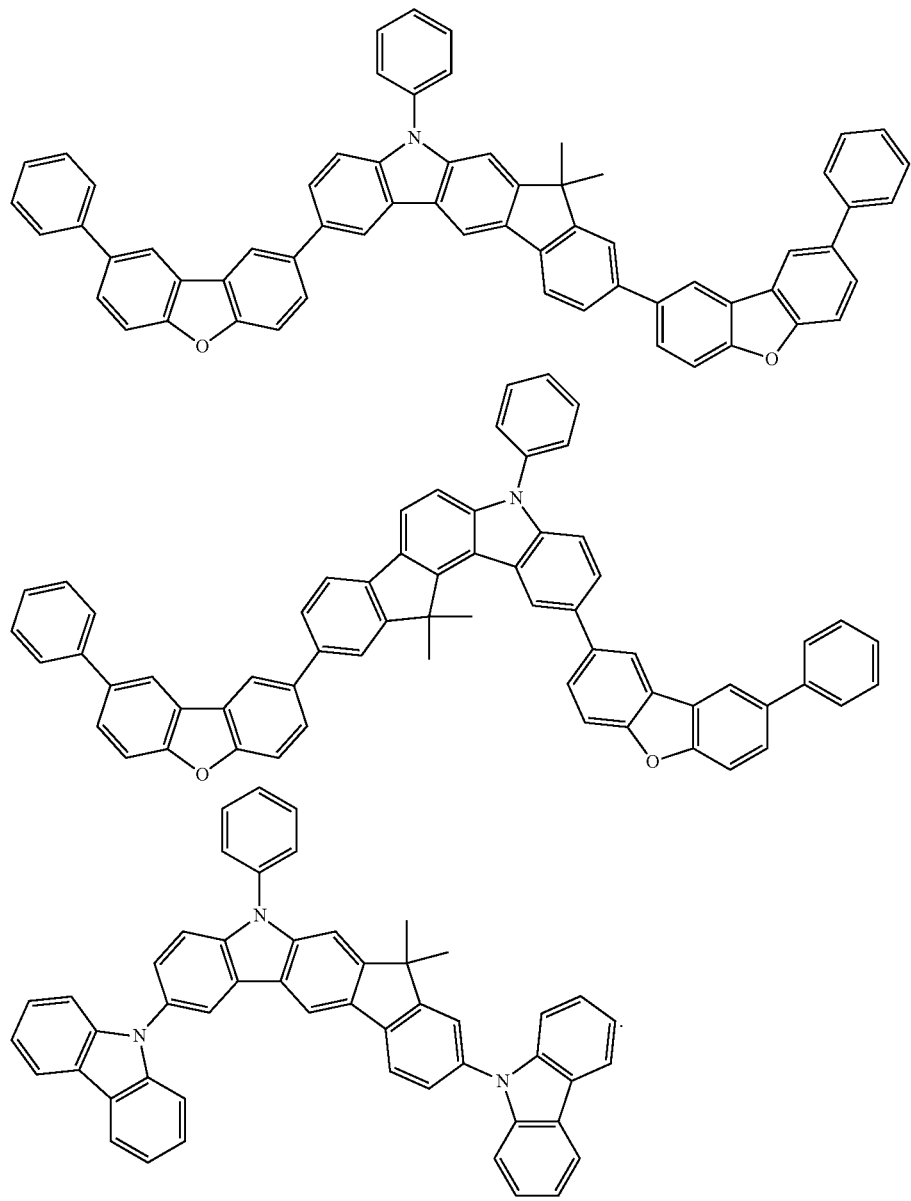

taken to mean methoxy, tri-fluoromethoxy, ethoxy, n-propoxy, i-propoxy, n-butoxy, i-butoxy, s-butoxy, t-butoxy or 2-methylbutoxy.

For the purposes of this invention, an aryl group contains 6 to 40 C atoms, preferably 6 to 25 C atoms, more preferably 6 to 20 C atoms; for the purposes of this invention, a heteroaryl group contains 1 to 39 C atoms and at least one heteroatom, preferably 2 to 25 C atoms and at least one heteroatom, more preferably 2 to 20 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, triazine, thiophene, or a polycyclic condensed aryl or heteroaryl group, for example naphthalene, anthracene, phenanthrene, benzanthracene, quinoline, isoquinoline, benzothiophene, benzofuran and indole, etc.

For the purposes of this invention, an aromatic ring system contains 6 to 60 C atoms, preferably 6 to 40 C atoms, more preferably 6 to 24 C atoms, in the ring system. For the purposes of this invention, a heteroaromatic ring system contains 1 to 79 C atoms and at least one heteroatom in the ring system, more preferably 2 to 40 C atoms and at least one heteroatom, most preferably 2 to 24 C atoms and at least one heteroatom, with the proviso that the sum of C atoms and heteroatoms is at least 5. The heteroatoms are preferably selected from N, O and/or S. For the purposes of this invention, an aromatic or heteroaromatic ring system is, in addition, intended to be taken to mean a system which does not necessarily contain only aryl or heteroaryl groups, but instead in which a plurality of aryl or heteroaryl groups may also be connected by a non-aromatic unit (preferably less than 10% of the atoms other than H), such as, for example, a C, N or O atom. Thus, for example, systems such as 9,9'-spirobifluorene, 9,9-diarylfluorene, triarylamine, diaryl ether, stilbene, etc. are also intended to be taken to be aromatic ring systems for the purposes of this invention, as are systems in which two or more aryl groups are connected, for example, by a linear or cyclic alkyl group or by a silyl group, and likewise biaryl or oligoaryl groups.

An aromatic or heteroaromatic ring system having 5-60 ring atoms, which may also in each case be substituted by the above-mentioned radicals R and which may be linked to the aromatic or heteroaromatic ring system via any desired positions, is taken to mean, in particular, groups derived from benzene, naphthalene, anthracene, phenanthrene, pyrene, chrysene, benzanthracene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, cis- or trans-indenocarbazole, cis- or trans-indolocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,54-azine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

In an embodiment, $X_1$ in the compound of the general formula (1) is preferably selected from $N(R^1)$, where $R^1$ is selected from an aryl or heteroaryl group having 5 to 40 ring atoms, each of which may be substituted by one or more radicals $R^2$, or an aromatic or heteroaromatic ring system having 5 to 60 ring atoms, which may in each case be substituted by one or more radicals $R^2$.

$X_2$ in the compound of the general formula (1) is on each occurrence, independently of one another, preferably selected from $C(R^1)_2$, $N(R^1)$ and S.

In a particularly preferred embodiment of the invention, $X_1$ in the compound of the general formula (1) stands for $N(R^1)$, where $R^1$ is selected from an aryl or heteroaryl group having 5 to 40 ring atoms, which may in each case be substituted by one or more radicals $R^2$, or an aromatic or heteroaromatic ring system having 5 to 60 ring atoms, which may in each case be substituted by one or more radicals $R^2$, and $X_2$ stands for $C(R^1)_2$.

$X_3$ in the compound of the general formula (1a) is on each occurrence, independently of one another, preferably selected from N or $C(R^1)$, particularly preferably N.

E is on each occurrence, independently of one another, preferably selected from a single covalent bond or a divalent bridge selected from $N(R^1)$, $C(R^1)_2$ and O. E is particularly preferably selected from a single covalent bond, $N(R^1)$ or $C(R^1)_2$. E very particularly preferably stands for a single covalent bond.

L preferably stands for an aromatic or heteroaromatic ring system having 5 to 24 aromatic ring atoms, which may be substituted by one or more radicals $R^1$, As already mentioned above in the definition, L does not necessarily have to contain only aromatic groups. Thus, for example, preference is also given to a group L which has the formula aryl-C(=O)-aryl, where aryl stands, identically or differently on each occurrence, for an aryl, biaryl, heteroaryl or biheteroaryl group having 5 to 12 aromatic ring atoms, preferably for a phenyl or biphenyl group. Groups L which are furthermore preferred are groups which represent a combination of phenyl groups and triazine groups, for example phenyl-triazine-phenyl, where these groups may also be substituted by one or more radicals $R^1$.

In the compound of the general formula (1), R is preferably selected from H, D, $N(Ar)_2$, preferably diphenylamino, a substituted or unsubstituted arylamine, a straight-chain alkyl group having 1 to 20 C atoms, preferably 1 to 10 C atoms, a branched alkyl group having 3 to 20 C atoms, preferably 1 to 10 C atoms, or an aromatic or heteroaromatic ring system having 5 to 40 ring atoms. The aromatic or heteroaromatic ring system here is preferably selected from substituted or unsubstituted phenyl, naphthyl, pyridine, triazine, pyrimidine, benzimidazole, thiophene, triphenylamine or combinations of these groups.

In the compound of the general formula (1), it is furthermore preferred for Ar to denote an aryl or heteroaryl group having 5 to 40 ring atoms, preferably substituted or unsubstituted phenyl, naphthyl, triazinyl, pyridyl, pyrimidyl or carbazole, particularly preferably phenyl.

A compound which is preferred in accordance with the invention is represented, for example, by the following formula (2) or formula (2'):

formula (2)
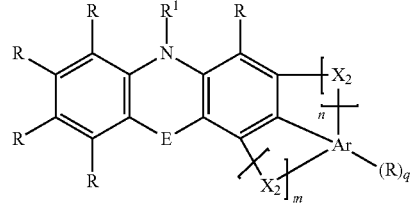

formula (2')
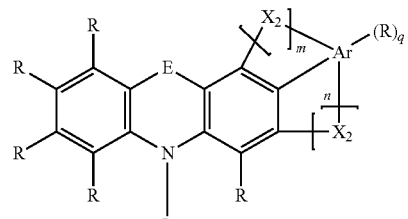

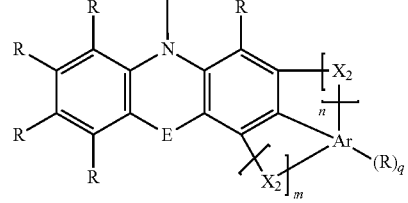

where the symbols and indices have the meanings indicated above.

Further preferred compounds within the general formula (1) are represented by the following compounds of the formulae (3), (4), (3') and (4'):

formula (3)
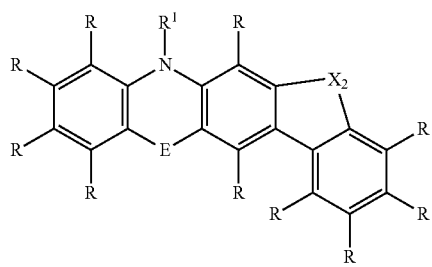

formula (4)
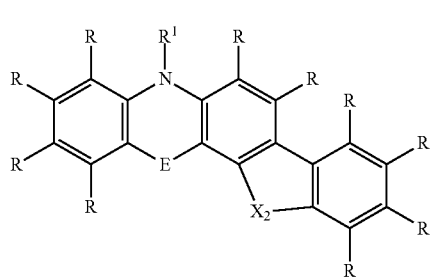

formula (3')
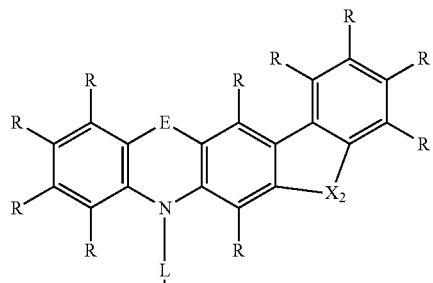

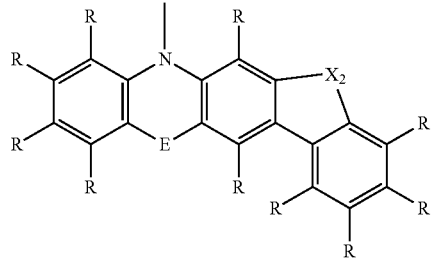

formula (4')
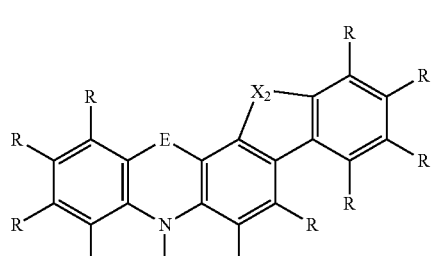

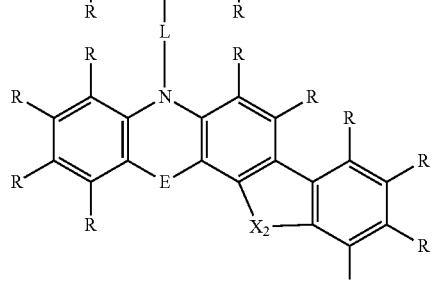

where the symbols and indices used have the meanings indicated above.

In yet a further embodiment, the compound of the formula (1) is selected from the following general structures:

formula (3a)
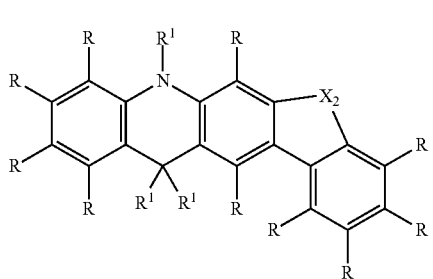

formula (3b)
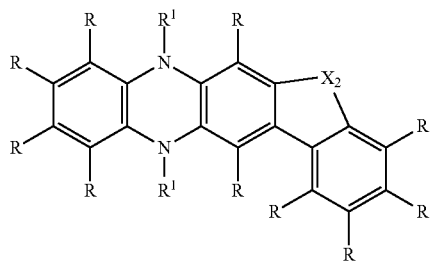

formula (3c)
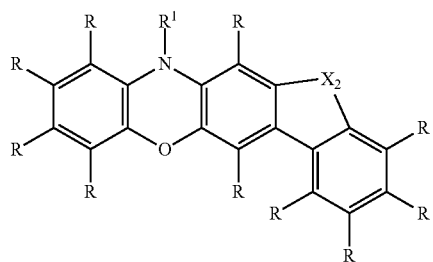

formula (3d)
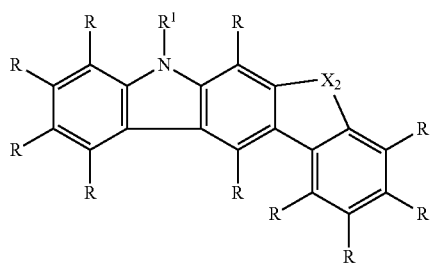

formula (4a)
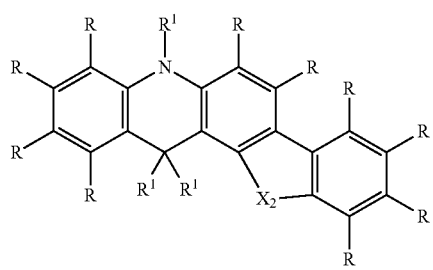

formula (4b)
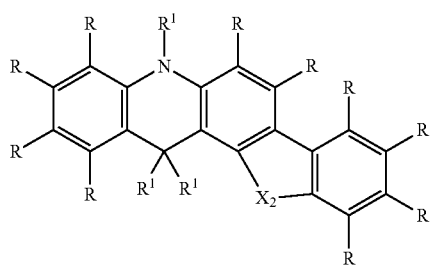

formula (4c)
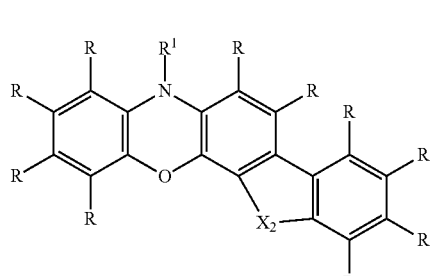

formula (4d)
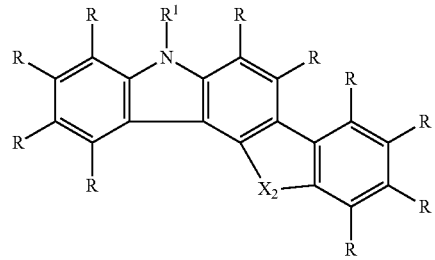

where the symbols and indices have the meanings indicated above and where $X_2$ is preferably selected from $C(R^1)_2$, $N(R^1)$ and S, with the proviso that $X_2$ in formula (3d) and formula (4d) does not stand for $N(R^1)$. $R^1$ here is preferably selected on each occurrence, independently of one another, from alkyl, substituted or unsubstituted triazine, pyridine, pyrimidine, pyrazine, phenyl, biphenyl, terphenyl, naphthyl, anthracenyl and carbazole. Furthermore, $R^1$ is preferably an aryl-C(=O)-aryl group, where aryl stands for an aryl or heteroaryl group having 5 to 10 aromatic ring atoms, preferably for phenyl. Two radicals $R^1$ here which are bonded to the same C atom together with the atom(s) to which they are bonded may also form an aliphatic, aromatic or heteroaromatic ring system, for example a fluorene.

Corresponding embodiments of the formula (1') can be constructed entirely analogously and are likewise preferred.

In formulae (3d) and (4d), it is preferred if none of the radicals R contains a carbazole group or a dibenzothiophene group.

In the formulae (3a) to (3d) and (4a) to (4d), $X_2$ very particularly preferably stands for $C(R^1)_2$.

Particular preference is given here to the following structures of the formulae (3e) and (4e):

formula (3e)
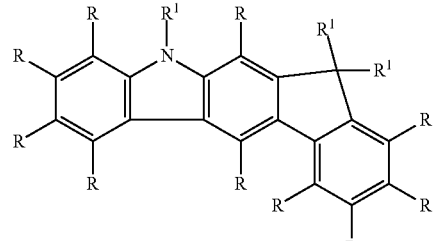

formula (4e)
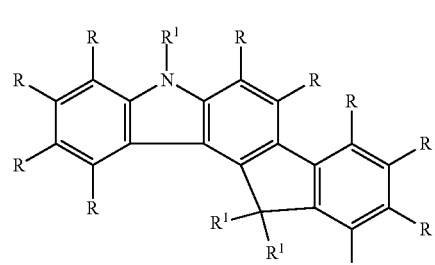

where the symbols and indices have the meanings indicated above. $R^1$ here is preferably selected on each occurrence, independently of one another, from alkyl, substituted or unsubstituted triazine, pyridine, pyrimidine, pyrazine, phenyl, biphenyl, terphenyl, naphthyl, anthracenyl and carbazole. Two radicals $R^1$ here which are bonded to the same C atom together with the atom(s) to which they are bonded may also form an aliphatic, aromatic or heteroaromatic ring, for example a fluorene.

Further particularly preferred compounds of the formula (1) are those which have at least one nitrogen heteroatom. The preferred positions for a nitrogen atom are represented by a Y in the structures shown below:

formula (5)

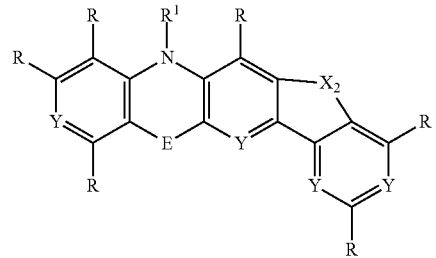

formula (6)

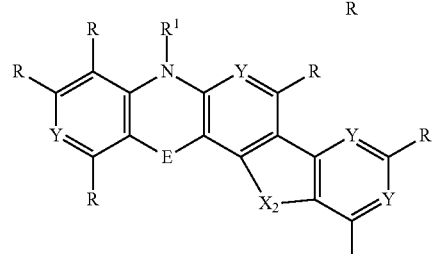

formula (5')

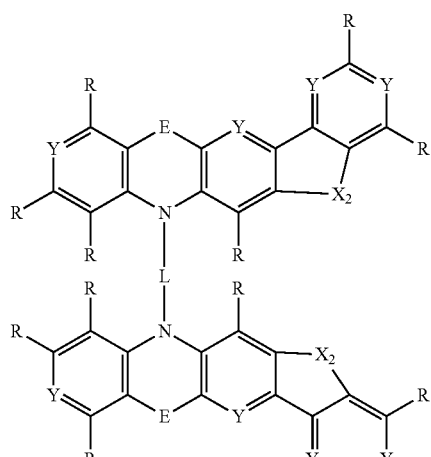

formula (6')

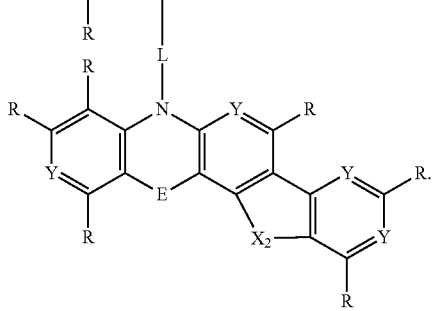

At least one group Y here stands for N and the remaining groups Y stand for CR. Otherwise, the symbols and indices used have the meanings indicated above.

Particularly preferred compounds are also the structures of the formulae (5a) to (5d) and (6a) to (6d) shown below:

formula (5a)

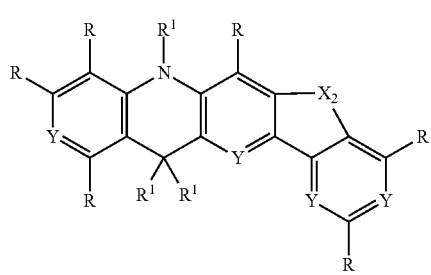

formula (5b)

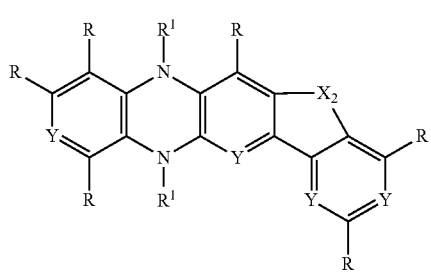

formula (5c)

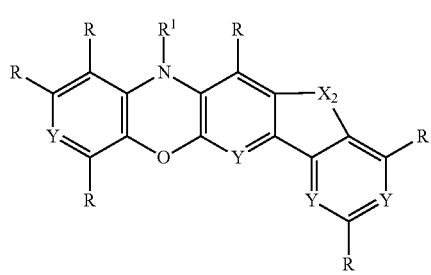

formula (5d)

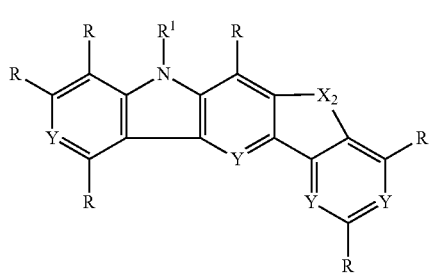

formula (6a)

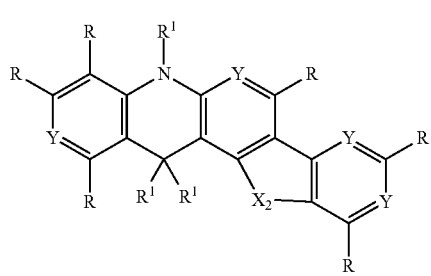

-continued formula (6b)
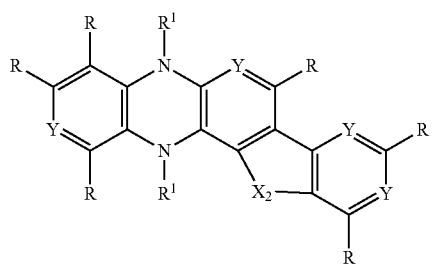

formula (6c)
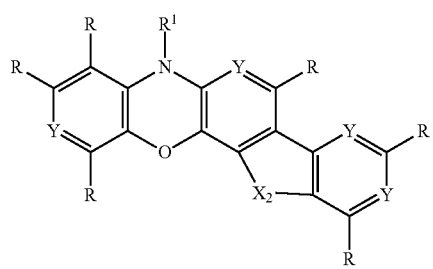

formula (6d)
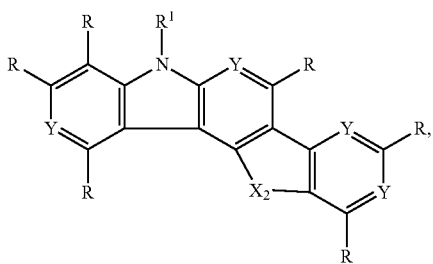

where the symbols and indices used have the meanings indicated above, at least one Y represents a nitrogen atom, and where $X_2$ is preferably selected from $C(R^1)_2$, $N(R^1)$ and S. $R^1$ here is preferably selected on each occurrence, independently of one another, from alkyl, substituted or unsubstituted triazine, pyridine, pyrimidine, pyrazine, phenyl, biphenyl, terphenyl, naphthyl, anthracenyl and carbazole. Two radicals $R^1$ here which are bonded to the same C atom may also form an aliphatic, aromatic or heteroaromatic ring system, for example a fluorene.

Corresponding embodiments of the formula (1') can be constructed entirely analogously and are likewise preferred.

For the purposes of the invention, preference is likewise given to the following structures:

formula (5e)
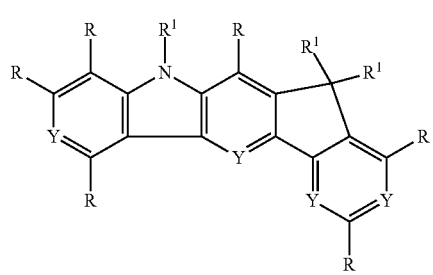

-continued formula (5f)
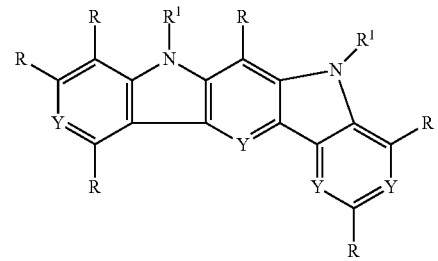

formula (6e)
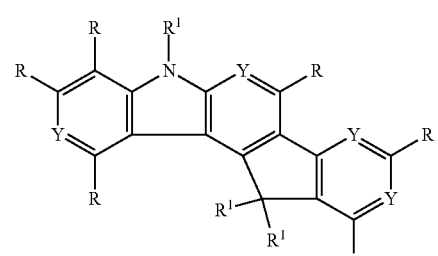

formula (6f)
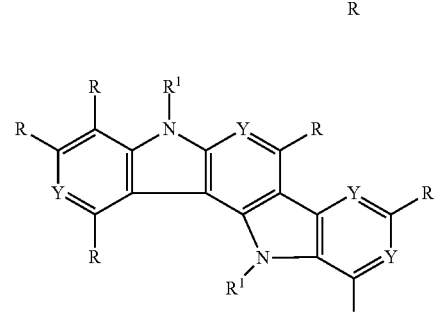

where the symbols and indices have the meanings indicated above. $R^1$ here is preferably selected on each occurrence, independently of one another, from alkyl, substituted or unsubstituted triazine, pyridine, pyrimidine, pyrazine, phenyl, biphenyl, terphenyl, naphthyl, anthracenyl and carbazole. Two radicals $R^1$ here which are bonded to the same C atom together with the atom(s) to which they are bonded may also form an aliphatic, aromatic or heteroaromatic ring system, for example a fluorene.

Corresponding embodiments of the formula (1') can be constructed entirely analogously and are likewise preferred.

Further particularly preferred compounds of the formula (1) are the following structures:

formula (3g)
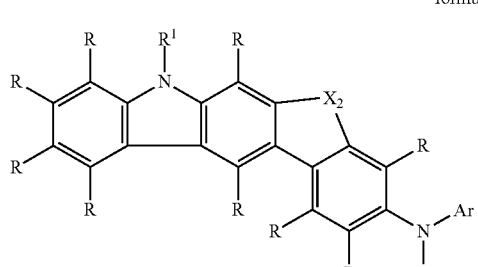

formula (3h)
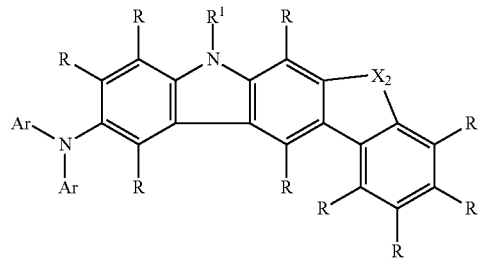

formula (3i)
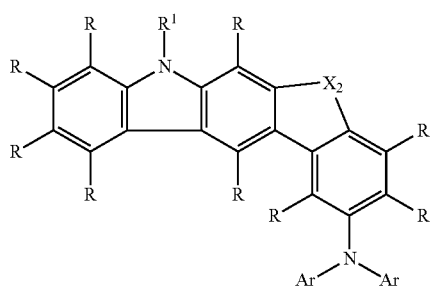

formula (3j)
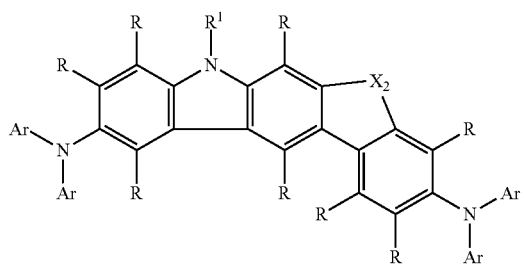

formula (3k)
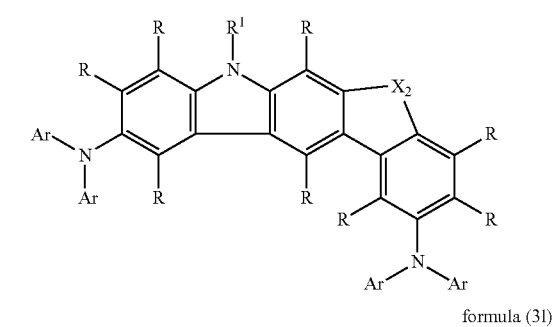

formula (3l)
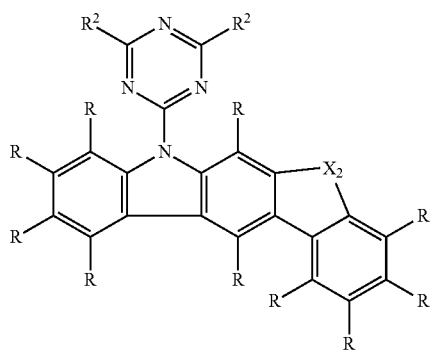

formula (3m)

formula (3n)

where the symbols and indices used have the meanings indicated above. $X_2$ here particularly preferably stands for $C(R^1)_2$. $R^1$ here is preferably selected on each occurrence, independently of one another, from alkyl, substituted or unsubstituted triazine, pyridine, pyrimidine, pyrazine, phenyl, biphenyl, terphenyl, naphthyl, anthracenyl and carbazole. Two radicals $R^1$ here which are bonded to the same C atom together with the atom(s) to which they are bonded may also form an aliphatic, aromatic or hetero aromatic ring system, for example a fluorene.

In yet a further embodiment of the invention, the compound according to the invention conforms to the general formula (7):

formula (7)

where the symbols and indices have the meanings indicated for formula (1), o and p are each, independently of one another, 0 or 1, and o+p=1 or 2.

In an embodiment, $X_1$ in the compound of the general formula (7) is preferably selected on each occurrence, independently of one another, from $N(R^1)$ or $C(R^1)_2$, where $R^1$ is selected from an aryl or heteroaryl group having 5 to 40 ring atoms which is substituted by $R^2$ or unsubstituted or an aromatic or heteroaromatic ring system having 5 to 40 ring atoms, which may be substituted by one or more radicals $R^2$.

$X_2$ in the compound of the general formula (7) is preferably selected on each occurrence, independently of one another, from $C(R^1)_2$, $N(R^1)$ or S.

Particularly preferably, $X_1$ stands for $N(R^1)$ and $X_2$ stands for $C(R^1)_2$ or $X_1$ stands for $C(R^1)_2$ and $X_2$ stands for $N(R^1)$.

In the compound of the general formula (7), R is preferably selected from H, D, $NAr_2$, a substituted or unsubstituted arylamine, a straight-chain alkyl group having 1 to 20 C atoms, preferably 1 to 10 C atoms, a branched alkyl group having 3 to 20 C atoms, preferably 3 to 10 C atoms, or an aromatic or heteroaromatic ring system having 5 to 40 ring atoms. The aromatic or heteroaromatic ring system here is preferably selected from phenyl, biphenyl, terphenyl, naphthyl, pyridine, triazine, pyrimidine, pyrazine, thiophene or triphenylamine, each of which may be substituted by one or more radicals $R^1$.

In the compound of the general formula (7), it is furthermore preferred for Ar to stand for an aryl or heteroaryl group, preferably phenyl, biphenyl, terphenyl, naphthyl, pyridinyl, triazinyl, pyrimidinyl, pyrazinyl, thiophenyl or substituted or unsubstituted carbazole, each of which may be substituted by one or more radicals R.

Preferred structures within the compound of the formula (7) are structures (7a) to (7d):


formula (7a)


formula (7b)

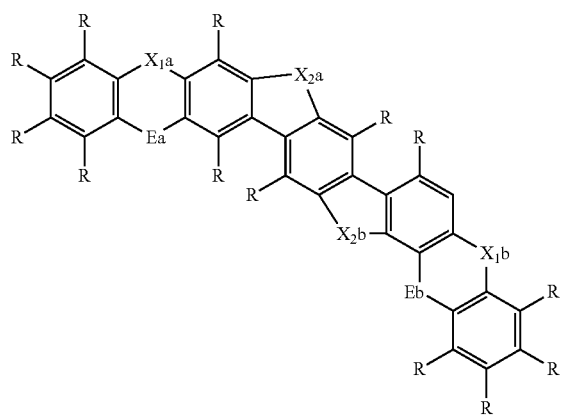

formula (7c)

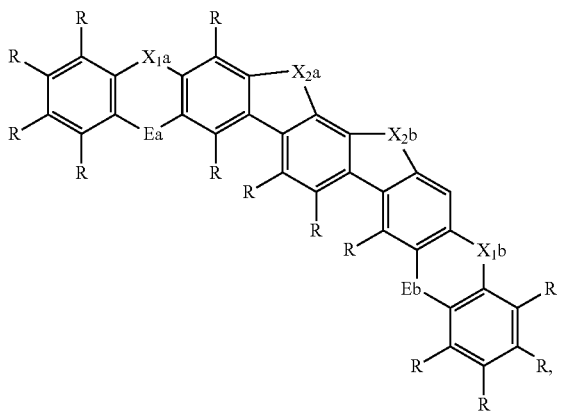

formula (7d)

where the symbols and indices used have the meanings indicated above, $X_1a$ and $X_1b$ are each on each occurrence, independently of one another, $C(R^1)_2$ or $N(R^1)$, Ea and Eb are on each occurrence, independently of one another, a covalent single bond, $C(R^1)_2$, $N(R^1)$ or O, and $X_2a$ and $X_2b$ are each selected, independently of one another, from $C(R^1)_2$, $N(R^1)$ or S, particularly preferably $C(R^1)_2$ and $N(R^1)$.

The possible combinations shown in Table 1 arise for the substituents $X_1a$, $X_1b$, Ea, Eb, $X_2a$ and $X_2b$:

TABLE 1

("—" denotes a covalent single bond):

| $X_1a$ | $X_1b$ | Ea | Eb | $X_2a$ | $X_2b$ |
|---|---|---|---|---|---|
| $C(R^1)_2$ | $C(R^1)_2$ | — | — | $C(R^1)_2$ | $C(R^1)_2$ |
| $C(R^1)_2$ | $C(R^1)_2$ | $C(R^1)_2$ | $C(R^1)_2$ | $C(R^1)_2$ | $C(R^1)_2$ |
| $C(R^1)_2$ | $C(R^1)_2$ | $N(R^1)$ | $N(R^1)$ | $C(R^1)_2$ | $C(R^1)_2$ |
| $C(R^1)_2$ | $C(R^1)_2$ | O | O | $C(R^1)_2$ | $C(R^1)_2$ |
| $C(R^1)_2$ | $C(R^1)_2$ | — | $C(R^1)_2$ | $C(R^1)_2$ | $C(R^1)_2$ |
| $C(R^1)_2$ | $C(R^1)_2$ | — | $N(R^1)$ | $C(R^1)_2$ | $C(R^1)_2$ |
| $C(R^1)_2$ | $C(R^1)_2$ | — | O | $C(R^1)_2$ | $C(R^1)_2$ |
| $C(R^1)_2$ | $C(R^1)_2$ | $C(R^1)_2$ | — | $C(R^1)_2$ | $C(R^1)_2$ |
| $C(R^1)_2$ | $C(R^1)_2$ | $C(R^1)_2$ | $N(R^1)$ | $C(R^1)_2$ | $C(R^1)_2$ |
| $C(R^1)_2$ | $C(R^1)_2$ | $C(R^1)_2$ | O | $C(R^1)_2$ | $C(R^1)_2$ |
| $C(R^1)_2$ | $C(R^1)_2$ | $N(R^1)$ | — | $C(R^1)_2$ | $C(R^1)_2$ |
| $C(R^1)_2$ | $C(R^1)_2$ | $N(R^1)$ | $C(R^1)_2$ | $C(R^1)_2$ | $C(R^1)_2$ |
| $C(R^1)_2$ | $C(R^1)_2$ | $N(R^1)$ | O | $C(R^1)_2$ | $C(R^1)_2$ |
| $C(R^1)_2$ | $C(R^1)_2$ | O | — | $C(R^1)_2$ | $C(R^1)_2$ |
| $C(R^1)_2$ | $C(R^1)_2$ | O | $C(R^1)_2$ | $C(R^1)_2$ | $C(R^1)_2$ |
| $C(R^1)_2$ | $C(R^1)_2$ | O | $N(R^1)$ | $C(R^1)_2$ | $C(R^1)_2$ |
| $C(R^1)_2$ | $N(R^1)$ | — | — | $C(R^1)_2$ | $C(R^1)_2$ |
| $C(R^1)_2$ | $N(R^1)$ | $C(R^1)_2$ | $C(R^1)_2$ | $C(R^1)_2$ | $C(R^1)_2$ |
| $C(R^1)_2$ | $N(R^1)$ | $N(R^1)$ | $N(R^1)$ | $C(R^1)_2$ | $C(R^1)_2$ |
| $C(R^1)_2$ | $N(R^1)$ | O | O | $C(R^1)_2$ | $C(R^1)_2$ |
| $C(R^1)_2$ | $N(R^1)$ | — | $C(R^1)_2$ | $C(R^1)_2$ | $C(R^1)_2$ |
| $C(R^1)_2$ | $N(R^1)$ | — | $N(R^1)$ | $C(R^1)_2$ | $C(R^1)_2$ |
| $C(R^1)_2$ | $N(R^1)$ | — | O | $C(R^1)_2$ | $C(R^1)_2$ |
| $C(R^1)_2$ | $N(R^1)$ | $C(R^1)_2$ | — | $C(R^1)_2$ | $C(R^1)_2$ |
| $C(R^1)_2$ | $N(R^1)$ | $C(R^1)_2$ | $N(R^1)$ | $C(R^1)_2$ | $C(R^1)_2$ |
| $C(R^1)_2$ | $N(R^1)$ | $C(R^1)_2$ | O | $C(R^1)_2$ | $C(R^1)_2$ |
| $C(R^1)_2$ | $N(R^1)$ | $N(R^1)$ | — | $C(R^1)_2$ | $C(R^1)_2$ |
| $C(R^1)_2$ | $N(R^1)$ | $N(R^1)$ | $C(R^1)_2$ | $C(R^1)_2$ | $C(R^1)_2$ |
| $C(R^1)_2$ | $N(R^1)$ | $N(R^1)$ | O | $C(R^1)_2$ | $C(R^1)_2$ |
| $C(R^1)_2$ | $N(R^1)$ | O | — | $C(R^1)_2$ | $C(R^1)_2$ |
| $C(R^1)_2$ | $N(R^1)$ | O | $C(R^1)_2$ | $C(R^1)_2$ | $C(R^1)_2$ |
| $C(R^1)_2$ | $N(R^1)$ | O | $N(R^1)$ | $C(R^1)_2$ | $C(R^1)_2$ |
| $N(R^1)$ | $C(R^1)_2$ | — | — | $C(R^1)_2$ | $C(R^1)_2$ |
| $N(R^1)$ | $C(R^1)_2$ | $C(R^1)_2$ | $C(R^1)_2$ | $C(R^1)_2$ | $C(R^1)_2$ |
| $N(R^1)$ | $C(R^1)_2$ | $N(R^1)$ | $N(R^1)$ | $C(R^1)_2$ | $C(R^1)_2$ |
| $N(R^1)$ | $C(R^1)_2$ | O | O | $C(R^1)_2$ | $C(R^1)_2$ |
| $N(R^1)$ | $C(R^1)_2$ | — | $C(R^1)_2$ | $C(R^1)_2$ | $C(R^1)_2$ |
| $N(R^1)$ | $C(R^1)_2$ | — | $N(R^1)$ | $C(R^1)_2$ | $C(R^1)_2$ |
| $N(R^1)$ | $C(R^1)_2$ | — | O | $C(R^1)_2$ | $C(R^1)_2$ |
| $N(R^1)$ | $C(R^1)_2$ | $C(R^1)_2$ | — | $C(R^1)_2$ | $C(R^1)_2$ |

TABLE 1-continued ("—" denotes a covalent single bond):

| X₁a | X₁b | Ea | Eb | X₂a | X₂b |
|---|---|---|---|---|---|
| N(R¹) | C(R¹)₂ | C(R¹)₂ | N(R¹) | C(R¹)₂ | C(R¹)₂ |
| N(R¹) | C(R¹)₂ | C(R¹)₂ | O | C(R¹)₂ | C(R¹)₂ |
| N(R¹) | C(R¹)₂ | N(R¹) | — | C(R¹)₂ | C(R¹)₂ |
| N(R¹) | C(R¹)₂ | N(R¹) | C(R¹)₂ | C(R¹)₂ | C(R¹)₂ |
| N(R¹) | C(R¹)₂ | N(R¹) | O | C(R¹)₂ | C(R¹)₂ |
| N(R¹) | C(R¹)₂ | O | — | C(R¹)₂ | C(R¹)₂ |
| N(R¹) | C(R¹)₂ | O | C(R¹)₂ | C(R¹)₂ | C(R¹)₂ |
| N(R¹) | C(R¹)₂ | O | N(R¹) | C(R¹)₂ | C(R¹)₂ |
| C(R¹)₂ | C(R¹)₂ | — | — | N(R¹) | C(R¹)₂ |
| C(R¹)₂ | C(R¹)₂ | C(R¹)₂ | C(R¹)₂ | N(R¹) | C(R¹)₂ |
| C(R¹)₂ | C(R¹)₂ | N(R¹) | N(R¹) | N(R¹) | C(R¹)₂ |
| C(R¹)₂ | C(R¹)₂ | O | O | N(R¹) | C(R¹)₂ |
| C(R¹)₂ | C(R¹)₂ | — | C(R¹)₂ | N(R¹) | C(R¹)₂ |
| C(R¹)₂ | C(R¹)₂ | — | N(R¹) | N(R¹) | C(R¹)₂ |
| C(R¹)₂ | C(R¹)₂ | — | O | N(R¹) | C(R¹)₂ |
| C(R¹)₂ | C(R¹)₂ | C(R¹)₂ | — | N(R¹) | C(R¹)₂ |
| C(R¹)₂ | C(R¹)₂ | C(R¹)₂ | N(R¹) | N(R¹) | C(R¹)₂ |
| C(R¹)₂ | C(R¹)₂ | C(R¹)₂ | O | N(R¹) | C(R¹)₂ |
| C(R¹)₂ | C(R¹)₂ | N(R¹) | — | N(R¹) | C(R¹)₂ |
| C(R¹)₂ | C(R¹)₂ | N(R¹) | C(R¹)₂ | N(R¹) | C(R¹)₂ |
| C(R¹)₂ | C(R¹)₂ | N(R¹) | O | N(R¹) | C(R¹)₂ |
| C(R¹)₂ | C(R¹)₂ | O | — | N(R¹) | C(R¹)₂ |
| C(R¹)₂ | C(R¹)₂ | O | C(R¹)₂ | N(R¹) | C(R¹)₂ |
| C(R¹)₂ | C(R¹)₂ | O | N(R¹) | N(R¹) | C(R¹)₂ |
| C(R¹)₂ | C(R¹)₂ | — | — | C(R¹)₂ | N(R¹) |
| C(R¹)₂ | C(R¹)₂ | C(R¹)₂ | C(R¹)₂ | C(R¹)₂ | N(R¹) |
| C(R¹)₂ | C(R¹)₂ | N(R¹) | N(R¹) | C(R¹)₂ | N(R¹) |
| C(R¹)₂ | C(R¹)₂ | O | O | C(R¹)₂ | N(R¹) |
| C(R¹)₂ | C(R¹)₂ | — | C(R¹)₂ | C(R¹)₂ | N(R¹) |
| C(R¹)₂ | C(R¹)₂ | — | N(R¹) | C(R¹)₂ | N(R¹) |
| C(R¹)₂ | C(R¹)₂ | — | O | C(R¹)₂ | N(R¹) |
| C(R¹)₂ | C(R¹)₂ | C(R¹)₂ | — | C(R¹)₂ | N(R¹) |
| C(R¹)₂ | C(R¹)₂ | C(R¹)₂ | N(R¹) | C(R¹)₂ | N(R¹) |
| C(R¹)₂ | C(R¹)₂ | C(R¹)₂ | O | C(R¹)₂ | N(R¹) |
| C(R¹)₂ | C(R¹)₂ | N(R¹) | — | C(R¹)₂ | N(R¹) |
| C(R¹)₂ | C(R¹)₂ | N(R¹) | C(R¹)₂ | C(R¹)₂ | N(R¹) |
| C(R¹)₂ | C(R¹)₂ | N(R¹) | O | C(R¹)₂ | N(R¹) |
| C(R¹)₂ | C(R¹)₂ | O | — | C(R¹)₂ | N(R¹) |
| C(R¹)₂ | C(R¹)₂ | O | C(R¹)₂ | C(R¹)₂ | N(R¹) |
| C(R¹)₂ | C(R¹)₂ | O | N(R¹) | C(R¹)₂ | N(R¹) |
| N(R¹) | N(R¹) | — | — | C(R¹)₂ | C(R¹)₂ |
| N(R¹) | N(R¹) | C(R¹)₂ | C(R¹)₂ | C(R¹)₂ | C(R¹)₂ |
| N(R¹) | N(R¹) | N(R¹) | N(R¹) | C(R¹)₂ | C(R¹)₂ |
| N(R¹) | N(R¹) | O | O | C(R¹)₂ | C(R¹)₂ |
| N(R¹) | N(R¹) | — | C(R¹)₂ | C(R¹)₂ | C(R¹)₂ |
| N(R¹) | N(R¹) | — | N(R¹) | C(R¹)₂ | C(R¹)₂ |
| N(R¹) | N(R¹) | — | O | C(R¹)₂ | C(R¹)₂ |
| N(R¹) | N(R¹) | C(R¹)₂ | — | C(R¹)₂ | C(R¹)₂ |
| N(R¹) | N(R¹) | C(R¹)₂ | N(R¹) | C(R¹)₂ | C(R¹)₂ |
| N(R¹) | N(R¹) | C(R¹)₂ | O | C(R¹)₂ | C(R¹)₂ |
| N(R¹) | N(R¹) | N(R¹) | — | C(R¹)₂ | C(R¹)₂ |
| N(R¹) | N(R¹) | N(R¹) | C(R¹)₂ | C(R¹)₂ | C(R¹)₂ |
| N(R¹) | N(R¹) | N(R¹) | O | C(R¹)₂ | C(R¹)₂ |
| N(R¹) | N(R¹) | O | — | C(R¹)₂ | C(R¹)₂ |
| N(R¹) | N(R¹) | O | C(R¹)₂ | C(R¹)₂ | C(R¹)₂ |
| N(R¹) | N(R¹) | O | N(R¹) | C(R¹)₂ | C(R¹)₂ |
| N(R¹) | C(R¹)₂ | — | — | N(R¹) | C(R¹)₂ |
| N(R¹) | C(R¹)₂ | C(R¹)₂ | C(R¹)₂ | N(R¹) | C(R¹)₂ |
| N(R¹) | C(R¹)₂ | N(R¹) | N(R¹) | N(R¹) | C(R¹)₂ |
| N(R¹) | C(R¹)₂ | O | O | N(R¹) | C(R¹)₂ |
| N(R¹) | C(R¹)₂ | — | C(R¹)₂ | N(R¹) | C(R¹)₂ |
| N(R¹) | C(R¹)₂ | — | N(R¹) | N(R¹) | C(R¹)₂ |
| N(R¹) | C(R¹)₂ | — | O | N(R¹) | C(R¹)₂ |
| N(R¹) | C(R¹)₂ | C(R¹)₂ | — | N(R¹) | C(R¹)₂ |
| N(R¹) | C(R¹)₂ | C(R¹)₂ | N(R¹) | N(R¹) | C(R¹)₂ |
| N(R¹) | C(R¹)₂ | C(R¹)₂ | O | N(R¹) | C(R¹)₂ |
| N(R¹) | C(R¹)₂ | N(R¹) | — | N(R¹) | C(R¹)₂ |
| N(R¹) | C(R¹)₂ | N(R¹) | C(R¹)₂ | N(R¹) | C(R¹)₂ |
| N(R¹) | C(R¹)₂ | N(R¹) | O | N(R¹) | C(R¹)₂ |
| N(R¹) | C(R¹)₂ | O | — | N(R¹) | C(R¹)₂ |
| N(R¹) | C(R¹)₂ | O | C(R¹)₂ | N(R¹) | C(R¹)₂ |
| N(R¹) | C(R¹)₂ | O | N(R¹) | N(R¹) | C(R¹)₂ |
| C(R¹)₂ | N(R¹) | — | — | N(R¹) | C(R¹)₂ |
| C(R¹)₂ | N(R¹) | C(R¹)₂ | C(R¹)₂ | N(R¹) | C(R¹)₂ |
| C(R¹)₂ | N(R¹) | N(R¹) | N(R¹) | N(R¹) | C(R¹)₂ |
| C(R¹)₂ | N(R¹) | O | O | N(R¹) | C(R¹)₂ |
| C(R¹)₂ | N(R¹) | — | C(R¹)₂ | N(R¹) | C(R¹)₂ |
| C(R¹)₂ | N(R¹) | — | N(R¹) | N(R¹) | C(R¹)₂ |
| C(R¹)₂ | N(R¹) | — | O | N(R¹) | C(R¹)₂ |
| C(R¹)₂ | N(R¹) | C(R¹)₂ | — | N(R¹) | C(R¹)₂ |
| C(R¹)₂ | N(R¹) | C(R¹)₂ | N(R¹) | N(R¹) | C(R¹)₂ |
| C(R¹)₂ | N(R¹) | C(R¹)₂ | O | N(R¹) | C(R¹)₂ |
| C(R¹)₂ | N(R¹) | N(R¹) | — | N(R¹) | C(R¹)₂ |
| C(R¹)₂ | N(R¹) | N(R¹) | C(R¹)₂ | N(R¹) | C(R¹)₂ |
| C(R¹)₂ | N(R¹) | N(R¹) | O | N(R¹) | C(R¹)₂ |
| C(R¹)₂ | N(R¹) | O | — | N(R¹) | C(R¹)₂ |
| C(R¹)₂ | N(R¹) | O | C(R¹)₂ | N(R¹) | C(R¹)₂ |
| C(R¹)₂ | N(R¹) | O | N(R¹) | N(R¹) | C(R¹)₂ |
| C(R¹)₂ | N(R¹) | — | — | C(R¹)₂ | N(R¹) |
| C(R¹)₂ | N(R¹) | C(R¹)₂ | C(R¹)₂ | C(R¹)₂ | N(R¹) |
| C(R¹)₂ | N(R¹) | N(R¹) | N(R¹) | C(R¹)₂ | N(R¹) |
| C(R¹)₂ | N(R¹) | O | O | C(R¹)₂ | N(R¹) |
| C(R¹)₂ | N(R¹) | — | C(R¹)₂ | C(R¹)₂ | N(R¹) |
| C(R¹)₂ | N(R¹) | — | N(R¹) | C(R¹)₂ | N(R¹) |
| C(R¹)₂ | N(R¹) | — | O | C(R¹)₂ | N(R¹) |
| C(R¹)₂ | N(R¹) | C(R¹)₂ | — | C(R¹)₂ | N(R¹) |
| C(R¹)₂ | N(R¹) | C(R¹)₂ | N(R¹) | C(R¹)₂ | N(R¹) |
| C(R¹)₂ | N(R¹) | C(R¹)₂ | O | C(R¹)₂ | N(R¹) |
| C(R¹)₂ | N(R¹) | N(R¹) | — | C(R¹)₂ | N(R¹) |
| C(R¹)₂ | N(R¹) | N(R¹) | O | C(R¹)₂ | N(R¹) |
| C(R¹)₂ | C(R¹)₂ | — | — | N(R¹) | N(R¹) |
| C(R¹)₂ | C(R¹)₂ | C(R¹)₂ | C(R¹)₂ | N(R¹) | N(R¹) |
| C(R¹)₂ | C(R¹)₂ | N(R¹) | N(R¹) | N(R¹) | N(R¹) |
| C(R¹)₂ | C(R¹)₂ | O | O | N(R¹) | N(R¹) |
| C(R¹)₂ | C(R¹)₂ | — | C(R¹)₂ | N(R¹) | N(R¹) |
| C(R¹)₂ | C(R¹)₂ | — | N(R¹) | N(R¹) | N(R¹) |
| C(R¹)₂ | C(R¹)₂ | — | O | N(R¹) | N(R¹) |
| C(R¹)₂ | C(R¹)₂ | C(R¹)₂ | — | N(R¹) | N(R¹) |
| C(R¹)₂ | C(R¹)₂ | C(R¹)₂ | N(R¹) | N(R¹) | N(R¹) |
| C(R¹)₂ | C(R¹)₂ | C(R¹)₂ | O | N(R¹) | N(R¹) |
| C(R¹)₂ | C(R¹)₂ | N(R¹) | — | N(R¹) | N(R¹) |
| C(R¹)₂ | C(R¹)₂ | N(R¹) | C(R¹)₂ | N(R¹) | N(R¹) |
| C(R¹)₂ | C(R¹)₂ | N(R¹) | O | N(R¹) | N(R¹) |
| C(R¹)₂ | C(R¹)₂ | O | — | N(R¹) | N(R¹) |
| C(R¹)₂ | C(R¹)₂ | O | C(R¹)₂ | N(R¹) | N(R¹) |
| C(R¹)₂ | C(R¹)₂ | O | N(R¹) | N(R¹) | N(R¹) |
| N(R¹) | N(R¹) | — | — | N(R¹) | C(R¹)₂ |
| N(R¹) | N(R¹) | C(R¹)₂ | C(R¹)₂ | N(R¹) | C(R¹)₂ |
| N(R¹) | N(R¹) | N(R¹) | N(R¹) | N(R¹) | C(R¹)₂ |
| N(R¹) | N(R¹) | O | O | N(R¹) | C(R¹)₂ |
| N(R¹) | N(R¹) | — | C(R¹)₂ | N(R¹) | C(R¹)₂ |
| N(R¹) | N(R¹) | — | N(R¹) | N(R¹) | C(R¹)₂ |
| N(R¹) | N(R¹) | — | O | N(R¹) | C(R¹)₂ |
| N(R¹) | N(R¹) | C(R¹)₂ | — | N(R¹) | C(R¹)₂ |
| N(R¹) | N(R¹) | C(R¹)₂ | N(R¹) | N(R¹) | C(R¹)₂ |
| N(R¹) | N(R¹) | C(R¹)₂ | O | N(R¹) | C(R¹)₂ |
| N(R¹) | N(R¹) | N(R¹) | — | N(R¹) | C(R¹)₂ |
| N(R¹) | N(R¹) | N(R¹) | C(R¹)₂ | N(R¹) | C(R¹)₂ |
| N(R¹) | N(R¹) | O | — | N(R¹) | C(R¹)₂ |
| N(R¹) | N(R¹) | O | C(R¹)₂ | N(R¹) | C(R¹)₂ |
| N(R¹) | N(R¹) | O | N(R¹) | N(R¹) | C(R¹)₂ |

TABLE 1-continued ("—" denotes a covalent single bond):

| $X_1a$ | $X_1b$ | Ea | Eb | $X_2a$ | $X_2b$ |
|---|---|---|---|---|---|
| $N(R^1)$ | $C(R^1)_2$ | — | — | $N(R^1)$ | $N(R^1)$ |
| $N(R^1)$ | $C(R^1)_2$ | $C(R^1)_2$ | $C(R^1)_2$ | $N(R^1)$ | $N(R^1)$ |
| $N(R^1)$ | $C(R^1)_2$ | $N(R^1)$ | $N(R^1)$ | $N(R^1)$ | $N(R^1)$ |
| $N(R^1)$ | $C(R^1)_2$ | O | O | $N(R^1)$ | $N(R^1)$ |
| $N(R^1)$ | $C(R^1)_2$ | — | $C(R^1)_2$ | $N(R^1)$ | $N(R^1)$ |
| $N(R^1)$ | $C(R^1)_2$ | — | $N(R^1)$ | $N(R^1)$ | $N(R^1)$ |
| $N(R^1)$ | $C(R^1)_2$ | — | O | $N(R^1)$ | $N(R^1)$ |
| $N(R^1)$ | $C(R^1)_2$ | $C(R^1)_2$ | — | $N(R^1)$ | $N(R^1)$ |
| $N(R^1)$ | $C(R^1)_2$ | $C(R^1)_2$ | $N(R^1)$ | $N(R^1)$ | $N(R^1)$ |
| $N(R^1)$ | $C(R^1)_2$ | $C(R^1)_2$ | O | $N(R^1)$ | $N(R^1)$ |
| $N(R^1)$ | $C(R^1)_2$ | $N(R^1)$ | — | $N(R^1)$ | $N(R^1)$ |
| $N(R^1)$ | $C(R^1)_2$ | $N(R^1)$ | $C(R^1)_2$ | $N(R^1)$ | $N(R^1)$ |
| $N(R^1)$ | $C(R^1)_2$ | $N(R^1)$ | O | $N(R^1)$ | $N(R^1)$ |
| $N(R^1)$ | $C(R^1)_2$ | O | — | $N(R^1)$ | $N(R^1)$ |
| $N(R^1)$ | $C(R^1)_2$ | O | $C(R^1)_2$ | $N(R^1)$ | $N(R^1)$ |
| $N(R^1)$ | $C(R^1)_2$ | O | $N(R^1)$ | $N(R^1)$ | $N(R^1)$ |
| $C(R^1)_2$ | $N(R^1)$ | — | — | $N(R^1)$ | $N(R^1)$ |
| $C(R^1)_2$ | $N(R^1)$ | $C(R^1)_2$ | $C(R^1)_2$ | $N(R^1)$ | $N(R^1)$ |
| $C(R^1)_2$ | $N(R^1)$ | $N(R^1)$ | $N(R^1)$ | $N(R^1)$ | $N(R^1)$ |
| $C(R^1)_2$ | $N(R^1)$ | O | O | $N(R^1)$ | $N(R^1)$ |
| $C(R^1)_2$ | $N(R^1)$ | — | $C(R^1)_2$ | $N(R^1)$ | $N(R^1)$ |
| $C(R^1)_2$ | $N(R^1)$ | — | $N(R^1)$ | $N(R^1)$ | $N(R^1)$ |
| $C(R^1)_2$ | $N(R^1)$ | — | O | $N(R^1)$ | $N(R^1)$ |
| $C(R^1)_2$ | $N(R^1)$ | $C(R^1)_2$ | — | $N(R^1)$ | $N(R^1)$ |
| $C(R^1)_2$ | $N(R^1)$ | $C(R^1)_2$ | $N(R^1)$ | $N(R^1)$ | $N(R^1)$ |
| $C(R^1)_2$ | $N(R^1)$ | $C(R^1)_2$ | O | $N(R^1)$ | $N(R^1)$ |
| $C(R^1)_2$ | $N(R^1)$ | $N(R^1)$ | — | $N(R^1)$ | $N(R^1)$ |
| $C(R^1)_2$ | $N(R^1)$ | $N(R^1)$ | $C(R^1)_2$ | $N(R^1)$ | $N(R^1)$ |
| $C(R^1)_2$ | $N(R^1)$ | $N(R^1)$ | O | $N(R^1)$ | $N(R^1)$ |
| $C(R^1)_2$ | $N(R^1)$ | O | — | $N(R^1)$ | $N(R^1)$ |
| $C(R^1)_2$ | $N(R^1)$ | O | $C(R^1)_2$ | $N(R^1)$ | $N(R^1)$ |
| $C(R^1)_2$ | $N(R^1)$ | O | $N(R^1)$ | $N(R^1)$ | $N(R^1)$ |

In yet a further embodiment of the invention, the compound according to the invention conforms to the general formula (8)

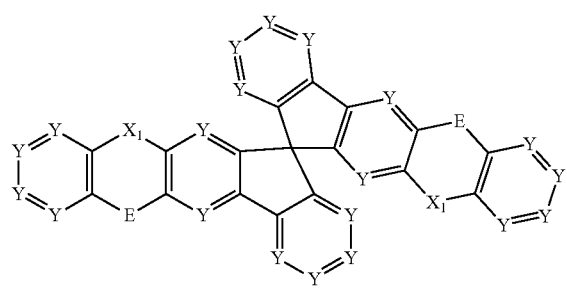

formula (8)

where the symbols used have the meanings indicated above.

In a preferred embodiment of the formula (8), $X_1$ stands for $N(R^1)$. In a further preferred embodiment of the formula (8), E stands for a single bond, $N(R^1)$ or $C(R^1)_2$, particularly preferably for a single bond. Very particularly preferably, $X_1$ stands for $N(R^1)_2$ and E stands for a single bond.

In a further preferred embodiment of the formula (8), a maximum of one or two groups Y stand for N and the remaining groups Y stand for CR. Very particularly preferably, all groups Y stand for CR.

Preferred embodiments of the formula (8) are the compounds of the following formula (8a):

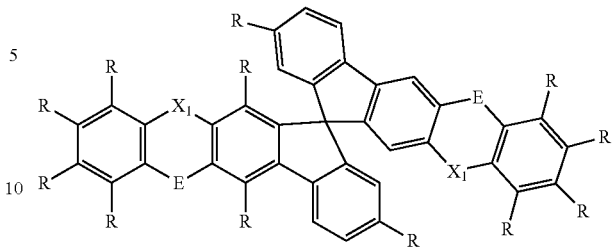

formula (8a)

where the symbols used have the meanings given above.

Particularly preferred embodiments of the formula (8) are the compounds of the following formula (8b):

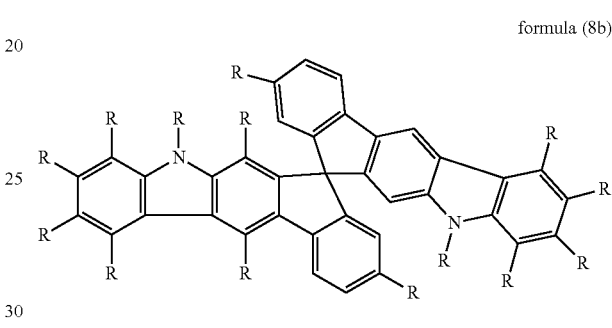

formula (8b)

where the symbols used have the meanings given above.

Very particularly preferred embodiments of the formula (8) are the compounds of the following formula (8c):

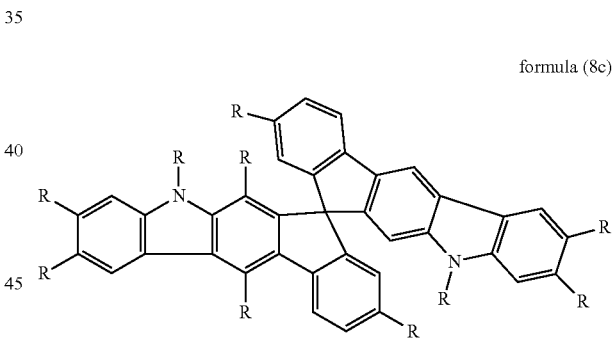

formula (8c)

where the symbols used have the meanings given above.

Examples of compounds of the formula (1) according to the invention are, for example, the structures shown below:

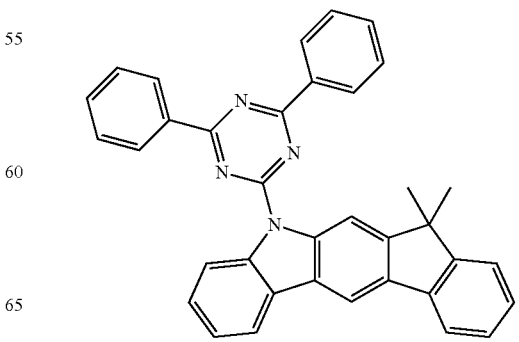

25
-continued
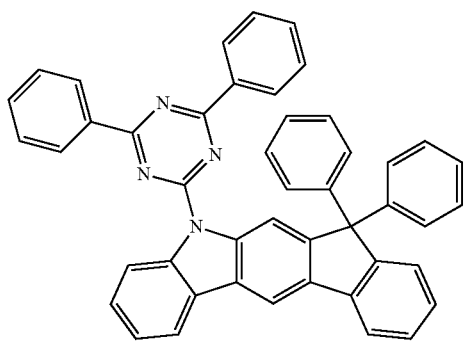
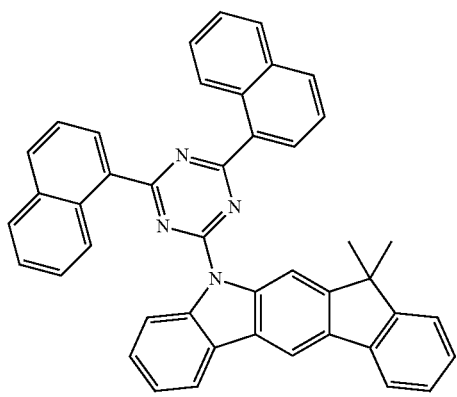
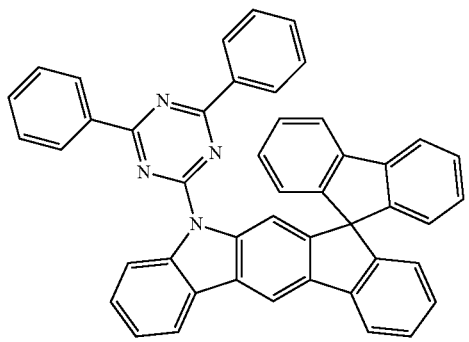
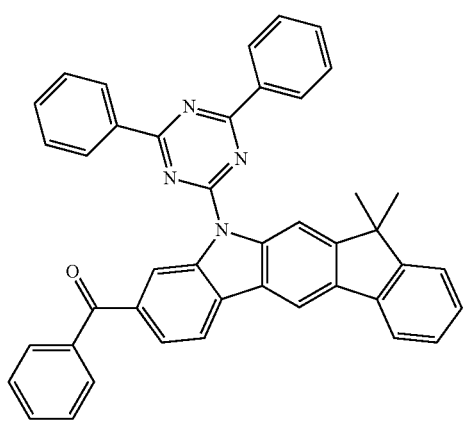
26
-continued
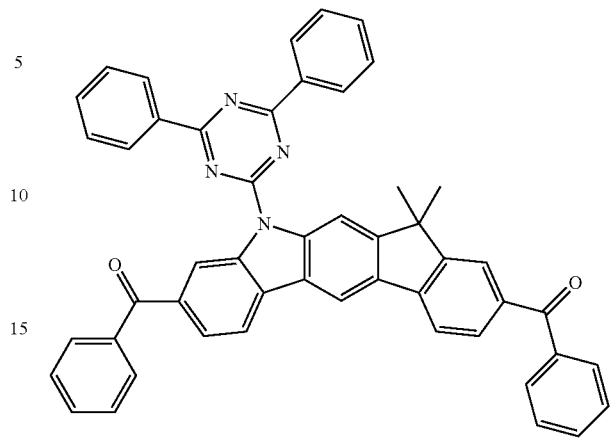
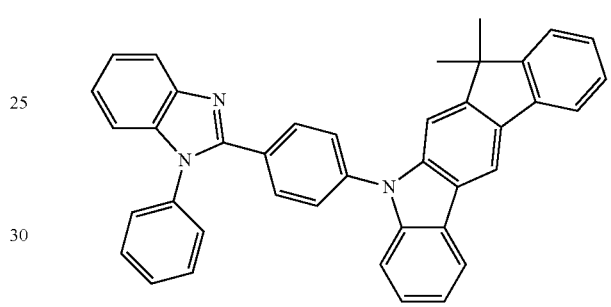
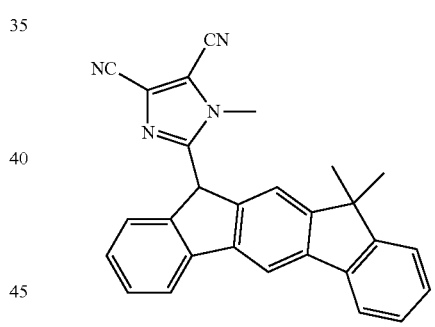
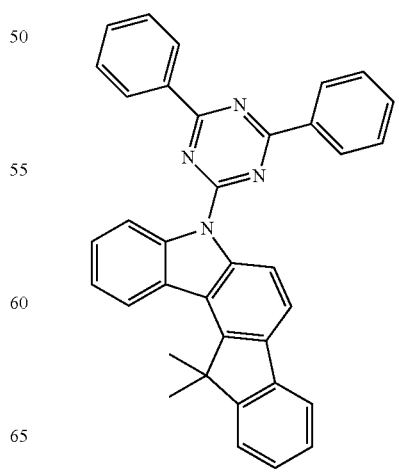

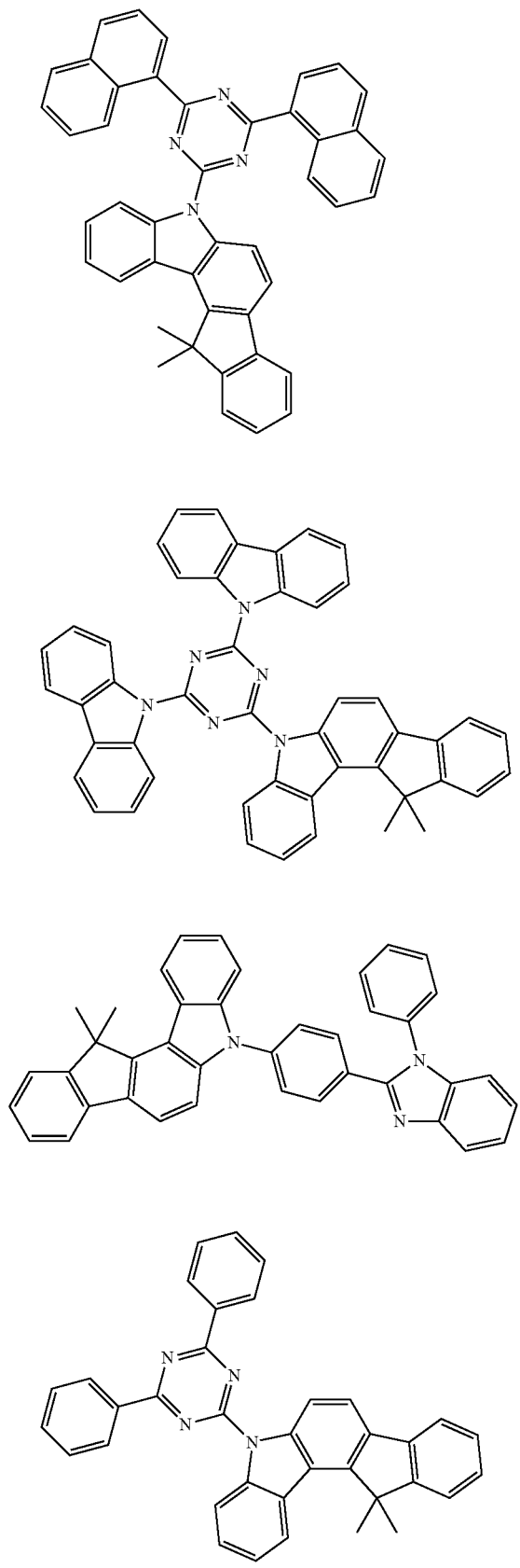
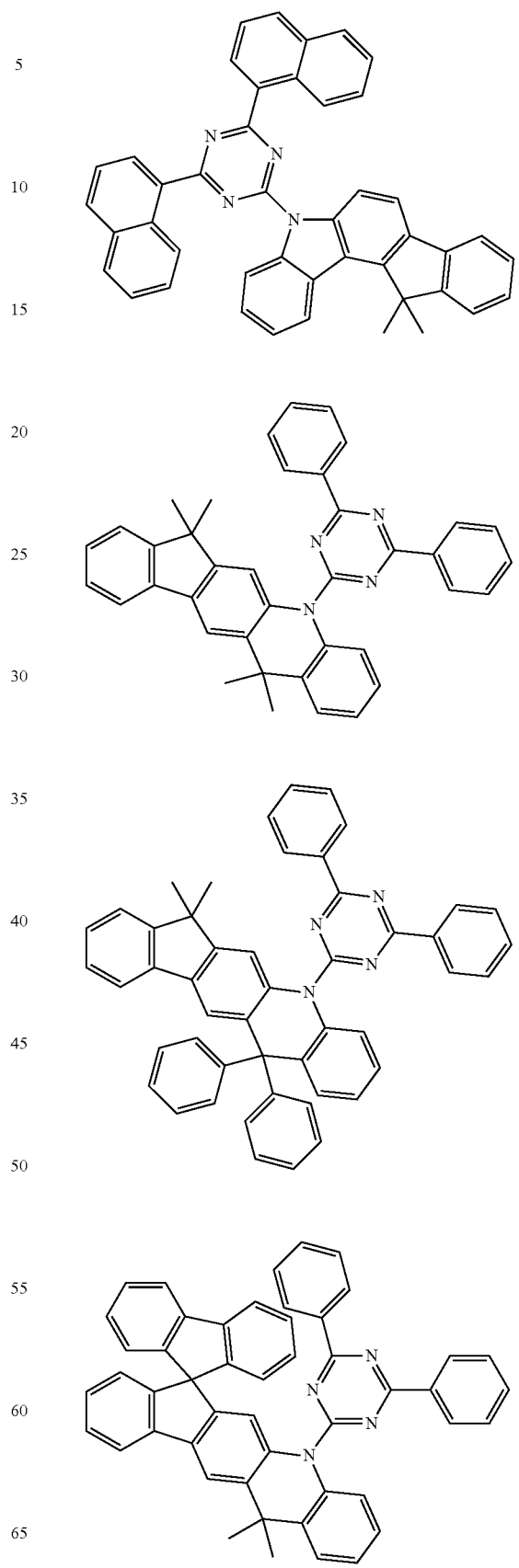

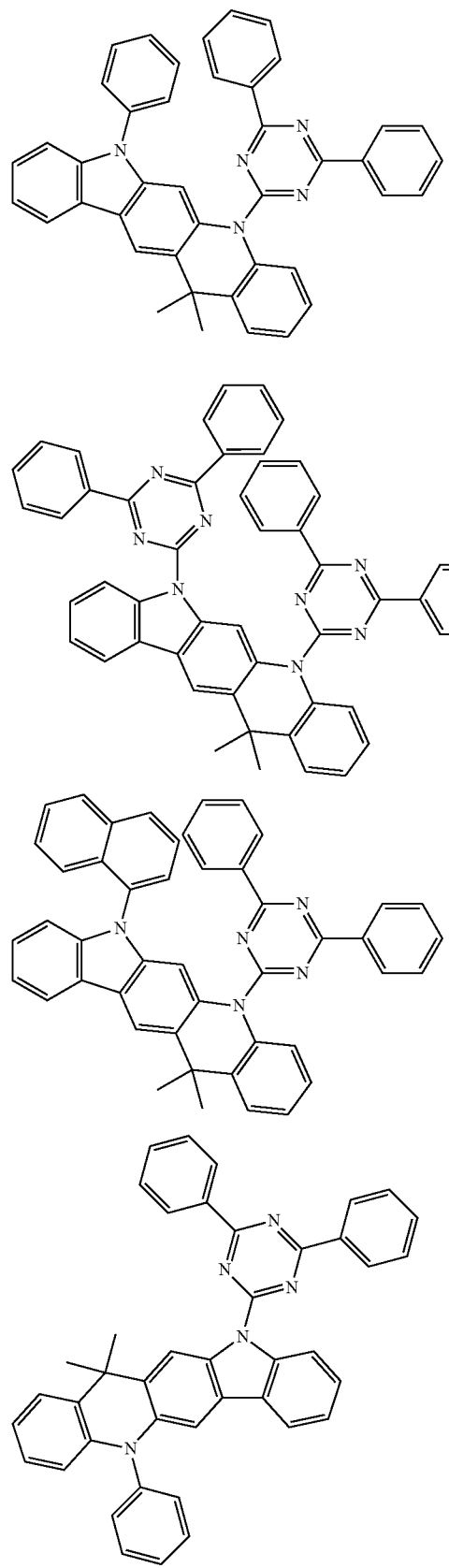
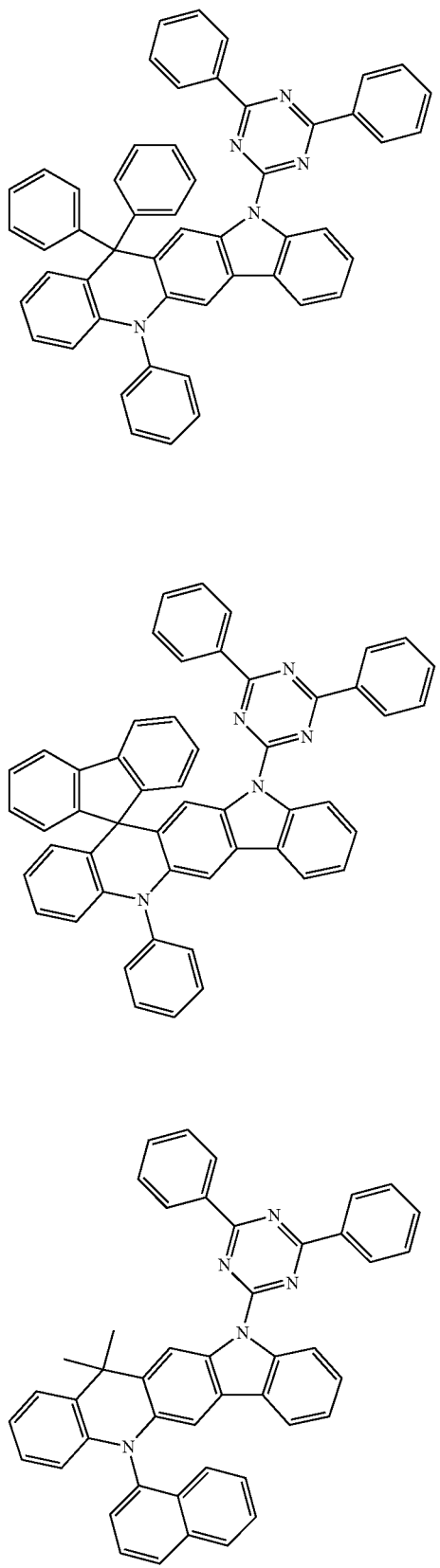

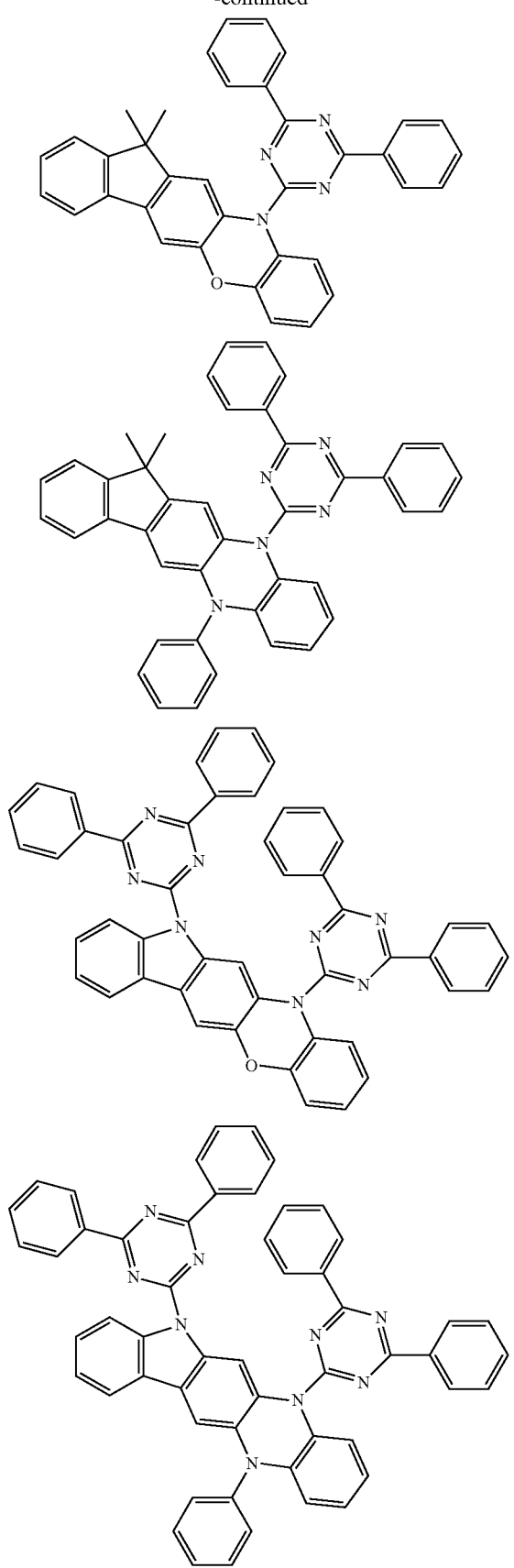
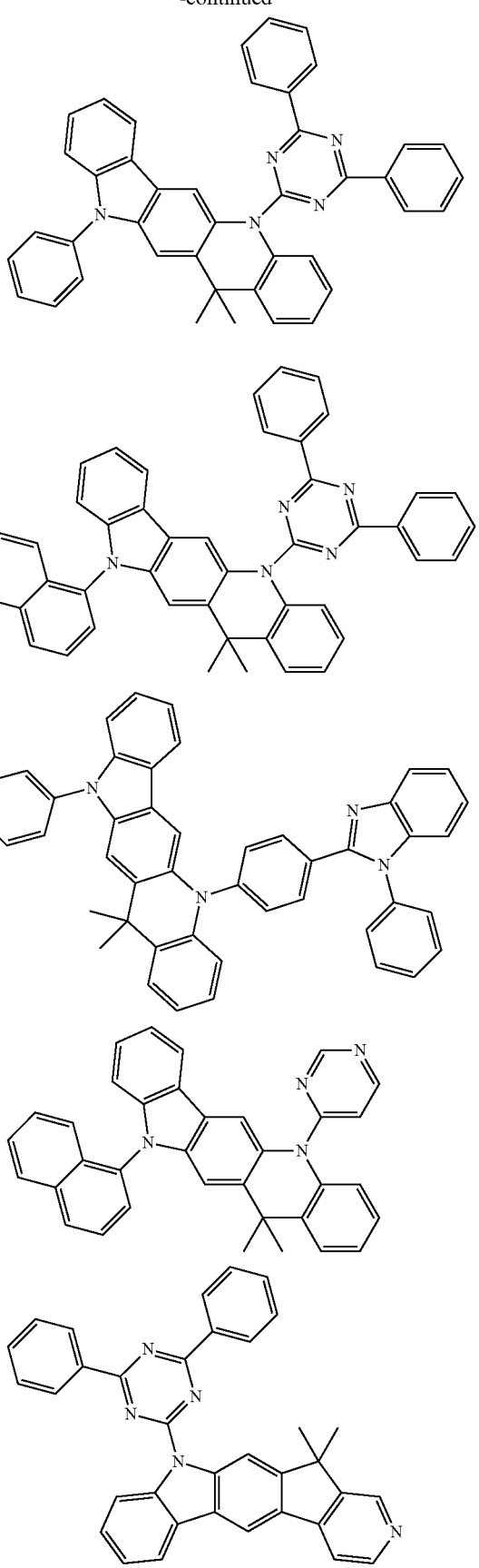

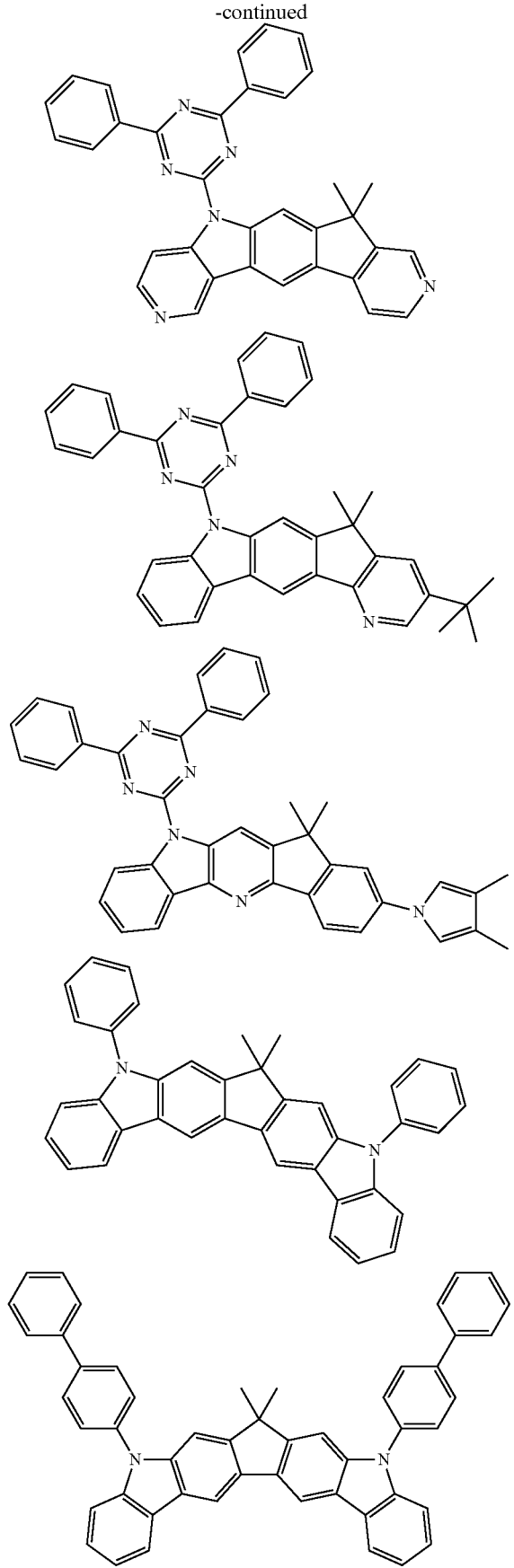
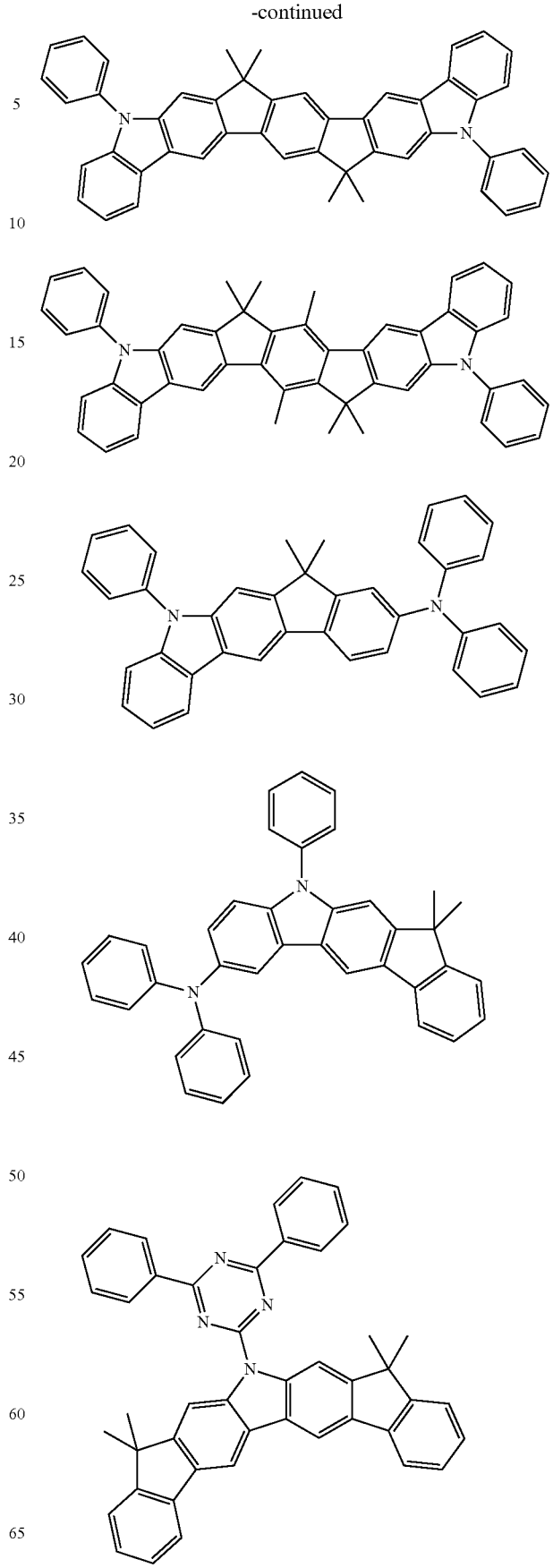

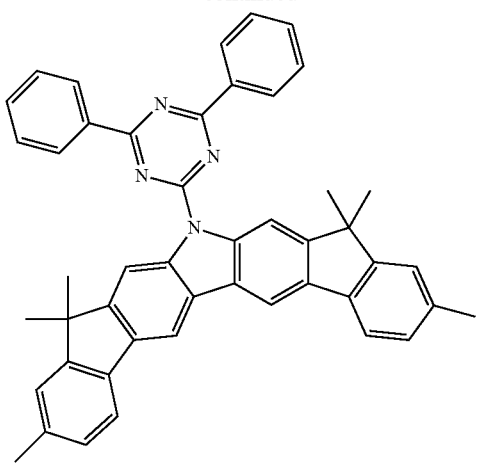
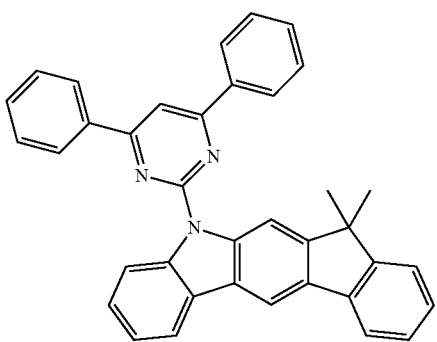
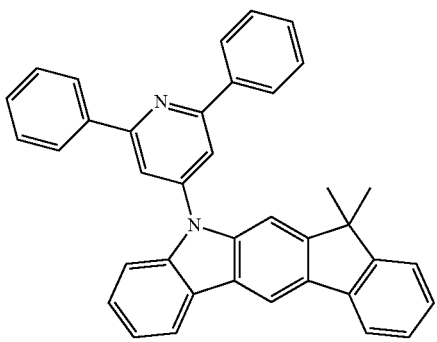
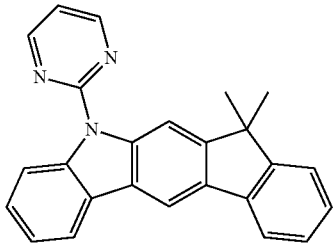
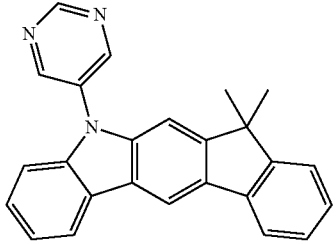
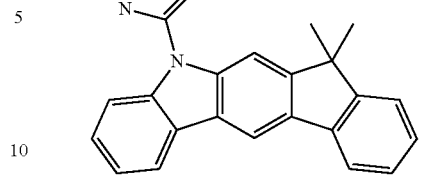
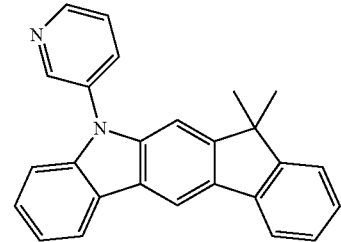
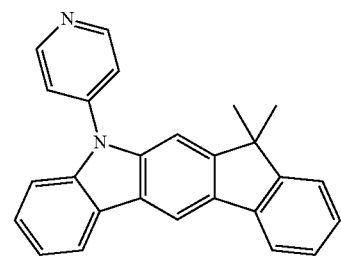
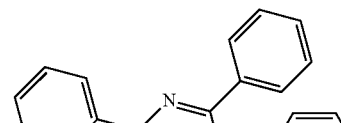
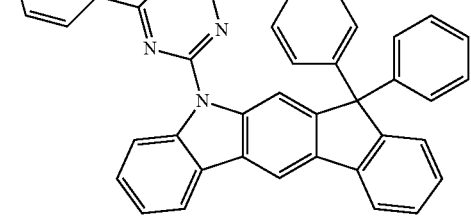

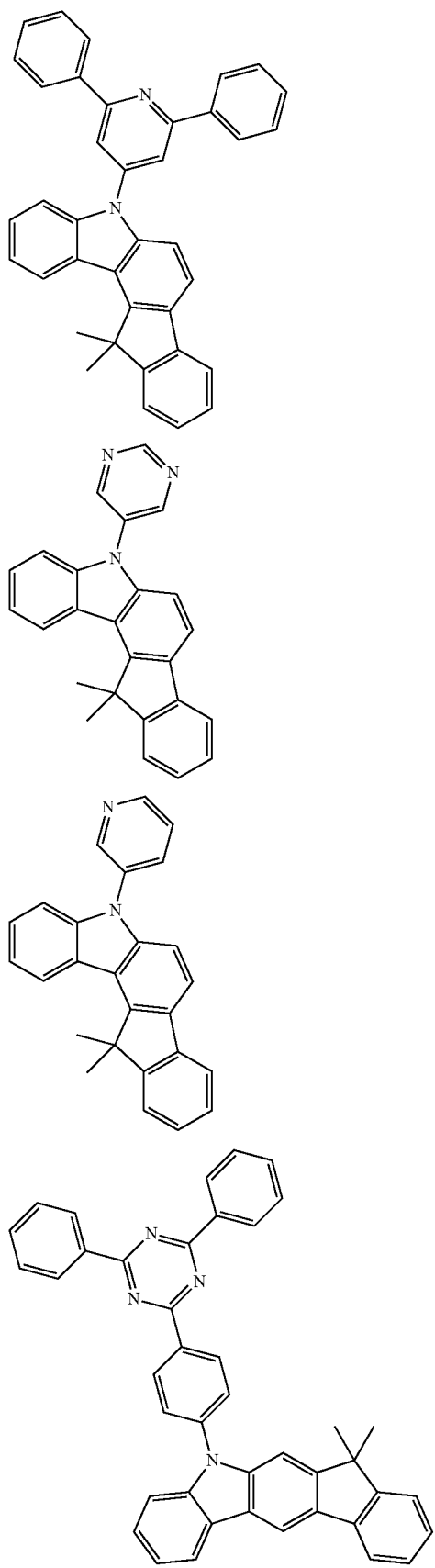
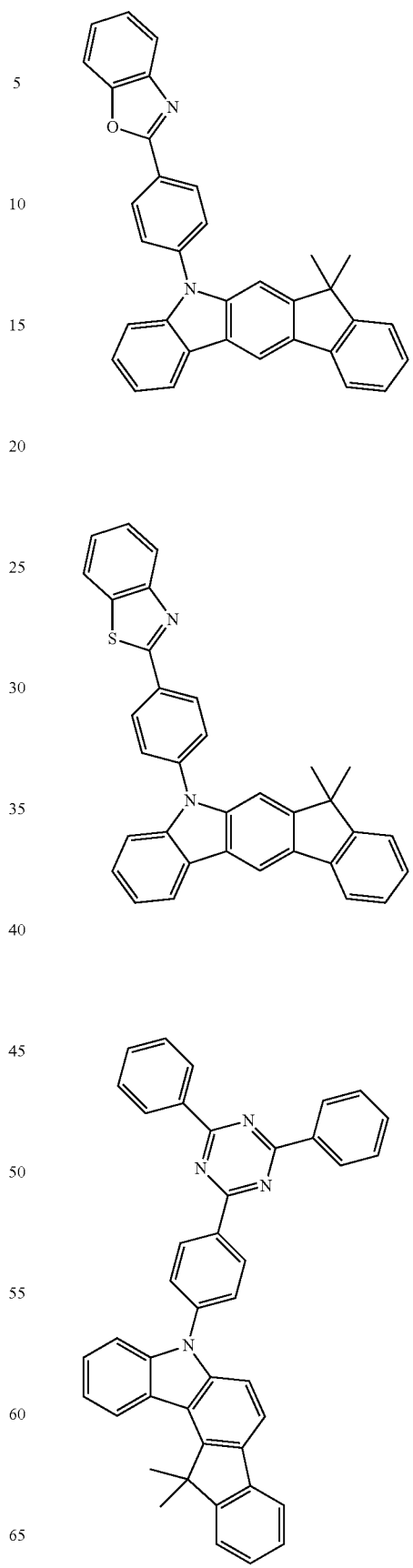

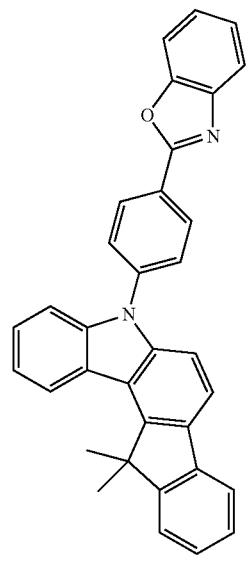
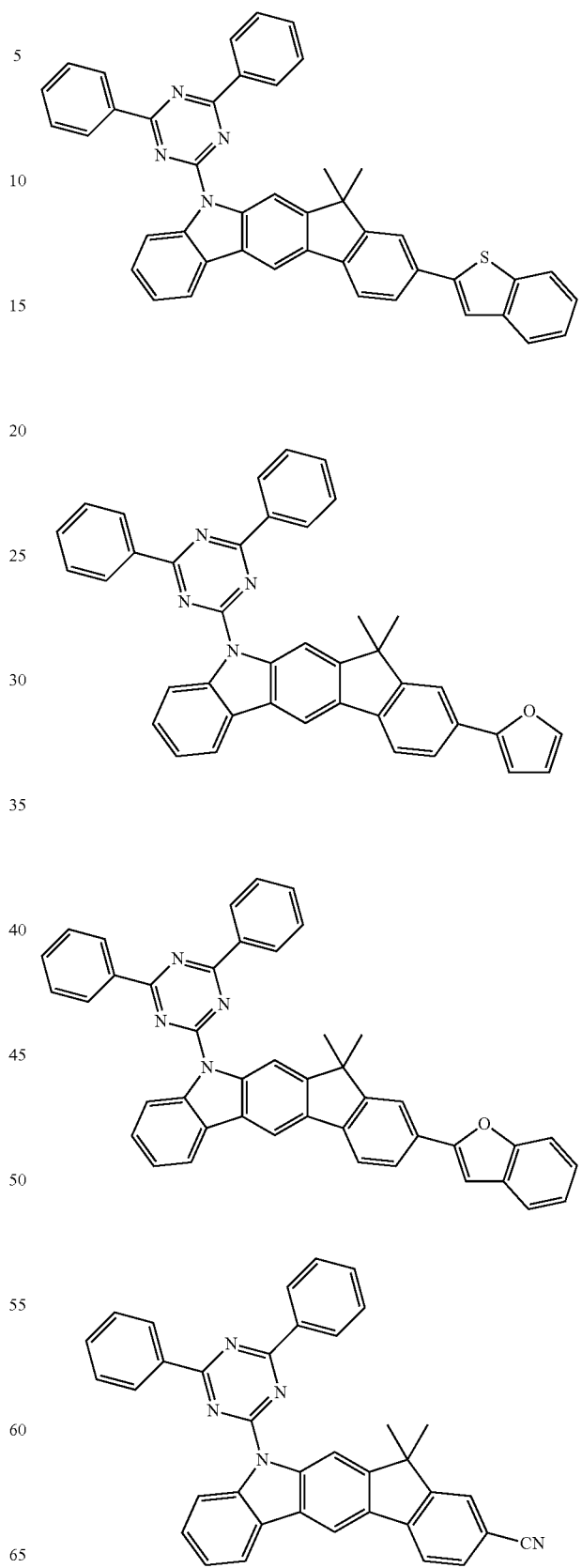

-continued
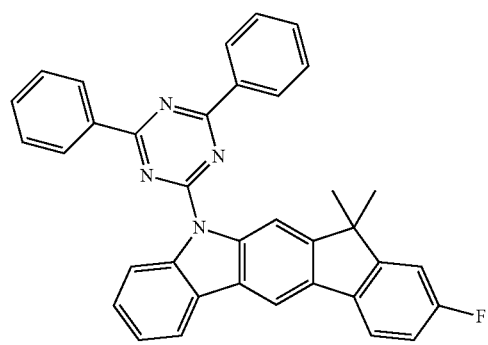
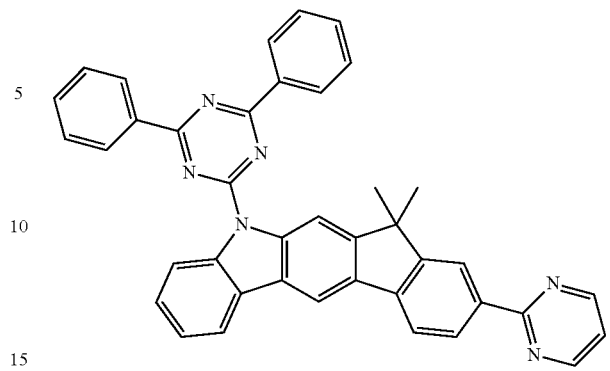
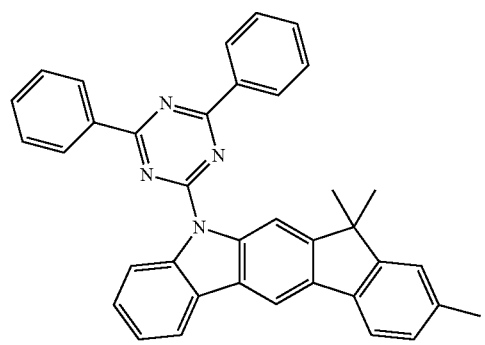
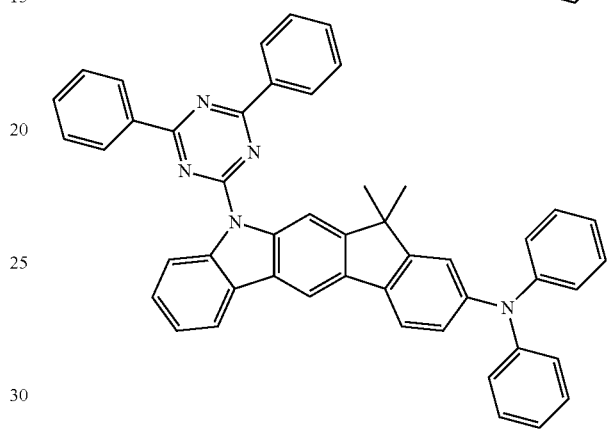
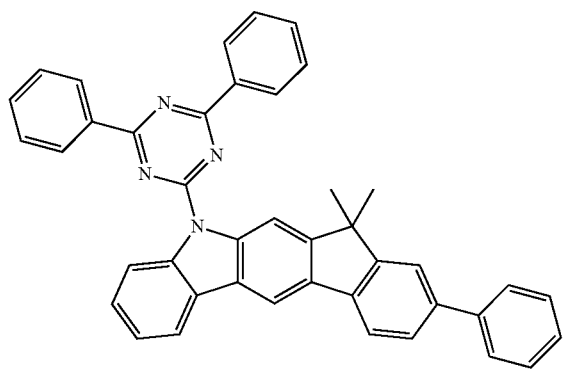
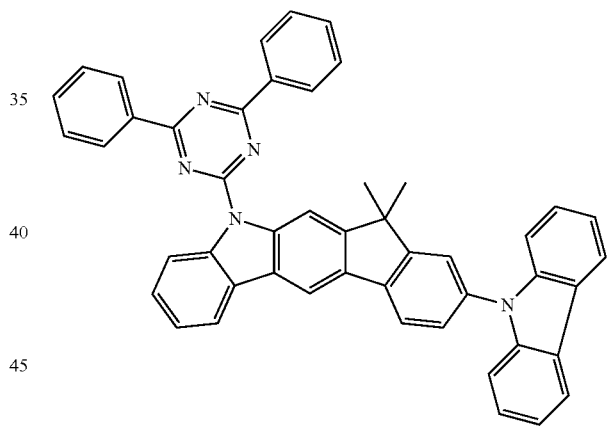
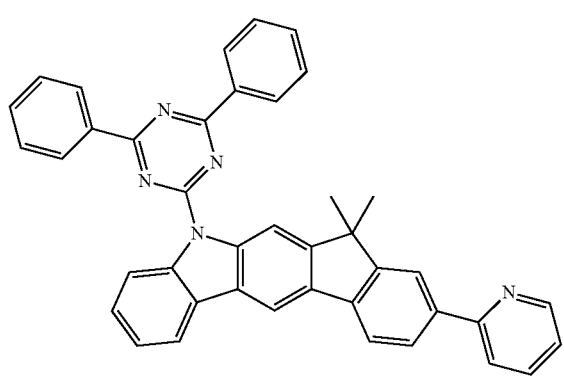
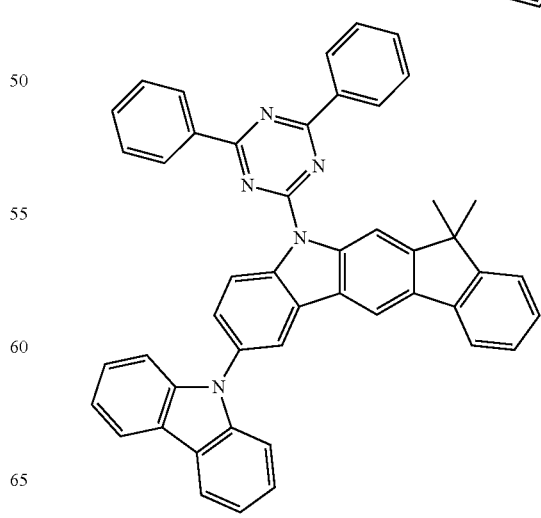

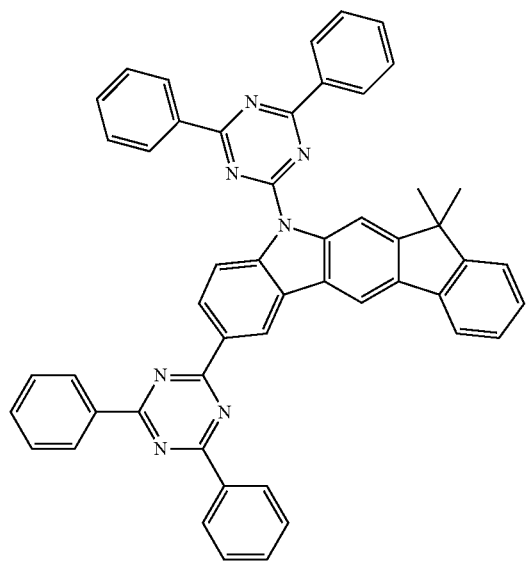
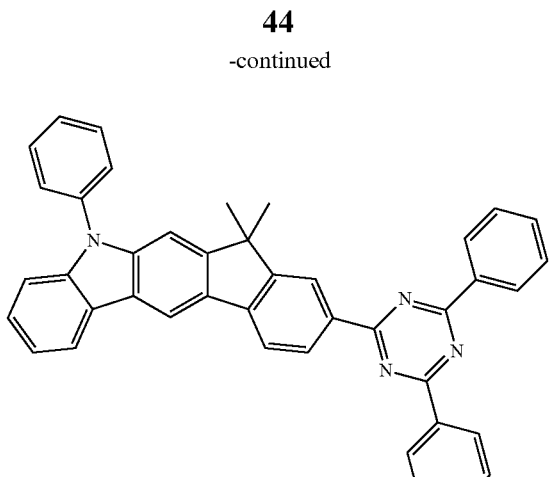
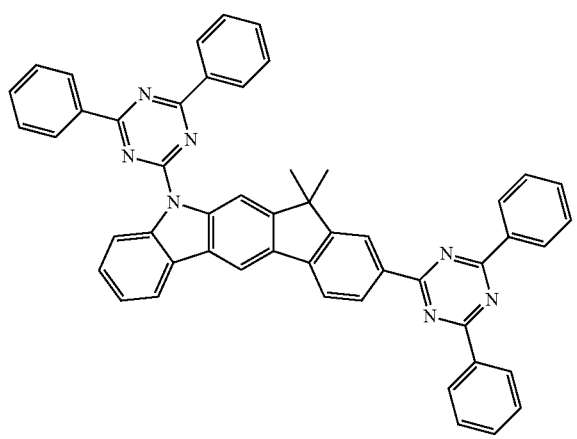
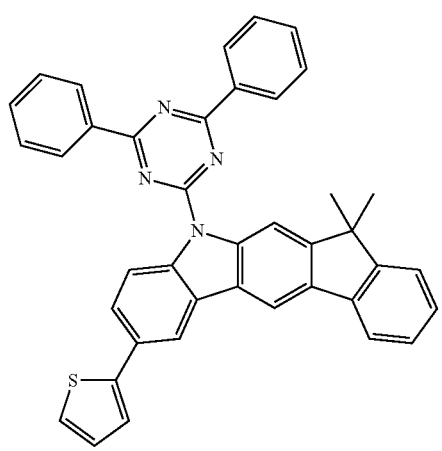
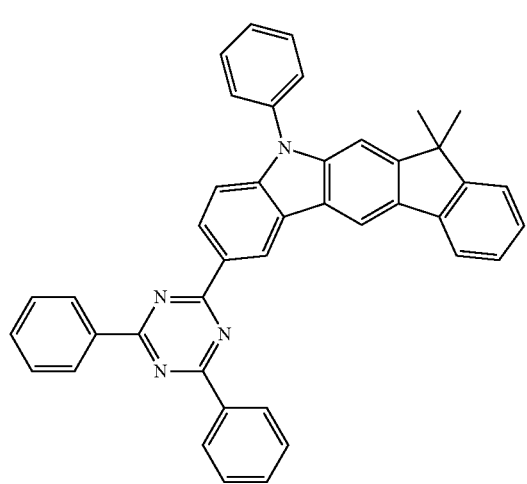 [SMILES: CC1(C)c2ccccc2-c2cc3c4cc(-c5nc(-c6ccccc6)nc(-c6ccccc6)n5)ccc4n(-c4ccccc4)c3cc21]
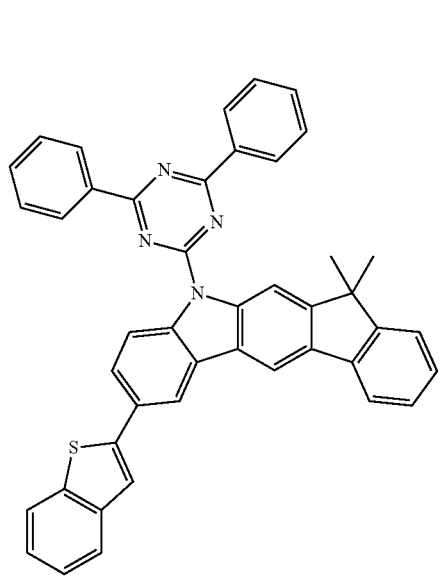

45
-continued
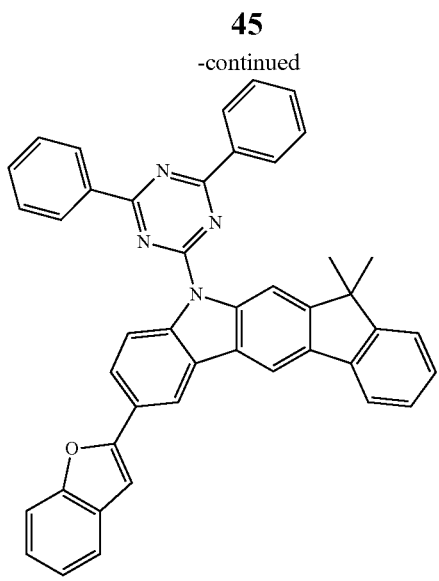
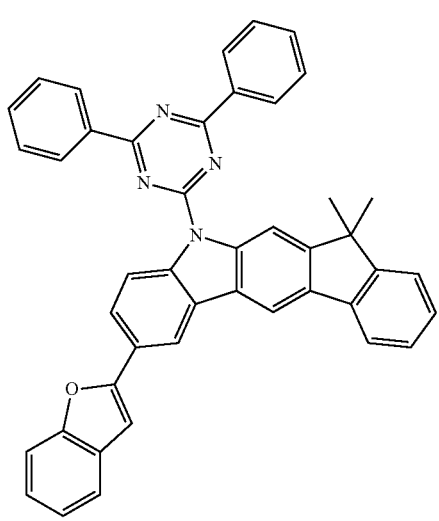
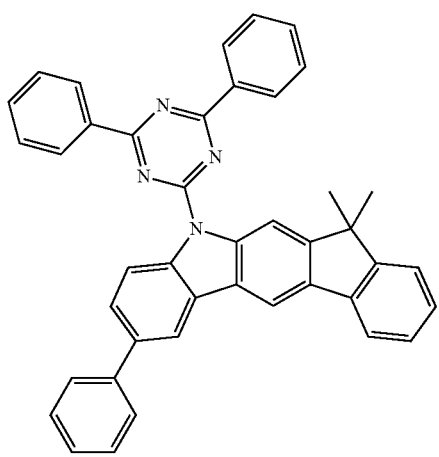
46
-continued
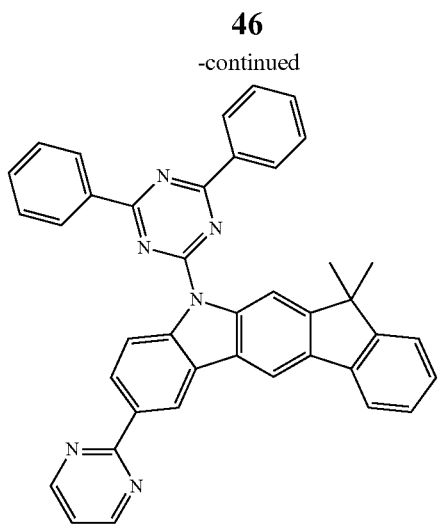
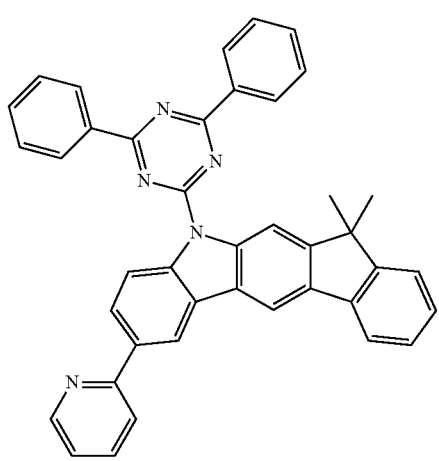
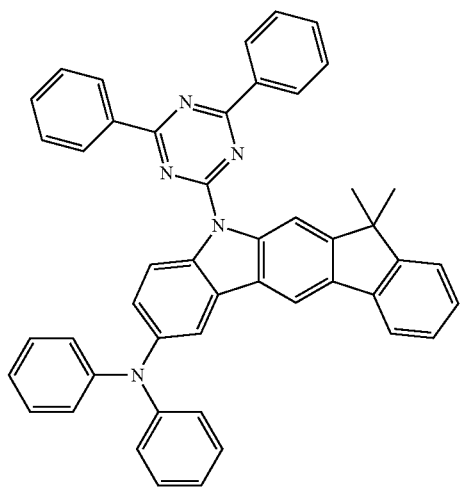

-continued
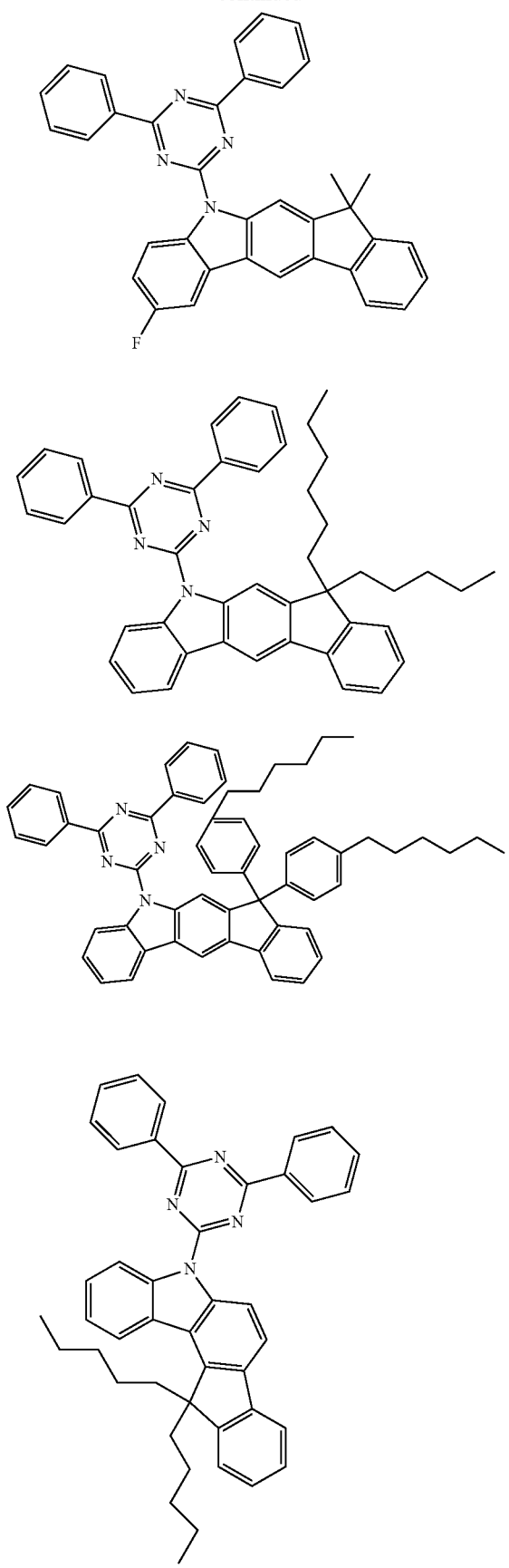
-continued
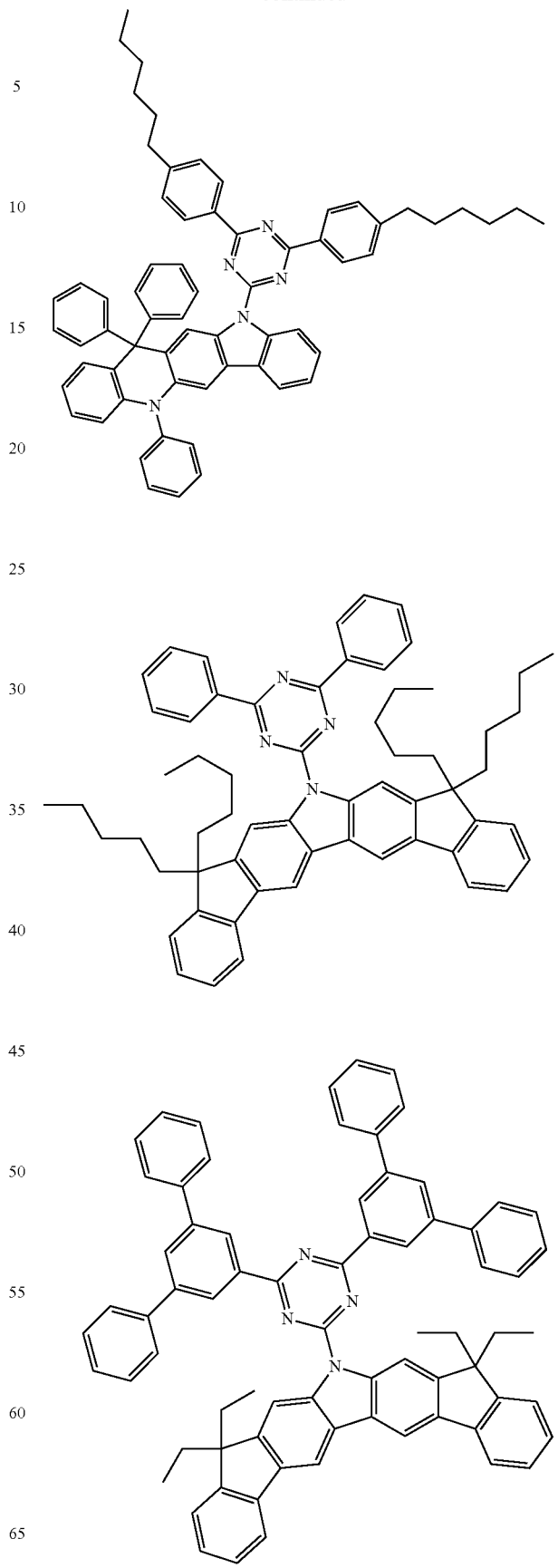

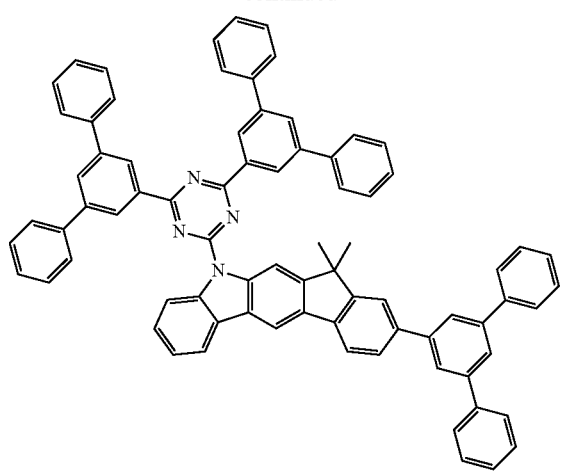
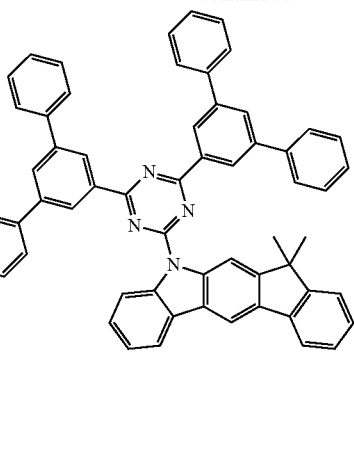
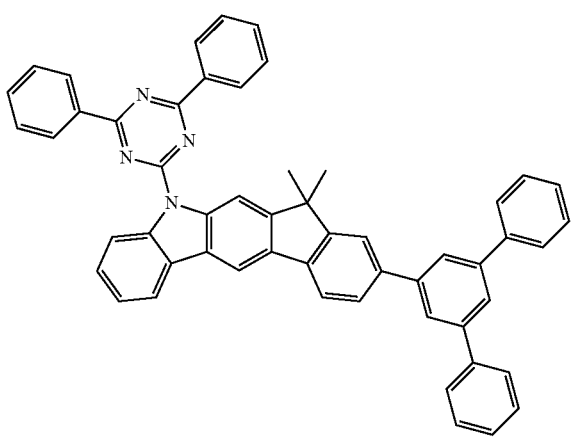
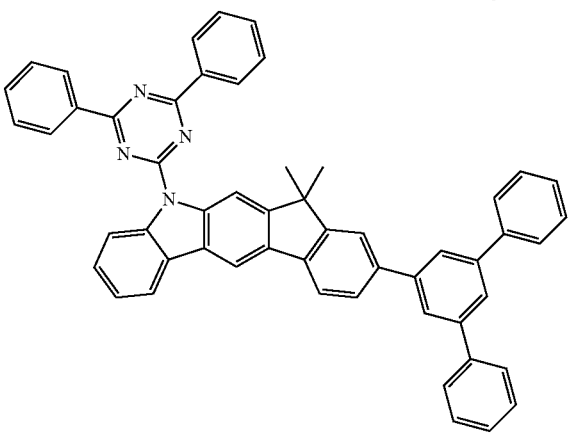
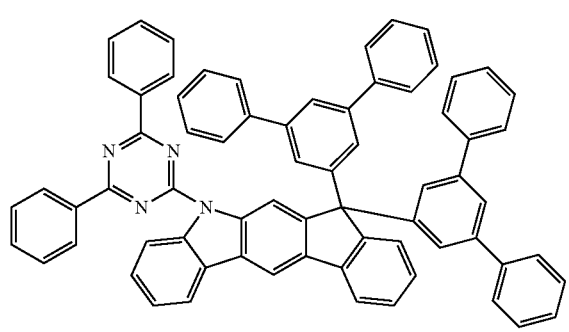
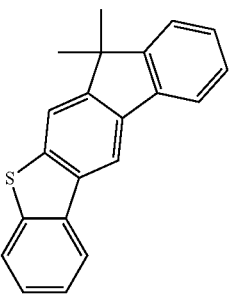
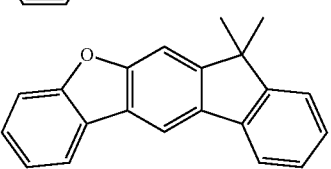
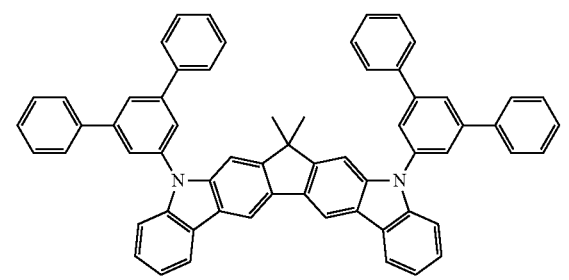
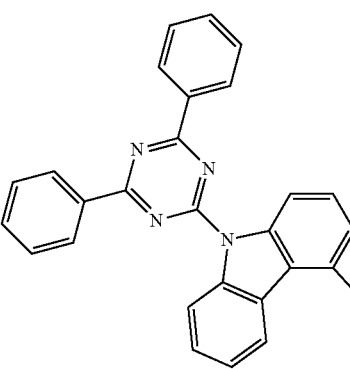

-continued
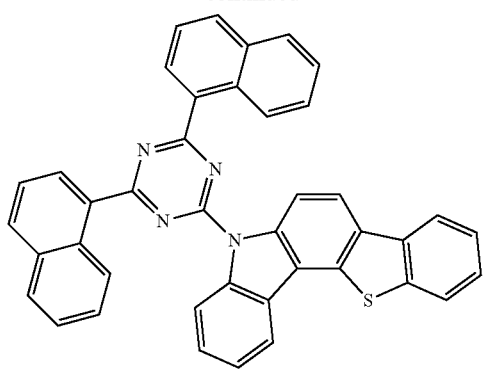
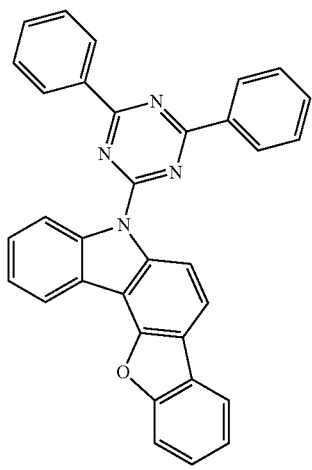
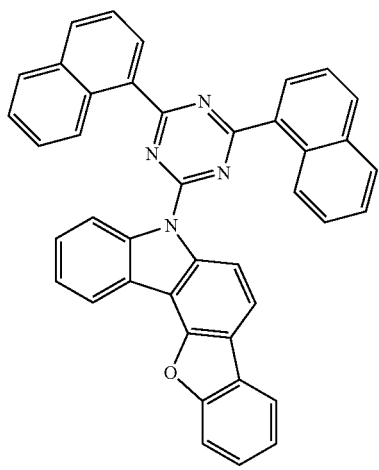
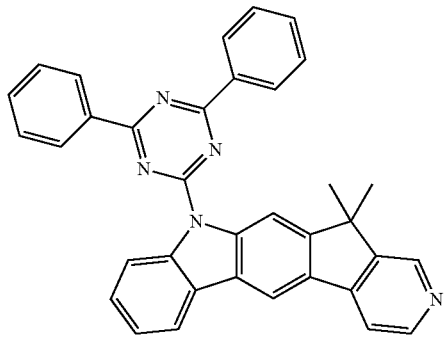
-continued
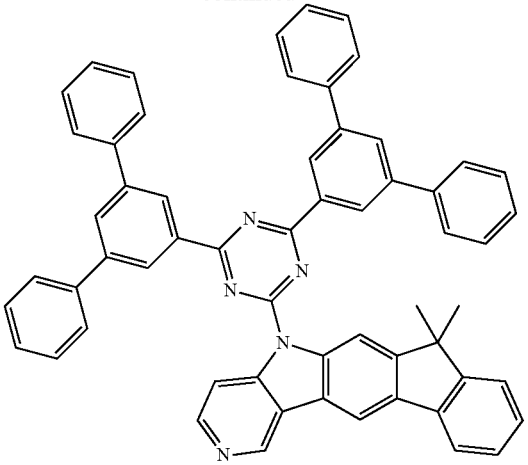
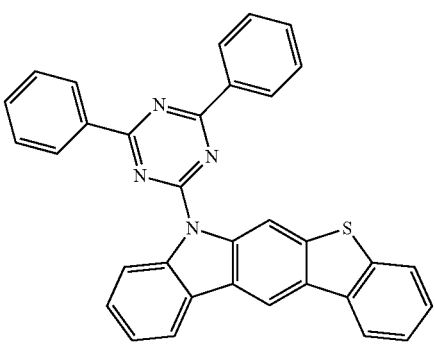
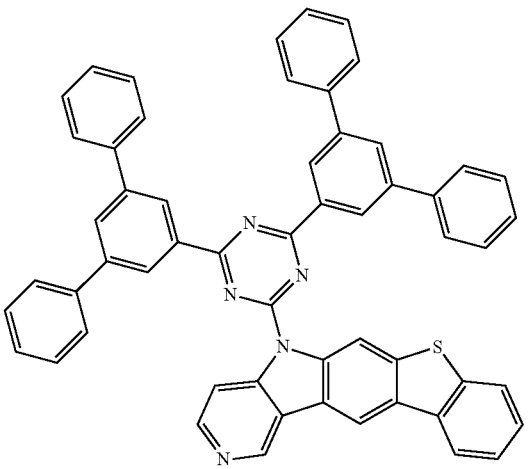
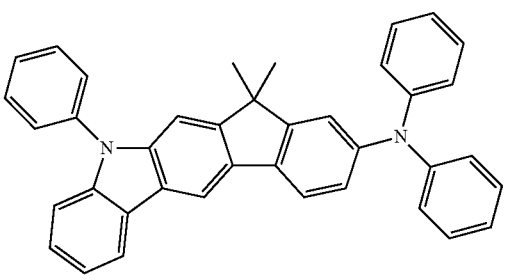

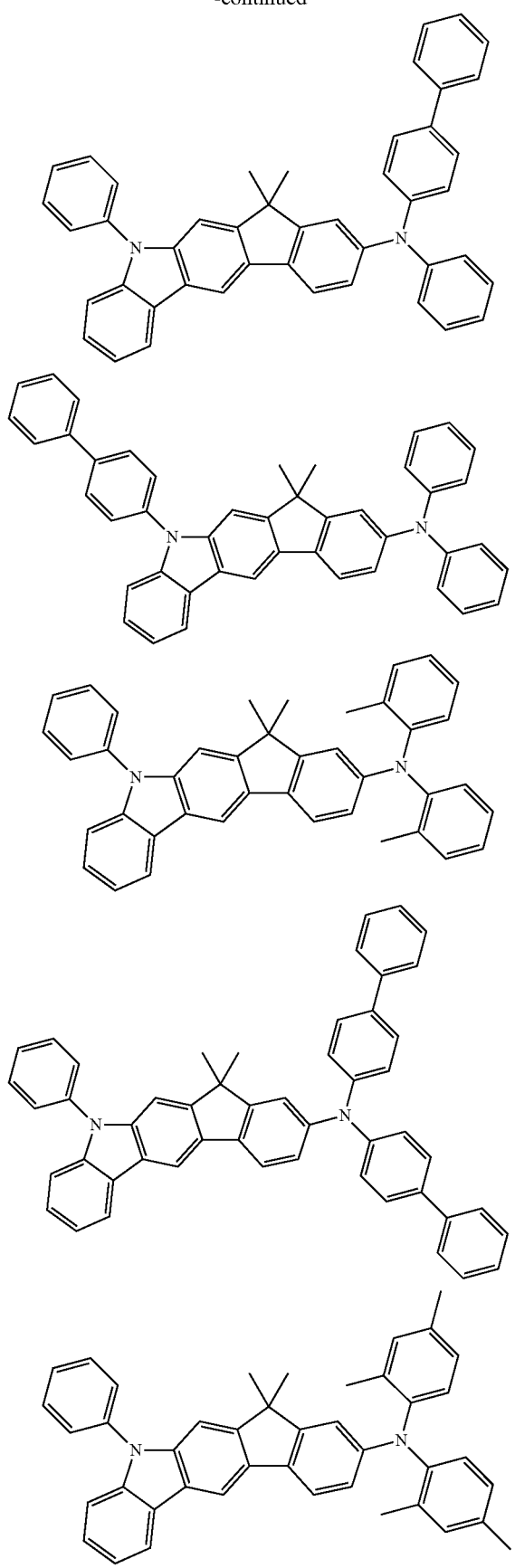
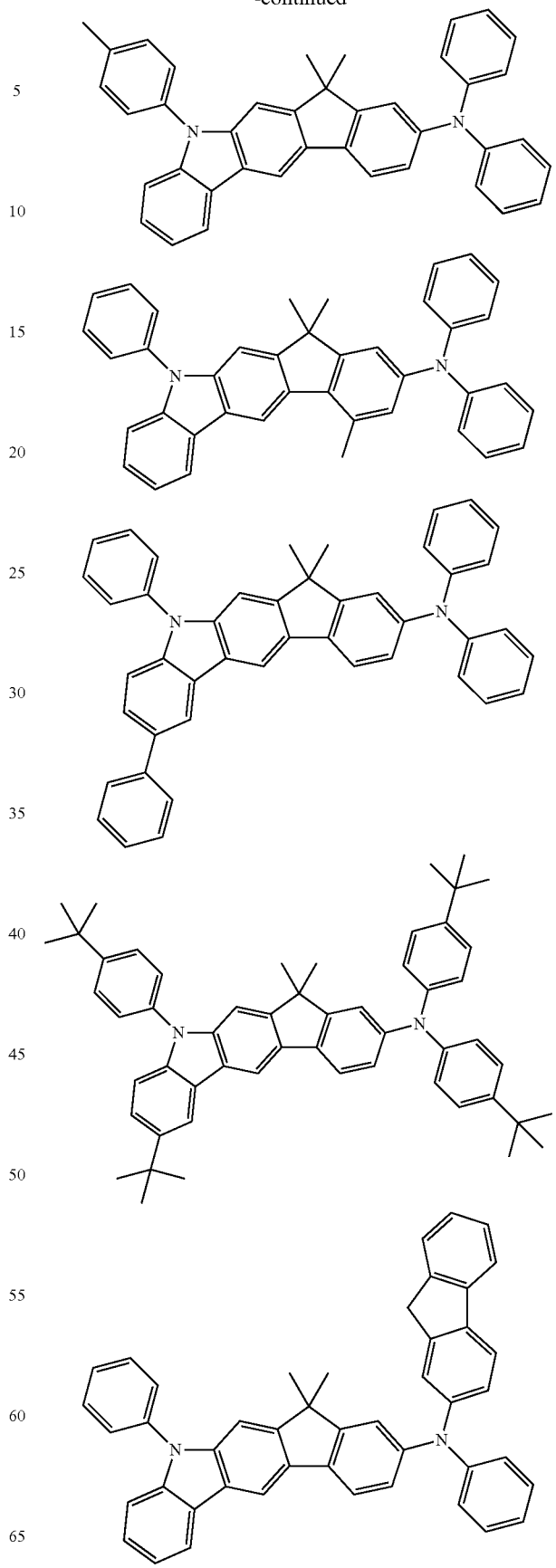

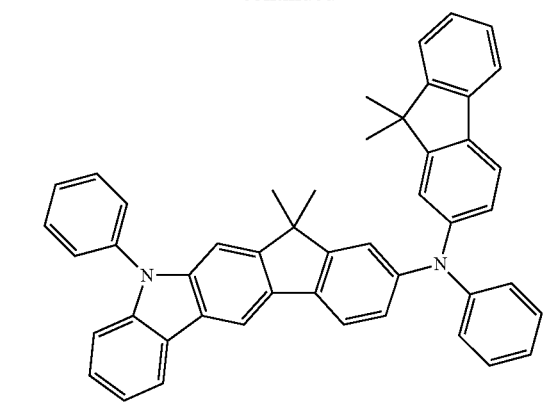
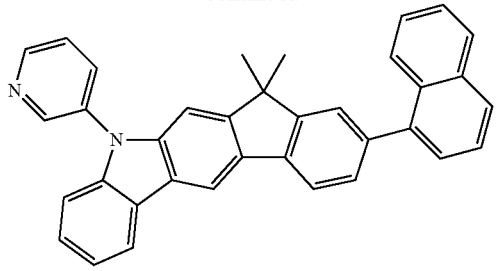
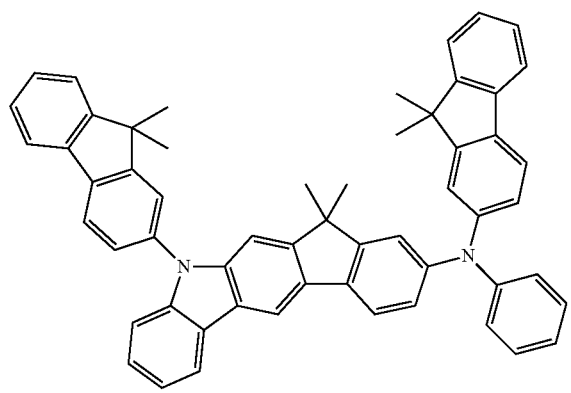
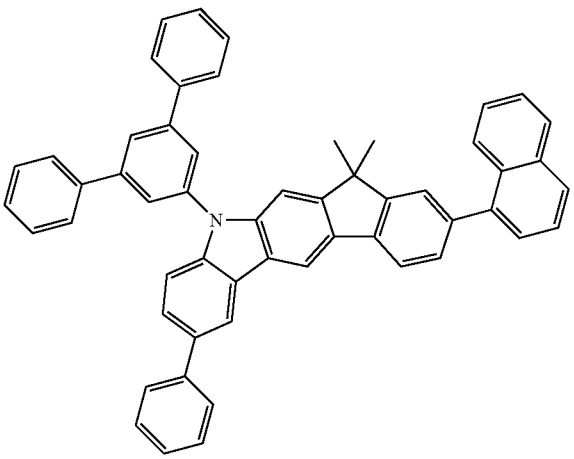
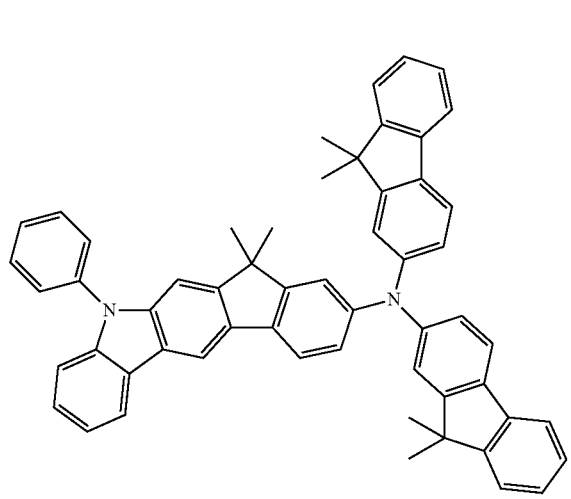
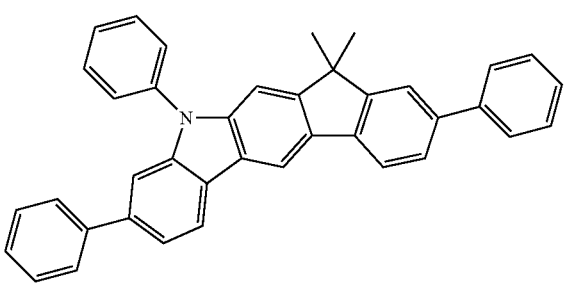
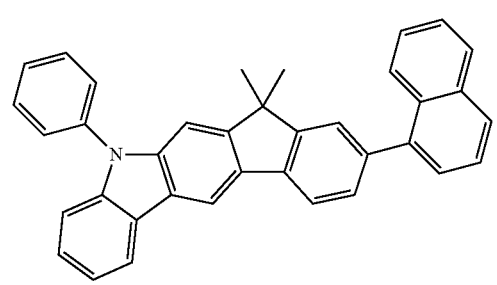
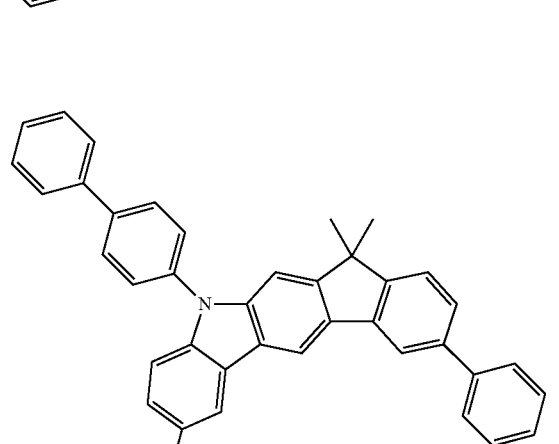

57
-continued
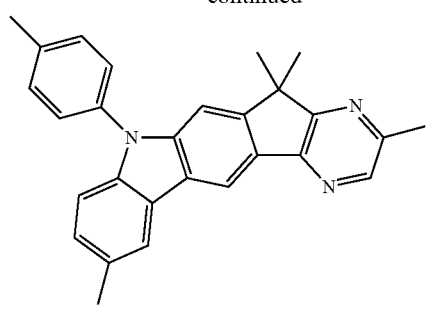
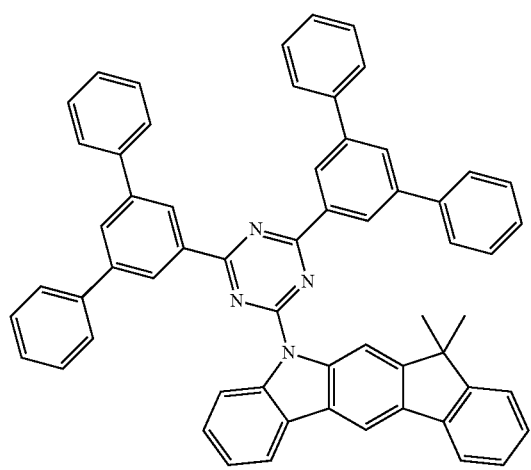
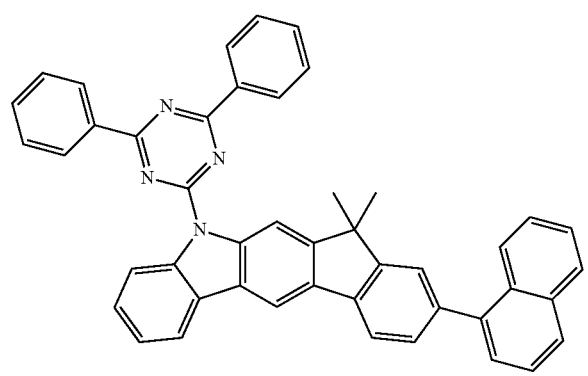
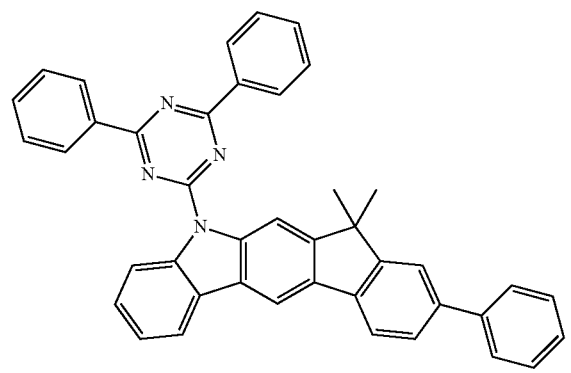
58
-continued
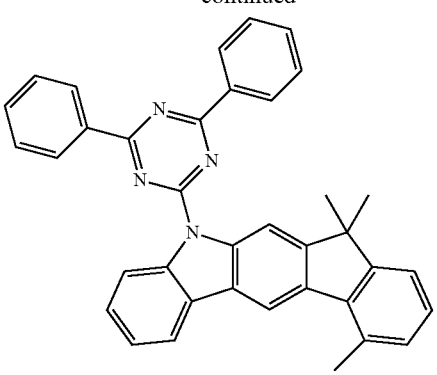
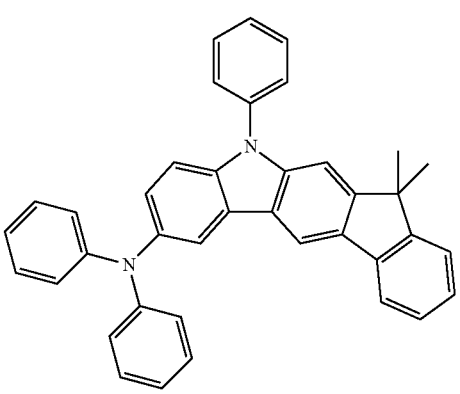
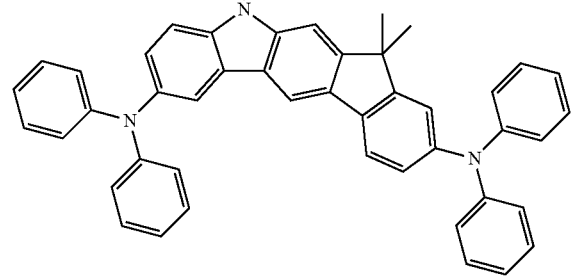
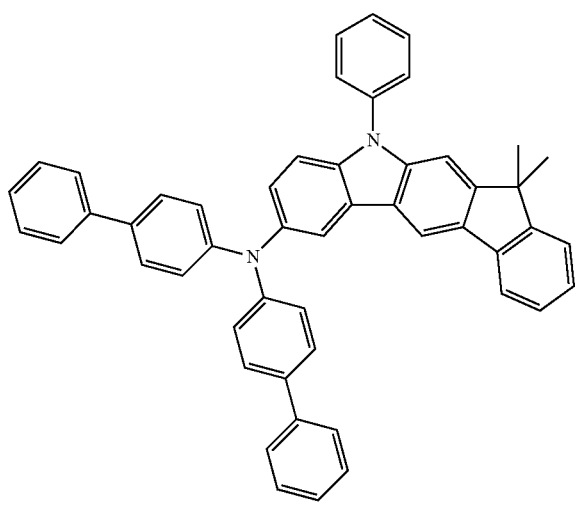

-continued
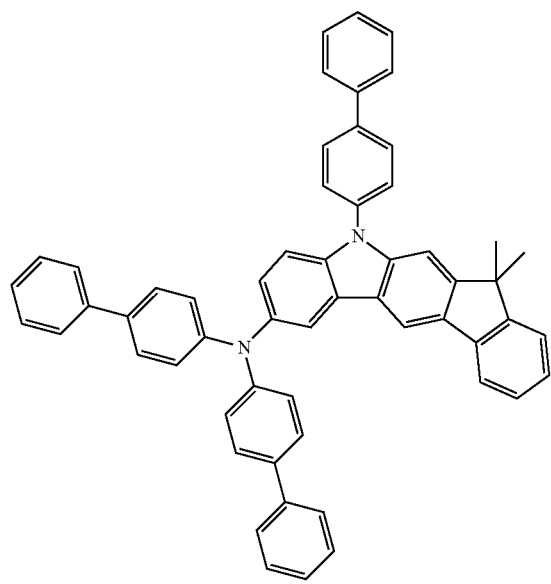
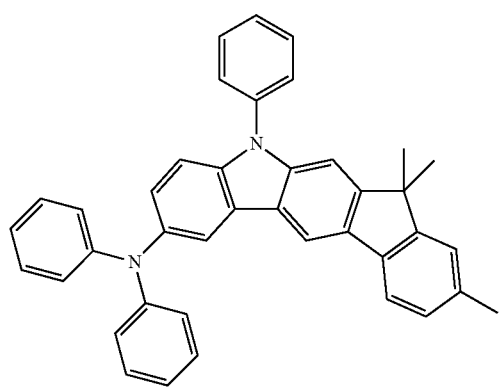
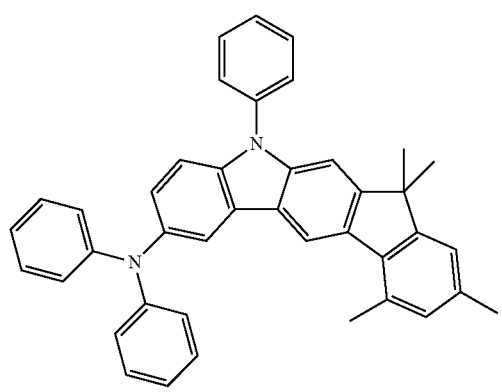
-continued
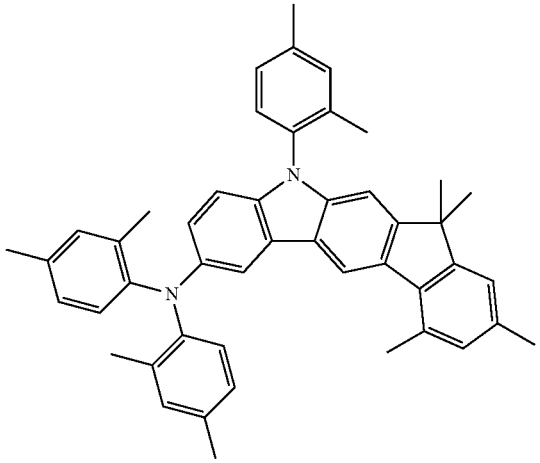
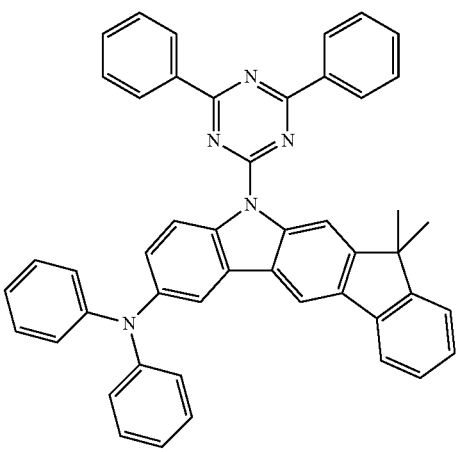
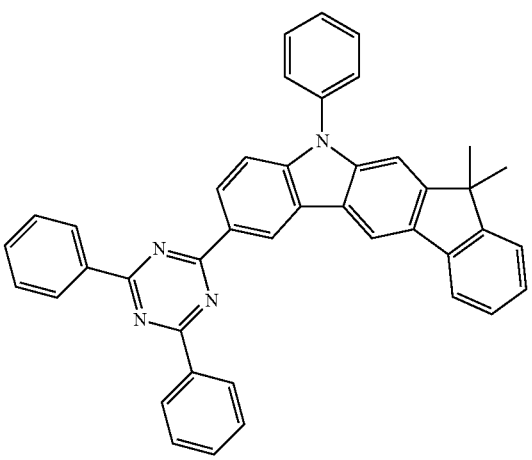

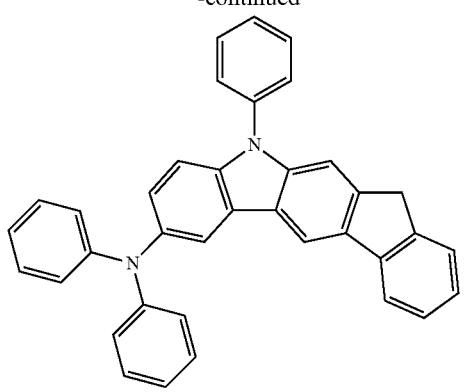
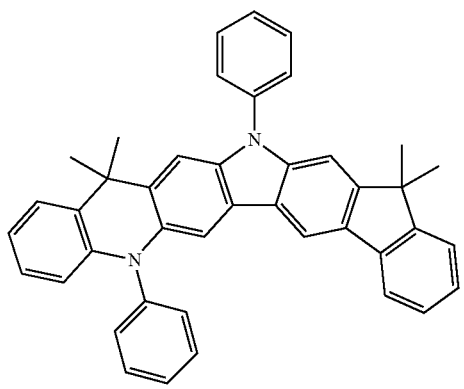
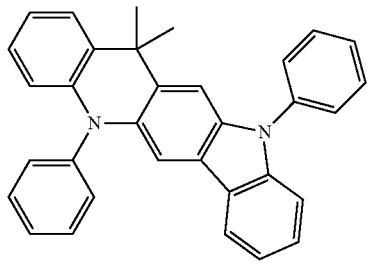
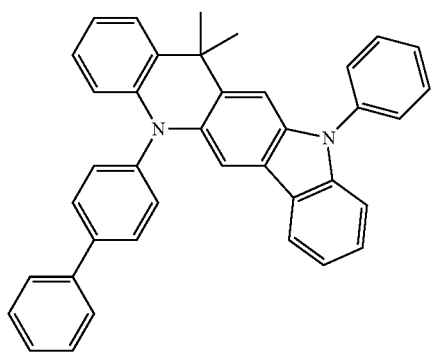
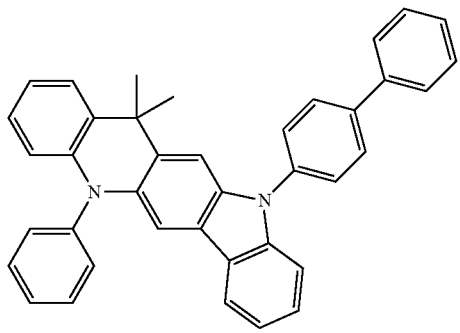
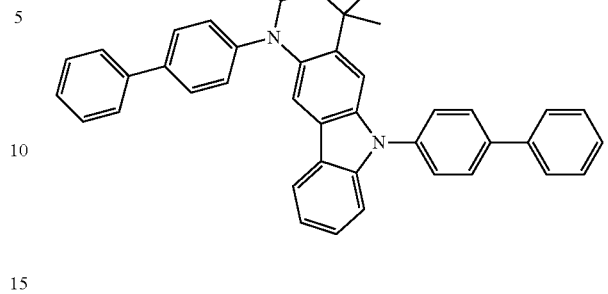
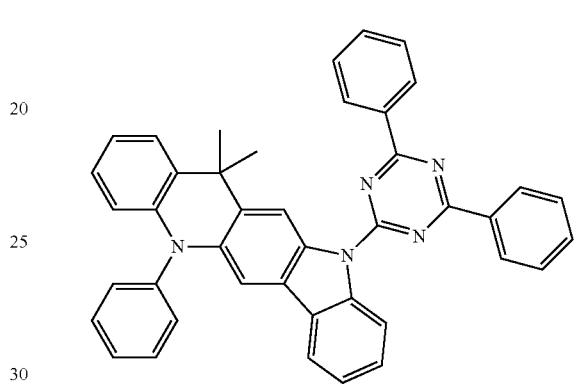
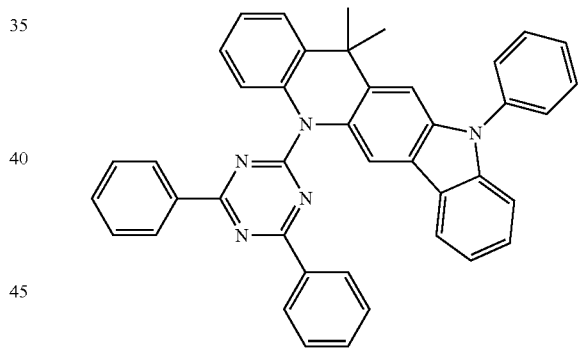
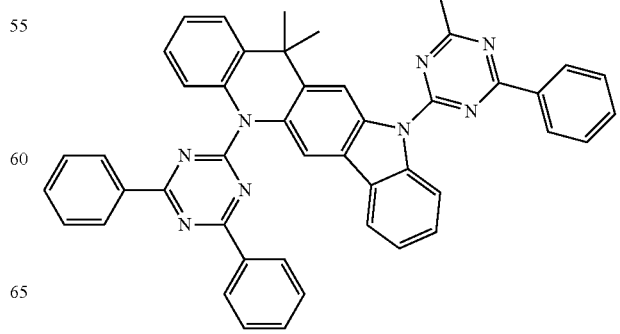

63
-continued
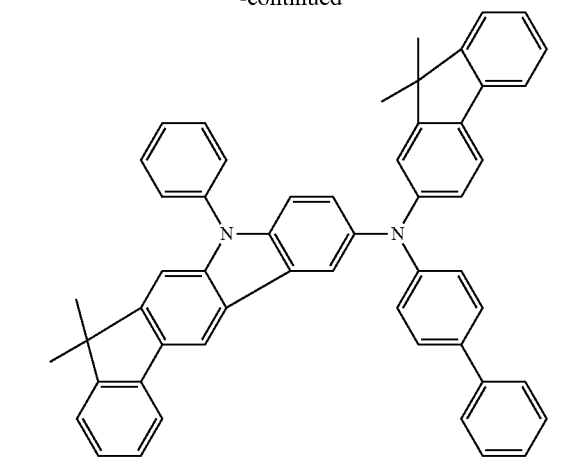
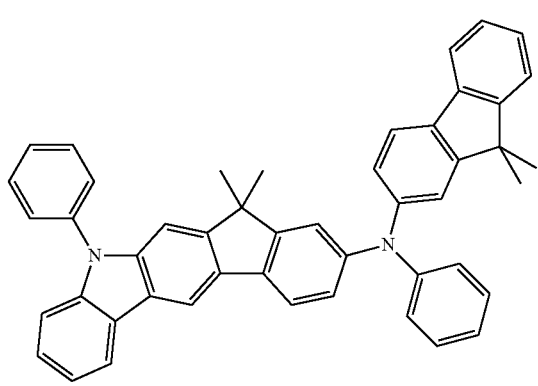
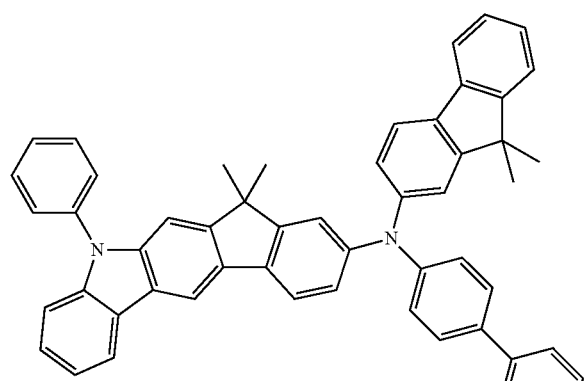
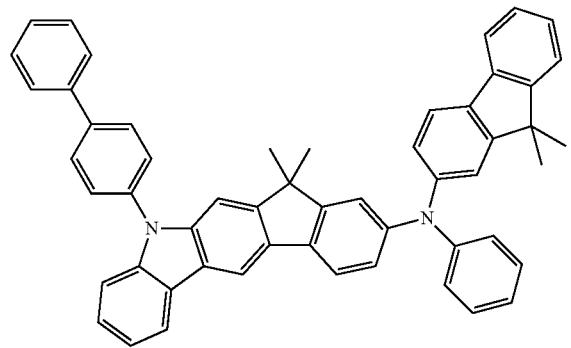
64
-continued
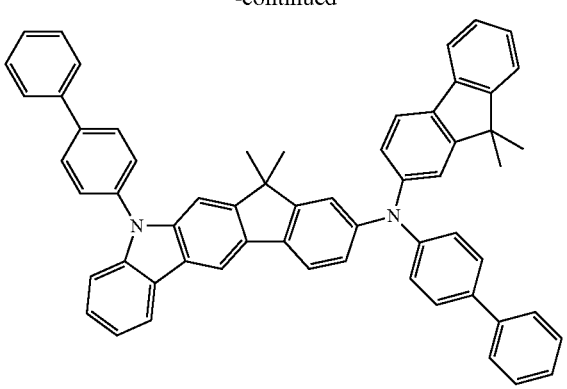
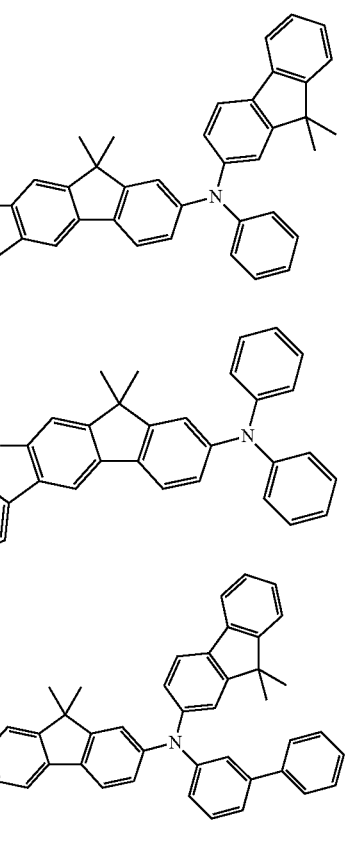

65
-continued
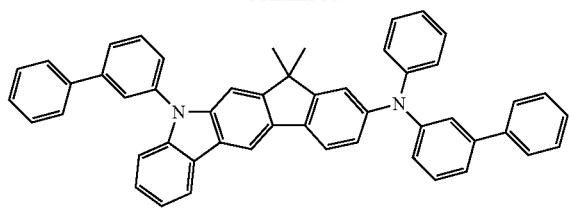
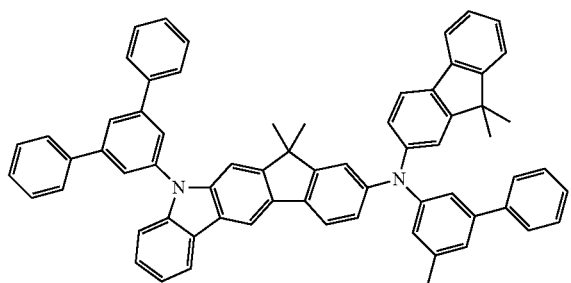
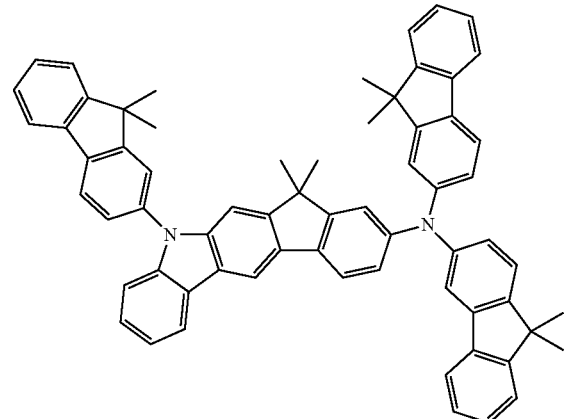
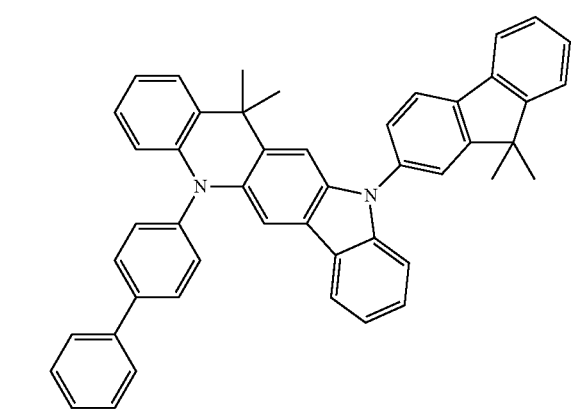
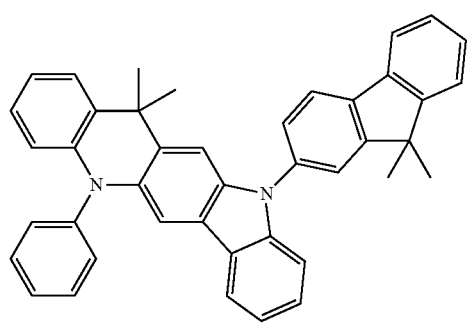
66
-continued
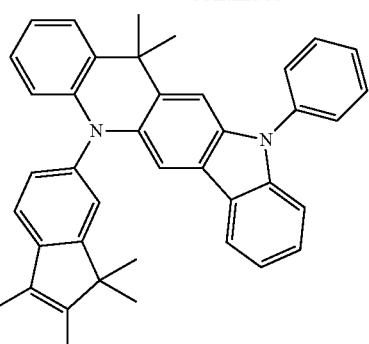
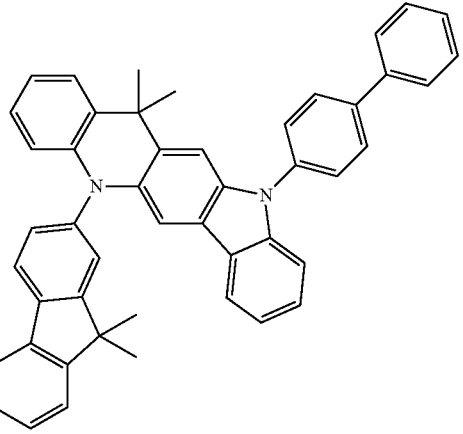
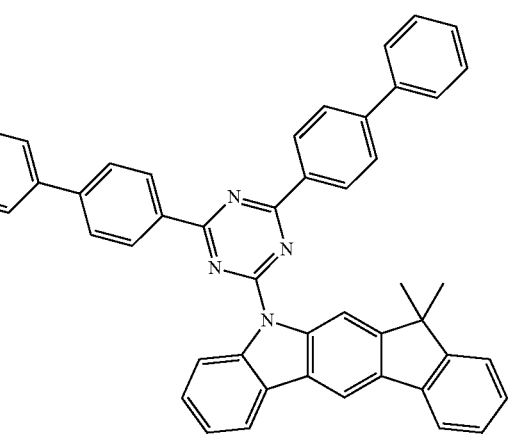
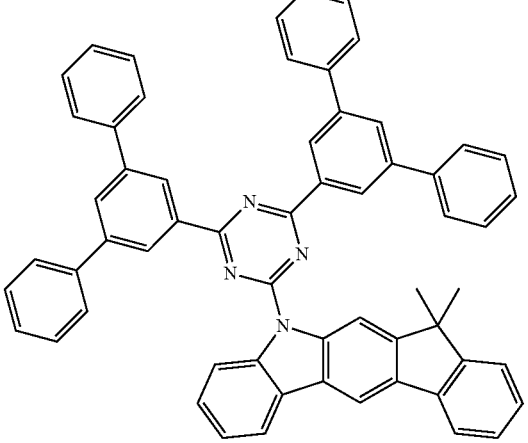

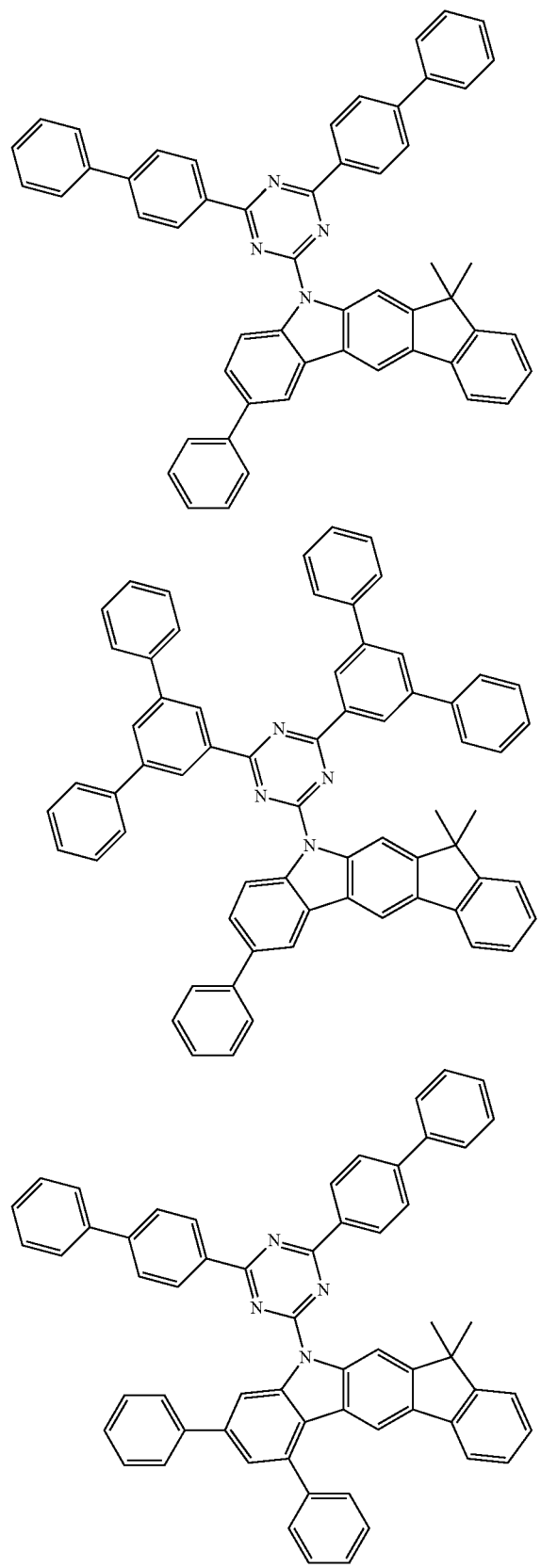
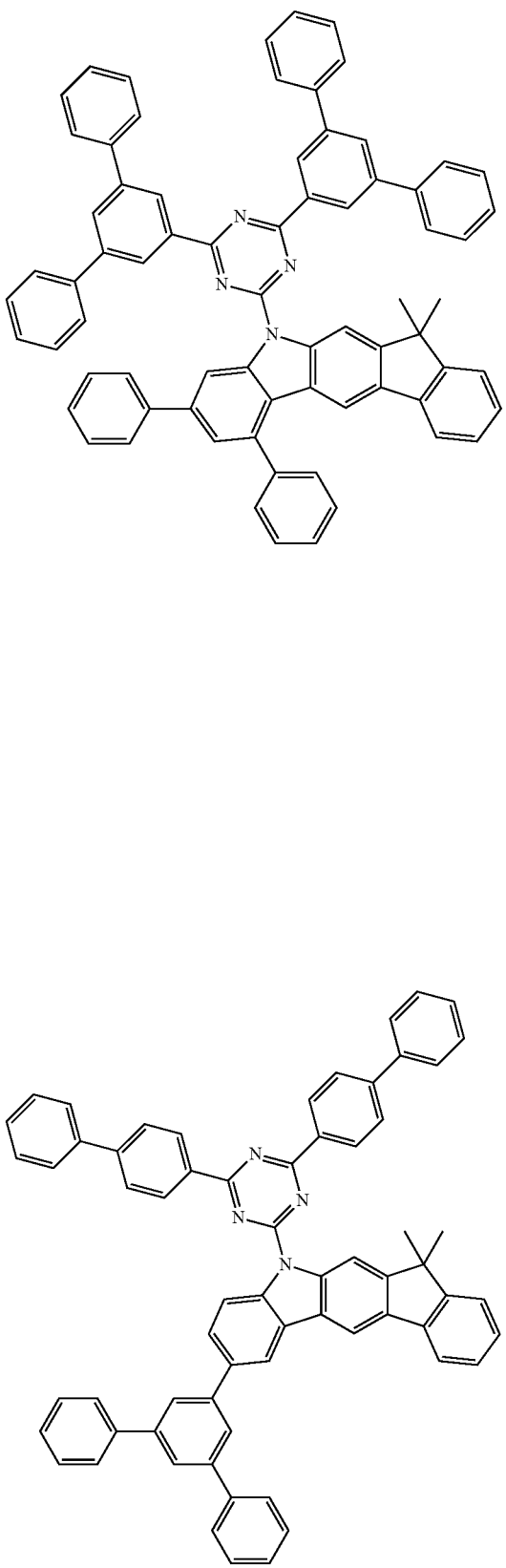

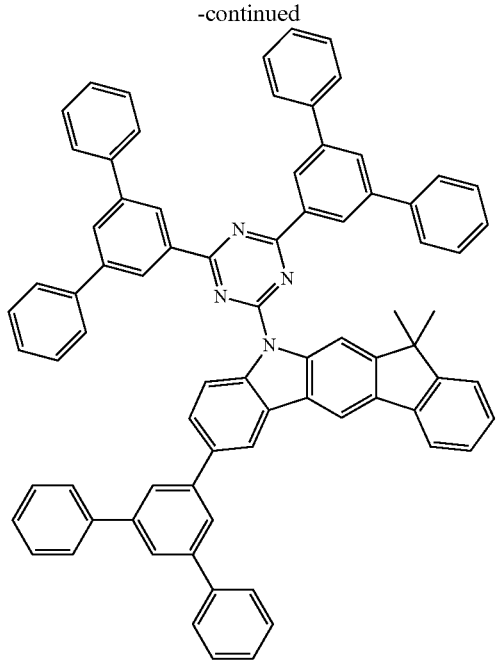
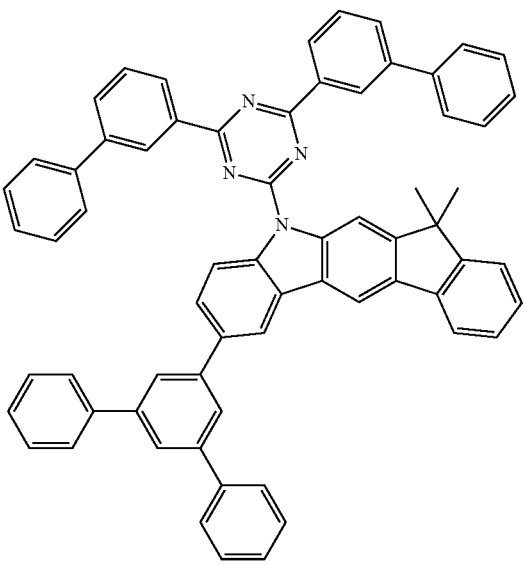
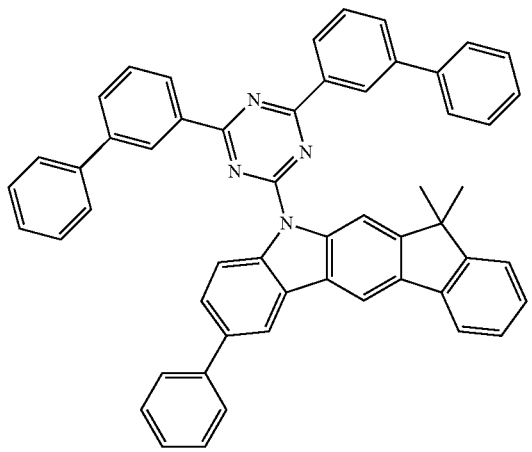
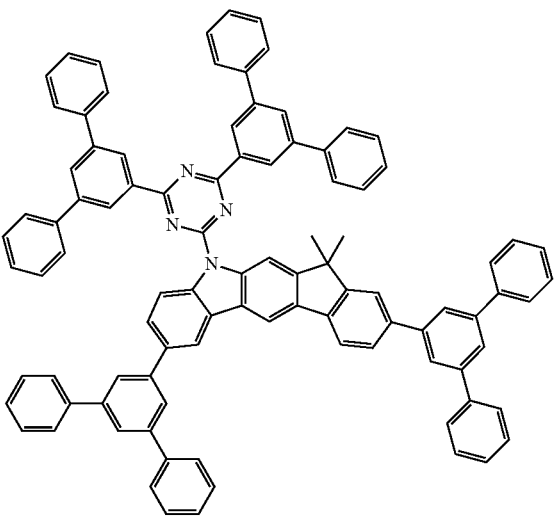
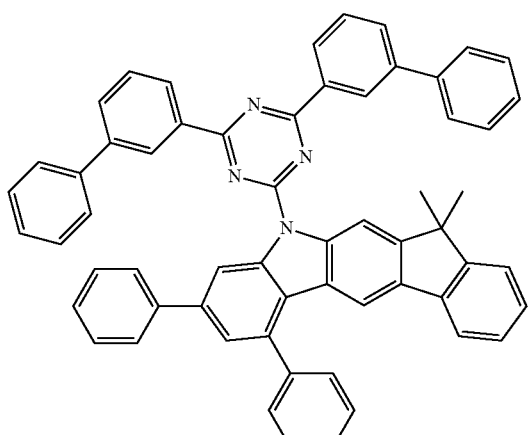
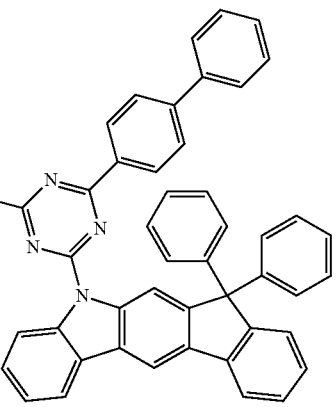

71
-continued
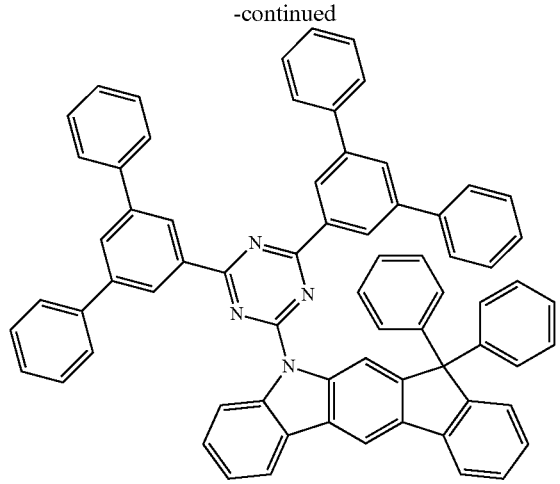
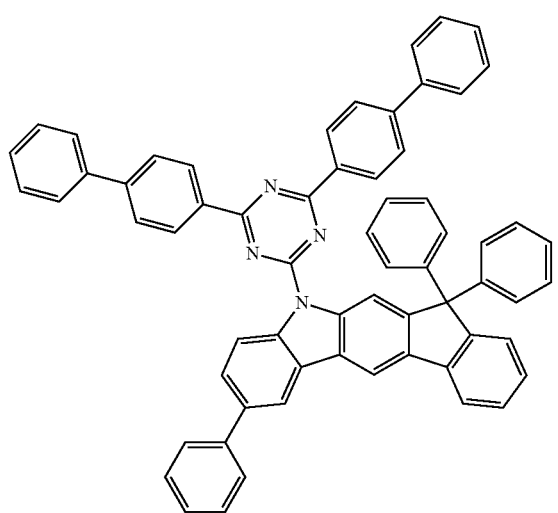
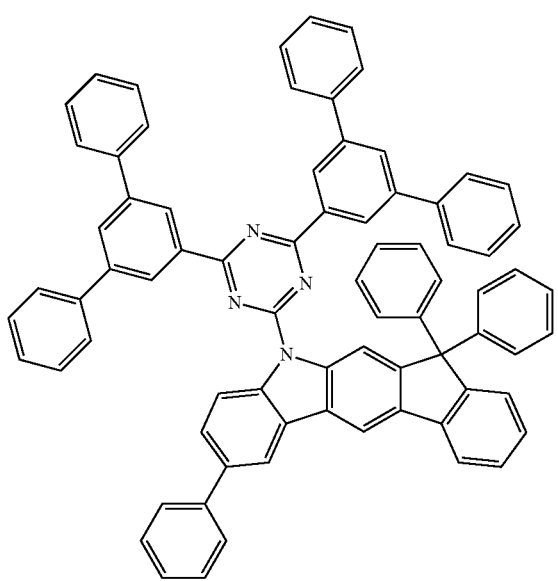
72
-continued
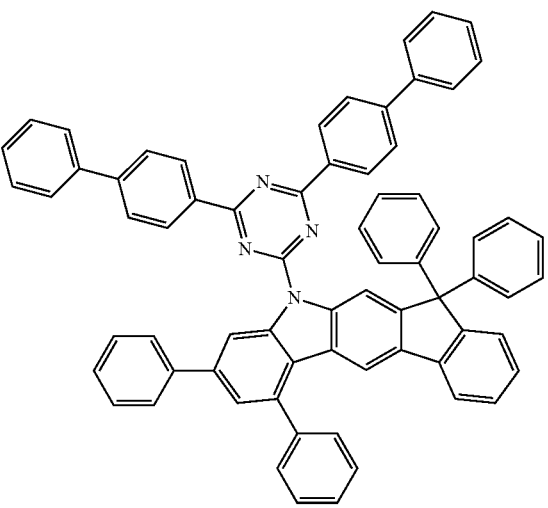
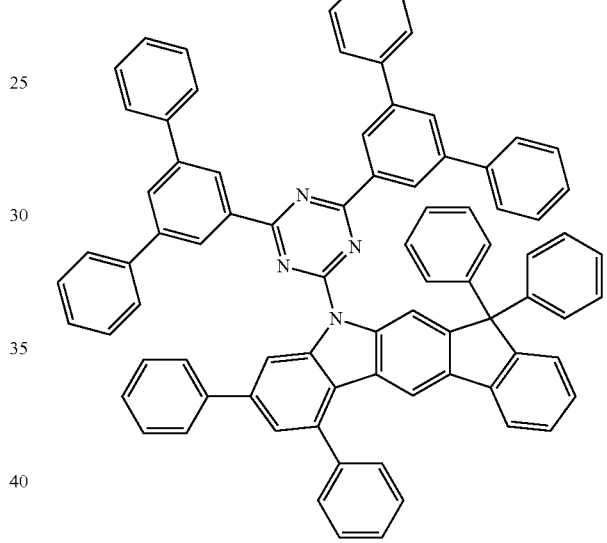
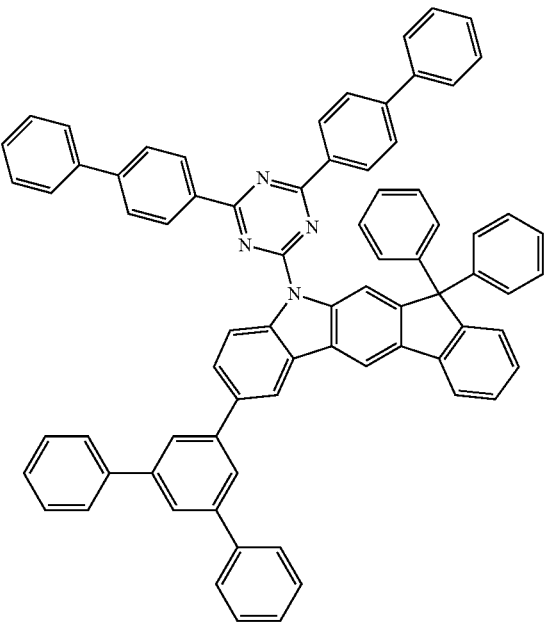

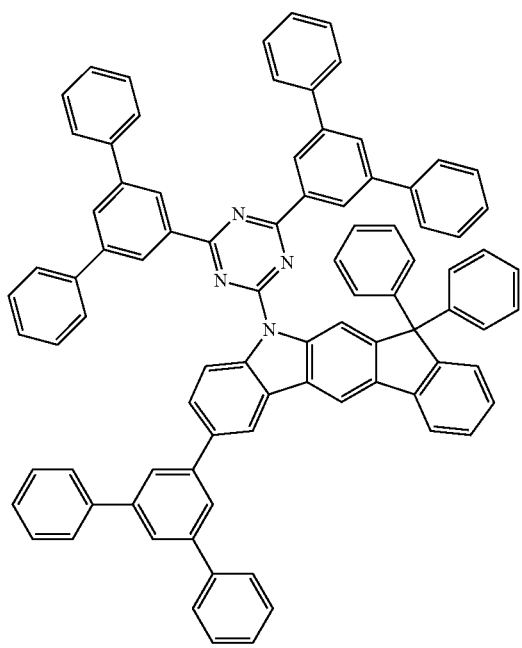
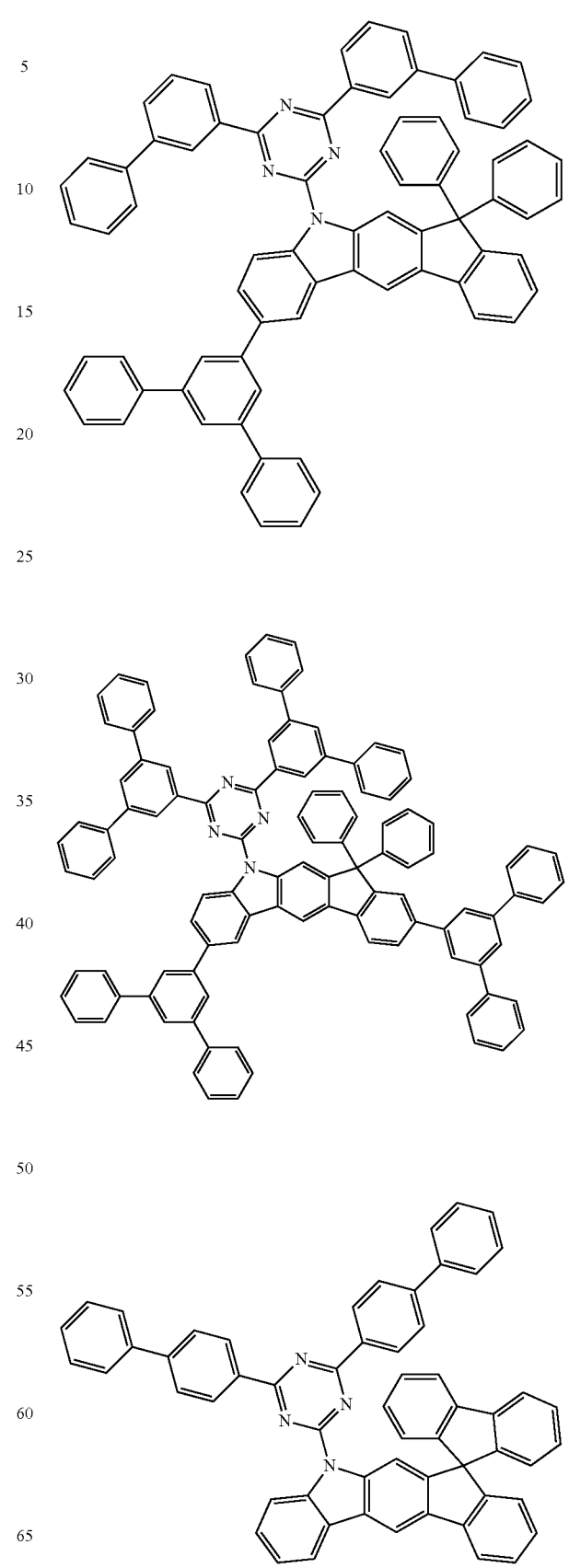

75
-continued
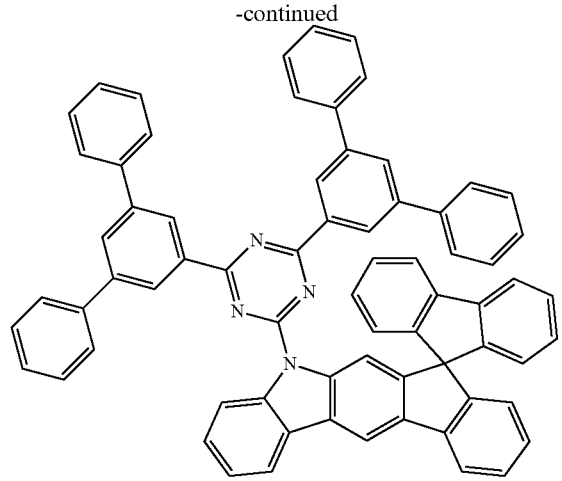
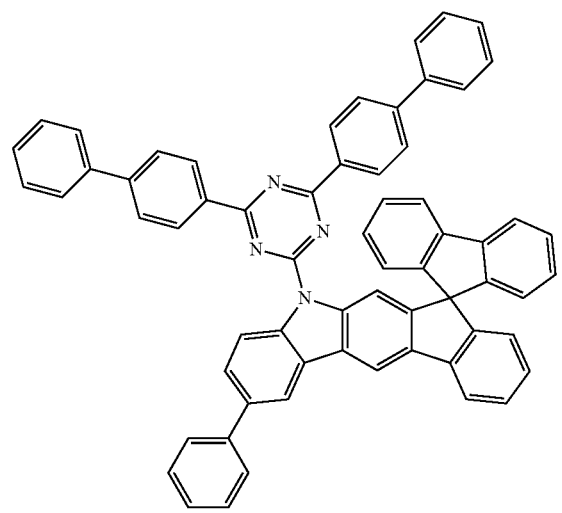
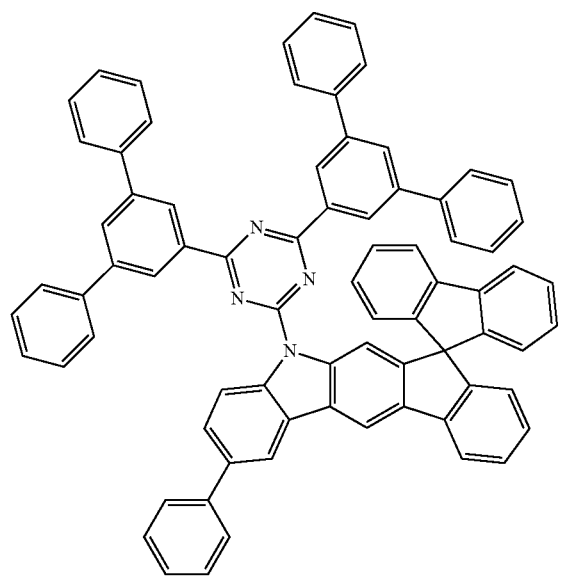
76
-continued
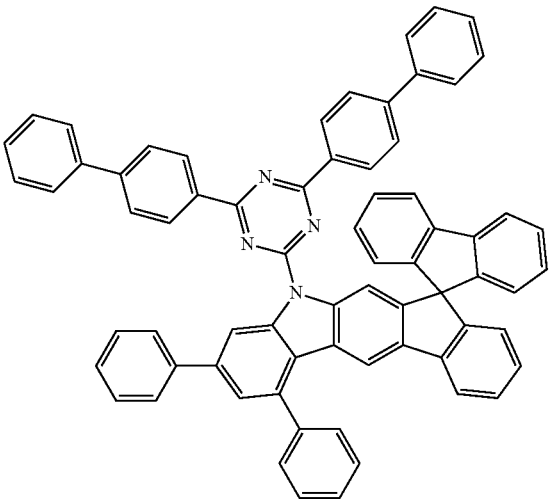
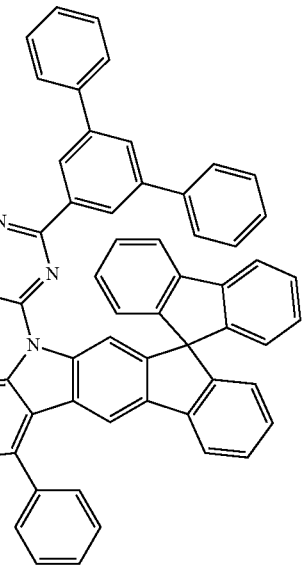
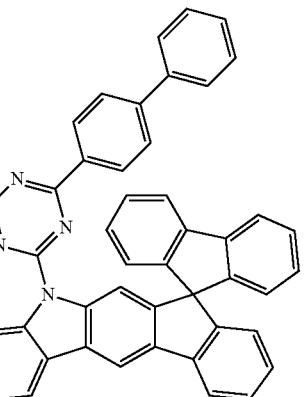

77
-continued
78
-continued
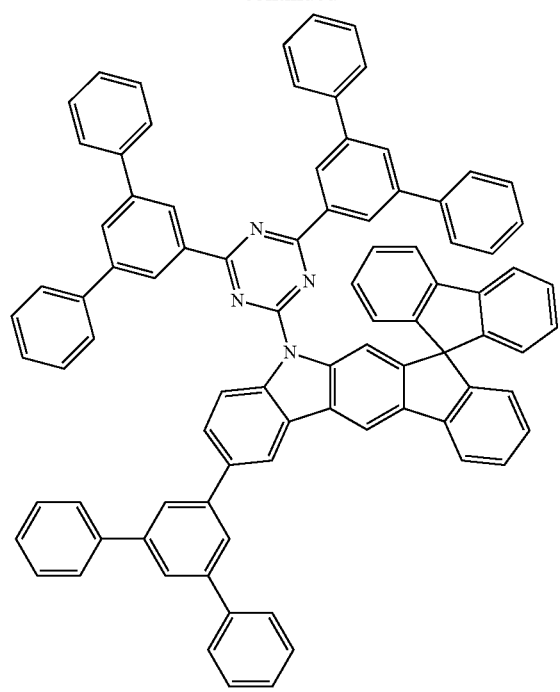
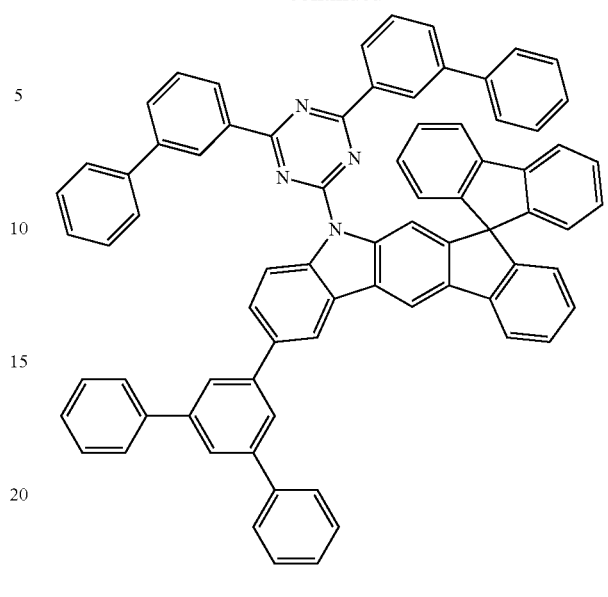
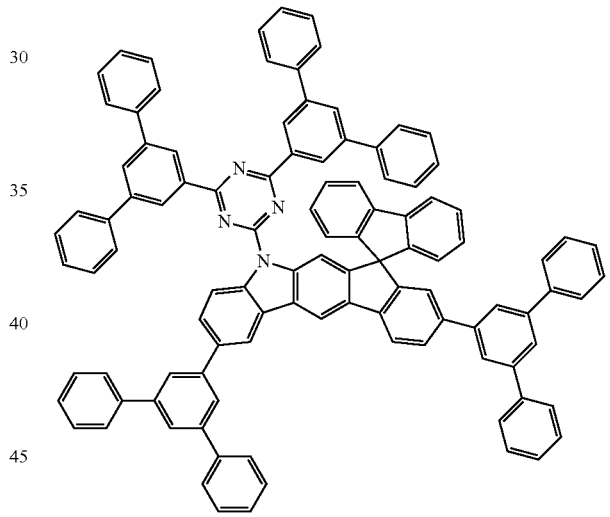
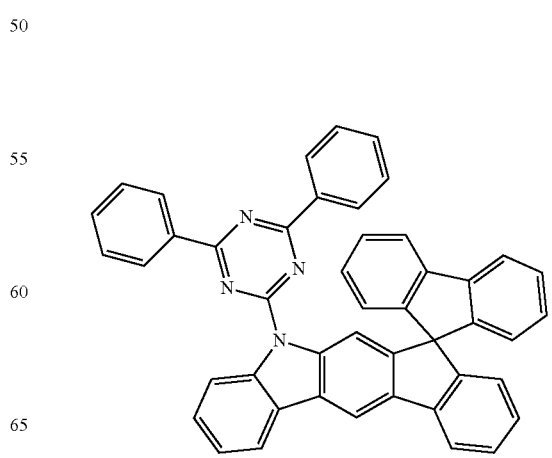

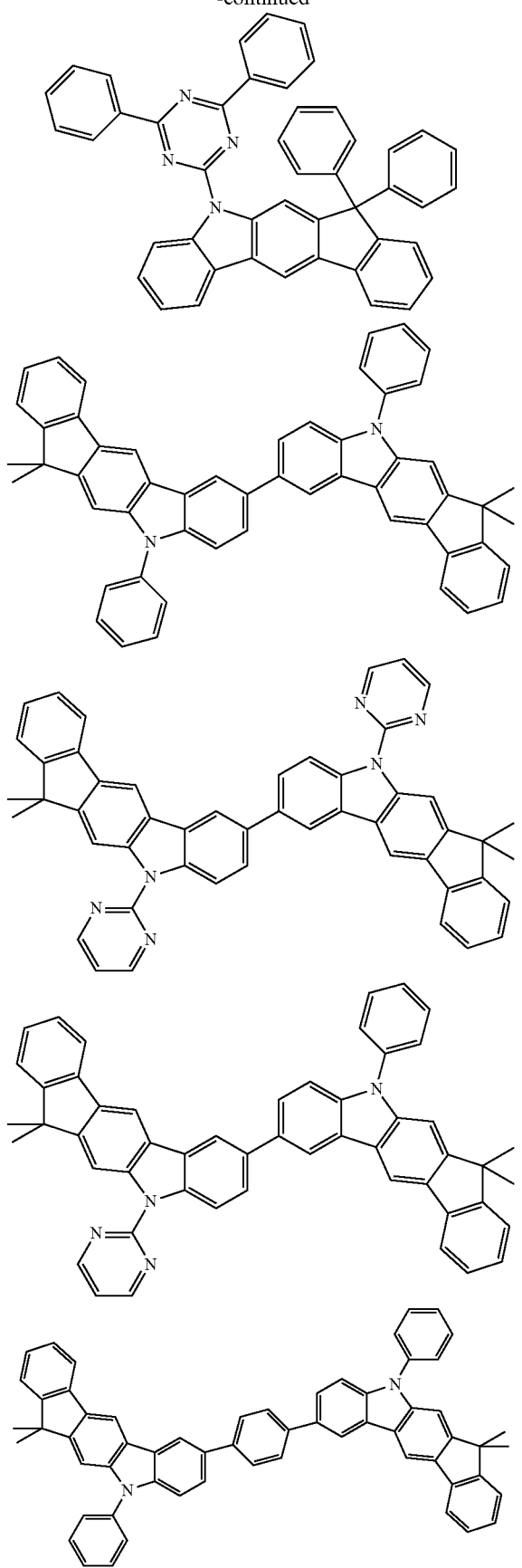
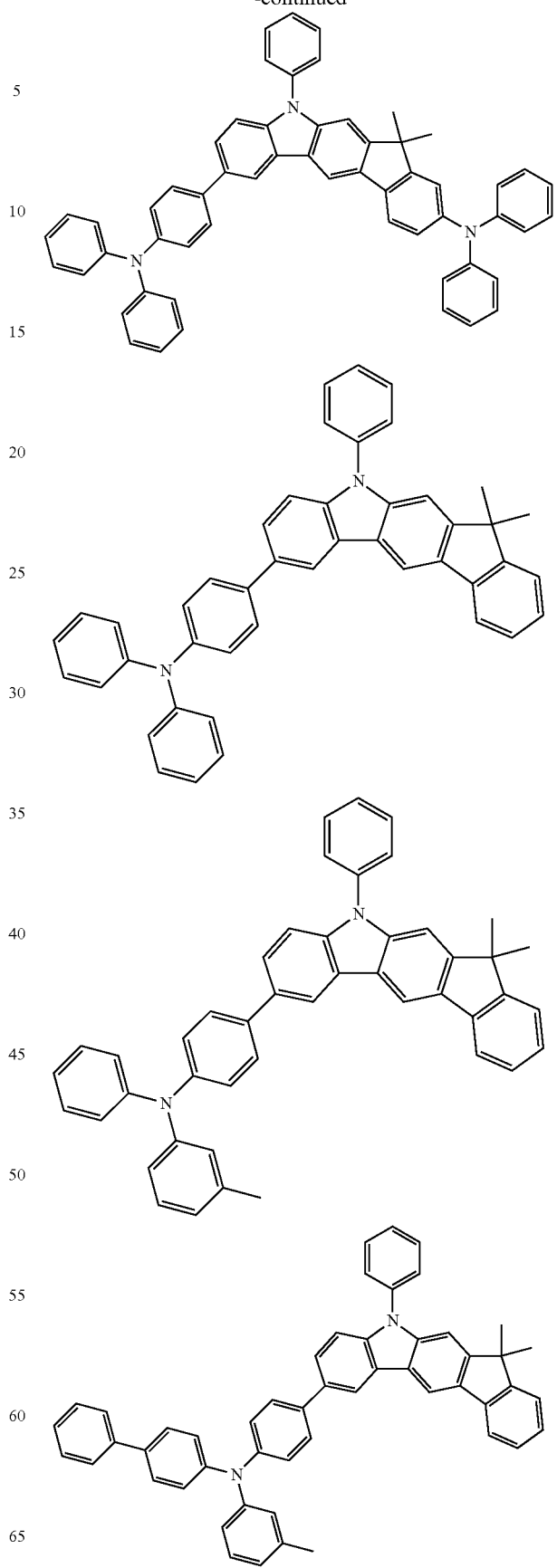

81
-continued
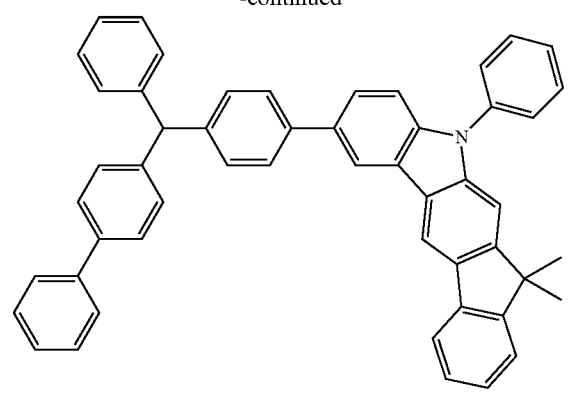
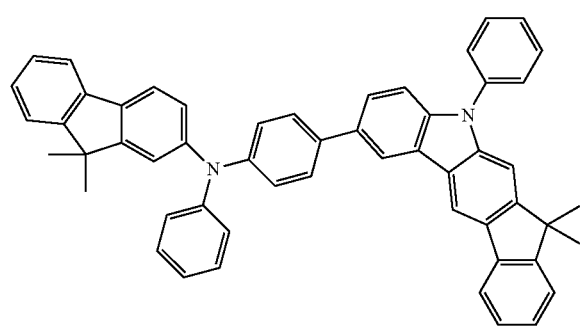
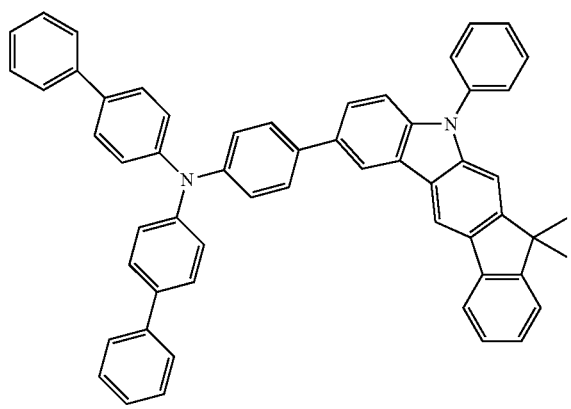
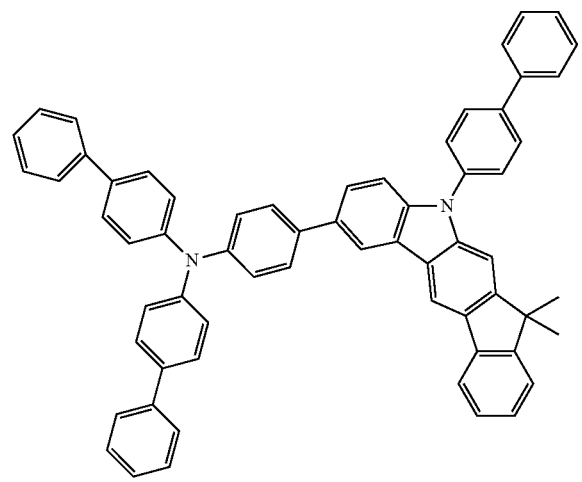
82
-continued
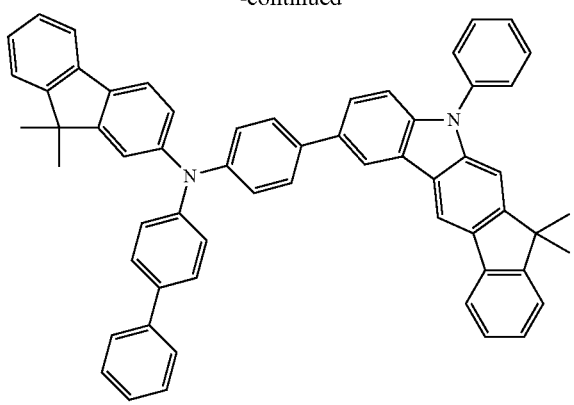
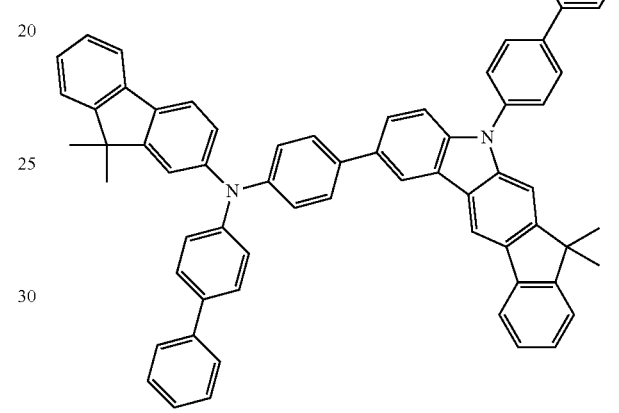
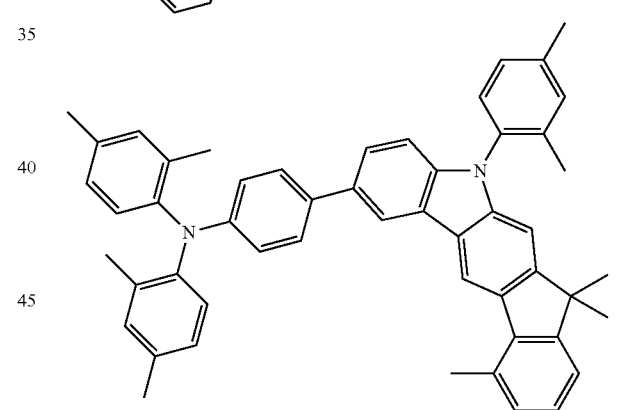
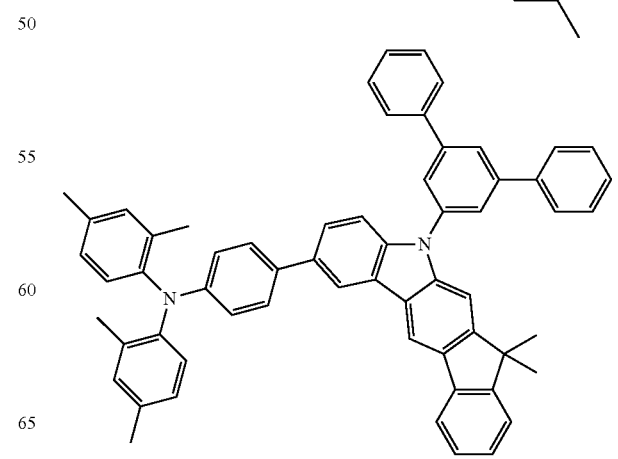

83
-continued
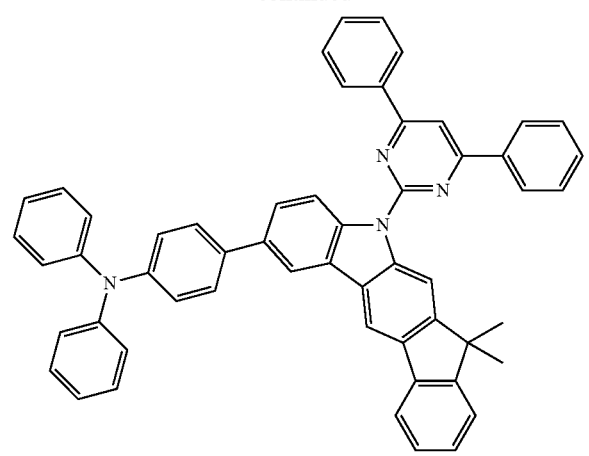
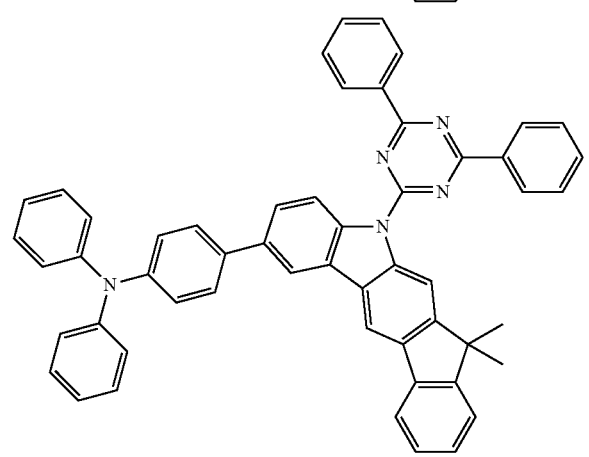
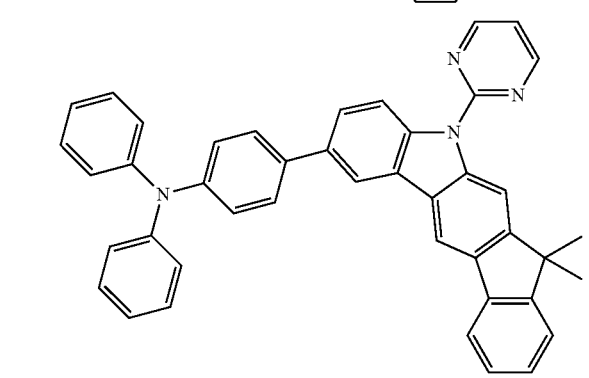
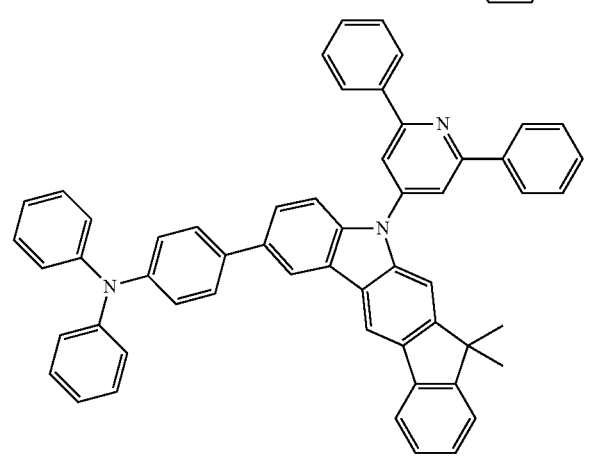
84
-continued
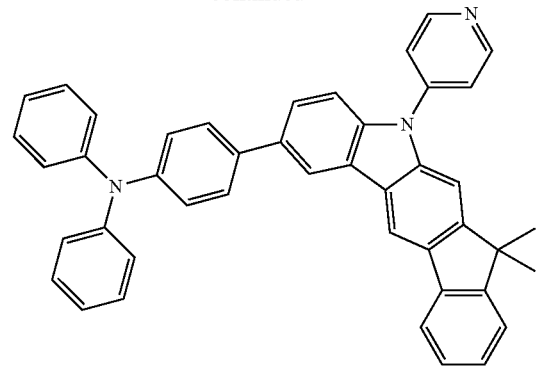
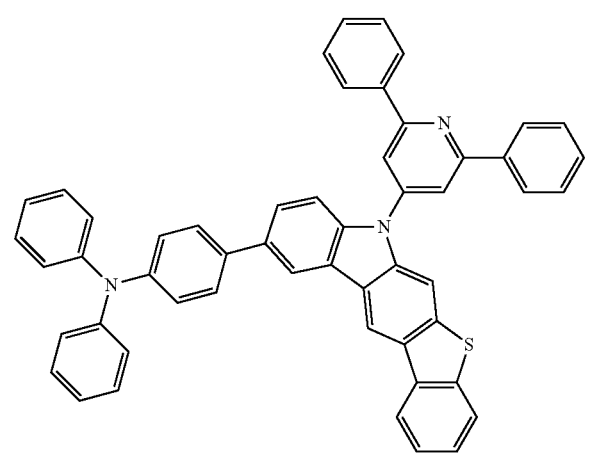
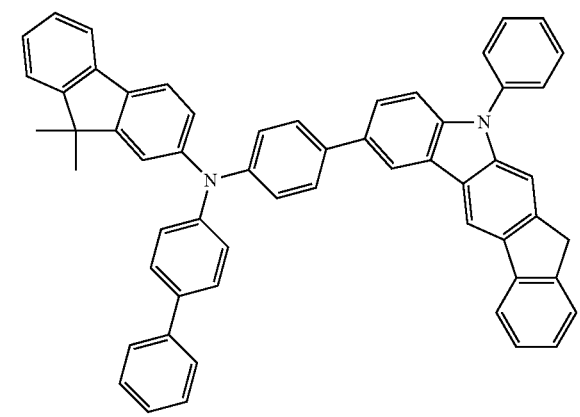
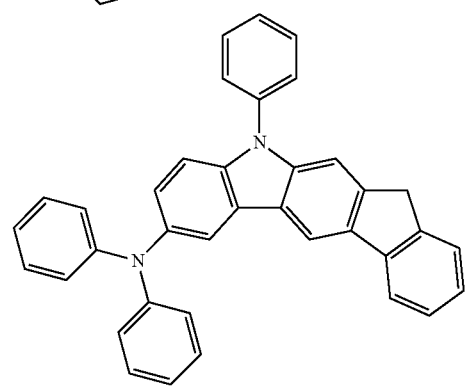

-continued
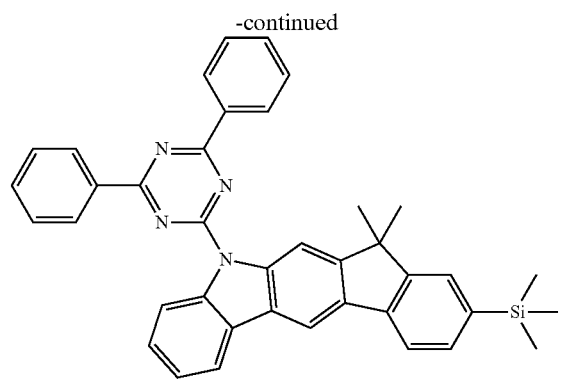
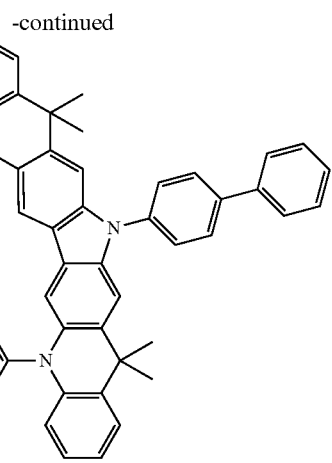
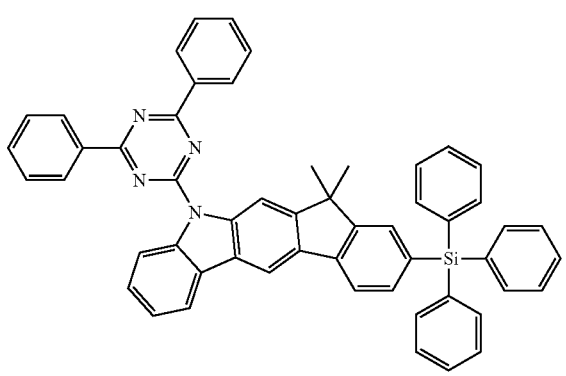
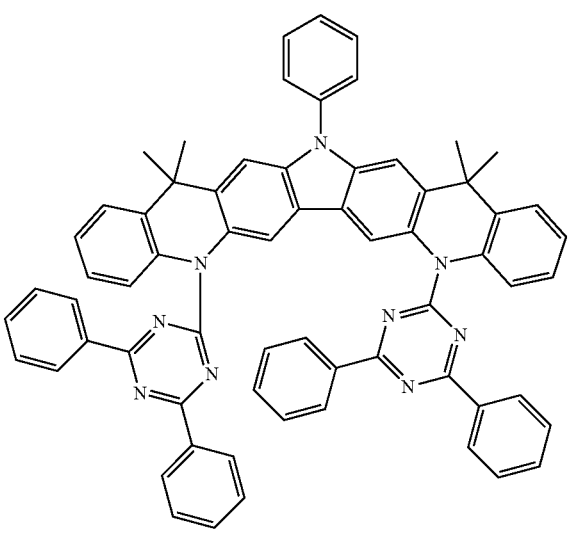
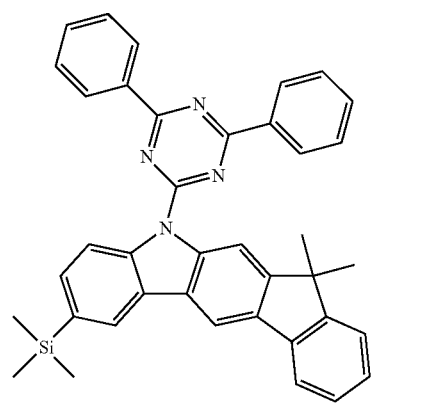
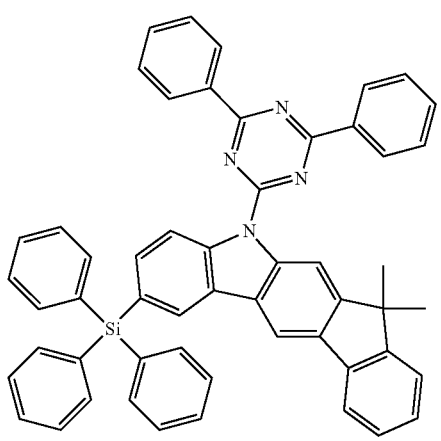
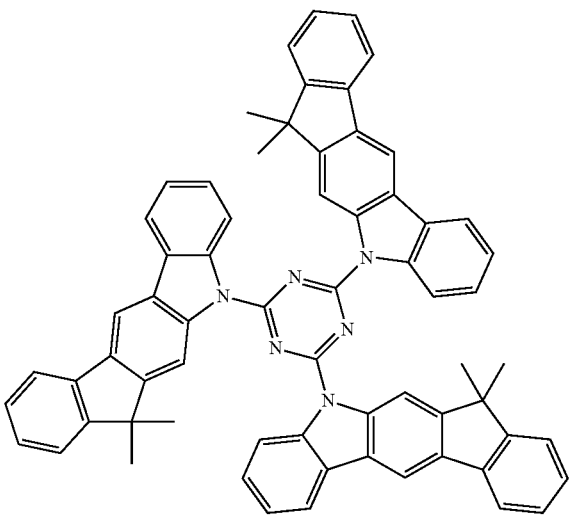

87
-continued
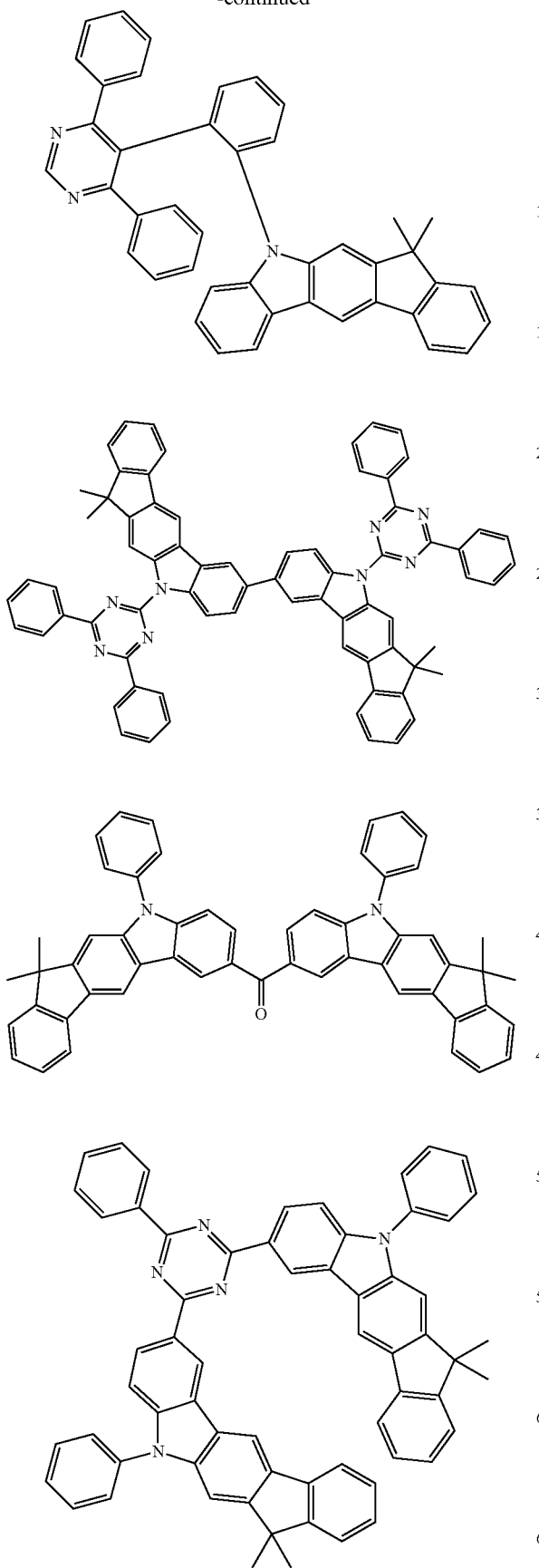
88
-continued
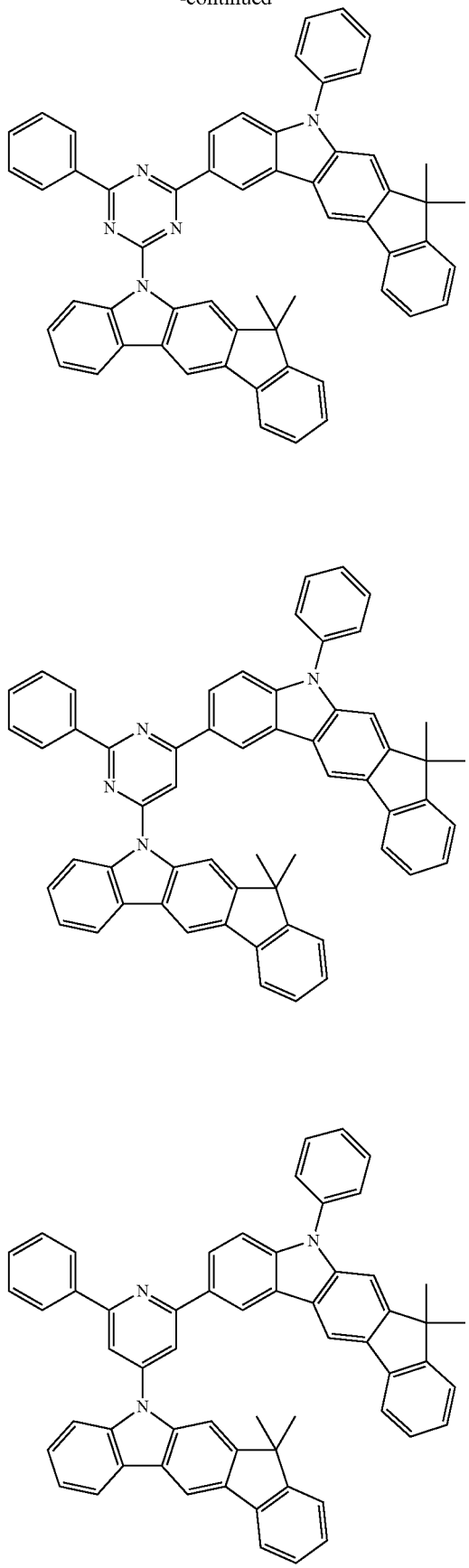

89
-continued
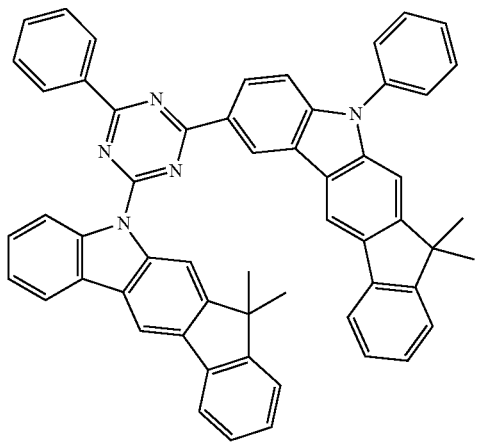
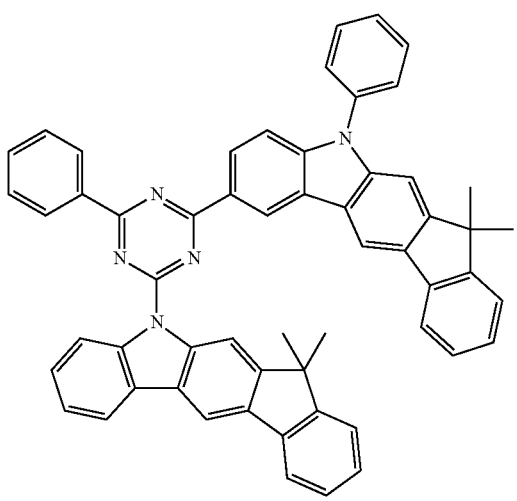
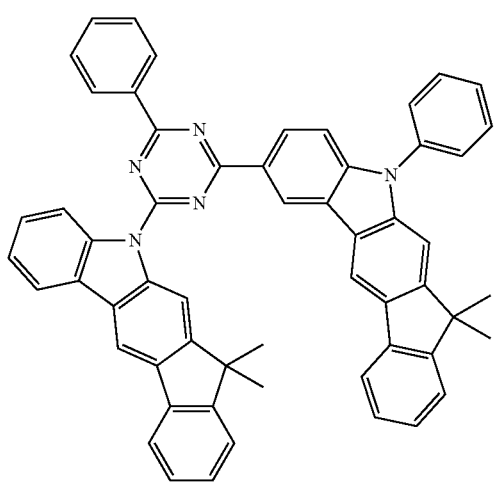
90
-continued
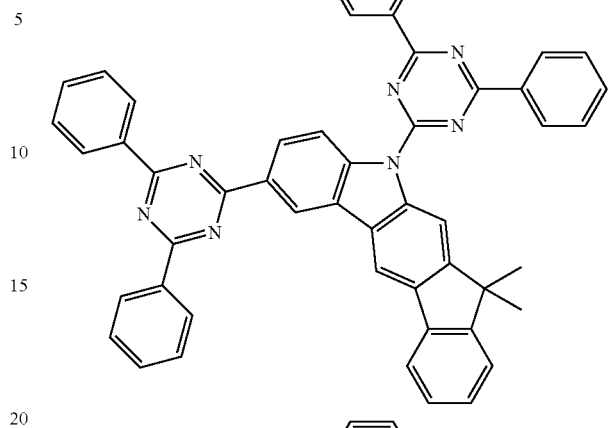
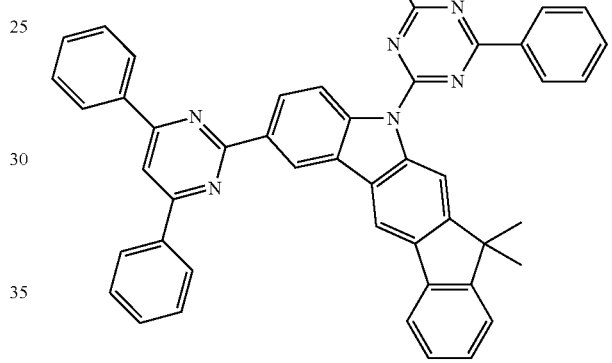
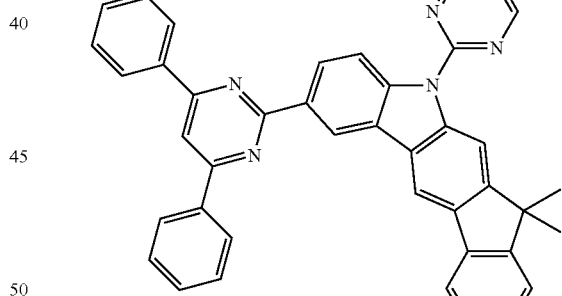
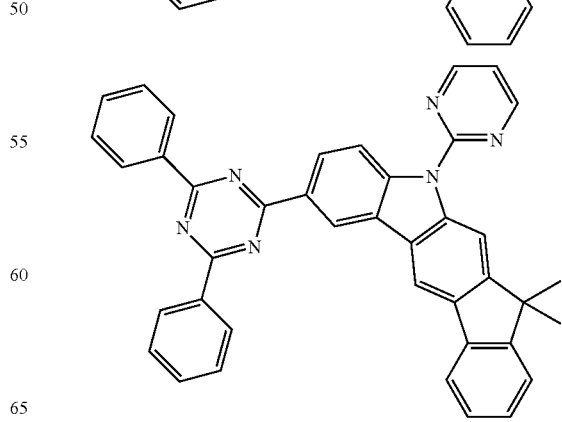

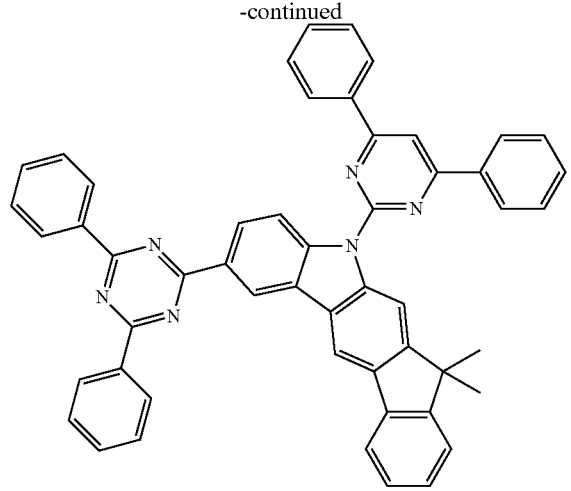
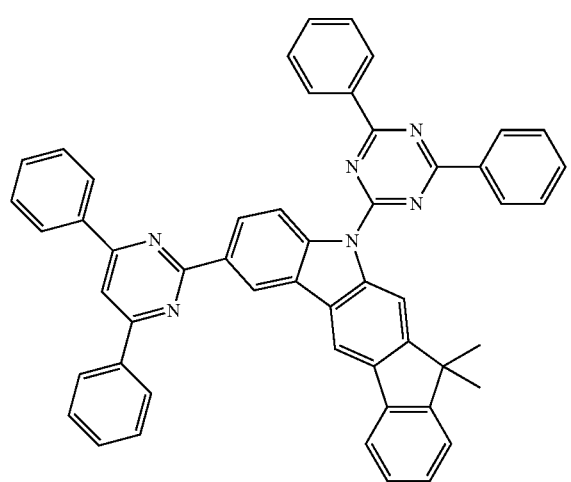
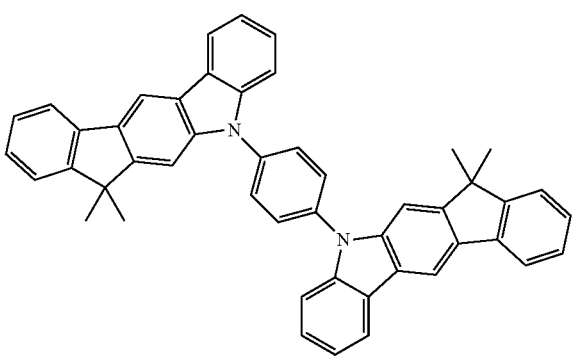
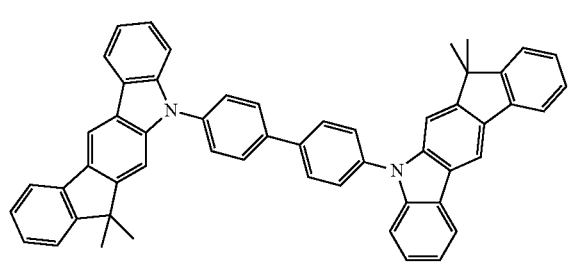
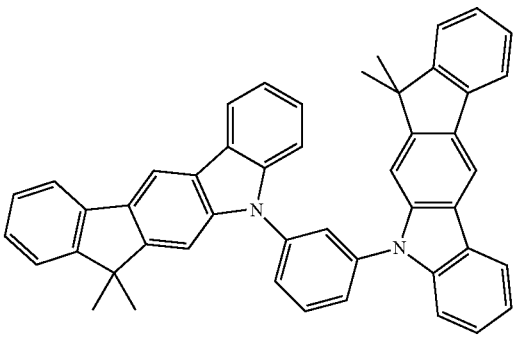
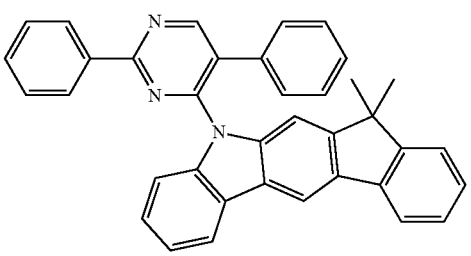
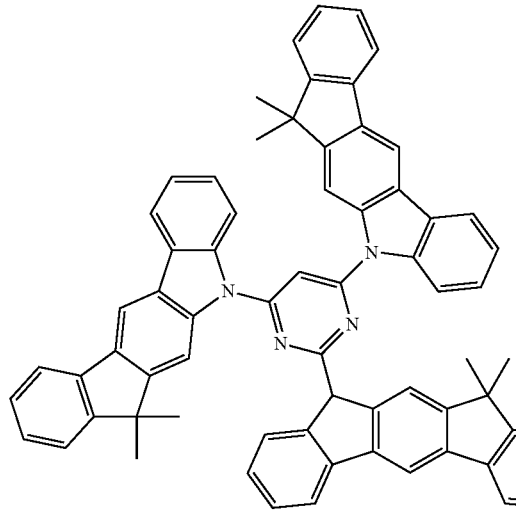
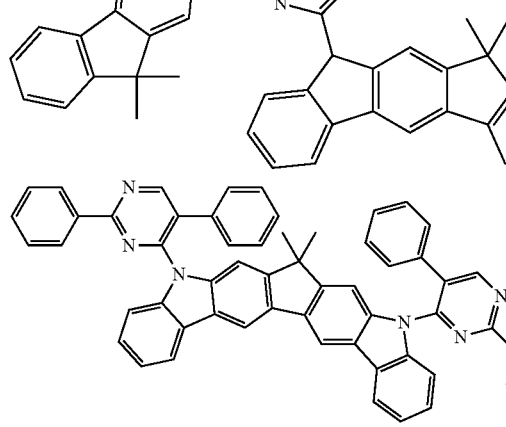
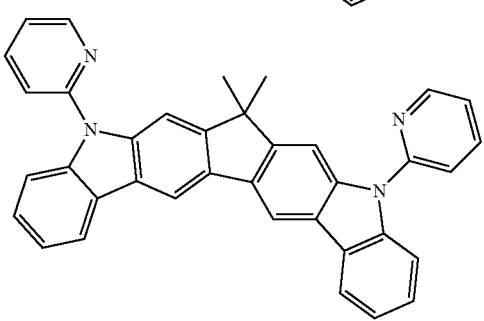

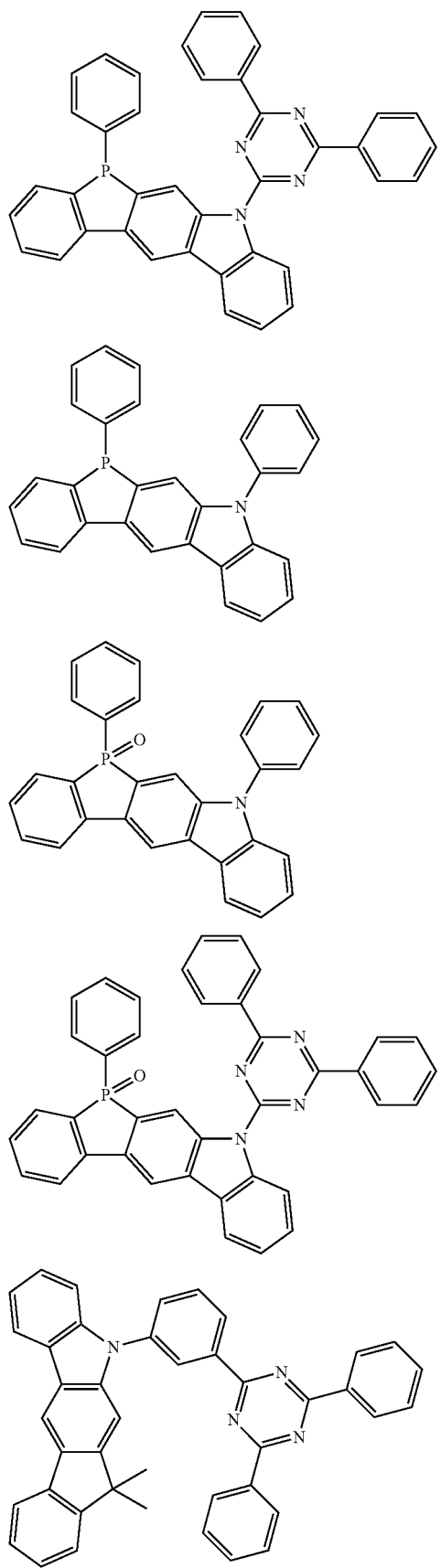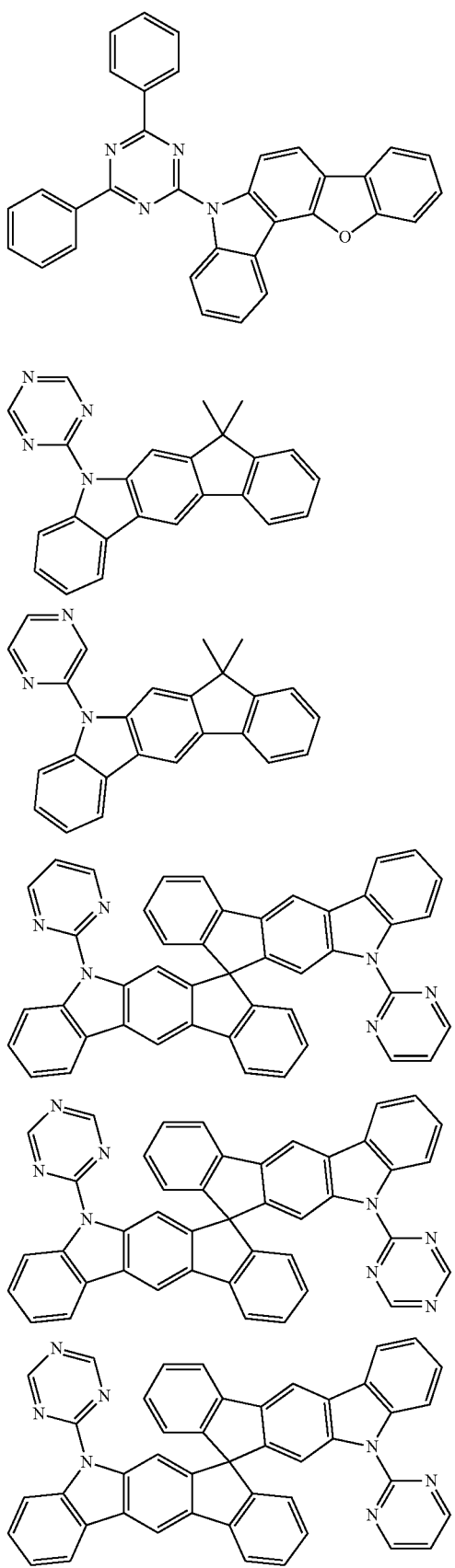

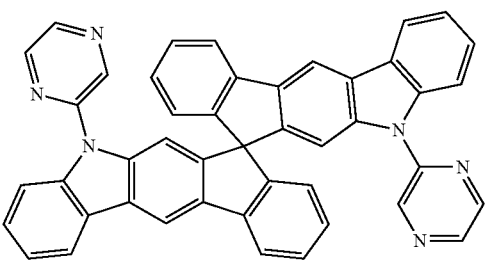
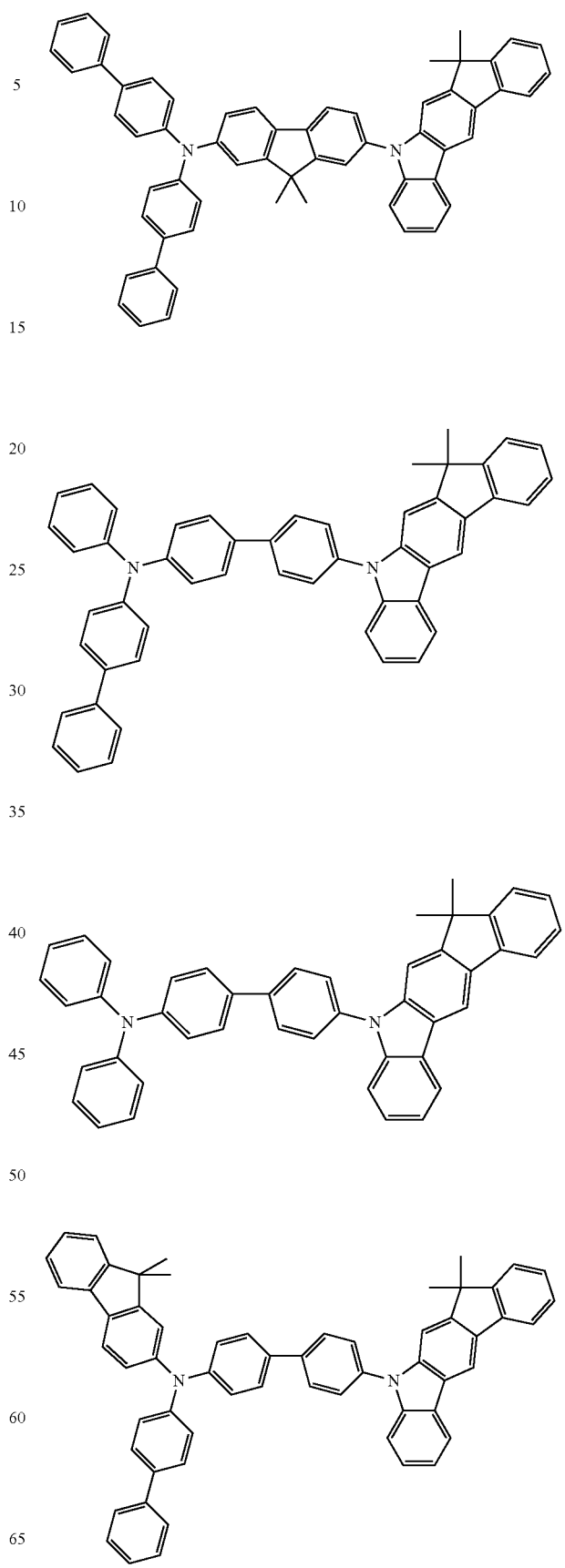

97
-continued
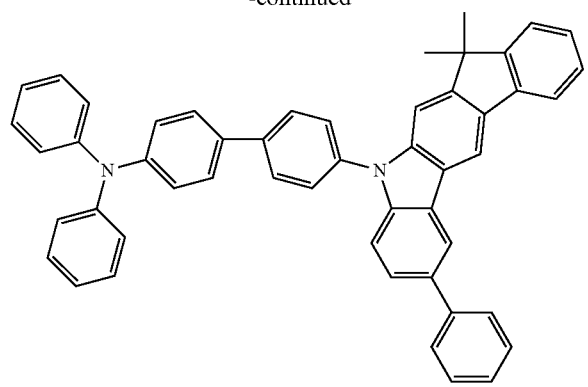
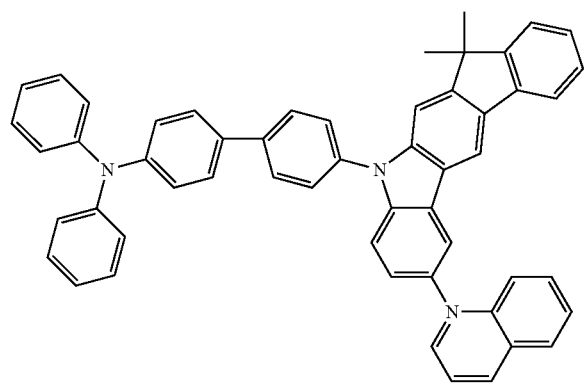
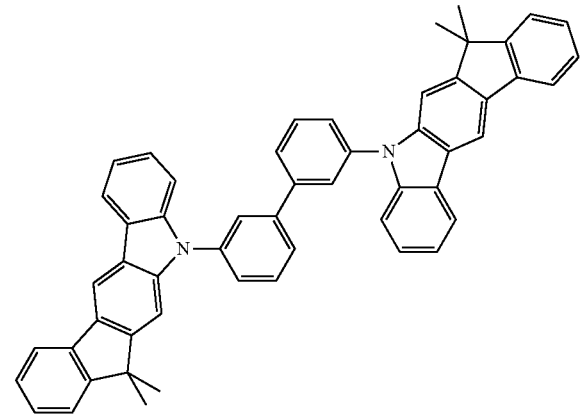
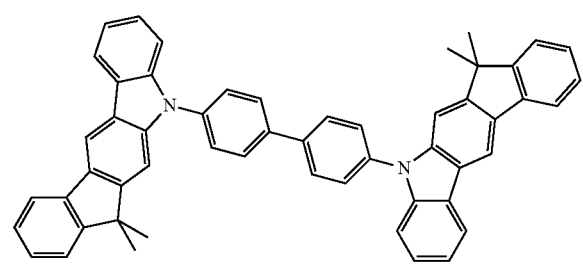
98
-continued
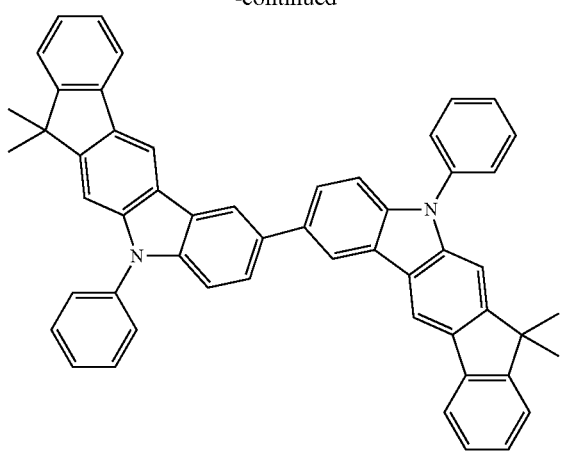
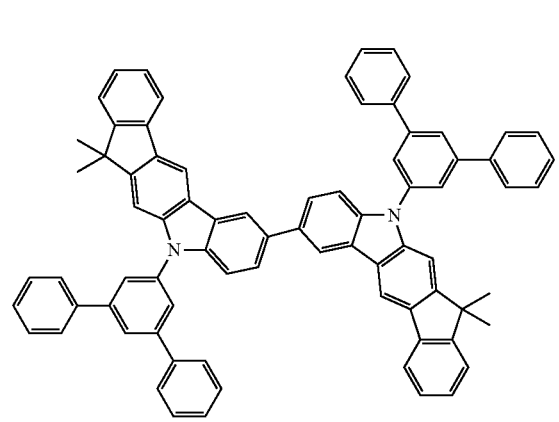
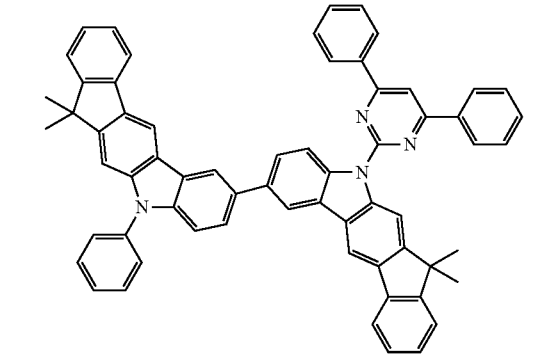
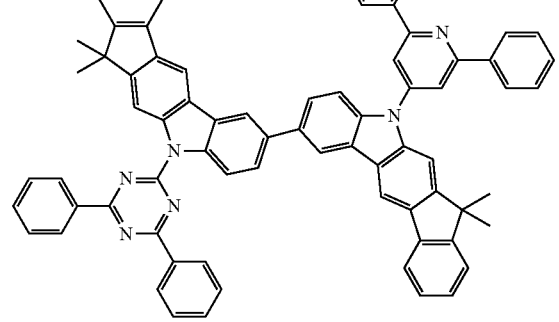

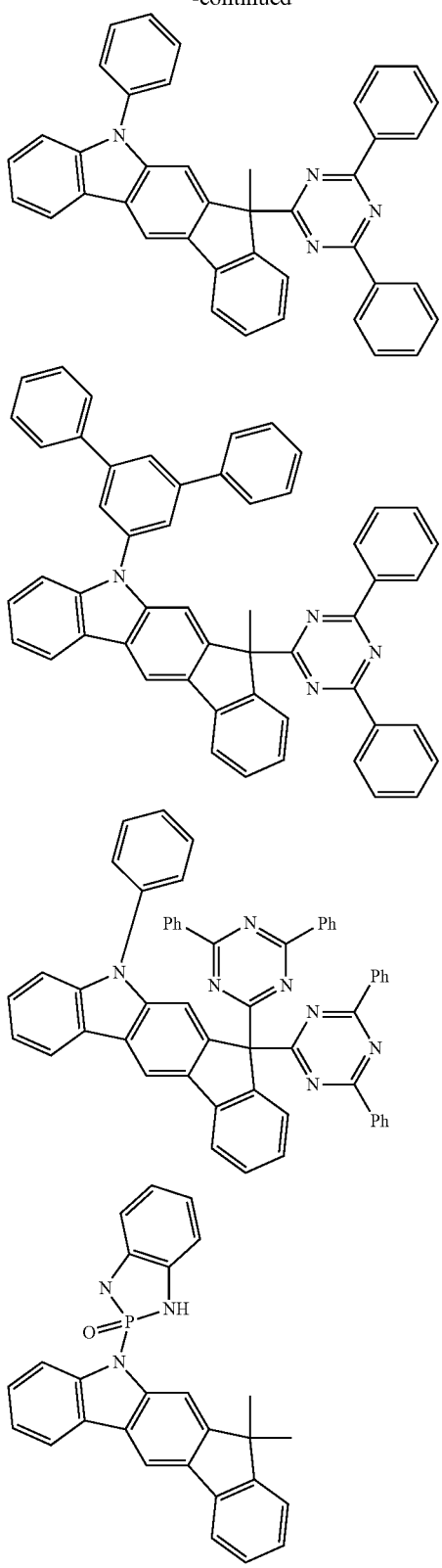

pound of the formula (1) containing a nitrogen atom as bridging atom is shown in general terms in Schemes 1 to 6 below.

As starting point, use can be made, for example, of (9-phenyl-9H-carbazol-3-yl)boronic acid (*Synlett,* 2006, 17, 2841-2845), p-aminobiphenyl (J. Am. Chem. Soc. 2008, 130(32), 10512-10514) and 2-bromo-9,9-dimethylfluorene (Synlett 2006, 5, 737-740):

Scheme 1:

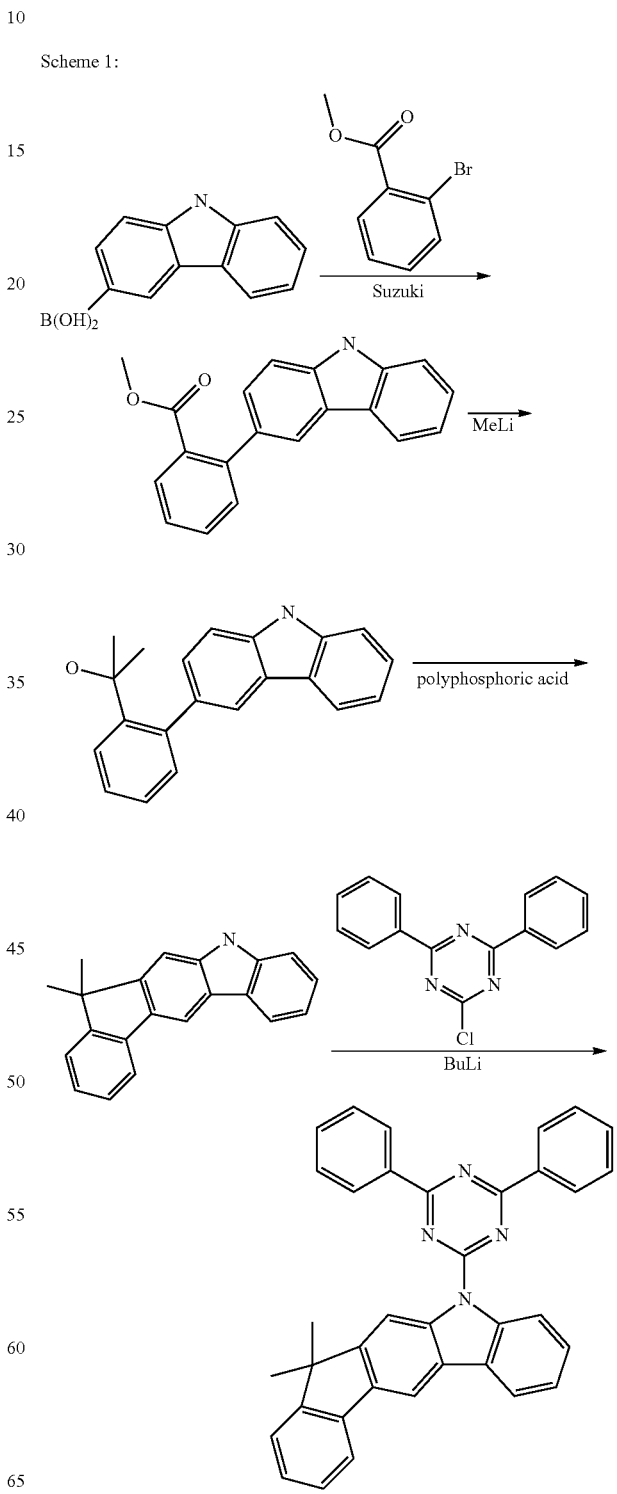

The compounds according to the invention can be prepared by synthetic steps known to the person skilled in the art, such as, for example, bromination, Suzuki coupling, Hartwig-Buchwald coupling, etc. The synthesis of a com- Scheme 2:
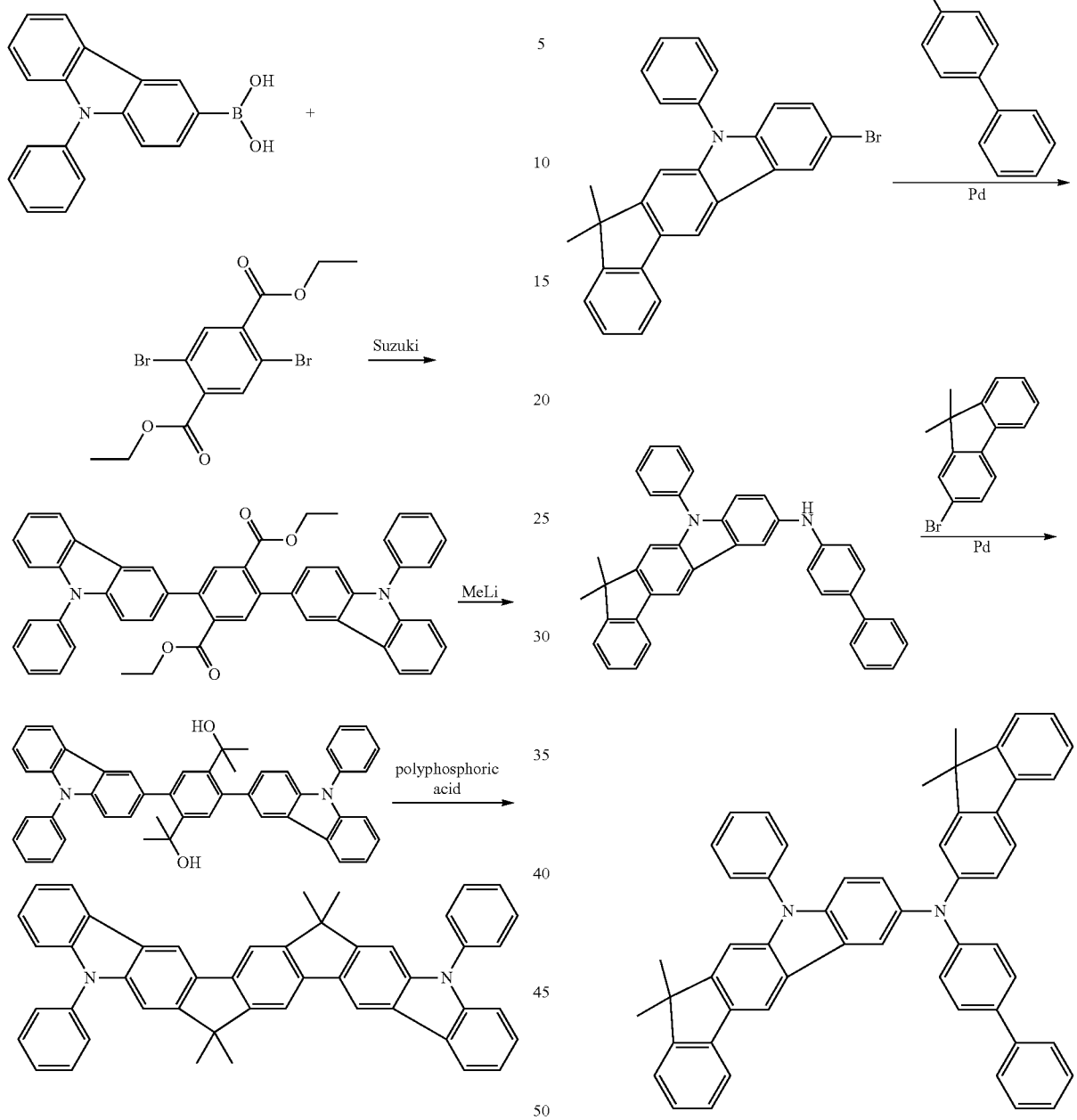
Scheme 3:
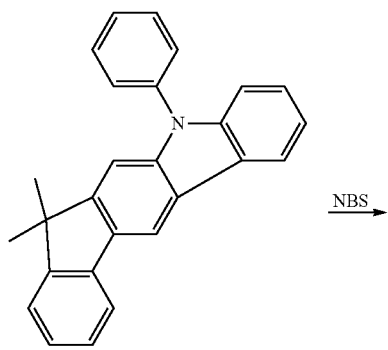
Scheme 4:
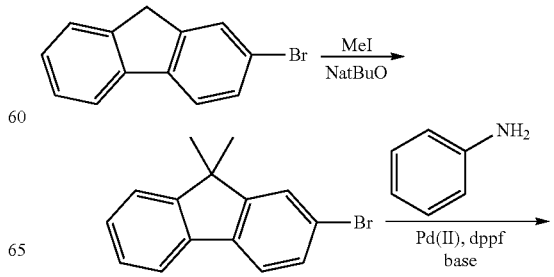

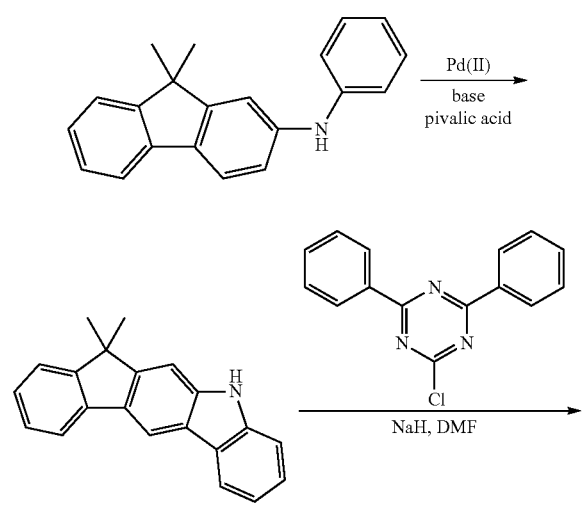
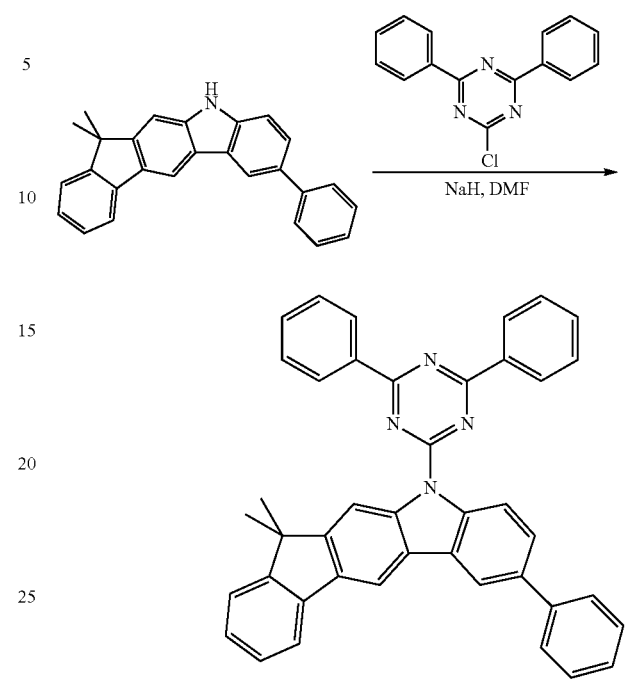
Scheme 5:
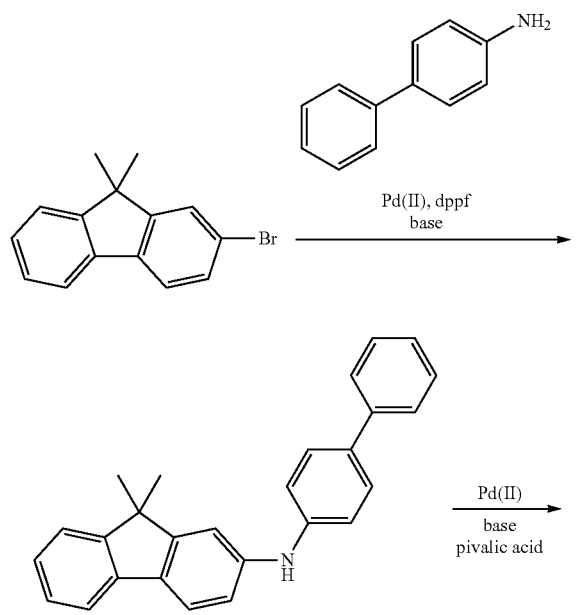
Scheme 6:
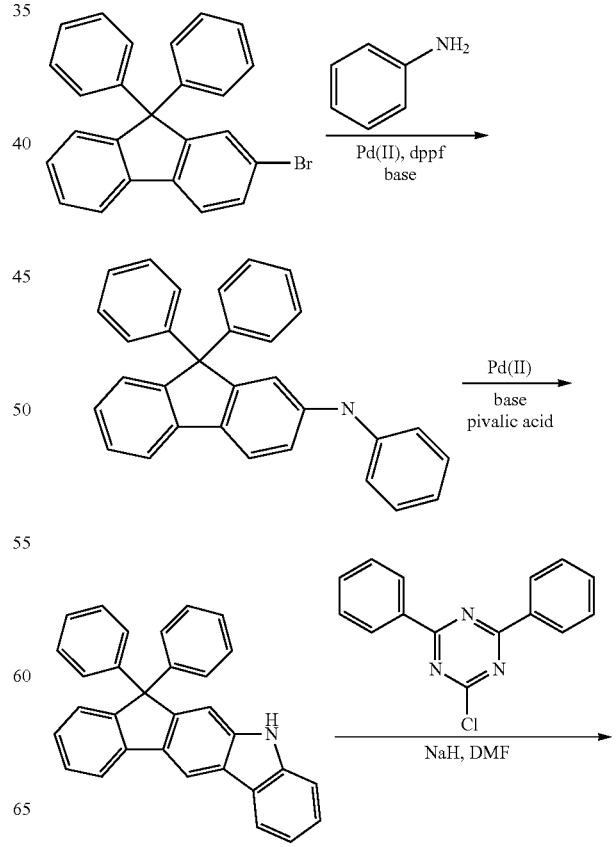

-continued

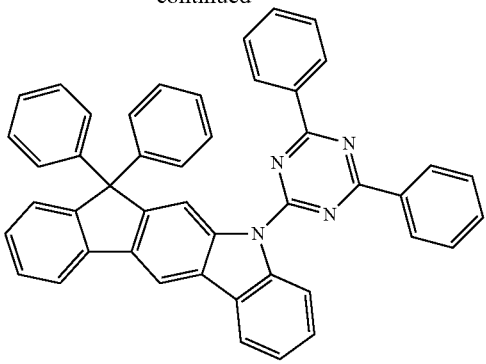

The example compounds according to the invention can also be synthesised analogously to the syntheses shown in Schemes 1 to 6 with variation of the substituents. For example, phenyl, biphenyl, terphenyl, naphthyl, pyridinyl, pyrimidinyl, anthracenyl and the like can be used instead of the triazine substituent as substituent on the nitrogen.

The invention furthermore relates to a process for the preparation of a compound of the general formula (1)

formula (1)

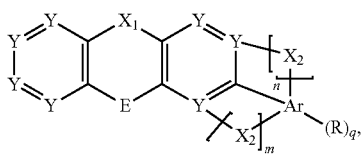

where the symbols and indices used have the meanings indicated above, characterised by the steps of:
a) reaction of a compound of the formula (I)

formula (I)

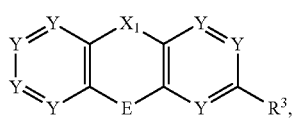

where $R^3$ is a reactive leaving group, preferably selected from bromine, iodine, chlorine, boronic acid, boronic acid ester, tosylate or triflate,
with a compound of the formula (II)

formula (II)

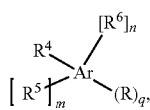

where $R^4$ is a reactive leaving group, preferably selected from bromine, iodine, chlorine, boronic acid, boronic acid ester, tosylate or triflate, or a functional reactive group, for example an amine. $R^5$ and $R^6$ are each, independently of one another, suitable for the formation of a bridge $X_2$, n and m are each, independently of one another, 0 or 1, where n m is greater than or equal to 1, for the formation of a compound of the formula (III)

formula (III)

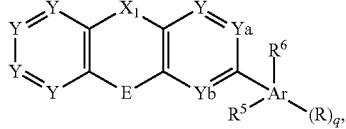

b) formation of the bridge $X_2$ by a suitable ring-closure reaction between $Y_a$ and/or $Y_b$ and $R^5$ and/or $R^6$ and optionally subsequent substitution on $X_1$ and/or $X_2$, with formation of the compound of the formula (1).

The compound of the formula (1) can be employed in electronic devices, in particular in organic electroluminescent devices. The precise use of the compounds here is dependent on the precise structure of the substituents.

The present invention therefore furthermore relates to the use of a compound of the formula (1) in an electronic device.

In a preferred embodiment of the invention, the compound of the formula (1) is employed in an emitting layer, preferably in a mixture with at least one further compound. It is preferred for the compound of the formula (1) in the mixture to be the matrix material.

In a preferred embodiment of the present invention, the compounds of the formula (1) are therefore employed as matrix material (host material) for dopants, preferably phosphorescent dopants. It is particularly preferred here for the compounds of the formula (1) to be employed as matrix material for dopants in an organic electroluminescent device.

An organic electroluminescent device is a device which comprises anode, cathode and at least one emitting layer which is arranged between the anode and the cathode. In addition, one or more electron-transport layers and one or more hole-transport layers may be present. An organic electroluminescent device according to the invention comprises at least one layer between the anode and cathode which comprises a compound of the formula (1), for example as matrix material, hole-transport material or electron-transport material. The matrix material preferably comprises an emitting compound. In this case, the layer is an emitting layer which comprises at least one emitter, preferably a phosphorescent emitter, and at least one compound of the above-mentioned formula (1).

In a further preferred embodiment of the invention, the organic electroluminescent device may also comprise a plurality of emitting layers, where at least one emitting layer comprises at least one compound of the formula (1) and at least one emitter, preferably a phosphorescent emitter.

The invention therefore furthermore also relates to mixtures of one or more compounds of the formula (1) as matrix material with one or more dopants, in particular emitting compounds.

The mixture of the compound of the formula (1) as matrix material and the emitter which is employed in the emitting layer preferably comprises between 99 and 50% by vol., preferably between 98 and 50% by vol., particularly preferably between 97 and 60% by vol., in particular between 95 and 85% by vol., of the compound of the formula (1), based on the entire mixture of emitter and matrix material. Correspondingly, the mixture comprises between 1 and 50% by vol., preferably between 2 and 50% by vol., particularly preferably between 3 and 40% by vol., in particular between 5 and 15% by vol., of the emitter, based on the entire mixture of emitter and matrix material.

Preference is furthermore also given to the use of a plurality of matrix materials as a mixture, where one matrix material is selected from compounds of the formula (1). Further suitable matrix materials which can be employed in combination with compounds of the formula (1) are, for example, ketones, phosphine oxides, sulfoxides and sulfones, for example in accordance with WO 2004/013080, WO 2004/093207, WO 2006/005627 or the unpublished application DE 102008033943.1, triarylamines, for example NPB, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, azacarbazoles, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with the unpublished application DE 102008036982.9, WO 2007/063754 WO 2008/056746 or WO 2010/015306, or zinc complexes, for example in accordance with EP 652273 or WO 2009/062578.

In a further preferred embodiment of the invention, the compound according to the invention is employed together with two phosphorescent emitters. The emitter which emits at shorter wavelength serves here as co-matrix for the emitter which emits at longer wavelength. Thus, for example, the compound according to the invention can be employed together with a green-phosphorescent and a red-phosphorescent emitter.

For the purposes of this invention, phosphorescence is taken to mean luminescence from an excited state of relatively high spin multiplicity, i.e. a spin state >1, in particular from an excited triplet state. For the purposes of this application, all luminescent transition-metal complexes and luminescent lanthanide complexes, in particular all iridium, platinum and copper complexes, are to be regarded as phosphorescent compounds.

Suitable phosphorescent compounds (=triplet emitters) are, in particular, compounds which emit light, preferably in the visible region, on suitable excitation and in addition contain at least one atom having an atomic number of greater than 20, preferably greater than 38 and less than 84, particularly preferably greater than 56 and less than 80, in particular a metal having this atomic number. The phosphorescence emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

Examples of the emitters described above are revealed by the applications WO 00/70655, WO 01/41512, WO 02/02714, WO 02/15645, EP 1191613, EP 1191612, EP 1191614, WO 05/033244, WO 05/019373, US 2005/0258742 and WO 2009/146770. Also suitable are the complexes in accordance with the unpublished applications DE 102008036247.6, DE 102008048336.2, DE 102008057050.8, DE 102008057051.6, DE 102009007038.9, DE 102009011223.5 and DE 102009013041.1. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

In a further embodiment of the present invention, the compounds of the formula (1) are employed as electron-transport material. Particularly preferred compounds in this case are compounds of the formula (1) which contain an electron-deficient heteroaromatic group, for example triazine or pyrimidine. Electron-deficient heteroaromatic groups are, for example, 5-membered heteroaromatic rings which contain at least 2 heteroatoms, or 6-membered heteroaromatic rings.

If the compounds of the formula (1) are employed as electron-transport material in an organic electroluminescent device, they can also be employed in accordance with the invention in combination with an organic alkali-metal compound. "In combination with an organic alkali-metal compound" here means that the compounds of the formula (1) and the alkali-metal compound are either in the form of a mixture in one layer or are present separately in two successive layers.

In a preferred embodiment of the invention, the compounds of the formula (1) and the organic alkali-metal compound are in the form of a mixture in one layer.

For the purposes of this invention, an organic alkali-metal compound is intended to be taken to mean a compound which contains at least one alkali metal, i.e. lithium, sodium, potassium, rubidium or caesium, and which furthermore contains at least one organic ligand.

Suitable organic alkali-metal compounds are, for example, the compounds disclosed in WO 2007/050301, WO 2007/050334 and EP 1144543. These are incorporated into the present application by way of reference.

Preferred organic alkali-metal compounds are the compounds of the following formula A:

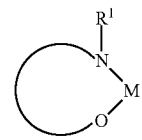

formula A where $R^1$ has the same meaning as described above, the curved line represents two or three atoms and bonds which are necessary to form a 5- or 6-membered ring with M, where these atoms may also be substituted by one or more radicals $R^1$, and M represents an alkali metal selected from lithium, sodium, potassium, rubidium and caesium.

It is possible here for the complex of the formula A to be in monomeric form, as depicted above, or for it to be in the form of aggregates, for example comprising two alkali-metal ions and two ligands, four alkali-metal ions and four ligands, six alkali-metal ions and six ligands or other aggregates.

Preferred compounds of the formula A are the compounds of the following formulae B and C:

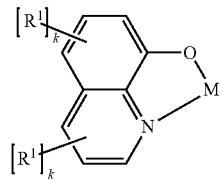

formula B formula C

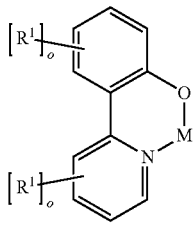

where k is equal to 0, 1, 2 or 3 and o is equal to 0, 1, 2, 3 or 4 and the other symbols used have the meanings mentioned above.

Further preferred organic alkali-metal compounds are the compounds of the following formula D:

formula D

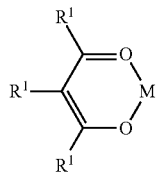

where the symbols used have the same meaning as described above.

The alkali metal is preferably selected from lithium, sodium and potassium, particularly preferably lithium and sodium, very particularly preferably lithium.

Particular preference is given to a compound of the formula B, in particular where M=lithium. Furthermore, the index k is very particularly preferably =0. The compound is thus very particularly preferably unsubstituted lithium quinolinate.

The organic electroluminescent device very particularly preferably comprises a mixture of a compound of the formula (1) containing an electron-deficient heteroaromatic group and an organic alkali-metal compound of the formula B, preferably where M=lithium, in particular unsubstituted lithium quinolinate.

Examples of suitable organic alkali-metal compounds are structures shown in the following table.

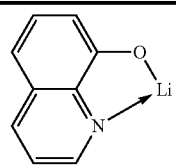

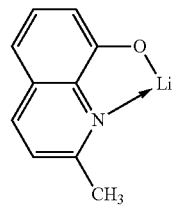

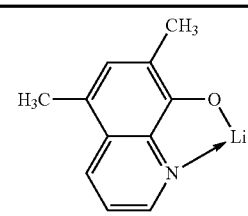

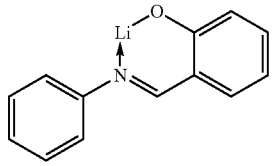

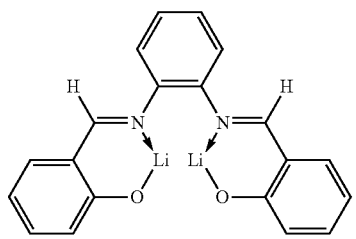

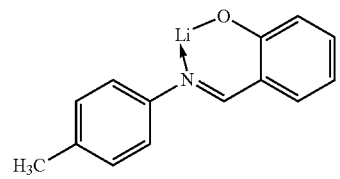

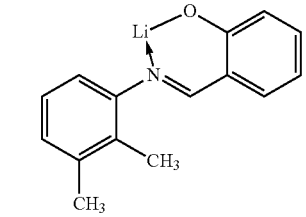

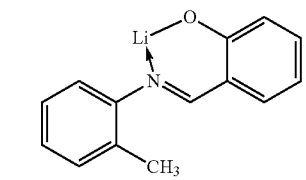

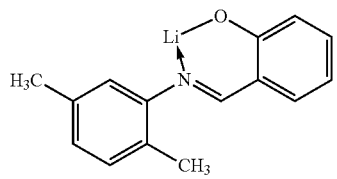

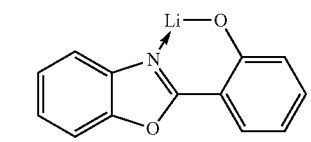

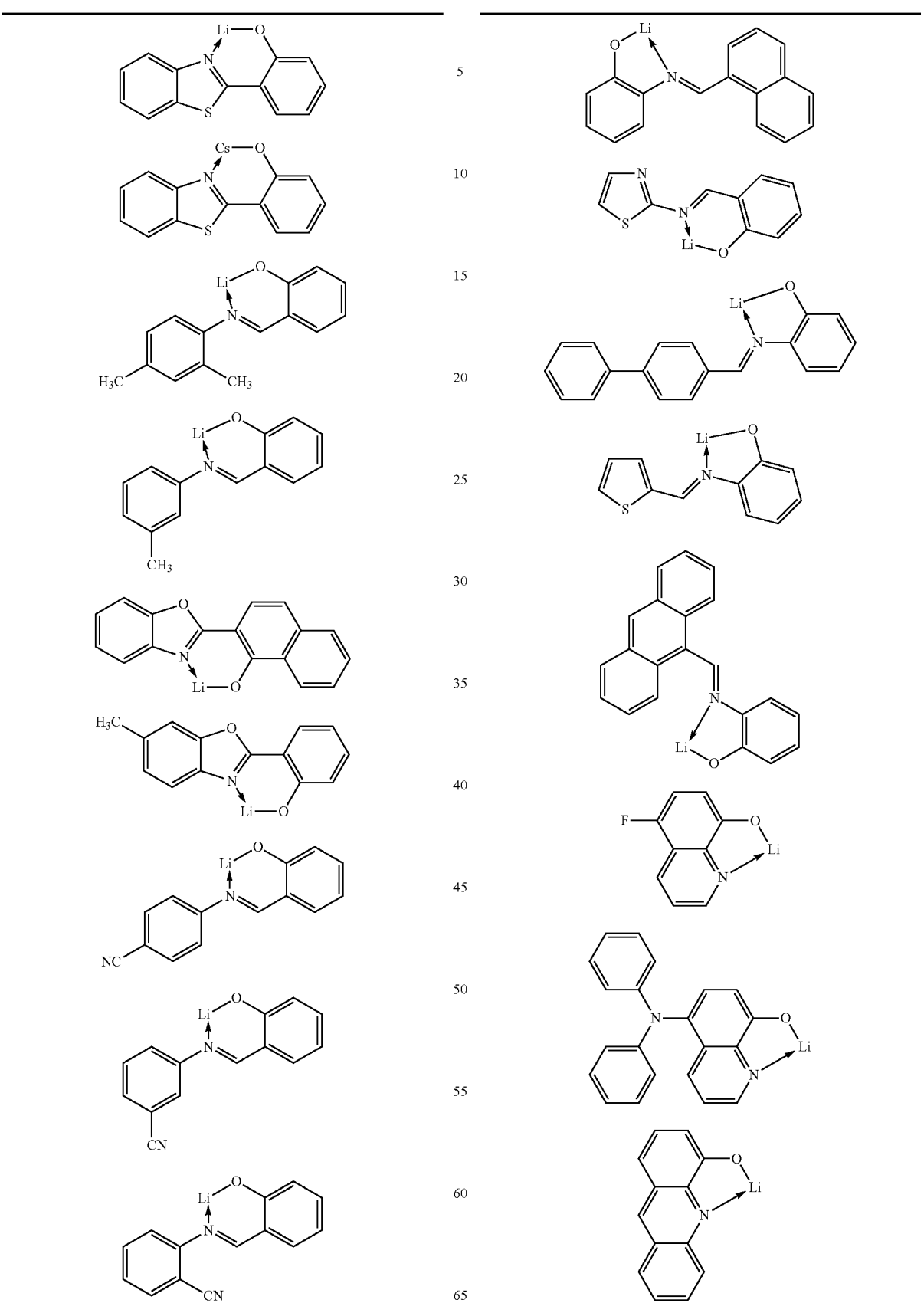

-continued
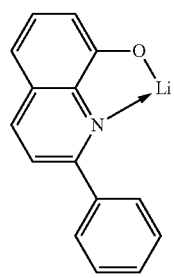
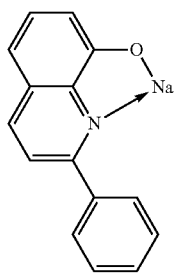
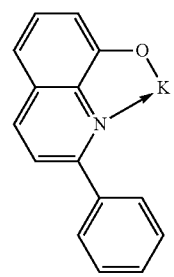
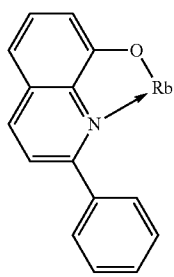
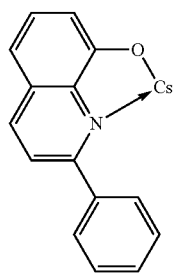
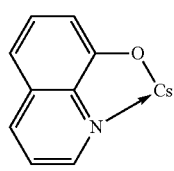
-continued
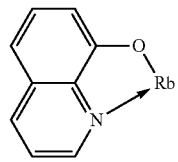
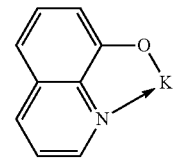
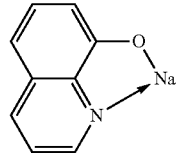
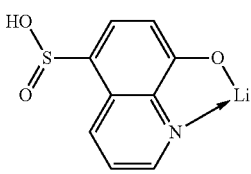
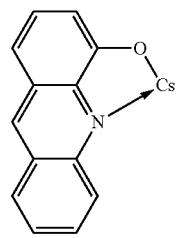
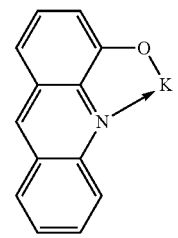
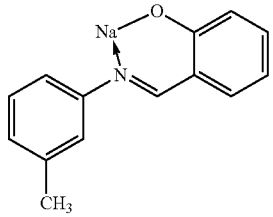
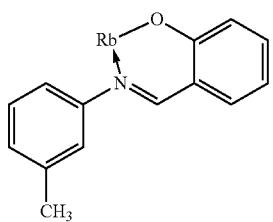

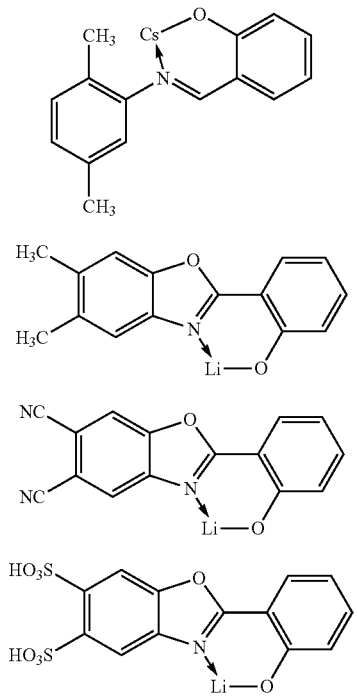

If the compound of the formula (1) and the organic alkali-metal compound are in the form of a mixture, the ratio of the compound of the formula (1) to the organic alkali-metal compound is preferably 20:80 to 80:20, particularly preferably 30:70 to 70:30, very particularly preferably 30:70 to 50:50, in particular 30:70 to 45:55.

If the compound of the formula (1) and the organic alkali-metal compound are in the form of a mixture, the layer thickness of this electron-transport layer is preferably between 3 and 150 nm, particularly preferably between 5 and 100 nm, very particularly preferably between 10 and 60 nm, in particular between 15 and 40 nm.

If the compound of the formula (1) and the organic alkali-metal compound are in the form of two successive layers, the layer thickness of the layer which comprises the compound of the formula (1) is preferably between 3 and 150 nm, particularly preferably between 5 and 100 nm, very particularly preferably between 10 and 60 nm, in particular between 15 and 40 nm. The layer thickness of the layer which comprises the organic alkali-metal compound and which is arranged between the layer comprising the compound of the formula (1) and the cathode is preferably between 0.5 and 20 nm, particularly preferably between 1 and 10 nm, very particularly preferably between 1 and 5 nm, in particular between 1.5 and 3 nm.

It is furthermore particularly preferred for the compound of the formula (1) to be employed as hole-transport material and/or as hole-injection material. This applies, in particular, if at least one R stands for a substituted or unsubstituted arylamine and/or if $X_1$ and/or $X_2$ stands for $N(R^1)$. The compounds are then preferably employed in a hole-transport layer and/or in a hole-injection layer. For the purposes of this invention, a hole-injection layer is a layer which is directly adjacent to the anode. For the purposes of this invention, a hole-transport layer is a layer which is between the hole-injection layer and the emission layer. If the compound of the formula (1) is used as hole-transport or hole-injection material, it may be preferred for it to be doped with electron-acceptor compounds, for example with $F_4$-TCNQ (tetrafluorotetracyanoquinodimethane) or with compounds as described in EP 1476881 or EP 1596445.

If the compound of the formula (1) is employed as hole-transport material in a hole-transport layer, a proportion of 100%, i.e. the use of this compound as pure material, may also be preferred.

Particular preference is also given to the use of the compound of the formula (1) in a hole-transport or -injection layer in combination with a layer which comprises a hexaazatriphenylene derivative, in particular hexa-cyano-hexaazatriphenylene (for example in accordance with EP 1175470). Thus, preference is given, for example, to a combination which looks as follows: anode-hexaazatriphenylene derivative-hole-transport layer, where the hole-transport layer comprises one or more compounds of the formula (1). It is likewise possible in this structure to use a plurality of successive hole-transport layers, where at least one hole-transport layer comprises at least one compound of the formula (1). A further preferred combination looks as follows: anode-hole-transport layer hexaazatriphenylene derivative-hole-transport layer, where at least one of the two hole-transport layers comprises one or more compounds of the formula (1). It is likewise possible in this structure for a plurality of successive hole-transport layers to be used instead of one hole-transport layer, where at least one hole-transport layer comprises at least one compound of the formula (1).

The invention furthermore relates to an electronic device comprising at least one compound of the formula (1) as defined above.

The electronic device is preferably selected from the group consisting of organic electroluminescent devices (OLEDs), organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic photoreceptors, organic laser diodes (O-lasers) or optically pumped lasers.

For the purposes of the invention, it is preferred for the compound of the formula (1) according to the invention to be employed as hole-transport material in a hole-transport layer and/or in a hole-injection layer in the electronic device and for the compounds of the formula (1) in these layers optionally to be doped with electron-acceptor compounds. In particular, the preferences mentioned above also apply here.

For the purposes of the invention, it is furthermore preferred for the compounds of the formula (1) according to the invention to be employed as electron-transport material in an electron-transport layer and/or as hole-blocking material in a hole-blocking layer and/or as matrix material, in particular as triplet matrix material, in an emitting layer in the electronic device. In particular, the preferences mentioned above also apply here.

The invention still furthermore relates to organic electronic devices comprising at least one compound of the formula (1) as defined above, in particular organic electroluminescent devices, comprising anode, cathode and at least one emitting layer, characterised in that at least one organic layer, which may be an emitting layer or another layer, comprises at least one compound of the formula (1) as defined above.

Preference is furthermore given to organic electroluminescent devices, characterised in that a plurality of emitting compounds are used in the same layer or in different layers. These compounds particularly preferably have in total a plurality of emission maxima between 380 nm and 750 nm, resulting overall in white emission, i.e. at least one further emitting compound which is able to fluoresce or phosphoresce and emits yellow, orange or red light is used in addition to the compound of the formula (1). Particular preference is given to three-layer systems, at least one layer of which comprises a compound of the formula (1) and where the layers exhibit blue, green and orange or red emission (for the basic structure see, for example, WO 05/011013). Broadband emitters can likewise be used for white-emitting OLEDs.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). In the case of multilayered structures, further metals which have a relatively high work function, such as, for example, Ag, can also be used in addition to the said metals, in which case combinations of the metals, such as, for example, Mg/Ag, Ca/Ag or Ba/Ag, are generally used. Preference is likewise given to metal alloys, in particular alloys comprising an alkali metal or alkaline-earth metal and silver, particularly preferably an alloy of Mg and Ag. It may also be preferred to introduce a thin interlayer of a material having a high dielectric constant between a metallic cathode and the organic semiconductor. Suitable for this purpose are, for example, alkali-metal or alkaline-earth metal fluorides, but also the corresponding oxides or carbonates (for example LiF, $Li_2O$, CsF, $Cs_2CO_3$, $BaF_2$, MgO, NaF, etc.). Organic metal compounds, such as, for example, lithium quinolinate, can also be used. The layer thickness of this layer is preferably between 0.5 and 5 nm.

The anode preferably comprises materials having a high work function. The anode preferably has a work function of greater than 4.5 eV against vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to enable either the irradiation of the organic material (O-SC) or the coupling-out of light (OLEDs/PLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

Apart from the cathode, anode and emitting layer, the organic electroluminescent device may also comprise further layers. These can be, for example: hole-injection layer, hole-transport layer, electron-blocking layer, exciton-blocking layer, hole-blocking layer, electron-transport layer, electron-injection layer and/or charge-generation layer. However, it should be pointed out at this point that each of these layers does not necessarily have to be present.

Preference is furthermore given to an organic electroluminescent device, characterised in that one or more layers are applied by means of a sublimation process, in which the materials are applied by vapour deposition in vacuum sublimation units at an initial pressure of less than $10^{-5}$ mbar, preferably less than $10^{-6}$ mbar. However, it should be noted that the initial pressure may also be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), inkjet printing or nozzle printing. Soluble compounds of the formula (1) are required for this purpose. High solubility can be achieved through suitable substitution of the compounds.

The organic electroluminescent device may also be produced as a hybrid system by applying one or more layers from solution and applying one or more other layers by vapour deposition. Thus, for example, it is possible to apply an emitting layer comprising a compound of the formula (1) and a phosphorescent dopant from solution and to apply a hole-blocking layer and/or an electron-transport layer on top by vacuum vapour deposition. The emitting layer comprising a compound of the formula (1) and a phosphorescent dopant can likewise be applied by vacuum vapour deposition, and one or more other layers can be applied from solution. Alternatively or in addition, it is also possible, for example, to apply an emitting layer from solution and to apply an electron-transport layer comprising a compound of the formula (1) on top, optionally in combination with an organic alkali-metal compound, by vacuum vapour deposition.

These processes are generally known to the person skilled in the art and can be applied by him without problems to organic electroluminescent devices comprising compounds of the formula (1) or the preferred embodiments mentioned above.

The present invention furthermore relates to mixtures comprising at least one phosphorescent emitter and at least one compound of the formula (1).

The present invention again furthermore relates to the use of compounds of the formula (1) as matrix material for phosphorescent emitters in an organic electroluminescent device.

The device is structured correspondingly (depending on the application), provided with contacts and finally hermetically sealed since the lifetime of devices of this type is drastically shortened in the presence of water and/or air.

The compounds according to the invention have the following surprising advantages over the prior art on use in organic electroluminescent devices:

1. The power efficiency of corresponding devices is increased compared with systems in accordance with the prior art.
2. The stability of corresponding devices is increased compared with systems in accordance with the prior art, which is evident, in particular, from a significantly longer lifetime.
3. The organic electroluminescent devices according to the invention simultaneously have a lower operating voltage.
4. The organic electroluminescent devices according to the invention have very high efficiency. The improved efficiency may be attributable to improved electron injection from the electron-transport layer into the emitting layer.

5. Surprisingly, it has additionally been found on use of the compounds of the formula (1) in vapour-deposition processes that the crystallinity of the compounds according to the invention is improved. Whereas the compounds in accordance with the prior art crystallise on the vapour-deposition source during vapour deposition and thus result in blockage of the source during extended vapour deposition, as occurs in industrial mass production, this phenomenon is not observed at all, or only to a minimal extent, in the case of the compounds according to the invention. The compounds according to the invention are therefore more suitable for use in mass production than are the compounds in accordance with the prior art.

The present application text and also the examples below are directed to the use of the compounds according to the invention in relation to OLEDs and the corresponding displays and illumination elements. In spite of this restriction of the description, it is possible for the person skilled in the art, without further inventive step, also to employ the compounds according to the invention for further uses in other electronic devices, for example for organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic photoreceptors or organic laser diodes (O-lasers), to mention but a few applications.

The present invention likewise relates to the use of the compounds according to the invention in the corresponding devices and to these devices themselves.

The invention will now be explained in greater detail by the following examples, without wishing to restrict it thereby.

EXAMPLES

The following syntheses are carried out under a protective-gas atmosphere in dried solvents, unless indicated otherwise. The compounds of the formula (1) according to the invention can be prepared by synthetic steps which are generally known to the person skilled in the art. The starting point used can be, for example, (9-phenyl-9H-carbazol-3-yl)boronic acid: *Synlett*, 2006, 17, 2841-2845, p-aminobiphenyl: J. Am. Chem. Soc. 2008, 130(32), 10512-10514, 2-bromo-9,9-dimethylfluorene: Synlett 2006, 5, 737-740.

Example 1

Synthesis of diethyl 2,5-bis(9-phenyl-9H-carbazol-3-yl)-terephthalate

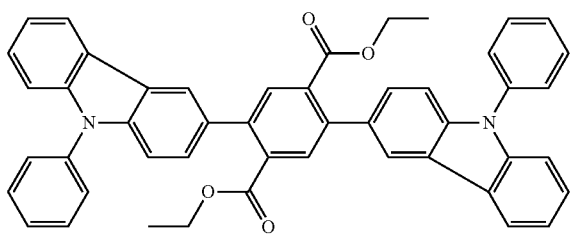 [SMILES: CCOC(=O)c1cc(-c2ccc3c(c2)c2ccccc2n3-c2ccccc2)c(C(=O)OCC)cc1-c1ccc2c(c1)c1ccccc1n2-c1ccccc1]

913 mg (3 mmol) of tri-o-tolylphosphine and then 112 mg (0.5 mmol) of palladium(II) acetate are added to a well-stirred suspension of 18.6 g (49.1 mmol) of diethyl 2,5-dibromoterephthalate, 38 g (102 mmol) of (9-phenyl-9H-carbazol-3-yl)boronic acid, 51 g (221 mmol) of tripotassium phosphate in a mixture of 380 ml of toluene, 190 ml of dioxane and 480 ml of water, and the mixture is subsequently heated under reflux for 16 h. After cooling to room temperature (RT), the precipitated solid is filtered off with suction, washed three times with 50 ml of toluene, three times with 50 ml of ethanol:water (1:1, v:v), and three times with 100 ml of ethanol and recrystallised three times from DMF (about 10 ml/g).

Yield: 22.6 g (32 mmol), 63.0%.

Example 2

Synthesis of 2-[4-(1-hydroxy-1-methylethyl)-2,5-bis(9-phenyl-9H-carbazol-3-yl)phenyl]propan-2-ol

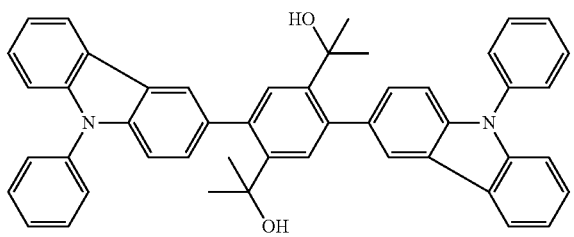 [SMILES: CC(C)(O)c1cc(-c2ccc3c(c2)c2ccccc2n3-c2ccccc2)c(C(C)(C)O)cc1-c1ccc2c(c1)c1ccccc1n2-c1ccccc1]

6.8 g (9.67 mmol) of diethyl 2,5-bis(9-phenyl-9H-carbazol-3-yl)terephthalate are dissolved in 40 ml of THF, 40 ml (42 mmol) of a 2 M solution of methyllithium in diethyl ether are added at −75° C., and the mixture is stirred at −75° C. for 3 h. After warming to RT, the mixture is hydrolysed using NH$_4$Cl solution, extracted with ethyl acetate and dried, and the solvent is removed under reduced pressure. The colourless solid which remains is recrystallised twice from toluene/EtOH, leaving 4.2 g (6.2 mmol), 62%, of the diol in the form of colourless crystals.

Example 3

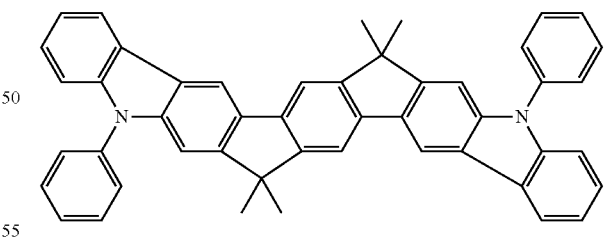

3.38 g (5 mmol) of 2-[4-(1-hydroxy-1-methylethyl)-2,5-bis(9-phenyl-9H-carbazol-3-yl)phenyl]propan-2-ol are dissolved in 30 ml of dichloromethane and cooled to 5° C., and a mixture of 4 g of polyphosphoric acid in 3 ml of methanesulfonic acid is added. After 30 min at 5° C., 50 ml of EtOH are added, and the mixture is heated at the boil for 1 h. The colourless precipitate is filtered off, washed twice with EtOH and heptane and recrystallised once from chlorobenzene, giving the product as a colourless solid (2 g, 4 mmol), 75%, which, according to RP-HPLC, has a purity of >99.9%.

Example 4

Synthesis of 7-bromo-12,12-dimethyl-10-phenyl-10, 12-dihydro-10-azaindeno[2,1-b]fluorene

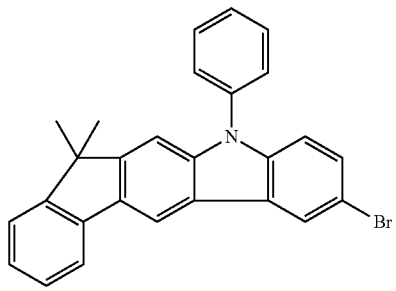 [SMILES: CC1(C)c2ccccc2-c2cc3c4cc(Br)ccc4n(-c4ccccc4)c3cc21]

9.51 g (54 mmol) of N-bromosuccinimide are added over the course of 15 min to a solution of 19.3 g (54 mmol) of 12,12-dimethyl-10-phenyl-10,12-dihydro-10-azaindeno[2,1-b]fluorene in 80 ml of chloroform at RT under a protective-gas atmosphere and with exclusion of light. The mixture is stirred for 6 h, 80 ml of sat. $Na_2CO_3$ soln. are subsequently added, and the organic phase is separated off and dried over $Na_2SO_4$. After removal of the solvent under reduced pressure, the residue is recrystallised, giving the product as a colourless solid in a yield of 20 g (45 mmol), 85%.

Example 5

Synthesis of biphenyl-4-yl-(12,12-dimethyl-10-phenyl-10,12-dihydro-10-azaindeno[2,1-b]fluoren-7-yl) amine

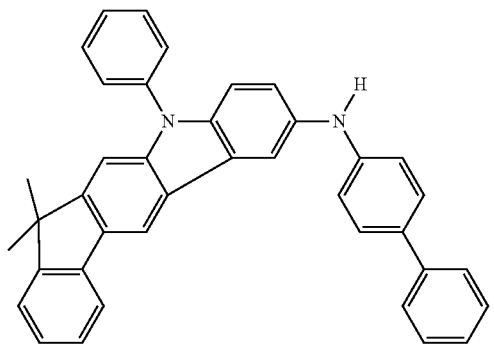 [SMILES: CC1(C)c2ccccc2-c2cc3c4cc(Nc5ccc(-c6ccccc6)cc5)ccc4n(-c4ccccc4)c3cc21]

A degassed solution of 175 g (400 mmol) of 7-bromo-12,12-dimethyl-10-phenyl-10,12-dihydro-10-azaindeno[2,1-b]fluorene and 67.7 g (401.8 mmol) of p-aminobiphenyl in 1000 ml of toluene is saturated with $N_2$ for 1 h. 2.47 g (4.45 mmol) of 1,1-bis(diphenylphosphino)ferrocene and 1 g (4.45 mmol) of $Pd(OAc)_2$ are then added to the solution, and 50.01 g (521.25 mmol) of NaO$^t$Bu in the solid state are subsequently added. The reaction mixture is heated under reflux for 5 h. After cooling to room temperature, 1000 ml of water are added. The organic phase is washed with 4×250 ml of $H_2O$, then dried using $MgSO_4$, and the solvent is removed under reduced pressure. The pure product is obtained by recrystallisation from dioxane as a colourless solid in a yield of 182 g (347 mmol), 87%.

Example 6

Synthesis of biphenyl-4-yl-(9,9-dimethyl-9H-fluoren-2-yl)-(12,12-dimethyl-10-phenyl-10,12-dihydro-10-azaindeno[2,1-b]fluoren-7-yl)amine

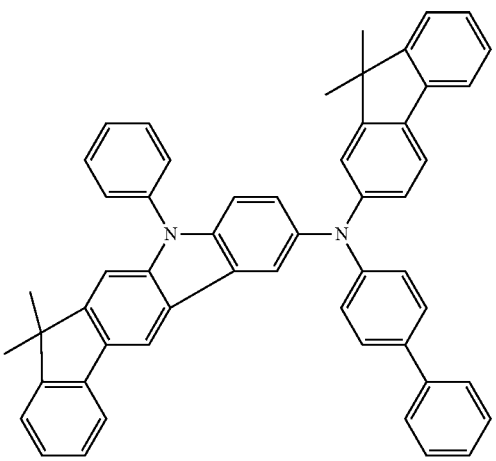 [SMILES: CC1(C)c2ccccc2-c2ccc(N(c3ccc(-c4ccccc4)cc3)c3ccc4c(c3)c3cc5c(cc3n4-c3ccccc3)C(C)(C)c3ccccc3-5)cc21]

190 µl (1 mmol) of di-tert-butylphosphine chloride and then 112 mg (0.5 mmol) of palladium(II) acetate are added to a suspension of 26.3 g (50 mmol) of biphenyl-4-yl-(12,12-dimethyl-10-phenyl-10,12-dihydro-10-azaindeno[2,1-b]fluoren-7-yl)amine, 13.3 g (49 mmol) of 2-bromo-9,9-dimethylfluorene and 7.7 g (80 mmol) of sodium tert-butoxide in 500 ml of toluene, and the mixture is subsequently heated under reflux for 5 h. After cooling to 60° C., 500 ml of water are added, the organic phase is separated off, filtered through silica gel, evaporated virtually to dryness under reduced pressure at 80° C., and 300 ml of ethanol are then added. After cooling, the solid is filtered off with suction and then recrystallised five times from dioxane. Yield: 31.5 g (43 mmol), 88%, purity 99.9% (HPLC).

Example 7

10-(4,6-Diphenyl-1,3,5-triazin-2-yl)-12,12-dimethyl-10,12-dihydro-10-azaindeno[2,1-b]fluorene Step a): Synthesis of bromo-9,9-dimethyl-9H-fluorene

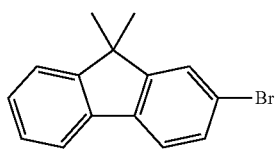 [SMILES: CC1(C)c2ccccc2-c2ccc(Br)cc21]

29.5 g (120.4 mmol) of 2-bromofluorene are dissolved in 220 ml of dried DMSO. 34.7 g of sodium tert-butoxide (361 mmol) are added, and the reaction mixture is heated to a temperature of 65° C. under a protective atmosphere. 22.5 ml of MeI (361 mmol) are subsequently added dropwise at this temperature, and the mixture is stirred for a further 4 h. After this time, 60 ml of a mixture of 120 ml of ammonia (conc.)/water (1/1, v/v) are added. The batch is heated to a temperature of 65° C. and stirred vigorously for a further 1 hour. After cooling to RT, the mixture is partitioned between ethyl acetate and water, and the aqueous phase is extracted twice with water and dried over Na$_2$SO$_4$. The residue which remains is evaporated. The yield is 30.7 g (112 mmol, 93%).

Step b): Synthesis of (9,9-dimethyl-9H-fluoren-2-yl)phenylamine

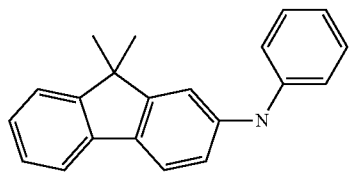 [SMILES: CC1(C)c2ccccc2-c2ccc(Nc3ccccc3)cc21]

50 g of bromo-9,9-dimethyl-9H-fluorene (183 mmol), 20 ml of aniline (220 mmol), 1.5 g of DPPF (2.7 mmol), 0.5 g of palladium(II) acetate and 45 g of sodium tert-butoxide (486 mmol) are heated at the boil in 1.5 l of toluene under a protective atmosphere for 18 h. The mixture is subsequently partitioned between toluene and water, and the organic phase is washed three times with water and dried over Na$_2$SO$_4$ and evaporated in a rotary evaporator. The residue which remains is recrystallised from heptane/ethyl acetate. The yield is 31.2 g (110 mmol, 52%).

Step c): Synthesis of 12,12-dimethyl-10,12-dihydro-10-azaindeno-[2,1-b]fluorene

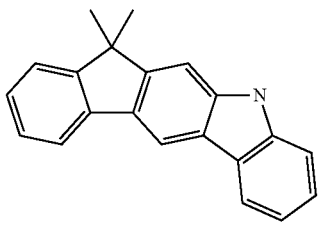 [SMILES: CC1(C)c2ccccc2-c2cc3c(cc21)[nH]c1ccccc13]

35 ml of pivalic acid are added to 10 g of (9,9-dimethyl-9H-fluoren-2-yl)phenylamine (35 mmol), 0.4 g of palladium (II) acetate (1.78 mmol) and 0.5 g of potassium carbonate (3.62 mmol), and the mixture is stirred at 120° C. for 9 h. After this time, 0.4 g of palladium(II) acetate (1.78 mmol) is added, and the mixture is stirred at 120° C. for a further 9 h. 200 ml of dichloromethane and 0.1 M Na$_2$CO$_3$ solution are then added. The mixture is partitioned between water and dichloromethane, the aqueous phase is extracted three times with dichloromethane, and the combined organic phases are dried over Na$_2$SO$_4$ and evaporated in a rotary evaporator. The residue is recrystallised from toluene/heptane. The yield is 5 g (5 mmol, 50%).

Step d): Synthesis of 10-(4,6-diphenyl-1,3,5-triazin-2-yl)-12,12-dimethyl-10,12-dihydro-10-azaindeno[2,1-b]fluorene

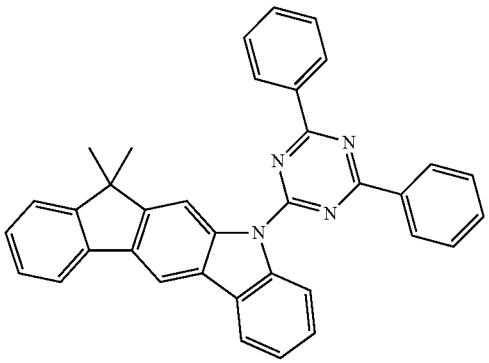 [SMILES: CC1(C)c2ccccc2-c2cc3c4ccccc4n(-c4nc(-c5ccccc5)nc(-c5ccccc5)n4)c3cc21]

8 g (28.2 mmol) of 12,12-dimethyl-10,12-dihydro-10-azaindeno[2,1-b]fluorene are dissolved in 225 ml of dimethylformamide under a protective-gas atmosphere, and 1.5 g of NaH, 60% in mineral oil (37.5 mmol), are added. After 1 h at room temperature, a solution of 2-chloro-4,6-diphenyl-1,3,5-triazine (8.5 g, 31.75 mmol) in 75 ml of dimethylformamide is added dropwise. The reaction mixture is then stirred at room temperature for 12 h. After this time, the reaction mixture is poured onto ice and extracted three times with dichloromethane. The combined organic phases are dried over Na$_2$SO$_4$ and evaporated. The residue is extracted with hot toluene. The yield is 12 g (23 mmol, 83%).

Example 9

Synthesis of 10-(4,6-diphenyl-1,3,5-triazin-2-yl)-12,12-dimethyl-7-phenyl-10,12-dihydro-10-azaindeno[2,1-b]fluorene Step a): Synthesis of biphenyl-4-yl-(9,9-dimethyl-9H-fluoren-2-yl)-amine

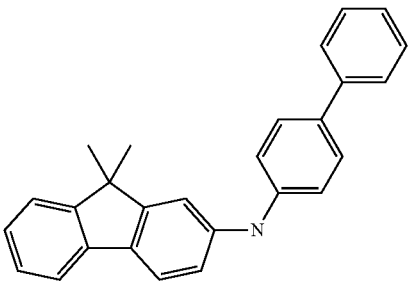 [SMILES: CC1(C)c2ccccc2-c2ccc(Nc3ccc(-c4ccccc4)cc3)cc21]

50 g of bromo-9,9-dimethyl-9H-fluorene (183 mmol), 38 g of p-phenylaniline (220 mmol), 1.5 g of DPPF (2.7 mmol), 0.5 g of palladium(II) acetate and 45 g of sodium tert-butoxide (486 mmol) are heated at the boil in 1.5 l of toluene under a protective-gas atmosphere for 18 h. The mixture is subsequently partitioned between toluene and water, and the organic phase is washed three times with water, dried over Na$_2$SO$_4$ and evaporated in a rotary evaporator. The residue which remains is recrystallised from heptane/ethyl acetate. The yield is 33 g (91.5 mmol, 50%).

Step b): Synthesis of 12,12-dimethyl-7-phenyl-10,12-dihydro-10-azaindeno[2,1-b]fluorene

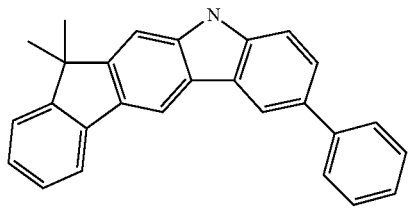 [SMILES: CC1(C)c2ccccc2-c2cc3c(cc21)[nH]c1ccc(-c2ccccc2)cc13]

50 ml of pivalic acid are added to 20 g of biphenyl-4-yl-(9,9-dimethyl-9H-fluoren-2-yl)amine (55.3 mmol), 1.2 g of palladium(II) acetate (5.5 mmol) and 0.8 g of potassium carbonate (5.5 mmol), and the mixture is stirred at 120° C. for 9 h. After this time, 1.2 g of palladium(II) acetate (5.5 mmol) are added, and the mixture is stirred at 120° C. for a further 9 h. 300 ml of dichloromethane and 0.1 M $Na_2CO_3$ solution are then added. The mixture is partitioned between water and dichloromethane, the aqueous phase is extracted three times with dichloromethane, and the combined organic phases are dried over $Na_2SO_4$ and evaporated in a rotary evaporator. The residue is recrystallised from toluene/heptane. The yield is 10 g (27.7 mmol, 50%).

Step c): Synthesis of 10-(4,6-diphenyl-1,3,5-triazin-2-yl)-12,12-dimethyl-7-phenyl-10,12-dihydro-10-azaindeno[2,1-b]fluorene

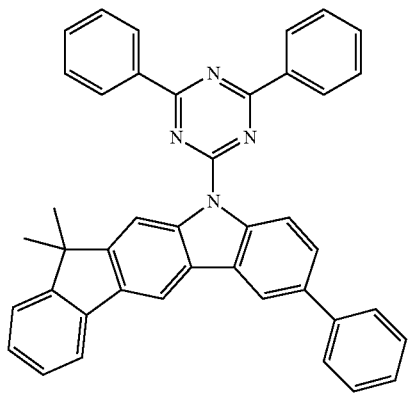 [SMILES: CC1(C)c2ccccc2-c2cc3c4cc(-c5ccccc5)ccc4n(-c4nc(-c5ccccc5)nc(-c5ccccc5)n4)c3cc21]

10 g (27.7 mmol) of 12,12-dimethyl-7-phenyl-10,12-dihydro-10-azaindeno[2,1-b]fluorene are dissolved in 275 ml of dimethylformamide under a protective-gas atmosphere, and 1.45 g of NaH, 60% in mineral oil (36 mmol), are added. After 1 h at room temperature, a solution of 2-chloro-4,6-diphenyl-1,3,5-triazine (8.2 g, 30.5 mmol) in 75 ml of dimethylformamide is added dropwise. The reaction mixture is then stirred at room temperature for 12 h. After this time, the reaction mixture is poured onto ice and extracted three times with dichloromethane. The combined organic phases are dried over $Na_2SO_4$ and evaporated. The residue is extracted with hot toluene. The yield is 14.7 g (24.9 mmol, 90%).

Example 10

Synthesis of 10-(4,6-diphenyl-1,3,5-triazin-2-yl)-12,12-diphenyl-10,12-dihydro-10-azaindeno[2,1-b]fluorene

Step a): Synthesis of (9,9-diphenyl-9H-fluoren-2-yl)phenylamine

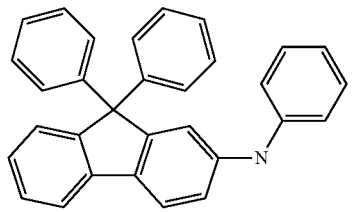 [SMILES: c1ccc(Nc2ccc3c(c2)C(c2ccccc2)(c2ccccc2)c2ccccc2-3)cc1]

40 g of bromo-9,9-diphenyl-9H-fluorene (100.7 mmol), 12 ml of aniline (121 mmol), 0.85 g of DPPF (1.5 mmol), 0.3 g of palladium(II) acetate and 25 g of sodium tert-butoxide (262 mmol) are heated at the boil in 1.5 l of toluene under a protective-gas atmosphere for 18 h. The mixture is subsequently partitioned between toluene and water, and the organic phase is washed three times with water, dried over $Na_2SO_4$ and evaporated in a rotary evaporator. The residue which remains is recrystallised from heptane/ethyl acetate. The yield is 26.8 g (65 mmol, 65%).

Step b): Synthesis of 12,12-diphenyl-10,12-dihydro-10-azaindeno[2,1-b]fluorene

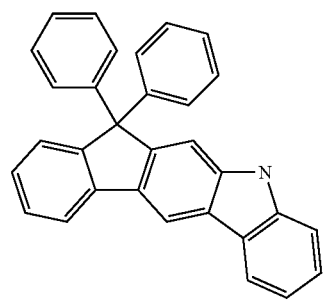 [SMILES: c1ccc(C2(c3ccccc3)c3ccccc3-c3cc4c(cc32)[nH]c2ccccc24)cc1]

50 ml of pivalic acid are added to 15 g of (9,9-diphenyl-9H-fluoren-2-yl)phenylamine (36.6 mmol), 0.9 g of palladium(II) acetate (3.66 mmol) and 0.5 g of potassium carbonate (3.66 mmol), and the mixture is stirred at 120° C. for 9 h. After this time, 0.9 g of palladium(II) acetate (3.66 mmol) is added, and the mixture is stirred at 120° C. for a further 9 h. 200 ml of dichloromethane and 0.1 M $Na_2CO_3$ solution are then added. The mixture is partitioned between water and dichloromethane, the aqueous phase is extracted three times with dichloromethane, and the combined organic phases are dried over $Na_2SO_4$ and evaporated in a rotary evaporator. The residue is recrystallised from toluene/heptane. The yield is 6 g (14.6 mmol, 40%).

Step c): Synthesis of 10-(4,6-diphenyl-1,3,5-triazin-2-yl)-12,12-diphenyl-10,12-dihydro-10-azaindeno[2,1-b]fluorene

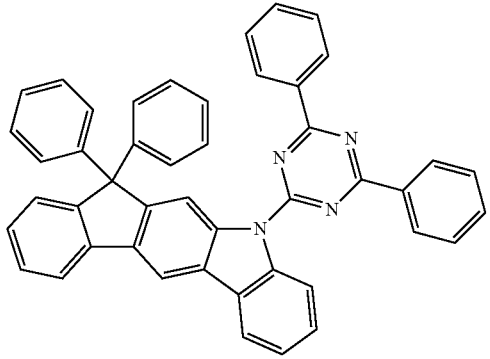 [SMILES: c1ccc(-c2nc(-c3ccccc3)nc(-n3c4ccccc4c4cc5c(cc43)C(c3ccccc3)(c3ccccc3)c3ccccc3-5)n2)cc1]

6 g (14.6 mmol) of 12,12-diphenyl-10,12-dihydro-10-azaindeno[2,1-b]fluorene are dissolved in 100 ml of dimethylformamide under a protective-gas atmosphere, and 0.76 g of NaH, 60% in mineral oil (19 mmol), is added. After 1 hour at room temperature, a solution of 2-chloro-4,6-diphenyl-1,3,5-triazine (4.3 g, 16 mmol) in 50 ml of dimethylformamide is added dropwise. The reaction mixture is then stirred at room temperature for 12 h. After this time, the reaction mixture is poured onto ice and extracted three times with dichloromethane. The combined organic phases are dried over $Na_2SO_4$ and evaporated. The residue is extracted with hot toluene. The yield is 8.1 g (12.7 mmol, 87%).

Example 11

10-(4,6-Diphenylpyrimidin-2-yl)-12,12-dimethyl-10,12-dihydro-10-azaindeno[2,1-b]fluorene Step a): 2-Chloro-4,6-diphenylpyrimidine

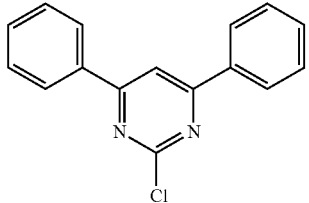 [SMILES: Clc1nc(-c2ccccc2)cc(-c2ccccc2)n1]

75 g (0.41 mmol) of 1,3,5-trichloropyrimidine, 100 g (0.82 mol) of phenylboronic acid and 625 ml of 4 M $NaHCO_3$ solution are suspended in 2.5 l of ethylene glycol dimethyl ether. 2.3 g (10.23 mmol) of $Pd(OAc)_2$ and 10.35 g (34 mmol) of $P(o-Tol)_3$ are added to this suspension, the reaction mixture is heated under reflux for 16 h. The mixture is subsequently partitioned between ethyl acetate and water, the organic phase is washed three times with water and dried over $Na_2SO_4$ and evaporated in a rotary evaporator. The residue which remains is recrystallised from heptane/ toluene. The yield is 43 g (0.15 mol, 38%).

Step b): 10-(4,6-Diphenylpyrimidin-2-yl)-12,12-dimethyl-10,12-dihydro-10-azaindeno[2,1-b]fluorene

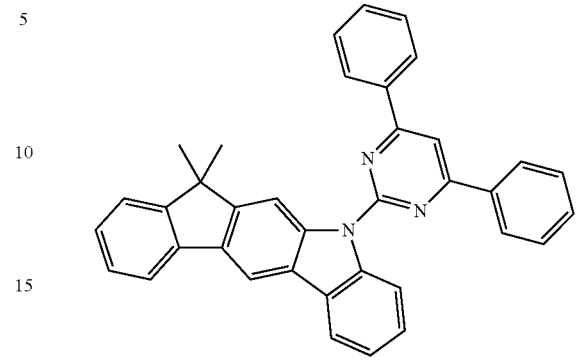

4.2 g of 60% NaH in mineral oil (0.106 mol) are dissolved in 300 ml of dimethylformamide under a protective-gas atmosphere. 30 g of 12,12-dimethyl-10,12-dihydro-10-azaindeno[2,1-b]fluorene (0.106 mol) are dissolved in 250 ml of DMF and added dropwise to the reaction mixture. After 1 h at room temperature, a solution of 2-chloro-4,6-diphenyl-1,3-pyrimidine (34.5 g, 0.122 mol) in 200 ml of THF is added dropwise. The reaction mixture is stirred at room temperature for 12 h, poured onto ice and extracted three times with dichloromethane. The combined organic phases are dried over $Na_2SO_4$ and evaporated. The residue is extracted with hot toluene, recrystallised from toluene/n-heptane and finally sublimed in a high vacuum, the purity is 99.9%. The yield is 23 g (43%).

Example 12

10-(4,6-Diphenyl-1,3,5-triazin-2-yl)-10,12-dihydro-10-azaindeno[2,1-b]-12,12-spirofluorene Step a): 10,12-Dihydro-10-azaindeno[2,1-b]-12,12-spirofluorene

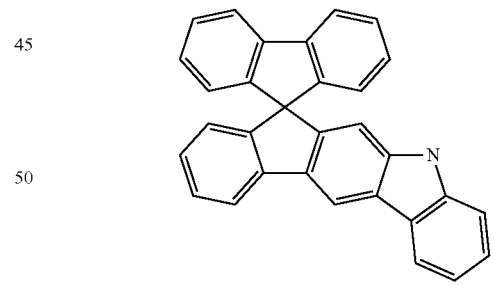

50 g of 2-bromo-9,9'-spirobifluorene (126 mmol), 14 ml of aniline (154 mmol), 1.1 g (2 mmol) of 1,1-bis(diphenylphosphino)ferrocene-palladium(II) dichloride complex with DCM, 0.4 g of palladium(II) acetate (1.78 mmol) and 31 g of sodium tert-butoxide (323 mmol) are heated at the boil in 1 l of toluene under a protective-gas atmosphere for 18 h. The mixture is subsequently partitioned between toluene and water, the organic phase is washed three times with water, dried over $Na_2SO_4$ and evaporated in a rotary evaporator. The residue of 2-aminophenyl-9,9'-spirobifluorene which remains is recrystallised from heptane/ethyl acetate. The yield is 50 g (114 mmol, 93%).

300 ml of pivalic acid are added to 30 g of 2-aminophenyl-9,9'-spirobifluorene (73.6 mmol), 1.6 g of palladium(II) acetate (7.4 mmol) and 1.6 g of potassium carbonate (11.4 mmol), and the mixture is stirred at 120° C. under air for 9 h. After this time, 1.6 g of palladium(II) acetate (7.4 mmol) are added, and the mixture is stirred at 120° C. for a further 9 h. 200 ml of dichloromethane and 0.1 M Na$_2$CO$_3$ solution are then added. The mixture is partitioned between water and dichloromethane, the aqueous phase is extracted three times with dichloromethane, the combined organic phases are dried over Na$_2$SO$_4$ and evaporated in a rotary evaporator. The residue is recrystallised from toluene/heptane. The yield is 11.9 g (29.4 mmol, 40%).

Step b): 10-(4,6-Diphenyl-1,3,5-triazin-2yl)-10,12-dihydro-10-azaindeno[2,1-b]-12,12-spirofluorene

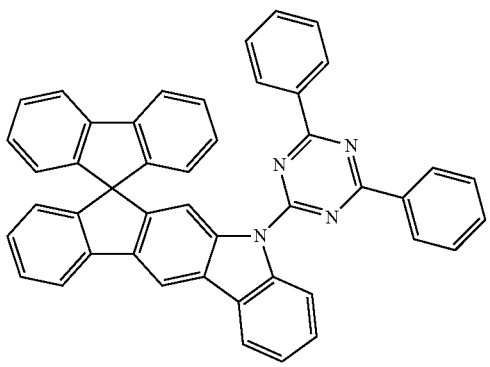 [SMILES: c1ccc(-c2nc(-c3ccccc3)nc(-n3c4ccccc4c4cc5c(cc43)C3(c4ccccc4-c4ccccc43)c3ccccc3-5)n2)cc1]

10 g (25 mmol) of 10,12-dihydro-10-azaindeno[2,1-b]-12,12-spirofluorene are dissolved in 100 ml of dimethylformamide under a protective-gas atmosphere, and 1.38 g of 60% NaH in mineral oil (34.5 mmol) are added. After 1 h at room temperature, a solution of 2-chloro-4,6-diphenyl-1,3,5-triazine (7.3 g, 27 mmol) in 100 ml of THF is added dropwise. The reaction mixture is stirred at room temperature for 12 h. After this time, the reaction mixture is poured onto ice and extracted three times with dichloromethane. The combined organic phases are dried over Na$_2$SO$_4$ and evaporated. The residue is extracted with hot toluene, recrystallised from toluene and finally sublimed in a high vacuum, the purity is 99.9%. The yield is 12 g (76%).

Example 13

10-(4,6-Bisbiphenyl-3-yl-1,3,5-triazin-2-yl)-12,12-dimethyl-10,12-dihydro-10-azaindeno[2,1-b]fluorene Step a): 2,4-Bisbiphenyl-3-yl-6-chloro-1,3,5-triazine

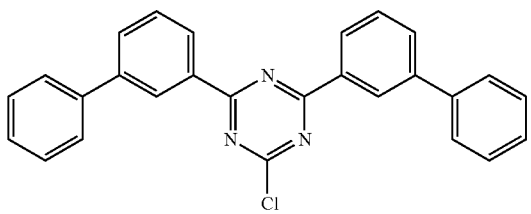 [SMILES: Clc1nc(-c2cccc(-c3ccccc3)c2)nc(-c2cccc(-c3ccccc3)c2)n1]

5.2 g of magnesium (0.215 mol) are initially introduced in a 500 ml four-necked flask, and a solution of 50 g of bromobiphenyl (214 mmol) in 200 ml of THF is slowly added dropwise. The reaction mixture is heated at the boil for 1.5 h and subsequently cooled to room temperature. In a second flask, cyanogen chloride (17.2 g, 93 mmol) in 150 ml of THF is initially introduced and cooled to 0° C. The cooled Grignard reagent is then added dropwise at this temperature, and the mixture is stirred at RT for 12 h. After this time, 150 ml of HCl are added to the reaction mixture, and the aqueous phase is extracted three times with dichloromethane. The combined organic phases are washed with water, dried over Na$_2$SO$_4$ and evaporated. The residue is recrystallised from EtOH. The yield is 32.8 g (78 mmol, 84%).

Step b): 10-(4,6-Bisbiphenyl-3-yl-1,3,5-triazin-2-yl)-12,12-dimethyl-10,12-dihydro-10-azaindeno[2,1-b]fluorene

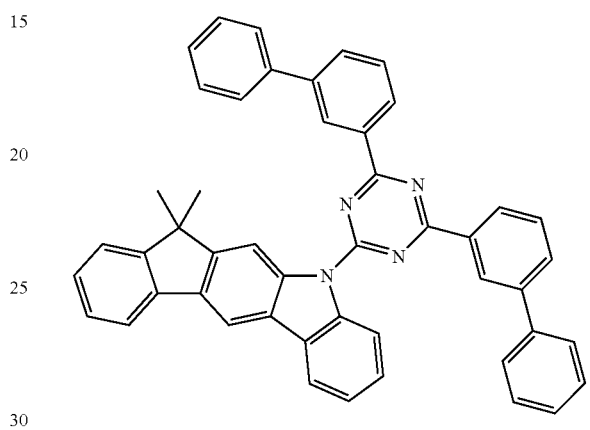

18.6 g (64.6 mmol) of 12,12-dimethyl-10,12-dihydro-10-azaindeno[2,1-b]fluorene are dissolved in 400 ml of dimethylformamide under a protective-gas atmosphere, and 3.1 g of 60% NaH in mineral oil (77.5 mmol) are added. After 1 h at room temperature, a solution of 2,4-bisbiphenyl-3-yl-6-chloro-1,3,5-triazine (32.6 g, 64.6 mmol) in 100 ml of THF is added dropwise. The reaction mixture is stirred at room temperature for 12 h. After this time, the reaction mixture is poured onto ice and extracted three times with dichloromethane. The combined organic phases are dried over Na$_2$SO$_4$ and evaporated. The residue is extracted with hot toluene, recrystallised from toluene and finally sublimed in a high vacuum, the purity is 99.9%. Yield: 41.5 g (61 mmol), 80% of theory.

Example 14

10-(4,6-Diphenyl-1,3,5-triazin-2-yl)-12,12,12',12'-tetramethyl-10,12-dihydro-12'H-[7,10']-bi[10-azaindeno[2,1-b]fluorenyl]

Step a): 7-Bromo-12,12-dimethyl-10,12-dihydro-10-azaindeno[2,1-b]fluorene

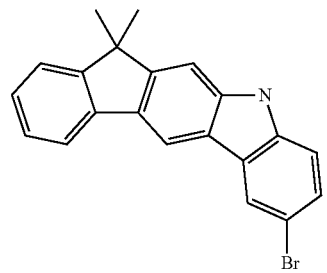 [SMILES: CC1(C)c2ccccc2-c2cc3c(cc21)[nH]c1ccc(Br)cc13]

66.5 g (234.6 mmol) of 12,12-dimethyl-10,12-dihydro-10-azaindeno[2,1-b]-fluorene are initially introduced in 1000 ml of acetonitrile. A solution of 41.7 g (234.6 mmol) of NBS in 500 ml of CH₃CN is subsequently added dropwise at −15° C. with exclusion of light, allowed to come to RT and stirred at this temperature for a further 4 h. 150 ml of water are subsequently added to the mixture, which is then extracted with CH₂Cl₂. The organic phase is dried over MgSO₄, and the solvents are removed in vacuo. The product is washed by stirring with hot hexane and filtered off with suction. Yield: 47.5 g (131 mmol), 55.9% of theory, purity according to ¹H-NMR approx. 97%.

Step b): 7-Bromo-10-(4,6-diphenyl-1,3,5-triazin-2-yl)-12,12-dimethyl-10,12-dihydro-10-azaindeno[2,1-b]fluorene

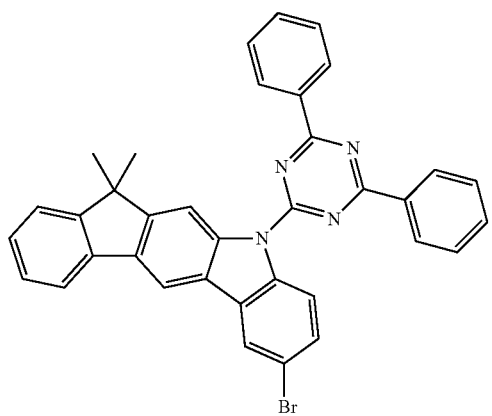 [SMILES: CC1(C)c2ccccc2-c2cc3c4cc(Br)ccc4n(-c4nc(-c5ccccc5)nc(-c5ccccc5)n4)c3cc21]

25.5 g (70.4 mmol) of 7-bromo-12,12-dimethyl-10,12-dihydro-10-azaindeno[2,1-b]fluorene are dissolved in 400 ml of dimethylformamide under a protective-gas atmosphere, and 3.1 g of 60% NaH in mineral oil (78 mol) are added. After 1 h at room temperature, a solution of 2-chloro-4,6-diphenyl-1,3,5-triazine (22.6 g, 84.5 mmol) in 100 ml of THF is added dropwise. The reaction mixture is stirred at room temperature for 12 h. After this time, the reaction mixture is poured onto ice and extracted three times with dichloromethane. The combined organic phases are dried over Na₂SO₄ and evaporated. The residue is recrystallised from toluene. Yield: 40 g (67 mmol), 95% of theory.

Step c): 10-(4,6-Diphenyl-1,3,5-triazin-2-yl)-12,12,12',12'-tetramethyl-10,12-dihydro-12'H-[7,10']bi[10-azaindeno[2,1-b]fluorenyl]

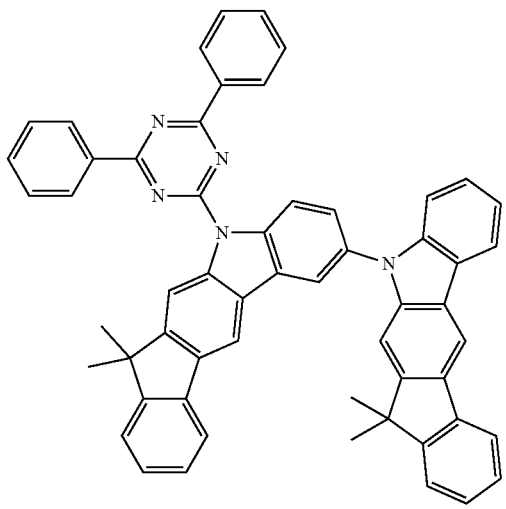 [SMILES: CC1(C)c2ccccc2-c2cc3c4ccccc4n(-c4ccc5c(c4)c4cc6c(cc4n5-c4nc(-c5ccccc5)nc(-c5ccccc5)n4)C(C)(C)c4ccccc4-6)c3cc21]

25 g (42.12 mmol) of 7-bromo-10-(4,6-diphenyl-1,3,5-triazin-2-yl)-12,12-dimethyl-10,12-dihydro-10-azaindeno[2,1-b]fluorene, 13.3 g (47 mmol) of 12,12-dimethyl-10,12-dihydro-10-azaindeno[2,1-b]fluorene and 29.2 g of Rb₂CO₃ are suspended in 250 ml of p-xylene. 0.95 g (4.2 mmol) of Pd(OAc)₂ and 12.6 ml of a 1 M tri-tert-butylphosphine solution are added to this suspension. The reaction mixture is heated under reflux for 16 h. After cooling, the organic phase is separated off, washed three times with 200 ml of water and subsequently evaporated to dryness. The residue is extracted with hot toluene, recrystallised from toluene and finally sublimed in a high vacuum, the purity is 99.9%. Yield: 25 g (31 mmol), 75% of theory.

Example 15

7-(3,6-Diphenylcarbazol-9-yl)-10-(4,6-diphenyl-1,3,5-triazin-2-yl)-12,12-dimethyl-10,12-dihydro-10-azaindeno[2,1-b]fluorene

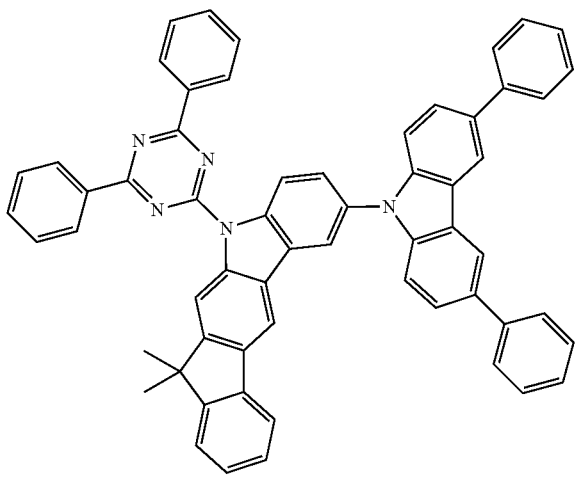 [SMILES: CC1(C)c2ccccc2-c2cc3c4cc(-n5c6ccc(-c7ccccc7)cc6c6cc(-c7ccccc7)ccc65)ccc4n(-c4nc(-c5ccccc5)nc(-c5ccccc5)n4)c3cc21]

20 g (33.7 mmol) of 7-bromo-10-(4,6-diphenyl-1,3,5-triazin-2-yl)-12,12-dimethyl-10,12-dihydro-10-azaindeno[2,1-b]fluorene, 12 g (37.6 mmol) of 3,6-diphenyl-9H-carbazole and 23.34 g of Rb₂CO₃ are suspended in 200 ml of p-xylene. 0.76 g (3.4 mmol) of Pd(OAc)₂ and 10.1 ml of a 1 M tri-tert-butylphosphine solution are added to this suspension. The reaction mixture is heated under reflux for 16 h. After cooling, the organic phase is separated off, washed three times with 200 ml of water and subsequently evaporated to dryness. The residue is extracted with hot toluene, recrystallised from toluene and finally sublimed in a high vacuum, the purity is 99.9%. Yield: 20 g (24 mmol), 72% of theory.

Example 16

7-(4,6-Diphenylpyrimidin-2-yl)-10-(4,6-diphenyl-1,3,5-triazin-2-yl)-12,12-dimethyl-10,12-dihydro-10-azaindeno[2,1-b]fluorene

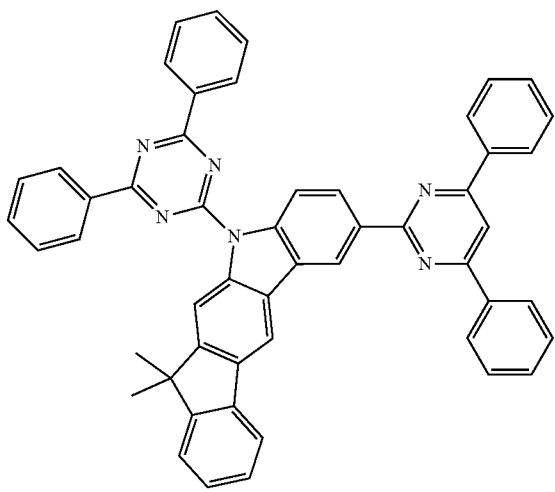 [SMILES: CC1(C)c2ccccc2-c2cc3c4cc(-c5nc(-c6ccccc6)cc(-c6ccccc6)n5)ccc4n(-c4nc(-c5ccccc5)nc(-c5ccccc5)n4)c3cc21]

40 g (67.4 mmol) of 7-bromo-10-(4,6-diphenyl-1,3,5-triazin-2-yl)-12,12-dimethyl-10,12-dihydro-10-azaindeno[2,1-b]fluorene, 17.1 g (67.4 mmol) of bis(pinacolato)diborane and 19.8 g of potassium acetate are suspended in 700 ml of dioxane. 2.8 g (3.4 mmol) of 1,1-bis(diphenylphosphino)ferrocenepalladium(II) dichloride complex with DOM are added to this suspension. The reaction mixture is heated under reflux for 16 h. After cooling, the organic phase is separated off, washed three times with 200 ml of water and subsequently evaporated to dryness. The residue is recrystallised from toluene. 30 g (46.8 mmol) of 10-(4,6-diphenyl-1,3,5-triazin-2-yl)-12,12-dimethyl-7-(4,4,5,5-tetramethyl-1,3,2-dioxaborolan-2-yl)-10,12-dihydro-10-azaindeno[2,1-b]fluorene, 11.2 g (42.15 mmol) of 2-chloro-4,6-diphenylpyrimidine and 9.9 g of sodium carbonate are suspended in 300 ml of dioxane, 300 ml of toluene and 100 ml of water, 2.7 g (2.3 mmol) of Pd(PPh$_3$)$_4$ are added to this suspension. The reaction mixture is heated under reflux for 5 h. After cooling, the precipitated solid is filtered off with suction, washed with water and ethanol and dried. The residue is extracted with hot toluene, recrystallised from toluene and finally sublimed in a high vacuum, the purity is 99.9%. Yield: 18 g, 59% of theory.

Example 17

10-(2,6-Diphenylpyridin-4-yl)-12,12-dimethyl-10,12-dihydro-10-azaindeno[2,1-b]fluorene Step a): 2,6-Dibromo-4-nitropyridine

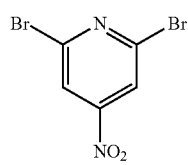

A solution of 50 g (211 mmol) of 2,6-dibromopyridine in 250 ml of trifluoroacetic acid is warmed to 90° C., 53 ml (515 mmol) of a 33% hydrogen peroxide solution are added dropwise. After 3 h, the reaction mixture is cooled and poured into 200 ml of ice-water. The filtrate is extracted three times with DCM, the combined organic phases are washed four times with a 0.5 M K$_2$CO$_3$ solution, dried over Na$_2$SO$_4$ and evaporated. The residue of 2,6-dibromopyridine 1-oxide (41.2 g) is employed further.

A solution of 20 g (78 mmol) of 2,6-dibromopyridine 1-oxide in 70 ml of H$_2$SO$_4$ is warmed to 40° C. Nitrating acid (70 ml of H$_2$SO$_4$ and 34 ml of fuming HNO$_3$) is added to the solution at this temperature. The reaction mixture is heated at 90° C. for 3 h. After cooling, the mixture is poured into 800 ml of ice-water. The precipitated solid is filtered off and washed with water. After drying, the 2,6-dibromo-4-nitropyridine 1-oxide (17.9 g) is suspended in 200 ml of chloroform, 6 ml of phosphorus tribromide (64 mmol) are added at room temperature, the mixture is stirred for 1 h and then heated under reflux for 2 days. After cooling, the solution is poured into 500 ml of ice-water and neutralised using solid NaHCO$_3$. The aqueous phase is separated off and extracted a number of times with CHCl$_3$, the combined organic phases are washed with a sodium thiosulfate solution and then with water, dried and evaporated. The residue is recrystallised from EtOH. Yield: 41.7 g (148 mmol), 70% of theory.

Step b): 10-(2,6-Diphenylpyridin-4-yl)-12,12-dimethyl-10,12-dihydro-10-azaindeno[2,1-b]fluorene

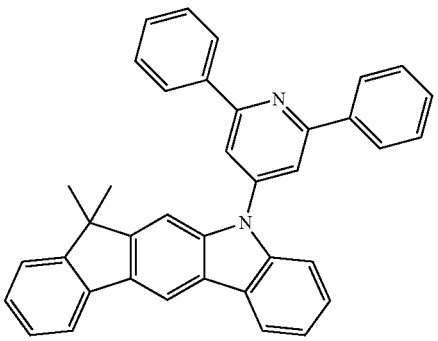 [SMILES: CC1(C)c2ccccc2-c2cc3c4ccccc4n(-c4cc(-c5ccccc5)nc(-c5ccccc5)c4)c3cc21]

20 g (70.7 mmol) of 12,12-dimethyl-10,12-dihydro-10-azaindeno[2,1-b]fluorene are dissolved in 50 ml of dimethylformamide under a protective-gas atmosphere, and 3.1 g of 60% NaH in mineral oil (78 mol) are added. After 1 h at room temperature, a solution of 2,6-dibromo-4-nitropyridine (20 g, 70.7 mmol) in 20 ml of DMF is added dropwise. The reaction mixture is stirred at room temperature for 12 h. After this time, the reaction mixture is poured onto ice and extracted three times with dichloromethane. The combined organic phases are dried over Na$_2$SO$_4$ and evaporated. The residue is recrystallised from toluene. Yield: 29.6 g (80 mmol), 95% of theory.

25 g (48 mmol) of 10-(2,6-dibromopyridin-4-yl)-12,12-dimethyl-10,12-dihydro-10-azaindeno[2,1-b]fluorene and 12.9 g of phenylboronic acid (106 mmol) are suspended in 300 ml of ethylene glycol dimethyl ether. 75 ml of a 2 M Na$_2$CO$_3$ solution are added to the reaction mixture. 2.8 g (2.4 mmol) of Pd(PPh$_3$)$_4$ are added to this suspension. The reaction mixture is heated under reflux for 12 h. After cooling, the precipitated solid is filtered off with suction and washed with water and ethanol and dried. The residue is extracted with hot toluene and recrystallised from toluene and finally sublimed in a high vacuum, the purity is 99.9%. Yield: 15 g, 60% of theory.

Example 18

12,12-Dimethyl-10-[2,2';6',2"]terpyridin-4'-yl-10,12-dihydro-10-azaindeno[2,1-b]fluorene

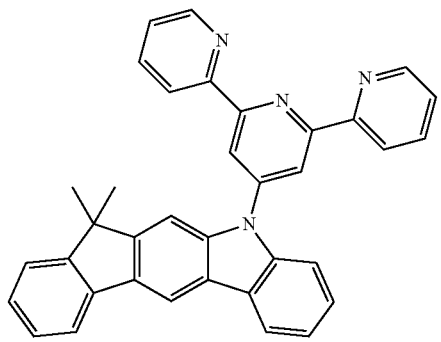 [SMILES: CC1(C)c2ccccc2-c2cc3c4ccccc4n(-c4cc(-c5ccccn5)nc(-c5ccccn5)c4)c3cc21]

15 g (29 mmol) of 10-(2,6-dibromopyridin-4-yl)-12,12-dimethyl-10,12-dihydro-10-azaindeno[2,1-b]fluorene and 0.7 g (0.6 mmol) of Pd(PPh$_3$)$_4$ are suspended in 50 ml of THF. 69 ml (34.7 mmol) of a pyridylzinc bromide/THF solution (0.5 M, 34.7 mmol) are slowly added dropwise to this suspension. The reaction mixture is stirred at room temperature for 12 h. The mixture is poured into an EDTA/Na$_2$CO$_3$ solution and extracted three times with Et$_2$O. The residue is suspended in 50 ml of THF together with 0.7 g (0.6 mmol) of Pd(PPh$_3$)$_4$, and 69 ml (34.7 mmol) of a pyridylzinc bromide/THF solution (0.5 M, 34.7 mmol) are slowly added dropwise. The reaction mixture is stirred at room temperature for 12 h. The mixture is poured into an EDTA/Na$_2$CO$_3$ solution and extracted three times with Et$_2$O. The residue is extracted with hot toluene, recrystallised from toluene and finally sublimed in a high vacuum, the purity is 99.9%. Yield: 7.5 g, 50% of theory.

Example 19

10-(3,5-Dipyrimidin-2-ylphenyl)-12,12-dimethyl-10,12-dihydro-10-azaindeno[2,1-b]fluorene Step a): 5-Iodo-1,3-bis(2'-pyrimidyl)benzene

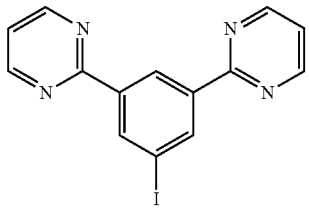 [SMILES: Ic1cc(-c2ncccn2)cc(-c2ncccn2)c1]

40 g (127 mmol) of tribromobenzene are dissolved in 800 ml of Et$_2$O, and the solution is cooled to −78° C. 88 ml (140 mmol) of n-BuLi (1.6 M solution in hexane) are added dropwise to this solution. After stirring at this temperature for 3 h, 19.4 ml of chlorotrimethylsilane are added dropwise, and the reaction mixture is stirred at room temperature for a further 1 h. The mixture is subsequently partitioned between heptane and water, the aqueous phase is extracted three times with heptane, dried over Na$_2$SO$_4$ and evaporated in a rotary evaporator. The residue which remains (31.4 g, 80% yield) is distilled and reacted further.

25 g (79.4 mmol) of 5-trimethylsilyl-1,3-bromobenzene, 37.7 g (159 mmol) of bis(pinacolato)diborane and 4 g of potassium acetate (350 mmol) are suspended in 700 ml of DMSO. 11.9 g (16 mmol) of 1,1-bis(diphenylphosphino)ferrocenepalladium(II) dichloride complex with DCM are added to this suspension. The reaction mixture is heated under reflux for 16 h. After cooling, the organic phase is separated off, washed three times with 200 ml of water and subsequently evaporated to dryness. The residue is recrystallised from toluene. Yield: 24 g, 75% of theory.

20 g (49.7 mmol) of dipinacolyl 5-trimethylsilylbenzene-1,3-bis(boronate) and 15.8 g of 2-bromopyrimidine (99.5 mmol) are suspended in 600 ml of ethylene glycol dimethyl ether. 100 ml of a 2 M Na$_2$CO$_3$ solution are added to the reaction mixture. 1.5 g (4.9 mmol) of Pd(PPh$_3$)$_4$ are added to this suspension. The reaction mixture is heated under reflux for 12 h. After cooling, the precipitated solid is filtered off with suction, washed with water and ethanol and dried. The residue is recrystallised from toluene. Yield: 9.5 g, 60% of theory.

15 g (49 mmol) of 5-trimethylsilyl-1,3-(2'-pyrimidyl)benzene are dissolved in 200 ml of dichloromethane under a protective-gas atmosphere, and 8.1 g of ICl (50 mol) are added at 0° C. The reaction mixture is then stirred at this temperature for 12 h. After this time, the reaction mixture is poured into water and extracted three times with dichloromethane. The combined organic phases are washed with a sodium dithionite solution, dried over Na$_2$SO$_4$ and evaporated. The residue is recrystallised from heptane/ethyl acetate. Yield: 12.6 g (80 mmol), 60% of theory.

Step b): 10-(3,5-Dipyrimidin-2-ylphenyl)-12,12-dimethyl-10,12-dihydro-10-azaindeno[2,1-b]fluorene

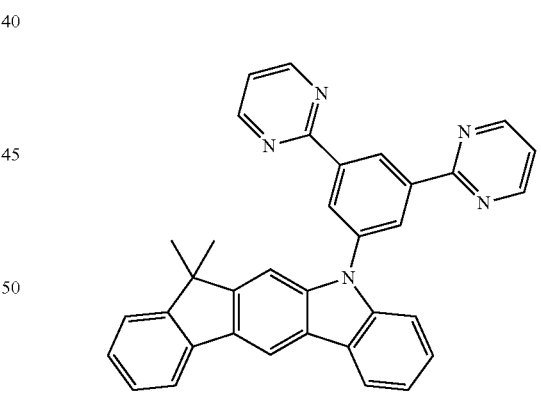

10.9 g (38.32 mmol) of 12,12-dimethyl-10,12-dihydro-10-azaindeno[2,1-b]fluorene, 12 g (38.32 mmol) of 5-iodo-1,3-(2'-pyrimidyl)benzene and 16 g of K$_2$CO$_3$ are suspended in 300 ml of p-xylene. 0.86 g (3.84 mmol) of Pd(OAc)$_2$ and 7.6 ml of a 1 M tri-tert-butylphosphine solution are added to this suspension. The reaction mixture is heated under reflux for 16 h. After cooling, the organic phase is separated off, washed three times with 200 ml of water and subsequently evaporated to dryness. The residue is extracted with hot toluene, recrystallised from toluene and finally sublimed in a high vacuum, the purity is 99.9%. Yield: 13.7 g (26.6 mmol), 80% of theory.

Example 20

10-(4,6-Bis[1,1';3',1"]terphenyl-5'-yl-1,3,5-triazin-2-yl)-12,12-dimethyl-10,12-dihydro-10-azaindeno[2,1-b]fluorene Step a): 2-Chloro-4,6-bis[1,1';3',1"]terphenyl-5'-yl-1,3,5-triazine

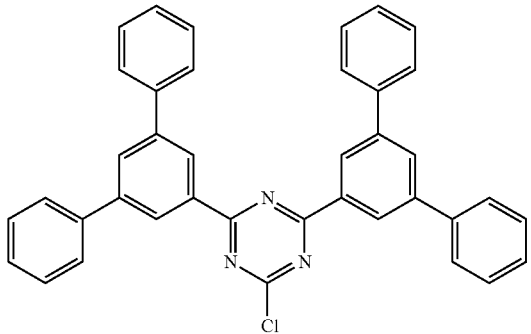 [SMILES: Clc1nc(-c2cc(-c3ccccc3)cc(-c3ccccc3)c2)nc(-c2cc(-c3ccccc3)cc(-c3ccccc3)c2)n1]

3.93 g of magnesium (162 mmol) are initially introduced into a 500 ml four-necked flask, and a solution of 50 g of 5'-bromo-[1,1';3',1"]terphenyl (162 mmol) in 150 ml of THF is slowly added dropwise. The reaction mixture is heated at the boil for 1.5 h and subsequently cooled to room temperature. In a second flask, cyanogen chloride (13 g, 70 mmol) is initially introduced in 150 ml of THF and cooled to 0° C. The cooled Grignard reagent is added dropwise at this temperature, and the mixture is stirred at RT for 12 h. After this time, 150 ml of HCl are added to the reaction mixture, and the aqueous phase is extracted three times with dichloromethane. The combined organic phases are washed with water, dried over $Na_2SO_4$ and evaporated. The residue is recrystallised from EtOH. The yield is 27.8 g (49 mol, 70%).

Step b): 10-(4,6-Bis[1,1';3',1"]terphenyl-5'-yl-1,3,5-triazin-2-yl)-12,12-dimethyl-10,12-dihydro-10-azaindeno[2,1-b]fluorene

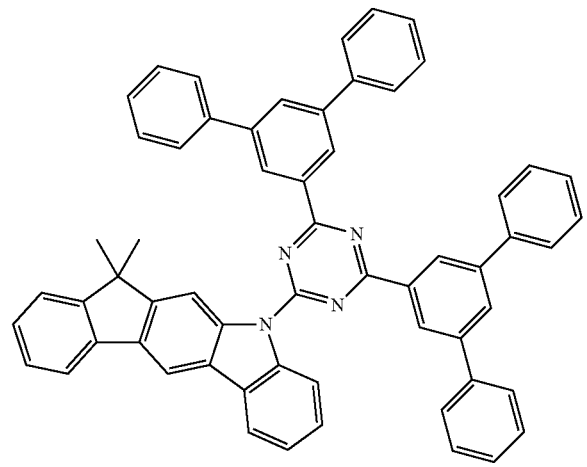 [SMILES: CC1(C)c2ccccc2-c2cc3c4ccccc4n(-c4nc(-c5cc(-c6ccccc6)cc(-c6ccccc6)c5)nc(-c5cc(-c6ccccc6)cc(-c6ccccc6)c5)n4)c3cc21]

11.3 g (40 mmol) of 12,12-dimethyl-10,12-dihydro-10-azaindeno[2,1-b]-fluorene are dissolved in 285 ml of dimethylformamide under a protective-gas atmosphere, and 1.9 g of 60% NaH in mineral oil (19 mmol) are added. After 1 h at room temperature, a solution of 2-chloro-4,6-bis[1,1'; 3',1"]terphenyl-5'-yl-1,3,5-triazine (25.1 g, 44 mmol) in 315 ml of dimethylformamide is added dropwise. The reaction mixture is stirred at room temperature for 12 h. After this time, the reaction mixture is poured onto ice and extracted three times with dichloromethane. The combined organic phases are dried over $Na_2SO_4$ and evaporated. The residue is extracted with hot toluene. The yield is 23 g (28 mmol, 70%).

Example 21

2,6-Bis(12,12-dimethyl-10-10,12-dihydro-10-azaindeno[2,1-b]fluorene)-4-phenyl-1,3,5-triazine

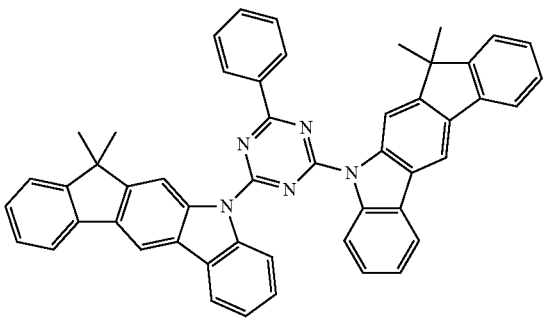 [SMILES: CC1(C)c2ccccc2-c2cc3c4ccccc4n(-c4nc(-c5ccccc5)nc(-n5c6ccccc6c6cc7c(cc65)C(C)(C)c5ccccc5-7)n4)c3cc21]

30 g (107.5 mmol) of 12,12-dimethyl-10,12-dihydro-10-azaindeno[2,1-b]-fluorene are dissolved in 185 ml of dimethylformamide under a protective-gas atmosphere, and 1.29 g of 60% NaH in mineral oil (129 mmol) are added. After 1 h at room temperature, a solution of 2,4-dichloro-6-phenyl-5'-yl-1,3,5-triazine (12.3 g, 54 mmol) in 125 ml of dimethylformamide is added dropwise. The reaction mixture is stirred at room temperature for 12 h. After this time, the reaction mixture is poured onto ice and extracted three times with dichloromethane. The combined organic phases are dried over $Na_2SO_4$ and evaporated. The residue is extracted with hot toluene, recrystallised and finally sublimed in a high vacuum, the purity is 99.9%. The yield is 23 g (32 mmol, 60%).

Example 22

12,12-Dimethyl-10-[1,1';3',1"]terphenyl-5'-yl-10,12-dihydro-10-azaindeno[2,1-b]fluorene

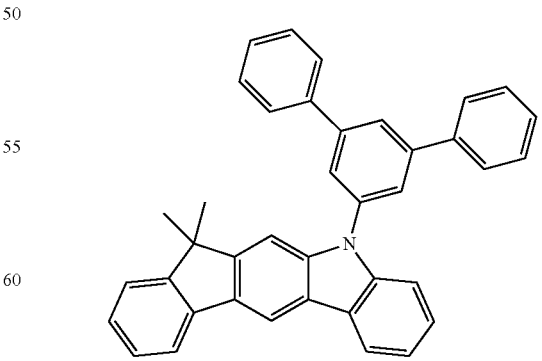

30 g (106 mmol) of 12,12-dimethyl-10,12-dihydro-10-azaindeno[2,1-b]fluorene, 13.3 g (114 mmol) of 5'-bromo-[1,1';3',1"]terphenyl and 30.5 g of NaOtBu are suspended in 1.5 l of p-xylene, 0.5 g (2.11 mmol) of Pd(OAc)$_2$ and 1.6 ml of a 1 M tri-tert-butylphosphine solution are added to this suspension. The reaction mixture is heated under reflux for 16 h. After cooling, the organic phase is separated off, washed three times with 200 ml of water and subsequently evaporated to dryness. The residue is extracted with hot toluene, recrystallised from toluene and finally sublimed in a high vacuum, the purity is 99.9%. The yield is 15.8 g (31 mmol, 72%).

Example 23

10-[3-(4,6-Diphenyl-1,3,5-triazin-2-yl)phenyl]-12,12-dimethyl-10,12-dihydro-10-azaindeno[2,1-b]fluorene

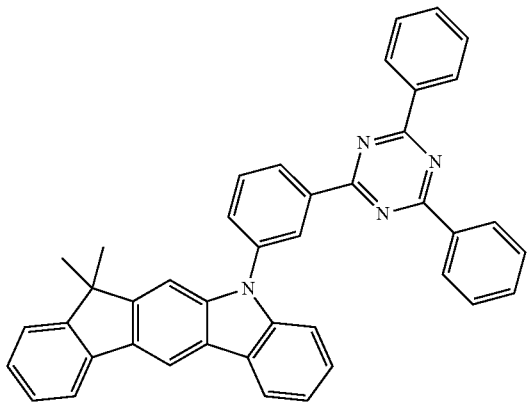 [SMILES: CC1(C)c2ccccc2-c2cc3c4ccccc4n(-c4cccc(-c5nc(-c6ccccc6)nc(-c6ccccc6)n5)c4)c3cc21]

19 g (67 mmol) of 12,12-dimethyl-10,12-dihydro-10-azaindeno[2,1-b]fluorene, 28.6 g (74 mmol) of 3-bromo-(4,6-diphenyl-1,3,5-triazin-2-yl)benzene and 19.3 g of NaOtBu are suspended in 1 l of p-xylene. 0.3 g (1.34 mmol) of Pd(OAc)$_2$ and 1.0 ml of a 1 M tri-tert-butylphosphine solution are added to this suspension. The reaction mixture is heated under reflux for 16 h. After cooling, dichloromethane is added, the organic phase is separated off, washed three times with 200 ml of water and subsequently evaporated to dryness. The residue is extracted with hot toluene and recrystallised from toluene and finally sublimed in a high vacuum, the purity is 99.9%. The yield is 25 g (43 mmol, 60%). 3-Bromo-(4,6-diphenyl-1,3,5-triazin-2-yl)benzene is prepared analogously to *J. Mater. Chem.* 2007, 17, 3714-3719.

Example 24

12-(4,6-Diphenyl-1,3,5-triazin-2-yl)-10,10-dimethyl-10,12-dihydro-3,12-diazaindeno[2,1-b]fluorene Step a): 10,10-Dimethyl-10,12-dihydro-3,12-diazaindeno[2,1-b]fluorene

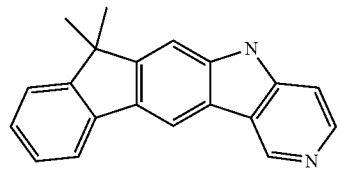 [SMILES: CC1(C)c2ccccc2-c2cc3c(cc21)[nH]c1ccncc13]

50 g of bromo-9,9-dimethyl-9H-fluorene (183 mmol), 19 ml of 4-aminopyridine (201 mmol), 1.5 g of DPPF (2.7 mmol), 0.5 g of palladium(II) acetate and 45 g of sodium tert-butoxide (486 mmol) are heated at the boil in 1.5 l of toluene under a protective-gas atmosphere for 18 h. The mixture is subsequently partitioned between toluene and water, the organic phase is washed three times with water, dried over Na$_2$SO$_4$ and evaporated in a rotary evaporator. The residue is recrystallised from heptane/ethyl acetate. The yield is 34 g (118 mmol, 65%).

70 ml of pivalic acid are added to 30 g of (9,9-dimethyl-9H-fluoren-2-yl)pyridin-4-ylamine (105 mmol), 2.35 g of palladium(II) acetate (10.5 mmol) and 1.44 g of potassium carbonate (10.5 mmol), and the mixture is stirred at 120° C. for 9 h. After this time, 2.35 g of palladium(II) acetate (10.5 mmol) are added, and the mixture is stirred at 120° C. for a further 9 h. 200 ml of dichloromethane and 0.1 M Na$_2$CO$_3$ solution are then added. The mixture is partitioned between water and dichloromethane, the aqueous phase is extracted three times with dichloromethane, the combined organic phases are dried over Na$_2$SO$_4$ and evaporated in a rotary evaporator. The residue is recrystallised from toluene/heptane. The yield is 13.4 g (13.5 mmol, 45%).

Step b): 12-(4,6-Diphenyl-1,3,5-triazin-2-yl)-10,10-dimethyl-10,12-dihydro-3,12-diazaindeno[2,1-b]fluorene

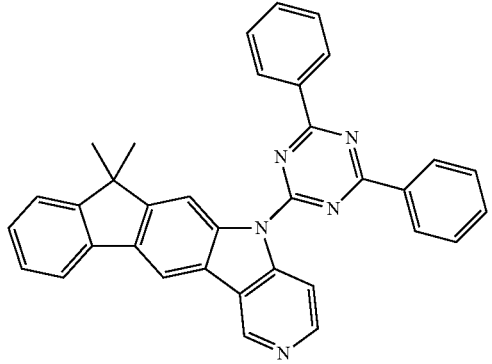 [SMILES: CC1(C)c2ccccc2-c2cc3c4cnccc4n(-c4nc(-c5ccccc5)nc(-c5ccccc5)n4)c3cc21]

10 g (35.17 mmol) of 10,10-dimethyl-10,12-dihydro-3,12-diazaindeno[2,1-b]fluorene are dissolved in 150 ml of dimethylformamide under a protective-gas atmosphere, and 1.7 g of 60% NaH in mineral oil (42.2 mmol) are added. After 1 h at room temperature, a solution of 2-chloro-4,6-diphenyl-1,3,5-triazine (10.7 g, 38.68 mmol) in 100 ml of THF is added dropwise. The reaction mixture is stirred at room temperature for 12 h. After this time, the reaction mixture is poured onto ice and extracted three times with dichloromethane. The combined organic phases are dried over Na$_2$SO$_4$ and evaporated. The residue is extracted with hot toluene, recrystallised from toluene and finally sublimed in a high vacuum, the purity is 99.9%. The yield is 14.4 g (80%).

Example 25

7-(4,6-Diphenyl-1,3,5-triazin-2-yl)-7H-12-oxa-7-azaindeno[1,2-a]fluorene

Step a): 7H-12-Oxa-7-azaindeno[1,2-a]fluorene

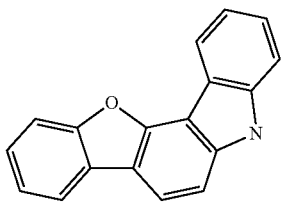 [SMILES: c1ccc2c(c1)[nH]c1ccc3c4ccccc4oc3c12]

30 g (120.5 mmol) of 1-iodo-2-nitrobenzene, 30.6 g (144.6 mmol) of dibenzofuran-4-boronic acid and 76.7 g of $K_3PO_4$ are suspended in 400 ml of toluene, 400 ml of dioxane and 400 ml of water. 1.35 g (6 mmol) of $Pd(OAc)_2$ and 5.5 g of o-tolylphosphine are added to this suspension, and the reaction mixture is heated under reflux for 16 h. After cooling, the organic phase is separated off, filtered through silica gel, washed three times with 200 ml of water and subsequently evaporated to dryness. The yield is 22.7 g (78 mmol), corresponding to 65% of theory.

20 g of 4-(2-nitrophenyl)dibenzofuran (69 mmol) and 48 ml of triethyl phosphite (276 mmol) are heated at the boil in 800 ml of 1,2-dichlorobenzene under a protective-gas atmosphere for 48 h. After this time, the remaining triethyl phosphite and the 1,2-dichlorobenzene are removed by distillation. The residue which remains is recrystallised from heptane/ethyl acetate. The yield is 13 g (45 mmol, 65%).

Step b): 7-(4,6-Diphenyl-1,3,5-triazin-2-yl)-7H-12-oxa-7-azaindeno[1,2-a]fluorene

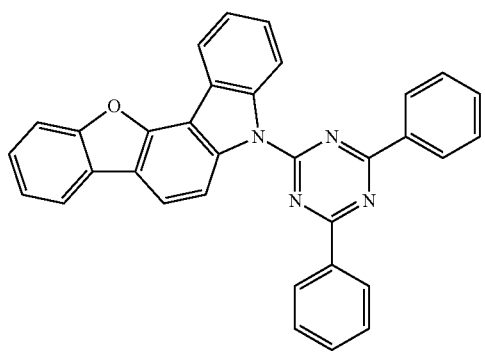 [SMILES: c1ccc(-c2nc(-c3ccccc3)nc(-n3c4ccccc4c4c5oc6ccccc6c5ccc43)n2)cc1]

13 g (50.5 mmol) of 7H-12-oxa-7-azaindeno[1,2-a]fluorene are dissolved in 150 ml of dimethylformamide under a protective-gas atmosphere, and 2.4 g of 60% NaH in mineral oil (60.6 mmol) are added. After 1 h at room temperature, a solution of 2-chloro-4,6-diphenyl-1,3,5-triazine (14.9 g, 55.6 mmol) in 100 ml of THF is added dropwise. The reaction mixture is stirred at room temperature for 12 h. After this time, the reaction mixture is poured onto ice and extracted three times with dichloromethane. The combined organic phases are dried over $Na_2SO_4$ and evaporated. The residue is extracted with hot toluene, recrystallised from toluene and finally sublimed in a high vacuum, the purity is 99.9%. The yield is 18.4 g (75%).

Example 26

10-Biphenyl-4-yl-7-(4,6-diphenyl-1,3,5-triazin-2-yl)-12,12-dimethyl-10,12-dihydro-10-azaindeno[2,1-b]fluorene Step a): 10-Biphenyl-4-yl-12,12-dimethyl-10,12-dihydro-10-azaindeno[2,1-b]fluorene

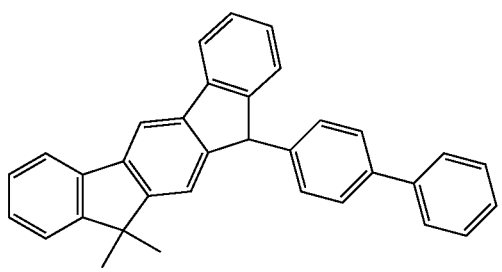 [SMILES: CC1(C)c2ccccc2-c2cc3c(cc21)C(c1ccc(-c2ccccc2)cc1)c1ccccc1-3]

20 g (70.58 mmol) of 12,12-dimethyl-10,12-dihydro-10-azaindeno[2,1-b]-fluorene and 24.6 g (105.87 mmol) of 4-bromobiphenyl are dissolved in toluene and degassed by introduction of a protective gas. 4.94 ml (4.94 mmol, 1 M solution in toluene) of tri-tert-butylphosphine, 633.8 mg (2.82 mmol) of $Pd(OAc)_2$ and 10.2 g (105.87 mmol) of NaOtBu are subsequently added. The solids are degassed in advance, the reaction mixture is subsequently degassed, and then stirred under reflux for 3 h. The warm reaction solution is filtered through Alox B (activity grade 1), washed with water, dried and evaporated. Crystallisation from toluene gives 15.6 g (50.8%) of the product as a white solid having a purity of 99.7%.

Step b): 10-Biphenyl-4-yl-7-bromo-12,12-dimethyl-10,12-dihydro-10-azaindeno[2,1-b]fluorene

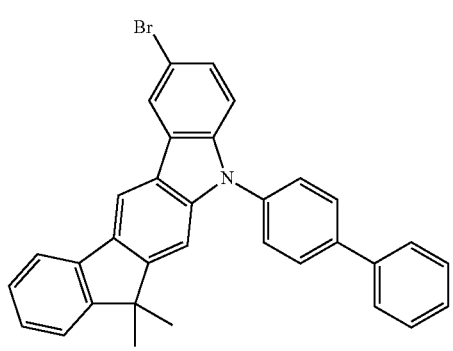 [SMILES: CC1(C)c2ccccc2-c2cc3c4cc(Br)ccc4n(-c4ccc(-c5ccccc5)cc4)c3cc21]

17.5 g (40.18 mmol) of 10-biphenyl-4-yl-12,12-dimethyl-10,12-dihydro-10-azaindeno[2,1-b]fluorene are suspended in 450 ml of acetonitrile, and 7.15 g (40.18 mmol) of N-bromosuccinimide are added in portions at −20° C. at such a rate that the reaction temperature does not rise above −20° C. The mixture is stirred for a further 18 h, during which the temperature is allowed to come to RT. The reaction mixture is subsequently evaporated in a rotary evaporator, dissolved in dichloromethane and washed with water. The residue is dried, evaporated and subsequently recrystallised from toluene to a purity of 99.3%, giving 10.9 g (53%) of the product as a white solid.

Step c): 10-Biphenyl-4-yl-7-boronic acid-12,12-dimethyl-10,12-dihydro-10-azaindeno[2,1-b]fluorene

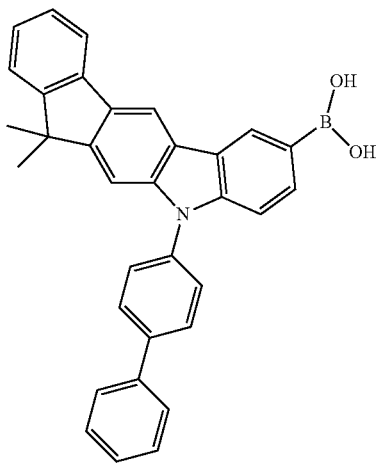 [SMILES: CC1(C)c2ccccc2-c2cc3c4cc(B(O)O)ccc4n(-c4ccc(-c5ccccc5)cc4)c3cc21]

26 g (51 mmol) of 10-biphenyl-4-yl-7-bromo-12,12-dimethyl-10,12-dihydro-10-azaindeno[2,1-b]fluorene are dissolved in 600 ml of dry THF, and the solution is cooled to −78° C. 26.2 ml (65.7 mmol/2.5 M in hexane) of n-BuLi are added over the course of approx. 5 min. at this temperature, and the mixture is subsequently stirred at −78° C. for a further 2.5 h. 7.3 ml (65.7 mmol) of trimethyl borate are added as rapidly as possible at this temperature, and the reaction mixture is slowly allowed to come to RT (about 18 h). The reaction solution is washed with water, and the precipitated solid and the organic phase are dried azeotropically with toluene. The crude product is washed by stirring with toluene/methylene chloride at about 40° C. and filtered off with suction, giving 20.1 g (83%) of the product as a white solid.

Step d): 10-Biphenyl-4-yl-7-(4,6-diphenyl-1,3,5-triazin-2-yl-12,12-dimethyl-10,12-dihydro-10-azaindeno[2,1-b]fluorene

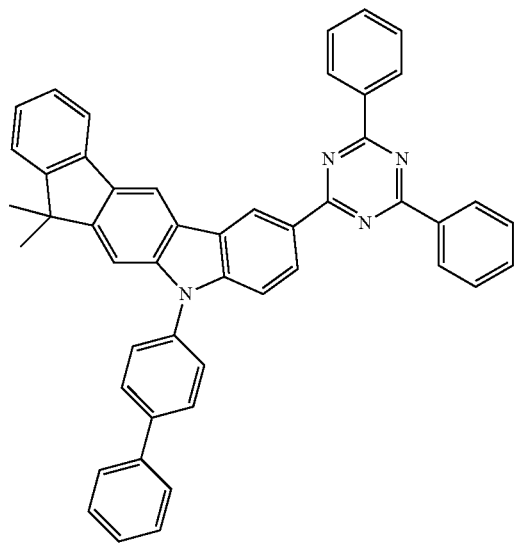 [SMILES: CC1(C)c2ccccc2-c2cc3c4cc(-c5nc(-c6ccccc6)nc(-c6ccccc6)n5)ccc4n(-c4ccc(-c5ccccc5)cc4)c3cc21]

20.1 g (42 mmol) of boronic acid and 15.5 g (52.4 mmol) of 2-chloro-4,6-diphenyl-1,3,5-triazine are dissolved in a degassed mixture of 135 ml of water, 315 ml of dioxane and 315 ml of toluene, and 5.33 g (50.31 mmol) of Na$_2$CO$_3$ are added. The reaction mixture is degassed, and 0.96 g (0.84 mmol) of Pd tetrakis(triphenylphosphine) is added. The mixture is refluxed for 18 h. After cooling, dichloromethane is added (heterogeneous mixture), the water phase is separated off, and the organic phase is evaporated azeotropically with toluene. The reaction product is crystallised from DMSO, giving, after sublimation, 5.3 g (18%) of the product having a purity of 99.98% as a white solid.

Example 27

Biphenyl-4-yl-(9,9-dimethyl-9H-fluoren-2-yl)-[4-(12,12-dimethyl-10-phenyl-10,12-dihydro-10-azaindeno[2,1-b]fluoren-7-yl)phenyl]amine

Step a): tert-Butyl 7-bromo-12,12-dimethyl-12H-10-azaindeno[2,1-b]fluorene-10-carboxylate

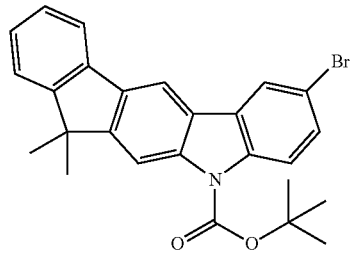 [SMILES: CC(C)(C)OC(=O)n1c2ccc(Br)cc2c2cc3c(cc21)C(C)(C)c1ccccc1-3]

35.5 g (98 mmol) of azaindenofluorene bromide are dissolved in 500 ml of dry THF, and 30.0 g (137.5 mmol) of BOC anhydride and 1.21 g (9.82 mmol) of DMAP are added. The mixture is heated under reflux for 1 h, water is added when the reaction is complete, and the mixture is extracted with dichloromethane, dried and evaporated. The yellow oil is washed by stirring with heptane, giving 35 g (77%) of the product as a white solid.

Step b): tert-Butyl 7-{4-[biphenyl-4-yl-(9,9-dimethyl-9H-fluoren-2-yl)amino]phenyl}-12,12-dimethyl-12H-10-azaindeno[2,1-b]fluorene-10-carboxylate

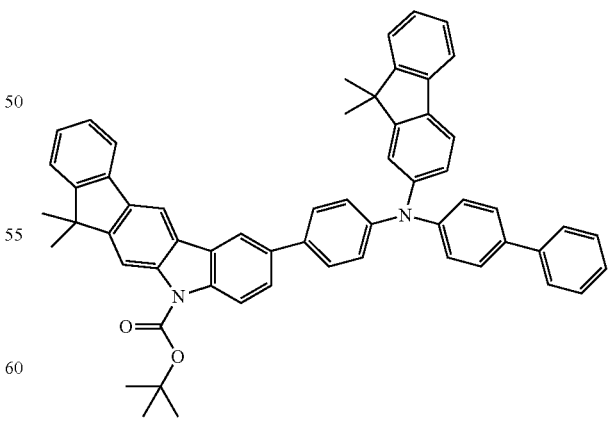

20.0 g (43.3 mmol) of tert-butyl 7-bromo-12,12-dimethyl-12H-10-azaindeno[2,1-b]fluorene-10-carboxylate and 22.9 g (47.6 mmol) of the corresponding triarylboronic acid are dissolved in 80 ml of toluene and degassed. 281 ml of a degassed 2 M K$_2$CO$_3$ and 2.5 g (2.2 mmol) of Pd(OAc)$_2$ are added. The reaction mixture is subsequently stirred at 80° C. under a protective-gas atmosphere. for 48 h Further toluene is added to the cooled solution, which is washed a number of times with water, dried and evaporated. The product is purified by column chromatography on silica gel with toluene/heptane (1:2), giving 27 g (67.5%) of the product as a white solid.

Step c): Biphenyl-4-yl-[4-(12,12-dimethyl-10,12-dihydro-10-azaindeno[2,1-b]fluoren-7-yl)phenyl]-(9,9-dimethyl-9H-fluoren-2-yl)amine

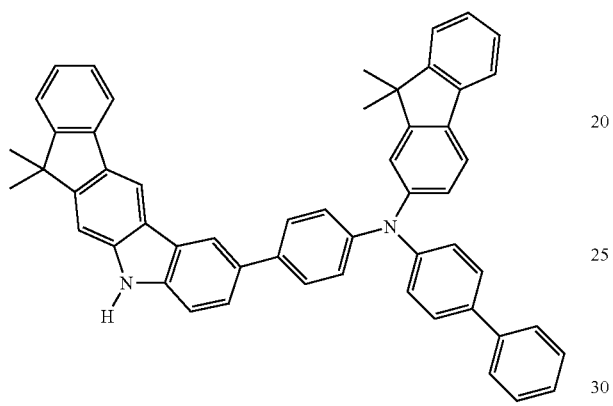

20.0 g (24.4 mmol) of tert-butyl 7-{4-[biphenyl-4-yl-(9,9-dimethyl-9H-fluoren-2-yl)amino]phenyl}-12,12-dimethyl-12H-10-azaindeno[2,1-b]fluorene-10-carboxylate are dissolved in 250 ml of dichloromethane and 2.65 ml (24.4 mmol) of anisole, and 5.4 ml of trifluoroacetic acid are subsequently added. The mixture is stirred at 40° C. for 3 h and, when the reaction is complete, neutralised by means of ice-water and 20% NaOH solution. The mixture is extracted with dichloromethane, dried and purified by recrystallisation from toluene/heptane, giving 15.7 g (89%) of the product as a white solid.

Step d): Biphenyl-4-yl-(9,9-dimethyl-9H-fluoren-2-yl)-[4-(12,12-dimethyl-10-phenyl-10,12-dihydro-10-azaindeno[2,1-b]fluoren-7-yl)phenyl]amine

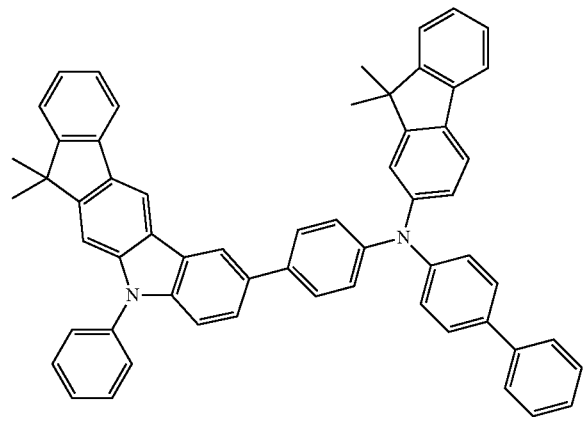 [SMILES: CC1(C)c2ccccc2-c2ccc(N(c3ccc(-c4ccccc4)cc3)c3ccc(-c4ccc5c(c4)c4cc6c(cc4n5-c4ccccc4)C(C)(C)c4ccccc4-6)cc3)cc21]

20.0 g (27.8 mmol) of biphenyl-4-yl-[4-(12,12-dimethyl-10,12-dihydro-10-azaindeno[2,1-b]fluoren-7-yl)phenyl]-(9,9-dimethyl-9H-fluoren-2-yl)-amine are dissolved in 500 ml of toluene with 4.39 ml (41.7 mmol) of bromobenzene and degassed, 1.94 ml (1.94 mmol/1 M in toluene) of tri-tert-butylphosphine, 249.8 mg of Pd(OAc)$_2$ and 4.01 g (41.7 mmol) of NaOtBu are added (solids are degassed in advance), and the mixture is stirred under reflux for 5 h. The warm (45° C.) mixture is filtered through Alox B (activity grade 1), washed with water, dried and evaporated. The crude product is extracted with heptane/toluene in a Soxhlet extractor and crystallised from heptane, giving, after sublimation, 14.7 g (67%) of the product as a yellowish solid having a purity of 99.9%.

Example 28

7-(4,6-Diphenyl-1,3,5-triazin-2-yl)-12,12-dimethyl-10-[1,1';3',1"]terphenyl-F-yl-10,12-dihydro-10-azaindeno[2,1-b]fluorene Step a): tert-Butyl 7-(4,6-diphenyl-1,3,5-triazin-2-yl)-12,12-dimethyl-12H-10-azaindeno[2,1-b]fluorene-10-carboxylate

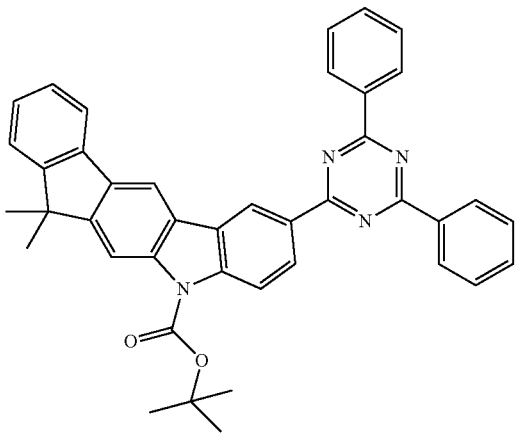 [SMILES: CC(C)(C)OC(=O)n1c2ccc(-c3nc(-c4ccccc4)nc(-c4ccccc4)n3)cc2c2cc3c(cc21)C(C)(C)c1ccccc1-3]

43.4 g (119.8 mmol) of 7-bromo-12,12-dimethyl-12H-10-azaindeno[2,1-b]fluorene, 33.5 g (131.8 mmol) of bis(pinacolato)diborane and 34.1 g (347.8 mmol) of potassium acetate are suspended in 770 ml of dioxane. 2.9 g (3.6 mmol) of 1,1-bis(diphenylphosphino)ferrocenepalladium(II) dichloride complex with DCM are added to this suspension. The reaction mixture is heated under reflux for 16 h. After cooling, the organic phase is separated off, washed three times with 200 ml of water and subsequently evaporated to dryness. The residue is recrystallised from toluene (39 g, 80% yield).

39 g (95 mmol) of the azaindenofluoreneboronic ester are dissolved in 1400 ml of dry acetonitrile, and 40.8 g (186.8 mmol) of BOC anhydride and 23.65 g (191.65 mmol) of DMAP are added. The mixture is heated under reflux for 1 h, water is added when the reaction is complete, and the mixture is extracted with dichloromethane, dried and evaporated. The yellow oil is washed by stirring with heptane, giving 37 g (75%) of the product as a white solid.

36.7 g (70.1 mmol) of the boronic ester, 19.3 g (72 mmol) of 2-chloro-4,6-diphenyl-1,3,5-triazine and 8.2 g of sodium carbonate are suspended in 900 ml of dioxane, 900 ml of toluene and 400 ml of water. 4.25 g (3.7 mmol) of Pd(PPh$_3$)$_4$ are added to this suspension. The reaction mixture is heated under reflux for 5 h. After cooling, the precipitated solid is filtered off with suction, washed with water and ethanol and dried. The residue is extracted with hot toluene and recrystallised from toluene. The purity is 99.9%. Yield: 36 g, 81% of theory.

Step b): 7-(4,6-Diphenyl-1,3,5-triazin-2-yl)-12,12-dimethyl-10-[1,1';3',1"]terphenyl-5'-yl-10,12-dihydro-10-azaindeno[2,1-b]fluorene

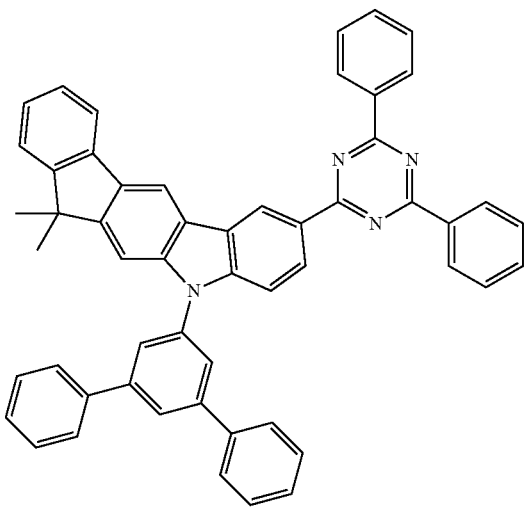 [SMILES: CC1(C)c2ccccc2-c2cc3c4cc(-c5nc(-c6ccccc6)nc(-c6ccccc6)n5)ccc4n(-c4cc(-c5ccccc5)cc(-c5ccccc5)c4)c3cc21]

34.4 g (56 mmol) of tert-butyl 7-(4,6-diphenyl-1,3,5-triazin-2-yl)-12,12-dimethyl-12H-10-azaindeno[2,1-b]fluorene-10-carboxylate are dissolved in 420 ml of anisole, and 11.5 ml of trifluoroacetic acid are subsequently added. The mixture is stirred at 40° C. for 3 h and, when the reaction is complete, neutralised by means of ice-water and 20% NaOH solution. The mixture is extracted with dichloromethane, dried and purified by recrystallisation from toluene/heptane, giving 20 g (70%) of the product as a white solid.

11.7 g (22.7 mmol) of the amine and 7.7 g (24.8 mmol) of bromoterphenyl are dissolved in 180 ml of xylene and degassed. 1.2 ml (1.2 mmol/1 M in toluene) of tri-tert-butylphosphine, 106 mg (0.47 mmol) of Pd(OAc)$_2$ and 5.9 g (61.5 mmol) of NaOtBu are added, and the mixture is stirred under reflux for 5 h. The warm (45° C.) mixture is filtered through Alox B (activity grade 1), washed with water, dried and evaporated. The crude product is extracted with heptane/toluene in a Soxhlet extractor and crystallised from heptane, giving, after sublimation, 10 g (65%) of the product as a yellowish solid having a purity of 99.9%.

Example 29

7-(4,6-Diphenyl-1,3,5-triazin-2-yl)-12,12-dimethyl-10-phenyl-10,12-dihydro-10-azaindeno[2,1-b]fluorene

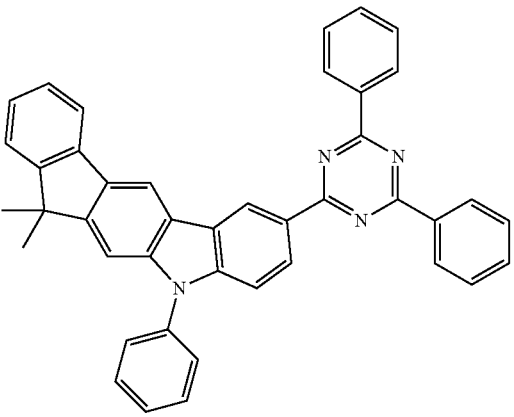 [SMILES: CC1(C)c2ccccc2-c2cc3c4cc(-c5nc(-c6ccccc6)nc(-c6ccccc6)n5)ccc4n(-c4ccccc4)c3cc21]

34.4 g (56 mmol) of tert-butyl 7-(4,6-diphenyl-1,3,5-triazin-2-yl)-12,12-dimethyl-12H-10-azaindeno[2,1-b]fluorene-10-carboxylate are dissolved in 420 ml of anisole, and 11.5 ml of trifluoroacetic acid are subsequently added. The mixture is stirred at 40° C. for 3 h and, when the reaction is complete, neutralised by means of ice-water and 20% NaOH solution. The mixture is extracted with dichloromethane, dried and purified by recrystallisation from toluene/heptane, giving 20 g (70%) of the product as a white solid.

8.1 g (15.8 mmol) of the amine and 1.7 ml (16.2 mmol) of bromobenzene are dissolved in 200 ml of xylene and degassed. 0.8 ml (0.8 mmol/1 M in toluene) of tri-tert-butylphosphine, 66 mg (0.29 mmol) of Pd(OAc)$_2$ and 4 g (42.6 mmol) of NaOtBu are added, and the mixture is stirred under reflux for 5 h. The warm (45° C.) mixture is filtered through Alox B (activity grade 1), washed with water, dried and evaporated. The crude product is extracted with heptane/toluene in a Soxhlet extractor and crystallised from heptane, giving, after sublimation, 5.6 g (60%) of the product as a yellowish solid having a purity of 99.9%.

Example 30

6,13-Bisbiphenyl-4-yl-11,11-dimethyl-11,13-dihydro-6H-6,13-diazaindeno[1,2-b]anthracene Step a): tert-Butyl 3-bromocarbazole-9-carboxylate

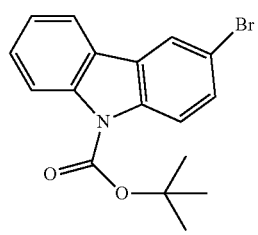 [SMILES: CC(C)(C)OC(=O)n1c2ccccc2c2cc(Br)ccc21]

150 g (0.85 mol) of carbazole are dissolved in 2.5 l of DMF, and 153.2 g (0.85 mol) of N-bromosuccinimide, dissolved in DMF, are slowly added at −10° C. When the reaction is complete, the DMF is removed in a rotary evaporator, and the precipitate is dissolved in dichloromethane, washed with water, dried and evaporated. The crude product is subsequently washed by stirring a number of times with hot Mesh/heptane (1:1), giving 141.6 g (67.5%) of the product as a white solid.

70.0 g (284 mmol) of the bromocarbazole are dissolved in 100 ml of dry THF, and 86.9 g (398.2 mmol) of BOC anhydride and 3.51 g (28.4 mmol) of DMAP are added. The mixture is stirred under reflux for 2.5 h, and, when the reaction is complete, water and dichloromethane are added at RT. The organic phase is separated off, dried and crystallised from heptane (ultrasound bath), giving 91.9 g (93.3%) of the product as a white solid.

Step b): tert-Butyl 3-(2-methoxycarbonylphenylamino)carbazole-9-carboxylate

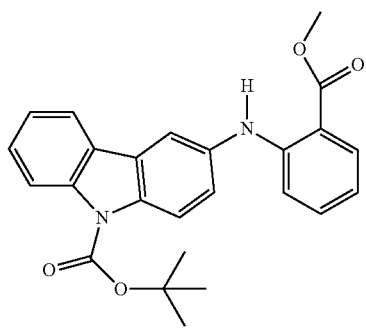 [SMILES: COC(=O)c1ccccc1Nc1ccc2c(c1)c1ccccc1n2C(=O)OC(C)(C)C]

50.0 g (144 mmol) of the BOC-protected bromocarbazole are dissolved in 1000 ml of dry toluene with 30.7 ml (238 mmol) of methyl anthranilate and degassed. 21.6 ml (21.6 mmol/1 M in toluene) of tris-tert-butylphosphine, degassed 2.6 g (11.5 mmol) of Pd(OAc)$_2$ and 81.3 g (249 mmol) of Cs$_2$CO$_3$ are added, and the reaction mixture is stirred under reflux for 2.5 h. The cooled reaction solution is filtered through silica gel, and the crude product is crystallised from Mesh/heptane (1:1), giving 45.5 g (76%) of the product as a white solid.

Step c): Methyl 2-(9H-carbazol-3-ylamino)benzoate

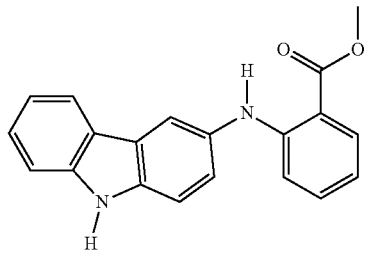 [SMILES: COC(=O)c1ccccc1Nc1ccc2[nH]c3ccccc3c2c1]

5.0 g (12 mmol) of the carbazole are dissolved in 50 ml of dichloromethane, and 2 ml (26 mmol) of trifluoroacetic acid and 0.26 ml (2.4 mmol) of anisole are added at RT, and the mixture is stirred at 40° C. for 2 h. When the reaction is complete, the mixture is carefully tipped into ice-water and adjusted as rapidly as possible to pH=7 using 20% NaOH. The mixture is extracted with dichloromethane, dried and evaporated. The residue is filtered through silica gel and washed by stirring with warm heptane, giving 3.24 g (85.3%) of the product as a white solid.

Step d): 11,11-Dimethyl-11,13-dihydro-6H-6,13-diazaindeno[1,2-b]anthracene

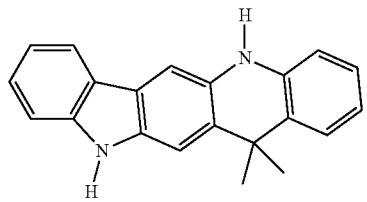 [SMILES: CC1(C)c2ccccc2Nc2cc3c(cc21)[nH]c1ccccc13]

10.0 g (31.6 mmol) of methyl 2-(9H-carbazol-3-ylamino)benzoate are dissolved in 300 ml of dry THF, and the solution is cooled to −78° C. 71.8 ml (158.0 mmol/2.2 M in diethyl ether) of MeLi are added dropwise at this temperature. The mixture is subsequently allowed to come to −40° C. over the course of 5 h and, when the reaction is complete, is carefully quenched using 50 ml of Mesh. The mixture is subsequently diluted with ethyl acetate and water, the organic phase is dried and evaporated in a rotary evaporator. The residue is washed by stirring with hot heptane, giving 7.7 g (77%) of the product as a white solid.

10.0 g (31.6 mmol) of the alcohol are dissolved in 150 ml of dichloromethane, and the solution is cooled to −20° C. 27.8 g (284 mmol) of polyphosphoric acid and 20.5 ml (316 mmol) of methanesulfonic acid are carefully mixed and added dropwise to the reaction mixture at −20° C. over the course of 15 min. When the reaction is complete, the reaction solution is carefully poured into ice-water, and the precipitate is filtered off with suction. The precipitate is rinsed with dichloromethane, giving, after drying in a vacuum drying cabinet, 6.7 g (71%) of the product as a white solid.

Step e): 6,13-Bisbiphenyl-4-yl-11,11-dimethyl-11,13-dihydro-6H-6,13-diazaindeno[1,2-b]anthracene

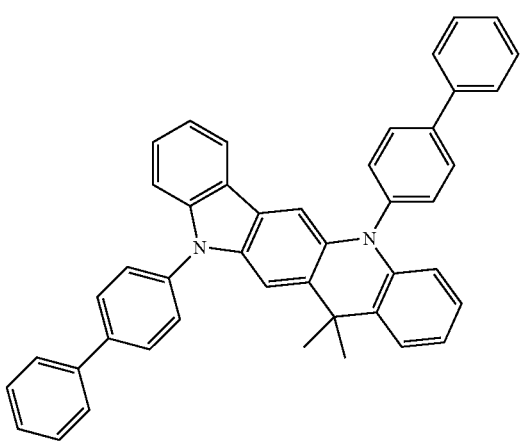 [SMILES: CC1(C)c2ccccc2N(c2ccc(-c3ccccc3)cc2)c2cc3c4ccccc4n(-c4ccc(-c5ccccc5)cc4)c3cc21]

20.0 g (67.0 mmol) of 11,11-dimethyl-11,13-dihydro-6H-6,13-diazaindeno[1,2-b]anthracene and 46.8 g (201.1 mmol)

of 4-bromobiphenyl are dissolved in 250 ml of toluene and degassed. 4.69 ml (4.69 mmol/1 M in toluene) of tri-tert-butylphosphine, degassed 19.3 g (201 mmol) of NaOtBu and 601 mg (2.68 mmol) of Pd(OAc)$_2$ are added, the mixture is subsequently degassed and heated under reflux for 10 h. When the reaction is complete, the warm mixture is filtered through Alox B (activity grade 1), washed with water, dried and evaporated. The residue is purified using toluene/heptane (1:1) in a Soxhlet extractor and crystallised from toluene, giving, after sublimation, 21.8 g (54%) of the product as a yellowish solid having a purity of 99.9%.

Example 31

10,10'-Di-(1,3-pyrimidin-2-yl)-10,10',12,12'-tetrahydro-10,10'-di(azaindeno[2,1-b]-12,12-spirofluorene Step a): 10,10',12,12'-Tetrahydro-10,10'-di(azaindeno[2,1-b]-12,12-spirofluorene

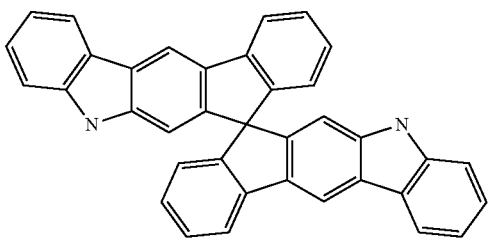 [SMILES: c1ccc2c(c1)-c1cc3c(cc1C21c2ccccc2-c2cc4c(cc21)[nH]c1ccccc14)[nH]c1ccccc13]

50 g of 2,2'-dibromo-9,9'-spirobifluorene (105.4 mmol), 21.2 ml of aniline (232 mmol), 2.9 g of DPPF (5.2 mmol), 1.18 g of palladium(II) acetate (5.3 mmol) and 50.7 g of sodium tert-butoxide (527 mmol) are heated at the boil in 1 l of toluene under a protective-gas atmosphere for 18 h. The mixture is subsequently partitioned between toluene and water, the organic phase is washed three times with water, dried over Na$_2$SO$_4$ and evaporated in a rotary evaporator. The residue of 2,2'-diaminophenyl-9,9'-spirobifluorene which remains is recrystallised from heptane/ethyl acetate. The yield is 42 g (80%).

300 ml of pivalic acid are added to 40 g of 2,2'-diaminophenyl-9,9'-spirobifluorene (80 mmol), 1.7 g of palladium (II) acetate (8 mmol) and 1.6 g of potassium carbonate (11.4 mmol), and the mixture is stirred at 120° C. under air for 9 h. After this time, 1.7 g of palladium(II) acetate (8 mmol) are added, and the mixture is stirred at 120° C. for a further 9 h. 200 ml of dichloromethane and 0.1 M Na$_2$CO$_3$ solution are then added. The mixture is partitioned between water and dichloromethane, the aqueous phase is extracted three times with dichloromethane, and the combined organic phases are dried over Na$_2$SO$_4$ and evaporated in a rotary evaporator. The residue is recrystallised from toluene/heptane. The yield is 19.8 g (40 mmol, 50%).

Step b): 10,10'-Di-(1,3-pyrimidin-2-yl)-10,10',12,12"-tetrahydro-10,10'-di(azaindeno[2,1-b]-12,12-spirofluorene

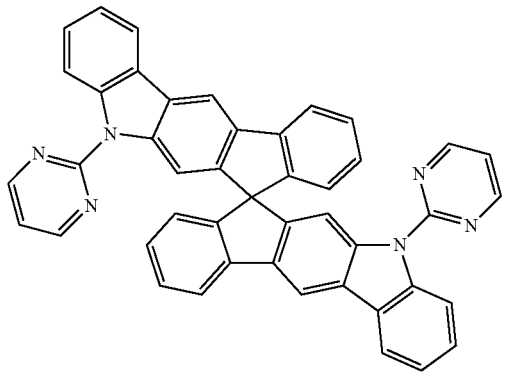 [SMILES: c1cnc(-n2c3ccccc3c3cc4c(cc32)C2(c3ccccc3-4)c3ccccc3-c3cc4c5ccccc5n(-c5ncccn5)c4cc32)nc1]

18 g (36.4 mmol) of 10,10',12,12'-tetrahydro-10,10'-di(azaindeno[2,1-b]-12,12-spirofluorene are dissolved in 200 ml of dimethylformamide under a protective-gas atmosphere, and 3.35 g of 60% NaH in mineral oil (83.7 mmol) are added. After 1 h at room temperature, a solution of 2-bromo-1,3-pyrimidine (12.7 g, 80 mmol) in 100 ml of THF is added dropwise. The reaction mixture is stirred at room temperature for 12 h. After this time, the reaction mixture is poured onto ice and extracted three times with dichloromethane. The combined organic phases are dried over Na$_2$SO$_4$ and evaporated. The residue is extracted with hot toluene, recrystallised from toluene and finally sublimed in a high vacuum, the purity is 99.9%. The yield is 19 g (80%).

Example 32

4,4'-Di(12,12-dimethyl-10,12-dihydro-10-azaindeno[2,1-b]fluoren-10-yl)biphenyl

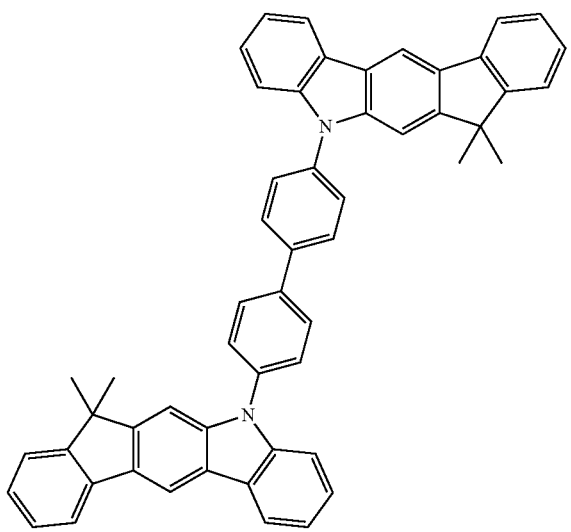 [SMILES: CC1(C)c2ccccc2-c2cc3c4ccccc4n(-c4ccc(-c5ccc(-n6c7ccccc7c7cc8c(cc76)C(C)(C)c6ccccc6-8)cc5)cc4)c3cc21]

30.3 g (107 mmol) of 12,12-dimethyl-10,12-dihydro-10-azaindeno[2,1-b]fluorene, 16.9 g (54.2 mmol) of 4,4'-dibromobiphenyl and 29.2 g (304 mmol) of NaOtBu are suspended in 1.35 l of p-xylene. 490 mg (2.1 mmol) of Pd(OAc)₂ and 1.7 ml (6.72 mmol) of a tri-tert-butylphosphine solution are added to this suspension. The reaction mixture is heated under reflux for 16 h. After cooling, the organic phase is separated off, washed three times with 200 ml of water and subsequently evaporated to dryness. The residue is extracted with hot toluene and recrystallised from toluene and finally sublimed in a high vacuum, the purity is 99.9%. The yield is 37.8 g (53 mmol, 90%).

Example 33

12,12,12',12'-Tetramethyl-10,10'-diphenyl-10,12,10', 12'-tetrahydro-[7,7']bi[10-azaindeno[2,1-b]fluorenyl]

Step a): tert-Butyl 7-bromo-12,12-dimethyl-12H-10-azaindeno[2,1-b]fluorene-10-carboxylate

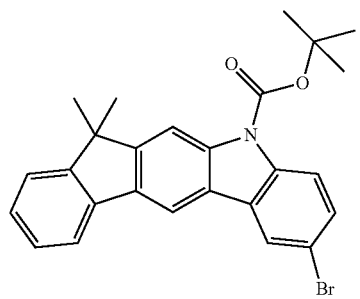 [SMILES: CC(C)(C)OC(=O)n1c2ccc(Br)cc2c2cc3c(cc21)C(C)(C)c1ccccc1-3]

35.5 g (98 mmol) of 7-bromo-12,12-dimethyl-10,12-dihydro-10-azaindeno-[2,1-b]fluorene are dissolved in 500 ml of dry THF, and 30.0 g (137.5 mmol) of BOC anhydride and 1.21 g (9.82 mmol) of DMAP are added. The mixture is heated under reflux for 1 h, water is added when the reaction is complete, and the mixture is extracted with dichloromethane, dried and evaporated. The yellow oil is washed by stirring with heptane, giving 35 g (77%) of the product as a white solid.

Step b): tert-Butyl 12,12-dimethyl-7-(4,4,5,5-tetramethyl-1,3,2-dioxaborolan-2-yl)-12H-10-azaindeno[2,1-b]fluorene-10-carboxylate

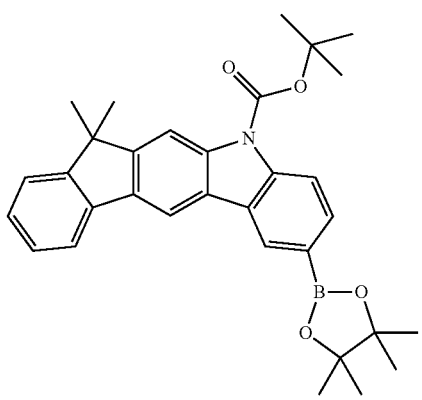 [SMILES: CC(C)(C)OC(=O)n1c2ccc(B3OC(C)(C)C(C)(C)O3)cc2c2cc3c(cc21)C(C)(C)c1ccccc1-3]

43.4 g (119.8 mmol) of 7-bromo-12,12-dimethyl-12H-10-azaindeno[2,1-b]fluorene, 33.5 g (131.8 mmol) of bis(pinacolato)diborane and 34.1 g (347.8 mmol) of potassium acetate are suspended in 770 ml of dioxane. 2.9 g (3.6 mmol) of 1,1-bis(diphenylphosphino)ferrocenepalladium(II) dichloride complex with DCM are added to this suspension. The reaction mixture is heated under reflux for 16 h. After cooling, the organic phase is separated off, washed three times with 200 ml of water and subsequently evaporated to dryness. The residue is recrystallised from toluene (39 g, 80% yield).

39 g (95 mmol) of the azaindenofluoreneboronic ester are dissolved in 1400 ml of dry acetonitrile, and 40.8 g (186.8 mmol) of BOC anhydride and 23.65 g (191.65 mmol) of DMAP are added. The mixture is heated under reflux for 1 h, water is added when the reaction is complete, and the mixture is extracted with dichloromethane, dried and evaporated. The yellow oil is washed by stirring with heptane, giving 37 g (75%) of the product as a white solid.

Step c): Di-tert-butyl 12,12,12',12'-tetramethyl-12H, 12'H-[7,7']bi[10-azaindeno[2,1-b]fluorenyl]-10,10'-dicarboxylate

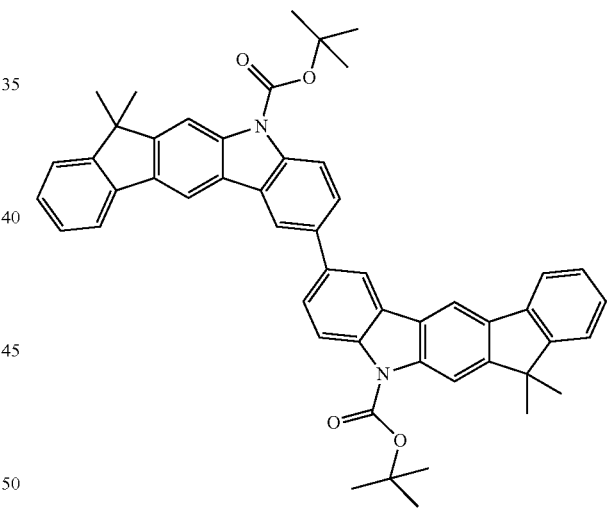

37 g (72.6 mmol) of the boronic ester, 33.6 g (72.6 mmol) of tert-butyl 7-bromo-12,12-dimethyl-12H-10-azaindeno[2,1-b]fluorene-10-carboxylate and 11.6 g of sodium carbonate are suspended in 900 ml of dioxane, 900 ml of toluene and 400 ml of water. 4.2 g (3.6 mmol) of Pd(PPh₃)₄ are added to this suspension. The reaction mixture is heated under reflux for 5 h. After cooling, the precipitated solid is filtered off with suction, washed with water and ethanol and dried. The residue is extracted with hot toluene and recrystallised from toluene. Yield: 47 g, 85% of theory.

Step d): 12,12,12',12'-Tetramethyl-10,10'-diphenyl-10,12,10',12'-tetrahydro-[7,7']bi[10-azaindeno[2,1-b]fluorenyl]

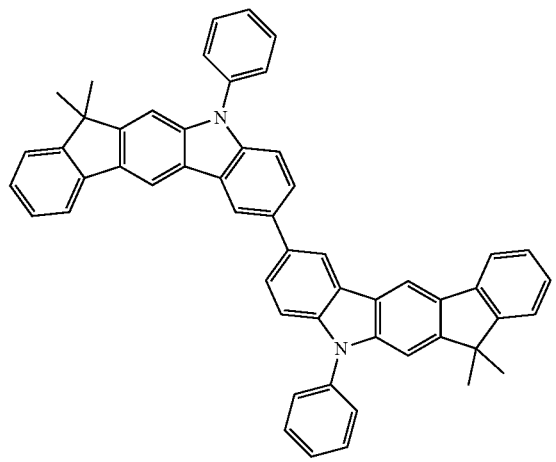 [SMILES: CC1(C)c2ccccc2-c2cc3c4cc(-c5ccc6c(c5)c5cc7c(cc5n6-c5ccccc5)C(C)(C)c5ccccc5-7)ccc4n(-c4ccccc4)c3cc21]

47 g (61.4 mmol) of di-tert-butyl 12,12,12',12'-tetramethyl-12H,12'H-[7,7']-bi[10-azaindeno[2,1-b]fluorenyl]-10,10'-dicarboxylate are dissolved in 500 ml of dichloromethane and 5 ml of anisole, and 13.7 ml of trifluoroacetic acid are subsequently added. The mixture is stirred at 40° C. for 3 h and, when the reaction is complete, neutralised by means of ice-water and 20% NaOH solution. The product is extracted with methylene chloride, dried and purified by recrystallisation from toluene, giving 32 g (90%) of the product as a solid.

32 g (56.7 mmol) of the amine are dissolved in 1 l of toluene with 22 g (141.7 mmol) of bromophenyl and degassed. 5.7 ml of tri-tert-butylphosphine solution (1 M in toluene), 640 mg (2.83 mmol) of Pd(OAc)₂ and 16.3 g (170 mmol) of NaOtBu are added, and the mixture is stirred under reflux for 5 h. The warm (45° C.) mixture is filtered through Alox B, washed with water, dried and evaporated. The crude product is extracted with toluene in a Soxhlet extractor and recrystallised, giving 28 g (70%) of the product as a yellowish solid. Finally, the solid is sublimed in a high vacuum, the purity is 99.9%.

Example 34

12,12-Dimethyl-10-[3,2';6',3"]terpyridin-4'-yl-10,12-dihydro-10-azaindeno[2,1-b]fluorene

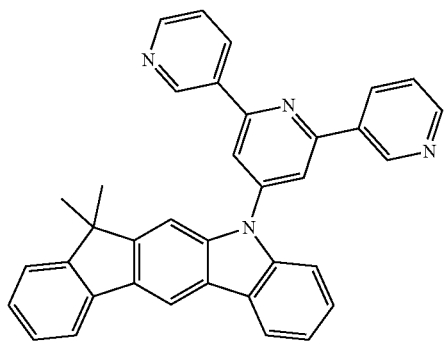 [SMILES: CC1(C)c2ccccc2-c2cc3c4ccccc4n(-c4cc(-c5cccnc5)nc(-c5cccnc5)c4)c3cc21]

11 ml (113 mmol) of 3-bromopyridine are dissolved in 225 ml of dry THF, the solution is cooled to −70° C., and 26.3 ml (115 mmol) of trimethyl borate are added. At this temperature, 46 ml (115 mmol/2.5 M in hexane) of n-BuLi are added to the reaction mixture over the course of about 10 min., and the mixture is subsequently stirred at −78° C. for a further 1 h. The temperature is allowed to rise to −40° C., and the mixture is stirred for a further 20 min, subsequently allowed to come to −20° C., during which 100 ml of 2 N hydrochloric acid are added dropwise. The organic phase is separated off, and the aqueous phase is adjusted to pH 7 using 4 N sodium hydroxide solution. The aqueous phase is saturated with sodium chloride and extracted three times with THF. The organic phases are combined and evaporated. Yield: 12.0 g (90% of theory).

20 g (38.6 mmol) of 10-(2,6-dibromopyridin-4-yl)-12,12-dimethyl-10,12-dihydro-10-azaindeno[2,1-b]fluorene and 10.4 g of 3-pyridineboronic acid (84.9 mmol) are suspended in 400 ml of ethylene glycol dimethyl ether, 85 ml of a 2 M Na₂CO₃ solution are added to the reaction mixture. 2.23 g (1.93 mmol) of Pd(PPh₃)₄ are added to this suspension. The reaction mixture is heated under reflux for 12 h. After cooling, the precipitated solid is filtered off with suction, washed with water and ethanol and dried. The residue is extracted with hot toluene, recrystallised from toluene and finally sublimed in a high vacuum, the purity is 99.9%. Yield: 12 g, 60% of theory.

Example 35

10-(2,6-Dipyrimidin-5-ylpyridin-4-yl)-12,12-dimethyl-10,12-dihydro-10-azaindeno[2,1-b]fluorene

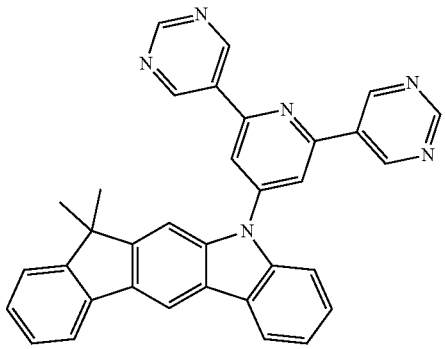 [SMILES: CC1(C)c2ccccc2-c2cc3c4ccccc4n(-c4cc(-c5cncnc5)nc(-c5cncnc5)c4)c3cc21]

30 g (189 mmol) of 5-bromopyrimidine are dissolved in 900 ml of dry THF, the solution is cooled to −78° C., and 87 ml (337 mmol) of trimethyl borate are added. At this temperature, 77.7 ml (194 mmol/2.5 M in hexane) of n-BuLi are added to the reaction mixture over the course of about 30 min, and the mixture is subsequently stirred at −78° C. for a further 4.5 h. 110 ml of water are then added to the reaction mixture, which is then slowly warmed to room temperature. The THF is removed in a rotary evaporator, and the aqueous phase is adjusted to pH 10 using 5% NaOH. The mixture is subsequently washed with diethyl ether. The water phase is adjusted to pH 4 using 48% HBr, and the precipitated solid is filtered off. Yield: 11 g (47% of theory).

15 g (29 mmol) of 10-(2,6-dibromopyridin-4-yl)-12,12-dimethyl-10,12-dihydro-10-azaindeno[2,1-b]fluorene and 7.9 g of 5-pyrimidineboronic acid (63.7 mmol) are suspended in 300 ml of ethylene glycol dimethyl ether. 65 ml of a 2 M Na₂CO₃ solution are added to the reaction mixture. 1.67 g (1.45 mmol) of Pd(PPh₃)₄ are added to this suspension. The reaction mixture is heated under reflux for 12 h. After cooling, the precipitated solid is filtered off with suction, washed with water and ethanol and dried. The residue is extracted with hot toluene and recrystallised from toluene and finally sublimed in a high vacuum, the purity is 99.9%. Yield: 8.5 g, 57% of theory.

Example 36

10-[4,6-Bis(4-tert-butylphenyl)-1,3,5-triazin-2-yl]-12,12-dimethyl-10,12-dihydro-10-azaindeno[2,1-b]fluorene Step a): 2,4-Bis(4-tert-butylphenyl)-6-chloro-1,3,5-triazine

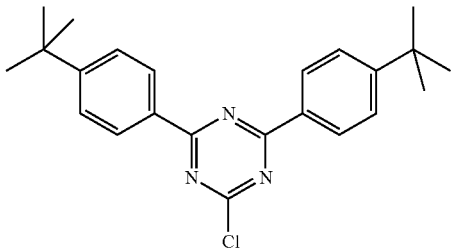 [SMILES: CC(C)(C)c1ccc(-c2nc(Cl)nc(-c3ccc(C(C)(C)C)cc3)n2)cc1]

5.7 g of magnesium (234.6 mmol) are initially introduced in a 500 ml four-necked flask, and a solution of 50 g of bromo-4-tert-butylbenzene (234.6 mmol) in 200 ml of THF is slowly added dropwise. The reaction mixture is heated at the boil for 1.5 h and subsequently cooled to room temperature. In a second flask, cyanogen chloride (18.8 g, 102 mmol) in 200 ml of THE is initially introduced and cooled to 0° C. The cooled Grignard reagent is added dropwise at this temperature, and the mixture is stirred at RT for 12 H. After this time, 150 ml of HCl are added to the reaction mixture, and the aqueous phase is extracted three times with dichloromethane. The combined organic phases are washed with water, dried over $Na_2SO_4$ and evaporated. The residue is recrystallised from EtOH. The yield is 31 g (81.6 mmol, 80%).

Step b): 10-[4,6-Bis(4-tert-butylphenyl)-1,3,5-triazin-2-yl]-12,12-dimethyl-10,12-dihydro-10-azaindeno[2,1-b]fluorene

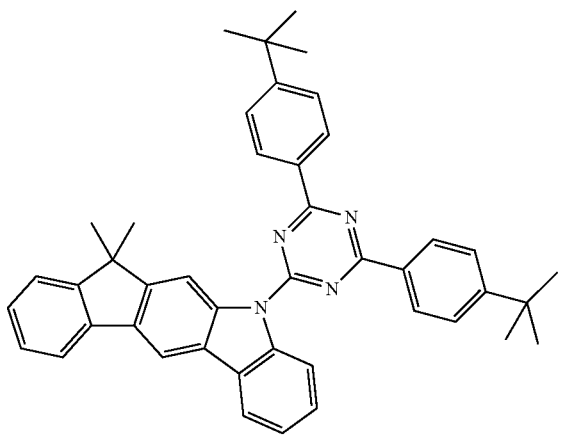 [SMILES: CC(C)(C)c1ccc(-c2nc(-c3ccc(C(C)(C)C)cc3)nc(-n3c4ccccc4c4cc5c(cc43)C(C)(C)c3ccccc3-5)n2)cc1]

12.5 g (44 mmol) of 12,12-dimethyl-10,12-dihydro-10-azaindeno[2,1-b]fluorene are dissolved in 200 ml of dimethylformamide under a protective-gas atmosphere, and 2.1 g of 60% NaH in mineral oil (52.7 mmol) are added. After 1 h at room temperature, a solution of 2,4-bis(4-tert-butylphenyl)-6-chloro-1,3,5-triazine (20 g, 52.7 mmol) in 100 ml of THF is added dropwise. The reaction mixture is stirred at room temperature for 12 h. After this time, the reaction mixture is poured onto ice and extracted three times with dichloromethane. The combined organic phases are dried over $Na_2SO_4$ and evaporated. The residue is extracted with hot toluene, recrystallised from toluene and finally sublimed in a high vacuum. Yield: 17 g, 60%. The purity is 99.9%.

Example 37

10-(4,6-Bis(3-([3,1';5,1"]terphen-1-yl)phen-1-yl)-1,3,5-triazin-2-yl)-12,12-dimethyl-10,12-dihydro-10-azaindeno[2,1-b]fluorene Step a): 2-Chloro-4,6-bis(3-([3,1';5,1"]terphen-1-yl)phen-1-yl)-1,3,5-triazin

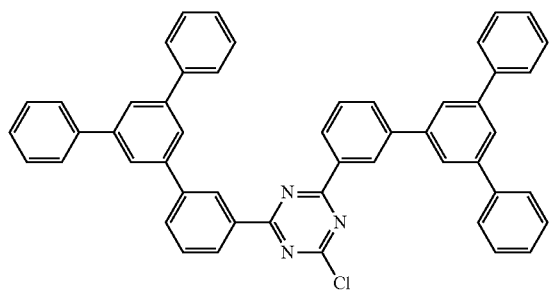 [SMILES: Clc1nc(-c2cccc(-c3cc(-c4ccccc4)cc(-c4ccccc4)c3)c2)nc(-c2cccc(-c3cc(-c4ccccc4)cc(-c4ccccc4)c3)c2)n1]

2.0 g of magnesium (81 mmol) are initially introduced in a 500 ml four-necked flask, and a solution of 31.2 g of 5'-(3-bromophenyl)-[1,1';3',1"]terphenyl (81 mmol) in 100 ml of THE is slowly added dropwise. The reaction mixture is heated at the boil for 1.5 h and subsequently cooled to room temperature. In a second flask, cyanogen chloride (6.4 g, 35 mmol) in 50 ml of THE is initially introduced and cooled to 0° C. The cooled Grignard reagent is added dropwise at this temperature, and the mixture is stirred at room temperature for 12 h. After this time, 150 ml of HCl are added to the reaction mixture, the aqueous phase is extracted three times with dichloromethane. The combined organic phases are washed with water and dried over $Na_2SO_4$ and evaporated. The residue is recrystallised from toluene. The yield is 6.8 g (9.4 mmol, 28%).

Step b): 10-(4,6-Bis(3-([3,1';5,1"]terphen-1-yl)phen-1-yl)-1,3,5-triazin-2-yl)-12,12-dimethyl-10,12-dihydro-10-azaindeno[2,1-b]fluorene

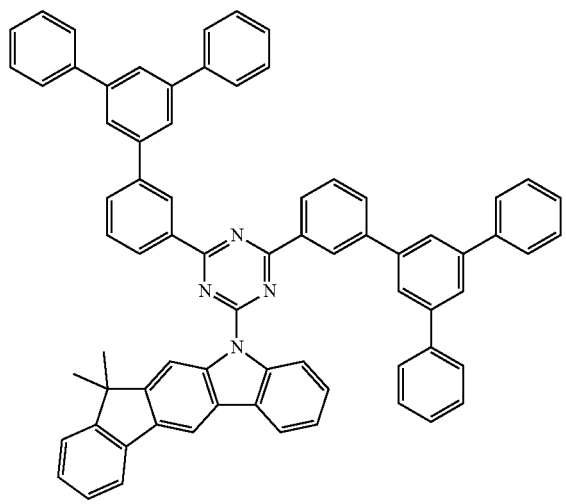 [SMILES: CC1(C)c2ccccc2-c2cc3c4ccccc4n(-c4nc(-c5cccc(-c6cc(-c7ccccc7)cc(-c7ccccc7)c6)c5)nc(-c5cccc(-c6cc(-c7ccccc7)cc(-c7ccccc7)c6)c5)n4)c3cc21]

8.0 g (28 mmol) of 12,12-dimethyl-10,12-dihydro-10-azaindeno[2,1-b]fluorene are dissolved in 210 ml of dimethylformamide under a protective-gas atmosphere, and 1.4 g of 60% NaH in mineral oil (35 mmol) are added. After 1 h at room temperature, a solution of 2-chloro-[4,6-bis-5'-(3-bromophenyl)-[1,1';3',1"]terphenyl-5'-yl]-1,3,5-triazine (22.5 g, 31 mmol) in 250 ml of dimethylformamide is added dropwise. The reaction mixture is stirred at room temperature for 12 h. After this time, the reaction mixture is poured onto ice and extracted three times with dichloromethane. The combined organic phases are dried over $Na_2SO_4$ and evaporated. The residue is recrystallised from heptane/toluene. The yield is 12.2 g (13 mmol, 44%).

Example 38

7-(3-([3,1';5,1"]Terphen-1-yl)phen-1-yl)-10-(4,6-diphenyl-1,3,5-triazin-2-yl)-12,12-dimethyl-10,12-dihydro-10-azaindeno[2,1-b]fluorene

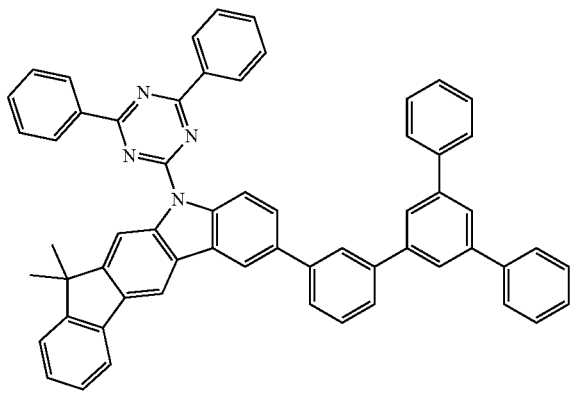 [SMILES: CC1(C)c2ccccc2-c2cc3c4cc(-c5cccc(-c6cc(-c7ccccc7)cc(-c7ccccc7)c6)c5)ccc4n(-c4nc(-c5ccccc5)nc(-c5ccccc5)n4)c3cc21]

25.0 g (42.1 mmol) of 7-bromo-10-(4,6-diphenyl-1,3,5-triazin-2-yl)-12,12-dimethyl-10,12-dihydro-10-azaindeno[2,1-b]fluorene and 19.9 g of 3-([3,1';5,1"]terphen-1-yl) phenyl 1-pinacolylboronate (46.3 mmol) are dissolved in 80 ml of toluene and degassed. 281 ml of a degassed 2 M $K_2CO_3$ and 2.4 g (2.1 mmol) of $Pd(PPh_3)_4$ are added. The reaction mixture is subsequently stirred at 80° C. for 48 h under a protective-gas atmosphere. Further toluene is added to the cooled solution, which is washed a number of times with water, dried and evaporated. The residue is recrystallised from heptane/toluene. The yield is 21.8 g (26.6 mmol, 63.2%).

Example 39

12-(4,6-Diphenyl-1,3,5-triazin-2-yl)-7-thia-12-azaindeno[1,2-a]fluorene

Step a): 2-(3-Nitrophenyl)dibenzothiophene

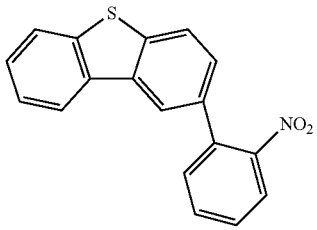 [SMILES: O=[N+]([O-])c1ccccc1-c1ccc2sc3ccccc3c2c1]

15.0 g of 2-bromodibenzothiophene (57.0 mmol) and 14.3 g of 2-nitrophenylboronic acid (85.5 mmol) are dissolved in 400 ml of toluene and degassed. 370 ml of a degassed 2 M $K_2CO_3$ and 1.6 g of $Pd(PPh_3)_4$ (1.4 mmol) are added. The reaction mixture is stirred at 80° C. for 48 h under a protective-gas atmosphere. Further toluene is added to the cooled solution, which is washed a number of times with water, dried and evaporated. The residue in the form of a yellowish oil is employed in the subsequent reaction without further purification. The yield is 16.9 g (55.4 mmol, 89%).

Step b): 12H-7-Thia-12-azaindeno[1,2-a]fluorene

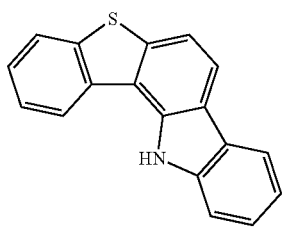 [SMILES: c1ccc2c(c1)[nH]c1c2ccc2sc3ccccc3c21]

21.0 g of 2-(3-nitrophenyl)dibenzothiophene (68.8 mmol) are dissolved in 140 ml of 1,2-dichlorobenzene. 30 ml of triethyl phosphite (172 mmol) are added. After 24 h at 135° C., the batch is allowed to cool and is evaporated in a rotary evaporator. The residue is purified by column chromatography on silica gel with heptane/ethyl acetate (3:1). The yield is 15.1 g (55.4 mmol, 81%).

Step c): 12-(4,6-Diphenyl-1,3,5-triazin-2-yl)-7-thia-12-azaindeno[1,2-a]fluorene

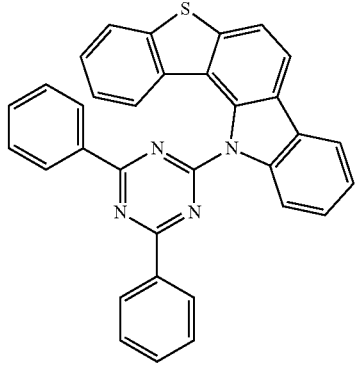 [SMILES: c1ccc(-c2nc(-c3ccccc3)nc(-n3c4ccccc4c4ccc5sc6ccccc6c5c43)n2)cc1]

15.1 g (55.4 mmol) of 12H-7-thia-12-azaindeno[1,2-a]fluorene are dissolved in 315 ml of dimethylformamide under a protective-gas atmosphere, and 2.4 g of 60% NaH in mineral oil (61 mmol) are added. After 1 h at room temperature, a solution of 2-chloro-[4,6-bisphenyl]-1,3,5-triazine (17.8 g, 66.5 mmol) in 80 ml of dimethylformamide is added dropwise. The reaction mixture is stirred at room temperature for 12 h. After this time, the reaction mixture is poured onto ice and extracted three times with dichloromethane. The combined organic phases are dried over Na$_2$SO$_4$ and evaporated. The residue is recrystallised from toluene. The yield after sublimation is 23.8 g (47.1 mmol, 85%) with a purity of 99.9%.

Example 40

7-{10-(4,6-Diphenyl-1,3,5-triazin-2-yl)-12,12-dimethyl-10,12-dihydro-10-azaindeno[2,1-b]fluorenyl}-12,12-dimethyl-10-phenyl-10,12-dihydro-10-azaindeno[2,1-b]fluorene Step a): tert-Butyl 7-{10-(4,6-diphenyl-1,3,5-triazin-2-yl)-12,12-dimethyl-10,12-dihydro-10-azaindeno[2,1-b]fluorenyl}-12,12-dimethyl-12H-azaindeno[2,1-b]fluorene-10-carboxylate

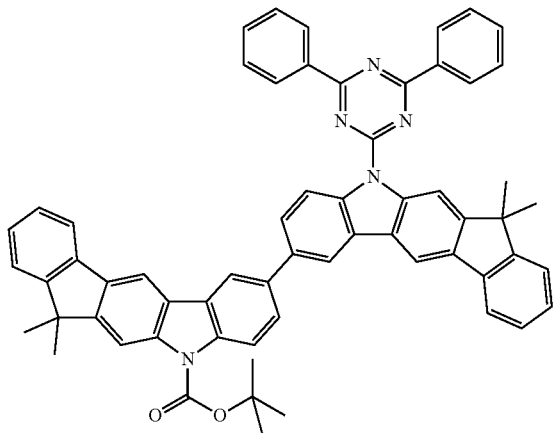 [SMILES: CC(C)(C)OC(=O)n1c2ccc(-c3ccc4c(c3)c3cc5c(cc3n4-c3nc(-c4ccccc4)nc(-c4ccccc4)n3)C(C)(C)c3ccccc3-5)cc2c2cc3c(cc21)C(C)(C)c1ccccc1-3]

21.0 g (41.2 mmol) of tert-butyl 12,12-dimethyl-7-(4,4,5,5-tetramethyl-1,3,2-dioxaborolan-2-yl)-12H-10-azaindeno[2,1-b]fluorene-10-carboxylate, 24.5 g (41.0 mmol) of 7-bromo-10-(4,6-diphenyl-1,3,5-triazin-2-yl)-12,12-dimethyl-10,12-dihydro-10-azaindeno[2,1-b]fluorene and 4.8 g of sodium carbonate are suspended in 500 ml of dioxane, 500 ml of toluene and 400 ml of water. 2.4 g (2.1 mmol) of Pd(PPh$_3$)$_4$ are added to this suspension. The reaction mixture is heated under reflux for 5 h. After cooling, the precipitated solid is filtered off with suction, washed with water and ethanol and dried. The residue is extracted with hot toluene and recrystallised from toluene. The yield is 32.1 g (36 mmol, 87%).

Step b): 7-{10-(4,6-Diphenyl-1,3,5-triazin-2-yl)-12,12-dimethyl-10,12-dihydro-10-azaindeno[2,1-b]fluorenyl}-12,12-dimethyl-10,12-dihydro-10-azaindeno[2,1-b]fluorene

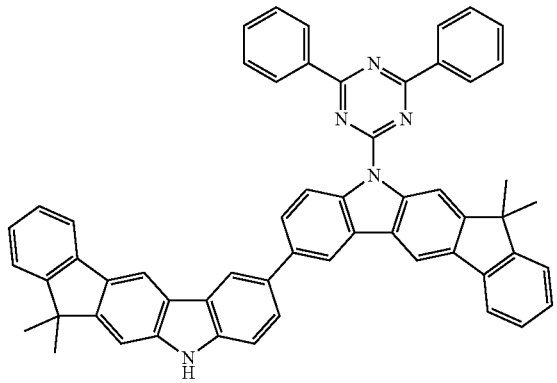 [SMILES: CC1(C)c2ccccc2-c2cc3c(cc21)[nH]c1ccc(-c2ccc4c(c2)c2cc5c(cc2n4-c2nc(-c4ccccc4)nc(-c4ccccc4)n2)C(C)(C)c2ccccc2-5)cc13]

30.2 g (34.0 mmol) of tert-butyl 7-{10-(4,6-diphenyl-1,3,5-triazin-2-yl)-12,12-dimethyl-10,12-dihydro-10-azaindeno[2,1-b]fluorenyl}-12,12-dimethyl-12H-10-azaindeno[2,1-b]fluorene-10-carboxylate are dissolved in 900 ml of toluene and 200 ml of anisole, and 50 ml of trifluoroacetic acid are subsequently added. The mixture is stirred at 40° C. for 3 h and, when the reaction is complete, neutralised by means of ice-water and 20% NaOH solution. The mixture is extracted with dichloromethane, dried and recrystallised from toluene. The yield is 23.6 g (30 mmol, 88%).

Step c): 7-{10-(4,6-Diphenyl-1,3,5-triazin-2-yl)-12,12-dimethyl-10,12-dihydro-10-azaindeno[2,1-b]fluorenyl}-12,12-dimethyl-10-phenyl-10,12-dihydro-10-azaindeno[2,1-b]fluorene

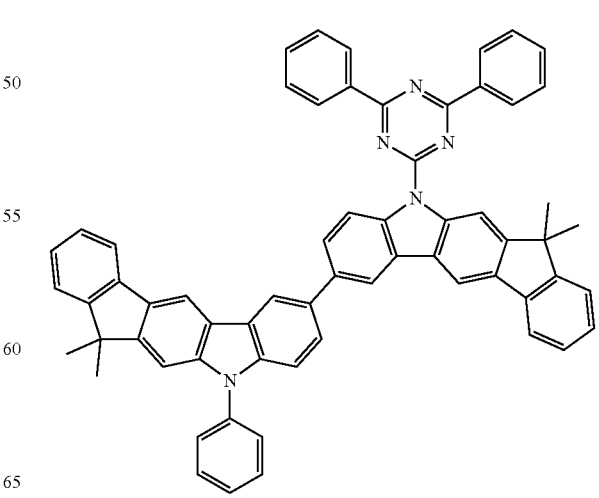

21.0 g (26 mmol) of 7-{10-(4,6-diphenyl-1,3,5-triazin-2-yl)-12,12-dimethyl-10,12-dihydro-10-azaindeno[2,1-b]fluorenyl}-12,12-dimethyl-10,12-dihydro-10-azaindeno[2,1-b]fluorene, 2.8 g (27 mmol) of bromobenzene and 6.8 g (71 mmol) of NaOtBu are suspended in 1000 ml of p-xylene. 0.11 g (0.5 mmol) of Pd(OAc)$_2$ and 0.33 ml of a 1 M tri-tert-butylphosphine solution are added to this suspension. The reaction mixture is heated under reflux for 16 h. After cooling, the organic phase is separated off, washed three times with 100 ml of water and subsequently evaporated to dryness. The residue is extracted with hot toluene, recrystallised from toluene and finally sublimed in a high vacuum. The yield is 15.3 g (18 mmol, 66.5%).

Example 41

4-(7-(4,6-Diphenyl-1,3,5-triazin-2-yl)-12,12-dimethyl-10,12-dihydro-10-azaindeno[2,1-b]fluoren-10-yl)-4'-(12,12-dimethyl-10,12-dihydro-10-azaindeno[2,1-b]fluoren-10-yl)biphenyl Step a): 4-(7-Bromo-12,12-dimethyl-10,12-dihydro-10-azaindeno[2,1-b]fluoren-10-yl)-4'-(12,12-dimethyl-10,12-dihydro-10-azaindeno-[2,1-b]fluoren-10-yl)biphenyl

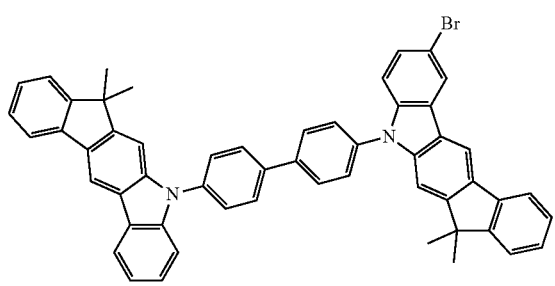 [SMILES: CC1(C)c2ccccc2-c2cc3c4ccccc4n(-c4ccc(-c5ccc(-n6c7ccc(Br)cc7c7cc8c(cc76)C(C)(C)c6ccccc6-8)cc5)cc4)c3cc21]

9.42 g (13.1 mmol) of 4,4'-bis(12,12-dimethyl-10,12-dihydro-10-azaindeno[2,1-b]fluoren-10-yl)biphenyl are initially introduced in 77 ml of THF. A solution of 2.36 g (13.2 mmol) of NBS in 25 ml of THF is subsequently added dropwise at −15° C. with exclusion of light, allowed to come to room temperature and stirred at this temperature for a further 4 h. 150 ml of water are subsequently added to the mixture, which is then extracted with CH$_2$Cl$_2$. The organic phase is dried over MgSO$_4$, and the solvents are removed in vacuo. The product is washed by stirring with hot ethanol and filtered off with suction. The yield is 7.5 g (9.4 mmol, 72%).

Step b): 4-(7-(4,4,5,5-Tetramethyl-1,3,2-dioxaborolan-2-yl)-12,12-dimethyl-10,12-dihydro-10-azaindeno[2,1-b]fluoren-10-yl)-4'-(12,12-dimethyl-10,12-dihydro-10-azaindeno[2,1-b]fluoren-10-yl)biphenyl

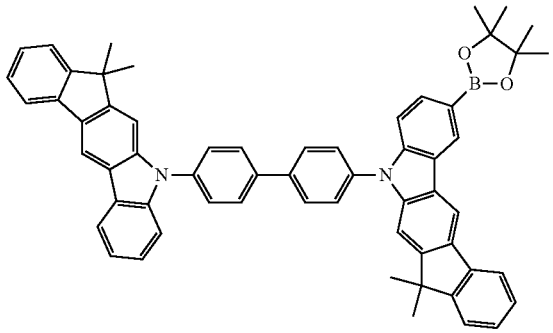 [SMILES: CC1(C)c2ccccc2-c2cc3c4ccccc4n(-c4ccc(-c5ccc(-n6c7ccc(B8OC(C)(C)C(C)(C)O8)cc7c7cc8c(cc76)C(C)(C)c6ccccc6-8)cc5)cc4)c3cc21]

7.1 g (9.0 mmol) of 4-(7-bromo-12,12-dimethyl-10,12-dihydro-10-azaindeno[2,1-b]fluoren-10-yl)-4'-(12,12-dimethyl-10,12-dihydro-10-azaindeno[2,1-b]fluoren-10-yl)biphenyl, 2.5 g (9.85 mmol) of bis(pinacolato)diborane and 2.6 g (26 mmol) of potassium acetate are suspended in 500 ml of dioxane. 0.22 g (0.27 mmol) of 1,1-bis(diphenylphosphino)ferrocenepalladium(II) dichloride complex with dichloromethane is added to this suspension. The reaction mixture is heated under reflux for 16 h. After cooling, the organic phase is separated off, washed three times with 150 ml of water and subsequently evaporated to dryness. The residue is recrystallised from toluene. The yield is 6.8 g (8 mmol, 90%).

Step c): 4-(7-(4,6-Diphenyl-1,3,5-triazin-2-yl)-12,12-dimethyl-10,12-dihydro-10-azaindeno[2,1-b]fluoren-10-yl)-4'-(12,12-dimethyl-10,12-dihydro-10-azaindeno[2,1-b]fluoren-10-yl)biphenyl

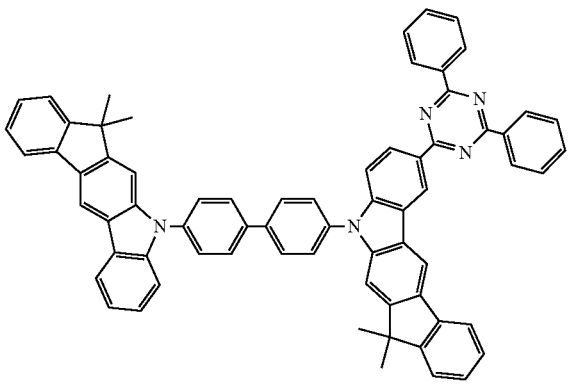 [SMILES: CC1(C)c2ccccc2-c2cc3c4ccccc4n(-c4ccc(-c5ccc(-n6c7ccc(-c8nc(-c9ccccc9)nc(-c9ccccc9)n8)cc7c7cc8c(cc76)C(C)(C)c6ccccc6-8)cc5)cc4)c3cc21]

6.0 g (7.0 mmol) of 4-(7-(4,4,5,5-tetramethyl-1,3,2-dioxaborolan-2-yl)-12,12-dimethyl-10,12-dihydro-10-azaindeno[2,1-b]fluoren-10-yl)-4'-(12,12-dimethyl-10,12-dihydro-10-azaindeno[2,1-b]fluoren-10-yl)biphenyl, 1.9 g (7.1 mmol) of 2-chloro-4,6-diphenyl-1,3,5-triazine and 0.83 g (7.8 mmol) of sodium carbonate are suspended in 400 ml of dioxane, 400 ml of toluene and 200 ml of water. 0.42 g (3.6 mmol) of Pd(PPh$_3$)$_4$ is added to this suspension. The reaction mixture is heated under reflux for 5 h. After cooling, the precipitated solid is filtered off with suction, washed with water and ethanol and dried. The residue is extracted with hot toluene, recrystallised from toluene and finally sublimed in a high vacuum. The yield after sublimation is 5.2 g (5 mmol, 77%) with a purity of 99.9%.

Example 42

7-Dibenzofuran-4-yl-10-(4,6-diphenyl-1,3,5-triazin-2-yl)-12,12-dimethyl-10,12-dihydro-10-azaindeno[2,1-b]fluorene Step a): 7-Dibenzofuran-4-yl-12,12-dimethyl-10,12-dihydro-10-azaindeno[2,1-b]fluorene

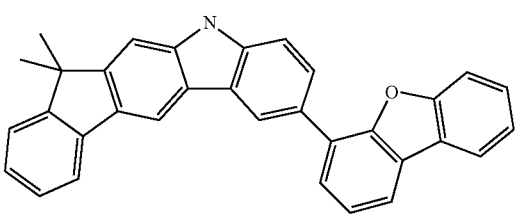 [SMILES: CC1(C)c2ccccc2-c2cc3c(cc21)[nH]c1ccc(-c2cccc4c2oc2ccccc24)cc13]

32 g (90.6 mmol) of 7-bromo-12,12-dimethyl-10,12-dihydro-10-azaindeno[2,1-b]fluorene, 19.9 g (94 mmol) of dibenzofuran-4-boronic acid and 164 ml of saturated NaHCO$_3$ solution are suspended in 1640 ml of toluene and 164 ml of ethanol. 1.9 g (1.6 mmol) of Pd(PPh)$_3$ are added to this suspension, and the reaction mixture is heated under reflux for 16 h. After cooling, the organic phase is separated off, filtered through silica gel, washed three times with 200 ml of water and subsequently evaporated to dryness. The yield is 26.7 g (59 mmol), corresponding to 65% of theory.

Step b): 7-Dibenzofuran-4-yl-10-(4,6-diphenyl-1,3,5-triazin-2-yl)-12,12-dimethyl-10,12-dihydro-10-azaindeno[2,1-b]fluorene

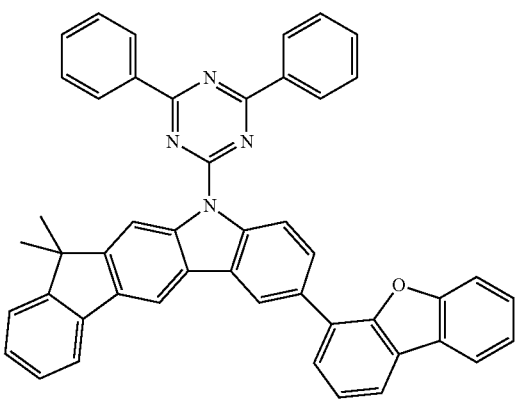 [SMILES: CC1(C)c2ccccc2-c2cc3c4cc(-c5cccc6c5oc5ccccc56)ccc4n(-c4nc(-c5ccccc5)nc(-c5ccccc5)n4)c3cc21]

16.6 g (58.78 mmol) of 7-dibenzofuran-4-yl-12,12-dimethyl-10,12-dihydro-10-azaindeno[2,1-b]fluorene are dissolved in 225 ml of dimethylformamide under a protective-gas atmosphere, and 2.8 g of 60% NaH in mineral oil (70 mmol) are added. After 1 h at room temperature, a solution of 2-chloro-4,6-diphenyl-1,3,5-triazine (18.6 g, 66.2 mmol) in 75 ml of dimethylformamide is added dropwise. The reaction mixture is stirred at room temperature for 12 h. After this time, the reaction mixture is poured onto ice and extracted three times with dichloromethane. The combined organic phases are dried over Na$_2$SO$_4$ and evaporated. The residue is extracted with hot toluene, recrystallised from dichloromethane/isopropanol and finally sublimed in a high vacuum, the purity is 99.9%. The yield is 18.3 g (27 mmol, 45.7%).

Example 43

10-[4-(3,6-Diphenylcarbazol-9-yl)-6-phenyl-1,3,5-triazin-2-yl]-12,12-dimethyl-10,12-dihydro-10-azaindeno[2,1-b]fluorene Step a): 9-(4-Chloro-6-phenyl-1,3,5-triazin-2-yl)-3,6-diphenyl-9H-carbazole

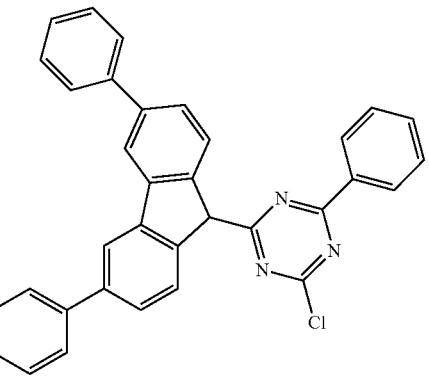

29.9 g (93.6 mmol) of 3,6-diphenyl-9H-carbazole are dissolved in 660 ml of THF under a protective-gas atmosphere, and 7.49 g of 60% NaH in mineral oil (187 mmol) are added. After 1 h at room temperature, a solution of 2,4-dichloro-6-phenyl-1,3,5-triazine (63.1 g, 279.3 mmol) in 300 ml of THF is added dropwise. The reaction mixture is stirred at room temperature for 12 h. After this time, the reaction mixture is poured onto ice and extracted three times with dichloromethane. The combined organic phases are dried over Na$_2$SO$_4$ and evaporated. The residue is extracted with hot toluene and recrystallised from dichloromethane/isopropanol. The yield is 28.4 g (56 mmol, 60%).

Step b): 10-[4-(3,6-Diphenylcarbazol-9-yl)-6-phenyl-1,3,5-triazin-2-yl]-12,12-dimethyl-10,12-dihydro-10-azaindeno[2,1-b]fluorene

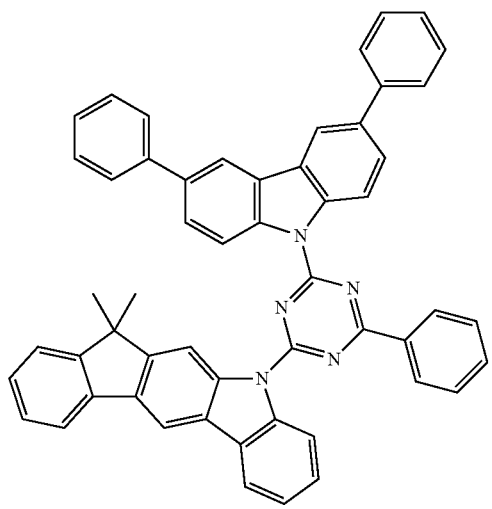 [SMILES: CC1(C)c2ccccc2-c2cc3c4ccccc4n(-c4nc(-c5ccccc5)nc(-n5c6ccc(-c7ccccc7)cc6c6cc(-c7ccccc7)ccc65)n4)c3cc21]

18.7 g (66.3 mmol) of 12,12-dimethyl-10,12-dihydro-10-azaindeno[2,1-b]fluorene are dissolved in 200 ml of dimethylformamide under a protective-gas atmosphere, and 5.3 g of 60% NaH in mineral oil (73 mmol) are added. After 1 h at room temperature, a solution of 9-(4-chloro-6-phenyl-1,3,5-triazin-2-yl)-3,6-diphenyl-9H-carbazole (40.5 g, 79.5 mmol) in 150 ml of dimethylformamide is added dropwise. The reaction mixture is stirred at room temperature for 12 h. After this time, the reaction mixture is poured onto ice and extracted three times with dichloromethane. The combined organic phases are dried over Na$_2$SO$_4$ and evaporated. The residue is extracted with hot toluene, recrystallised from dichloromethane/isopropanol and finally sublimed in a high vacuum, the purity is 99.9%. The yield is 21.4 g (28 mmol, 42%).

Example 44

Step a): Bis(9,9-dimethyl-9H-fluoren-2-yl)amine

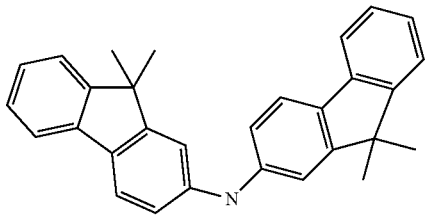 [SMILES: CC1(C)c2ccccc2-c2ccc(Nc3ccc4c(c3)C(C)(C)c3ccccc3-4)cc21]

81 g of 2-bromo-9,9-dimethyl-9H-fluorene (300 mmol), 93 g of 2-amino-9,9-dimethyl-9H-fluorene (444 mmol), 5 g of DPPF (9 mmol), 2 g of palladium(II) acetate and 86 g of sodium tert-butoxide (486 mmol) are heated at the boil for 18 h in 1.5 l of toluene under a protective-gas atmosphere. The mixture is subsequently partitioned between toluene and water, the organic phase is washed three times with water, dried over Na$_2$SO$_4$ and evaporated in a rotary evaporator.

The residue which remains is recrystallised from heptane/ethyl acetate. The yield is 93 g (231 mmol, 77%).

Step b): Reaction of bis(9,9-dimethyl-9H-fluoren-2-yl)amine with palladium

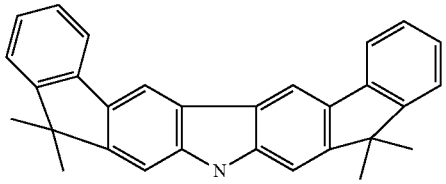 [SMILES: CC1(C)c2ccccc2-c2cc3c(cc21)[nH]c1cc2c(cc13)-c1ccccc1C2(C)C]

35 ml of pivalic acid are added to 10 g of (9,9-dimethyl-9H-fluoren-2-yl)phenylamine (35 mmol), 0.4 g of palladium (II) acetate (1.78 mmol) and 0.5 g of potassium carbonate (3.62 mmol), and the mixture is stirred at 120° C. for 9 h. After this time, 0.4 g of palladium(II) acetate (1.78 mmol) is added, and the mixture is stirred at 120° C. for a further 9 h. 200 ml of dichloromethane and 0.1 M Na$_2$CO$_3$ solution are then added. The mixture is partitioned between water and dichloromethane, the aqueous phase is extracted three times with dichloromethane, and the combined organic phases are dried over Na$_2$SO$_4$ and evaporated in a rotary evaporator. The residue is recrystallised from toluene/heptane. The yield is 5 g (5 mmol, 50%).

Step c): Reaction with diphenyl-1,3,5-triazine

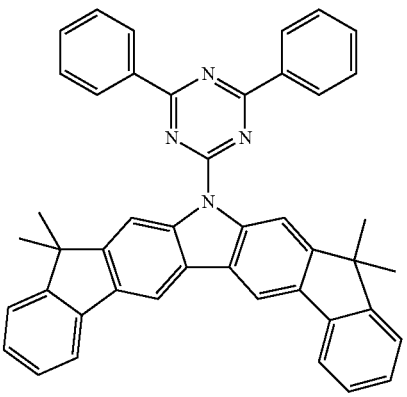 [SMILES: CC1(C)c2ccccc2-c2cc3c4cc5c(cc4n(-c4nc(-c6ccccc6)nc(-c6ccccc6)n4)c3cc21)C(C)(C)c1ccccc1-5]

25 g (62.5 mmol) of product b) are dissolved in 200 ml of dimethylformamide under a protective-gas atmosphere, and 7.7 g of 60% NaH in mineral oil (194 mmol) are added. After 1 h at room temperature, a solution of 2-chloro-4,6-diphenyl-1,3,5-triazine (25 g, 68 mmol) in 300 ml of dimethylformamide is added dropwise. The reaction mixture is stirred at room temperature for 12 h. After this time, the reaction mixture is poured onto ice and extracted three times with dichloromethane. The combined organic phases are dried over Na$_2$SO$_4$ and evaporated. The residue is extracted with hot toluene, recrystallised from dichloromethane/isopropanol and finally sublimed in a high vacuum, the purity is 99.9%. The yield is 17 g (27 mmol, 44%).

Example 45

Bis[3'-(10,10-dimethyl-10H-3,12-diazaindeno[2,1-b]fluoren-12-yl)biphenyl-3-yl]methanone Step a): 10,10-Dimethyl-10,12-dihydro-3,12-diazaindeno[2,1-b]fluorene

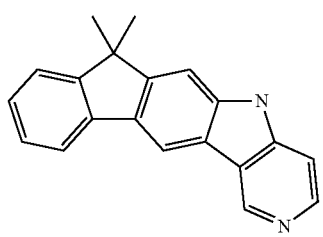 [SMILES: CC1(C)c2ccccc2-c2cc3c(cc21)[nH]c1ccncc13]

62.5 g of 2-bromo-9,9-dimethyl-9H-fluorene (230 mmol), 29.6 g of 3-chloropyridin-4-ylamine (230 mmol), 1.9 g (3.5 mmol) of 1,1-bis(diphenylphosphino)ferrocene, 0.6 g of palladium(II) acetate (2.8 mmol) and 57.2 g of sodium tert-butoxide (598 mmol) are heated at the boil for 18 h in 1.5 l of toluene under a protective-gas atmosphere. The mixture is subsequently partitioned between toluene and water, the organic phase is washed three times with water, dried over Na$_2$SO$_4$ and evaporated in a rotary evaporator. The residue of (3-chloropyridin-4-yl)-(9,9-dimethyl-9H-fluoren-2-yl)amine which remains is recrystallised from toluene/ethyl acetate. The yield is 66.4 g (207 mmol, 90%).

500 ml of dioxane are added to 42 g of (3-chloropyridin-4-yl)-(9,9-dimethyl-9H-fluoren-2-yl)amine (130 mmol), 1.46 g of palladium(II) acetate (6.5 mmol) and 75 g of sodium tert-butoxide (780 mmol), 7.8 ml of a 1 M solution of P(t-Bu)$_3$ in toluene (7.8 mmol), and the mixture is stirred at 105° C. under nitrogen for 24 h. 200 ml of dichloromethane and 0.1 M Na$_2$CO$_3$ solution are then added. The mixture is partitioned between water and dichloromethane, the aqueous phase is extracted three times with dichloromethane, the combined organic phases are dried over Na$_2$SO$_4$ and evaporated in a rotary evaporator. The residue is recrystallised from toluene/heptane. The yield is 18.5 g (65.1 mmol, 50%).

Step b): Bis(3'-bromobiphenyl-3-yl)methanone

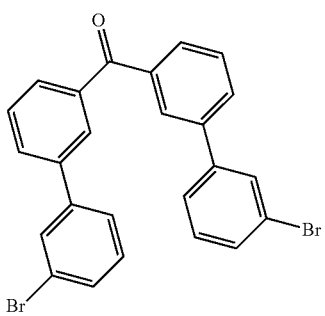 [SMILES: O=C(c1cccc(-c2cccc(Br)c2)c1)c1cccc(-c2cccc(Br)c2)c1]

The corresponding Grignard reagent is prepared from a solution of 31.5 g (101 mmol) of 3,3'-dibromobiphenyl, 1 ml of 1,2-dichloroethane and 30 ml of 1,2-dimethoxyethane in 300 ml of THF and 2.8 g (115 mmol) of magnesium at the boiling temperature. A solution of 26.06 g (101 mmol) of 3-bromo-3'-cyanobiphenyl in a mixture of 130 ml of THF and 130 ml of toluene is added dropwise to this Grignard solution at 0-5° C. over the course of 20 min. The mixture is subsequently heated under reflux for 16 h. After cooling, the reaction mixture is evaporated to dryness. The solid is taken up in 1100 ml of NMP and heated under reflux for 24 h with 40 ml of water and 5 ml of glacial acetic acid. A mixture of 600 ml of methanol and 600 ml of 1 N hydrochloric acid is added, and the precipitated solid is separated off by filtration and dried. The crude product is recrystallised three times from toluene/heptane. The yield, with a purity of >97% according to HPLC, is 34.8 g (70.7 mmol), corresponding to 70.1% of theory.

Step c): Bis[3'-(10,10-dimethyl-10H-3,12-diazaindeno[2,1-b]fluoren-12-yl)biphenyl-3-yl]methanone

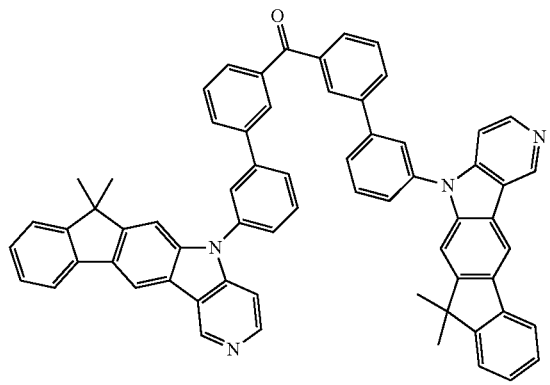 [SMILES: CC1(C)c2ccccc2-c2cc3c4cnccc4n(-c4cccc(-c5cccc(C(=O)c6cccc(-c7cccc(-n8c9ccncc9c9cc%10c(cc98)C(C)(C)c8ccccc8-%10)c7)c6)c5)c4)c3cc21]

11.6 g (23.5 mmol) of bis(3'-bromobiphenyl-3-yl)methanone, 13.36 g (47 mmol) of 10,10-dimethyl-10,12-dihydro-3,12-diazaindeno[2,1-b]fluorene and 29.2 g of Rb$_2$CO$_3$ are suspended in 250 ml of p-xylene. 0.95 g (4.2 mmol) of Pd(OAc)$_2$ and 12.6 ml of a 1 M tri-tert-butylphosphine solution are added to this suspension. The reaction mixture is heated under reflux for 24 h. After cooling, the organic phase is separated off, washed three times with 200 ml of water and subsequently evaporated to dryness. The residue is extracted with hot toluene and recrystallised three times from toluene and finally sublimed in a high vacuum, giving 10.56 g (14.7 mmol), corresponding to 50% of theory. The purity is 99.9%.

Example 46

[3'-(12,12-Dimethyl-12H-10-azaindeno[2,1-b]fluoren-10-yl)biphenyl-3-yl]phenylmethanone Step a): (3'-Bromobiphenyl-3-yl)phenylmethanone

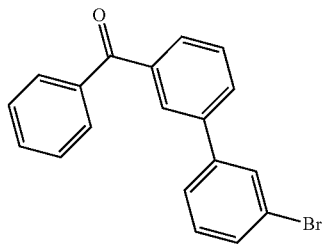 [SMILES: O=C(c1ccccc1)c1cccc(-c2cccc(Br)c2)c1]

The corresponding Grignard reagent is prepared from a solution of 31.5 g (101 mmol) of 3,3'-dibromobiphenyl and 1 ml of 1,2-dichloroethane in 30 ml of 1,2-dimethoxyethane and 300 ml of THF and 2.8 g (115 mmol) of magnesium at the boiling temperature. A solution of 10.4 g (101 mmol) of benzonitrile in a mixture of 130 ml of THF and 130 ml of toluene is added dropwise to this Grignard solution at 0-5° C. over the course of 20 min. The mixture is subsequently heated under reflux for 16 h. After cooling, the reaction mixture is evaporated to dryness. The solid is taken up in 1000 ml of NMP and heated under reflux for 12 h with 40 ml of water and 2 ml of glacial acetic acid. A mixture of 600 ml of methanol and 600 ml of 1 N hydrochloric acid is added, and the precipitated solid is separated off by filtration and dried. The crude product is recrystallised from toluene/heptane. The yield, with a purity of >98% according to HPLC, is 27.1 g (80.5 mmol), corresponding to 79.7% of theory.

Step b): [3'-(12,12-Dimethyl-12H-10-azaindeno[2,1-b]fluoren-10-yl)biphenyl-3-yl]phenylmethanone

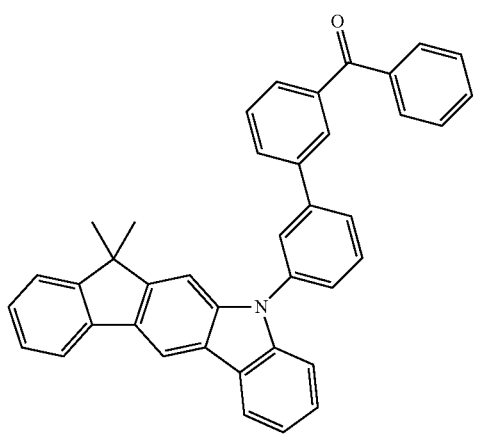 [SMILES: CC1(C)c2ccccc2-c2cc3c4ccccc4n(-c4cccc(-c5cccc(C(=O)c6ccccc6)c5)c4)c3cc21]

15.8 g (47 mmol) of (3'-bromobiphenyl-3-yl)phenylmethanone, 13.36 g (47 mmol) of 10,10-dimethyl-10,12-dihydro-3,12-diazaindeno[2,1-b]fluorene and 29.2 g of Rb₂CO₃ are suspended in 250 ml of p-xylene. 0.95 g (4.2 mmol) of Pd(OAc)₂ and 12.6 ml of a 1 M tri-tert-butylphosphine solution are added to this suspension. The reaction mixture is heated under reflux for 24 h. After cooling, the organic phase is separated off, washed three times with 150 ml of water and subsequently evaporated to dryness. The residue is extracted with hot toluene, recrystallised three times from toluene and finally sublimed in a high vacuum, giving 14.2 g (26.3 mmol), corresponding to 56% of theory. The purity is 99.9%.

Example 47

Bis[3'-(12,12-dimethyl-12H-10-azaindeno[2,1-b]fluoren-10-yl)biphenyl-3-yl]methanone

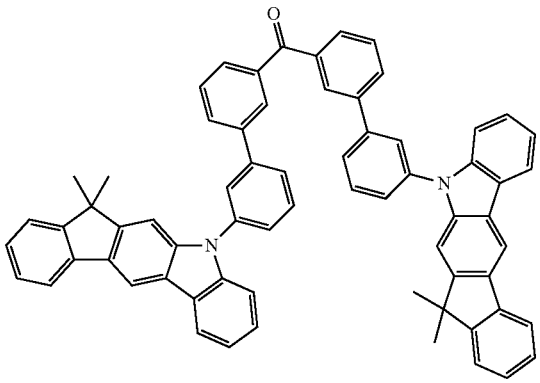 [SMILES: CC1(C)c2ccccc2-c2cc3c4ccccc4n(-c4cccc(-c5cccc(C(=O)c6cccc(-c7cccc(-n8c9ccccc9c9cc%10c(cc98)C(C)(C)c8ccccc8-%10)c7)c6)c5)c4)c3cc21]

11.6 g (23.5 mmol) of bis(3'-bromobiphenyl-3-yl)methanone, 13.36 g (47 mmol) of 12,12-dimethyl-10,12-dihydro-10-azaindeno[2,1-b]fluorene and 29.2 g of Rb₂CO₃ are suspended in 250 ml of p-xylene. 0.95 g (4.2 mmol) of Pd(OAc)₂ and 12.6 ml of a 1 M tri-tert-butylphosphine solution are added to this suspension. The reaction mixture is heated under reflux for 24 h. After cooling, the organic phase is separated off, washed three times with 200 ml of water and subsequently evaporated to dryness. The residue is extracted with hot toluene, recrystallised three times from toluene and finally sublimed in a high vacuum, giving 14.56 g (16.2 mmol), corresponding to 70% of theory. The purity is 99.9%.

Example 48

[3'-(12,12-Dimethyl-10-phenyl-10,12-dihydro-10-azaindeno[2,1-b]fluoren-7-yl)biphenyl-3-yl]phenylmethanone Step a): tert-Butyl 7-(3'-benzoylbiphenyl-3-yl)-12,12-dimethyl-12H-10-azaindeno[2,1-b]fluorene-10-carboxylate

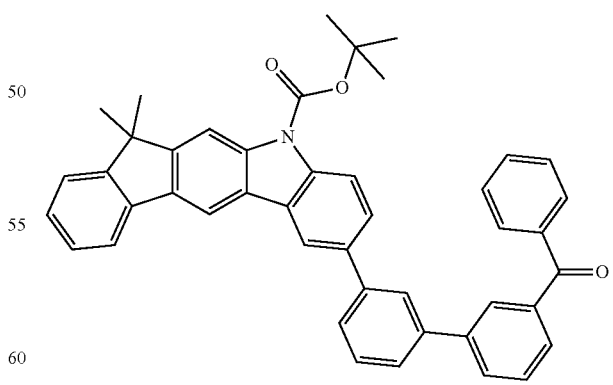

16.8 g (33.0 mmol) of tert-butyl 12,12-dimethyl-7-(4,4,5,5-tetramethyl-1,3,2-dioxaborolan-2-yl)-12H-10-azaindeno[2,1-b]fluorene-10-carboxylate, 13.4 g (40 mmol) of (3'-bromobiphenyl-3-yl)phenylmethanone and 11.6 g of sodium carbonate are suspended in 900 ml of dioxane, 900 ml of toluene and 400 ml of water. 4.2 g (3.6 mmol) of Pd(PPh$_3$)$_4$ are added to this suspension. The reaction mixture is heated under reflux for 7 h. After cooling, the precipitated solid is filtered off with suction and washed with water and ethanol and dried. The residue is extracted with hot toluene and recrystallised from toluene. Yield: 14.7 g (23 mmol), 70% of theory.

Step b): [3'-(12,12-Dimethyl-10-phenyl-10,12-di-hydro-10-azaindeno[2,1-b]fluoren-7-yl)biphenyl-3-yl]phenylmethanone

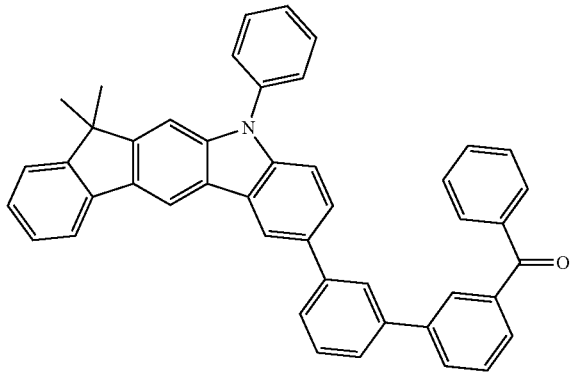 [SMILES: CC1(C)c2ccccc2-c2cc3c4cc(-c5cccc(-c6cccc(C(=O)c7ccccc7)c6)c5)ccc4n(-c4ccccc4)c3cc21]

12.8 g (20.1 mmol) of tert-butyl 7-(3'-benzoylbiphenyl-3-yl)-12,12-dimethyl-12H-10-azaindeno[2,1-b]fluorene-10-carboxylate are dissolved in 250 ml of dichloromethane and 3 ml of anisole, and 4.5 ml of trifluoroacetic acid are subsequently added. The mixture is stirred at 40° C. for 3 h and, when the reaction is complete, neutralised by means of ice-water and 20% NaOH solution. The mixture is extracted with dichloromethane, dried and purified by recrystallisation from toluene, giving 9.6 g (17.9 mmol) (89%) of the product as a solid.

9.6 g (17.9 mmol) of [3'-(12,12-dimethyl-10,12-dihydro-10-azaindeno[2,1-b]fluoren-7-yl)biphenyl-3-yl]phenylmethanone are dissolved in 300 ml of toluene with 3.14 g (20 mmol) of bromobenzene and degassed. 1.9 ml of tri-tert-butylphosphine solution (1 M in toluene), 214 mg (0.94 mmol) of Pd(OAc)$_2$ and 5.4 g (56.7 mmol) of NaOtBu are added, and the mixture is stirred under reflux for 7 h. The warm (45° C.) mixture is filtered through Alox B, washed with water, dried and evaporated. The crude product is extracted with toluene in a Soxhlet extractor and recrystallised from toluene/heptane, giving 7.4 g (12.1 mmol, 60%) of the product as a white solid. Finally, the product is sublimed in a high vacuum, the purity is 99.9%.

Example 49

Step a)

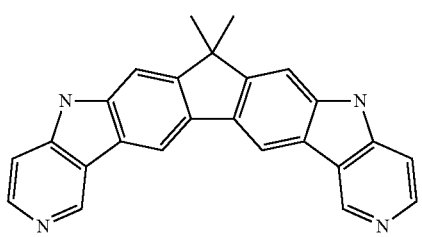 [SMILES: CC1(C)c2cc3[nH]c4ccncc4c3cc2-c2cc3c(cc21)[nH]c1ccncc13]

40.48 g of 2,7-dibromo-9,9-dimethyl-9H-fluorene (115 mmol), 29.6 g of 3-chloropyridin-4-ylamine (230 mmol), 1.91 g (3.5 mmol) of 1,1-bis(diphenylphosphino)ferrocene, 0.64 g of palladium(II) acetate (2.8 mmol) and 57.2 g of sodium tert-butoxide (598 mmol) are heated at the boil in 1.6 l of toluene under a protective-gas atmosphere for 24 h. The mixture is subsequently partitioned between toluene and water, the organic phase is washed three times with water, dried over Na$_2$SO$_4$ and evaporated in a rotary evaporator. The residue of N,N'-bis(3-chloropyridin-4-yl)-9,9-dimethyl-9H-fluorene-2,7-diamine is recrystallised from toluene/ethyl acetate. The yield is 36.4 g (81 mmol, 70.8%).

300 ml of dioxane are added to 29 g of N,N'-bis(3-chloropyridin-4-yl)-9,9-dimethyl-9H-fluorene-2,7-diamine (65 mmol), 0.73 g of palladium(II) acetate (3.25 mmol) and 37.5 g of sodium tert-butoxide (390 mmol), 3.9 ml of a 1 M solution of PBu-t$_3$ in toluene (3.9 mmol), and the mixture is stirred at 105° C. under nitrogen for 48 h. 100 ml of dichloromethane and 0.1 M Na$_2$CO$_3$ solution are then added. The mixture is partitioned between water and dichloromethane, the aqueous phase is extracted three times with dichloromethane, the combined organic phases are dried over Na$_2$SO$_4$ and evaporated in a rotary evaporator. The residue is recrystallised from toluene/heptane. The yield is 12.9 g (34.45 mmol, 53%).

Step b)

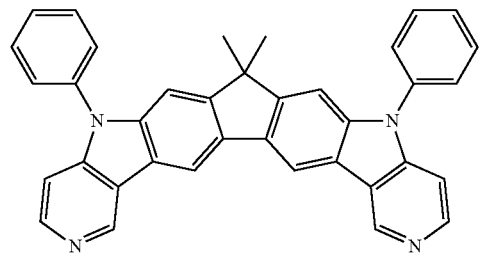 [SMILES: CC1(C)c2cc3c(cc2-c2cc4c5cnccc5n(-c5ccccc5)c4cc21)c1cnccc1n3-c1ccccc1]

5.21 g (13.9 mmol) of the product from step a) are dissolved in 500 ml of toluene with 4.39 ml (41.7 mmol) of bromobenzene and degassed. 1.94 ml (194 mmol/1 M in toluene) of tri-tert-butylphosphine, 249.8 mg of Pd(OAc)$_2$ and 4.01 g (41.7 mmol) of NaOt-Bu are added, and the mixture is stirred under reflux for 12 h. The warm (40° C.) mixture is filtered through Alox B (activity grade 1), washed with water, dried and evaporated. The crude product is extracted with heptane/toluene in a Soxhlet extractor, recrystallised from toluene, giving 4.75 g (9.2 mmol) (66%) of the product as a yellowish solid. The product is finally sublimed in a high vacuum, the purity is 99.9%.

Example 50

Step a)

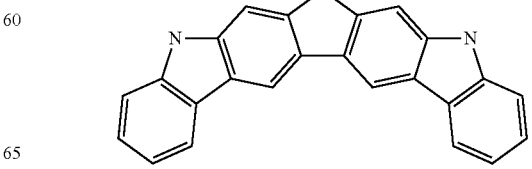

40.48 g of 2,7-dibromo-9,9-dimethyl-9H-fluorene (115 mmol), 21.4 g (21.5 ml) of aniline (230 mmol), 1.91 g (3.5 mmol) of 1,1-bis(diphenylphosphino)ferrocene, 0.64 g of palladium(II) acetate (2.8 mmol) and 57.2 g of sodium tert-butoxide (598 mmol) are heated at the boil in 1.3 l of toluene under a protective-gas atmosphere for 20 h. The mixture is subsequently partitioned between toluene and water, the organic phase is washed three times with water, dried over Na$_2$SO$_4$ and evaporated in a rotary evaporator. The residue of N,N'-bis(2-chlorophenyl)-9,9-dimethyl-9H-fluorene-2,7-diamine which remains is recrystallised from toluene/ethyl acetate. The yield is 32.5 g (73 mmol, 63.5%).

300 ml of dioxane are added to 28.9 g of N,N'-bis(2-chlorophenyl)-9,9-dimethyl-9H-fluorene-2,7-diamine (65 mmol), 0.73 g of palladium(II) acetate (3.25 mmol) and 37.5 g of sodium tert-butoxide (390 mmol), 3.9 ml of a 1 M solution of P(t-Bu)$_3$ in toluene (3.9 mmol), and the mixture is stirred at 105° C. under nitrogen for 48 h. 100 ml of dichloromethane and 0.1 M Na$_2$CO$_3$ solution are then added. The mixture is partitioned between water and dichloromethane, the aqueous phase is extracted three times with dichloromethane, the combined organic phases are dried over Na$_2$SO$_4$ and evaporated in a rotary evaporator. The residue is recrystallised from toluene/heptane. The yield is 7.9 g (21.32 mmol, 57.3%).

Step b

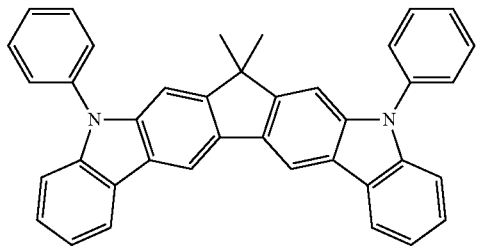 [SMILES: CC1(C)c2cc3c(cc2-c2cc4c5ccccc5n(-c5ccccc5)c4cc21)c1ccccc1n3-c1ccccc1]

5.6 g (15 mmol) of the product from step a) are dissolved in 300 ml of toluene with 4.39 ml (41.7 mmol) of bromobenzene and degassed. 1.94 ml (1.94 mmol/1 M in toluene) of tri-tert-butylphosphine, 252 mg of Pd(OAc)$_2$ and 4.1 g (41.7 mmol) of NaOt-Bu are added, and the mixture is stirred under reflux for 10 h. The mixture is filtered through Alox B (activity grade 1), washed with water, dried and evaporated. The crude product is extracted with toluene in a Soxhlet extractor, recrystallised from toluene/heptane, giving 5.7 g (10.9 mmol, 72.5%) of the product as a white solid. Finally, the product is sublimed in a high vacuum, the purity is 99.9%.

Example 51

Step a)

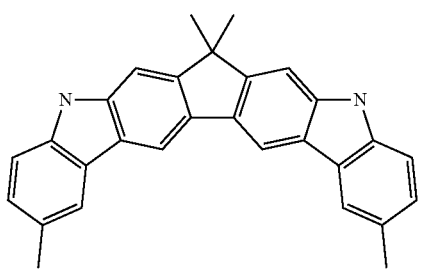 [SMILES: Cc1ccc2[nH]c3cc4c(cc3c2c1)-c1cc2c(cc1C4(C)C)[nH]c1ccc(C)cc12]

40.48 g of 2,7-dibromo-9,9-dimethyl-9H-fluorene (115 mmol), 24.7 g of p-toluidine (230 mmol), 1.91 g (3.5 mmol) of 1,1-bis(diphenylphosphino)ferrocene, 0.64 g of palladium(II) acetate (2.8 mmol) and 57.2 g of sodium tert-butoxide (598 mmol) are heated at the boil in 1.3 l of toluene under a protective-gas atmosphere for 20 h. The mixture is subsequently partitioned between toluene and water, the organic phase is washed three times with water and dried over Na$_2$SO$_4$ and evaporated in a rotary evaporator. The residue of N,N'-bis(2-chloro-4-methylphenyl)-9,9-dimethyl-9H-fluorene-2,7-diamine which remains is recrystallised from toluene/EtOH. The yield is 29.95 g (63 mmol, 63.5%).

300 ml of dioxane are added to 2.95 g of N,N'-bis(2-chlorophenyl)-9,9-dimethyl-9H-fluorene-2,7-diamine (63 mmol), 0.73 g of palladium(II) acetate (3.25 mmol) and 37.5 g of sodium tert-butoxide (390 mmol), 3.9 ml of a 1 M solution of P(t-Bu)$_3$ in toluene (3.9 mmol), and the mixture is stirred at 105° C. under nitrogen for 48 h. 100 ml of dichloromethane and 0.1 M Na$_2$CO$_3$ solution are then added. The mixture is partitioned between water and dichloromethane, the aqueous phase is extracted three times with dichloromethane, the combined organic phases are dried over Na$_2$SO$_4$ and evaporated in a rotary evaporator. The residue is recrystallised from toluene/heptane. The yield is 15.1 g (37.5 mmol, 59.5%).

Step b)

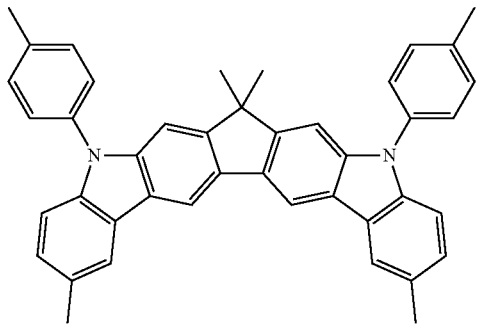 [SMILES: Cc1ccc(-n2c3ccc(C)cc3c3cc4c(cc32)C(C)(C)c2cc3c(cc2-4)c2cc(C)ccc2n3-c2ccc(C)cc2)cc1]

6.8 g (17 mmol) of the product from step a) are dissolved in 300 ml of toluene with 4.4 ml (41.7 mmol) of 4-methylbromobenzene and degassed. 1.94 ml (1.94 mmol/1 M in toluene) of tri-tert-butylphosphine, 252 mg of Pd(OAc)$_2$ and 4.1 g (41.7 mmol) of NaOBu-t are added, and the mixture is stirred under reflux for 10 h. The mixture is filtered through Alox B (activity grade 1), washed with water, dried and evaporated. The crude product is extracted with toluene in a Soxhlet extractor, recrystallised from toluene/heptane, giving 4.8 g (8.3 mmol, 49%) of the product as a white solid. Finally, the product is sublimed in a high vacuum, the purity is 99.9%.

Example 52

Bisbiphenyl-4-yl-[4'-(12,12-dimethyl-12H-10-azaindeno[2,1-b]fluoren-10-yl)biphenyl-4-yl]amine Step a): 10-(4'-Bromobiphenyl-4-yl)-12,12-dimethyl-10,12-dihydro-10-azaindeno[2,1-b]fluorene

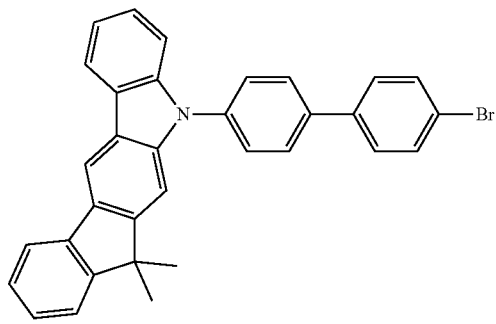 [SMILES: CC1(C)c2ccccc2-c2cc3c4ccccc4n(-c4ccc(-c5ccc(Br)cc5)cc4)c3cc21]

20 g (70.58 mmol) of 12,12-dimethyl-10,12-dihydro-10-azaindeno[2,1-b]fluorene and 33 g (105.87 mmol) of 4,4'-dibromobiphenyl are dissolved in toluene and degassed by introduction of a protective gas. 4.94 ml (4.94 mmol/1 M solution in toluene) of tri-tert-butylphosphine, 633.8 mg (2.82 mmol) of Pd(OAc)$_2$ and 10.2 g (105.87 mmol) of NaOtBu are subsequently added. The solids are degassed in advance, the reaction mixture is subsequently degassed and then stirred under reflux for 5 h. The warm reaction solution is filtered through Alox B (activity grade 1), washed with water, dried and evaporated. Crystallisation from toluene gives 15.6 g (30.4 mmol) (43%) of the product as a white solid.

Step b): Bisbiphenyl-4-yl-[4'-(12,12-dimethyl-12H-10-azaindeno[2,1-b]fluoren-10-yl)biphenyl-4-yl]amine

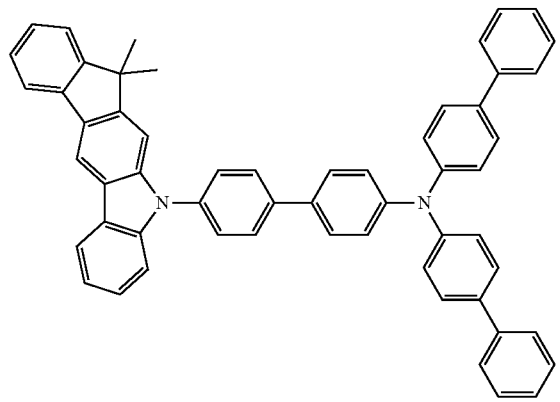 [SMILES: CC1(C)c2ccccc2-c2cc3c4ccccc4n(-c4ccc(-c5ccc(N(c6ccc(-c7ccccc7)cc6)c6ccc(-c7ccccc7)cc6)cc5)cc4)c3cc21]

10 g (19.4 mmol) of 10-(4'-bromobiphenyl-4-yl)-12,12-dimethyl-10,12-dihydro-10-azaindeno[2,1-b]fluorene are dissolved in 300 ml of toluene with 9.6 g (30 mmol) of bis(4-biphenylyl)amine and degassed. 1.94 ml (1.94 mmol/1 M in toluene) of tri-tert-butylphosphine, 252 mg of Pd(OAc)$_2$ and 4.1 g (41.7 mmol) of NaOt-Bu are added, and the mixture is stirred under reflux for 10 h. The mixture is filtered through Alox B (activity grade 1), washed with water, dried and evaporated. The crude product is extracted with toluene in a Soxhlet extractor, recrystallised from toluene/heptane, giving 6.7 g (8.9 mmol, 46%) of the product as a yellow solid. Finally, the product is sublimed in a high vacuum, the purity is 99.9%.

Example 53

Step a):
2,4-Bis(3-bromophenyl)-6-phenyl-1,3,5-triazine

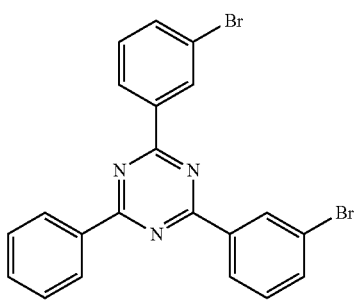 [SMILES: Brc1cccc(-c2nc(-c3ccccc3)nc(-c3cccc(Br)c3)n2)c1]

49 ml (392 mmol) of benzoyl chloride, 52.3 g (392 mmol) of AlCl$_3$ and 8.5 ml of thionyl chloride are initially introduced in 500 ml of 1,2-dichlorobenzene under a protective-gas atmosphere. 150 g (824 mmol) of bromobenzonitrile, dissolved in 300 ml of 1,2-dichlorobenzene, are added dropwise to this solution at room temperature via a dropping funnel, the mixture is subsequently stirred at 100° C. for 1 h, then at 40° C. for 18 h. After this time, 1.5 l of Mesh are added to the reaction mixture, and the residue is separated off. The residue is washed by stirring with hot Mesh, giving 59 g (126 mmol) (32%) of the product.

Step b): Reaction with diphenyl-1,3,5-triazine

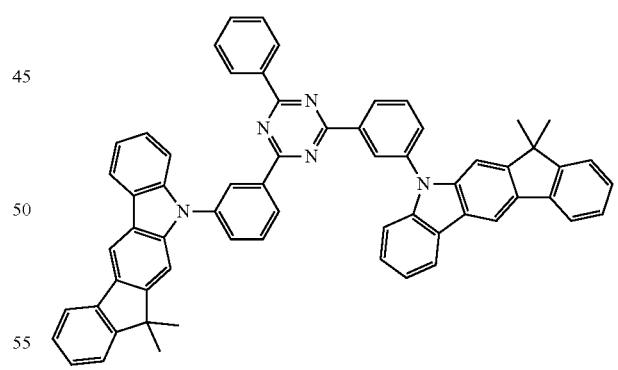

10.9 g (23.5 mmol) of 2,4-bis(3-bromophenyl)-6-phenyl-1,3,5-triazine, 13.3 g (47 mmol) of 12,12-dimethyl-10,12-dihydro-10-azaindeno[2,1-b]-fluorene and 29.2 g of Rb$_2$CO$_3$ are suspended in 250 ml of p-xylene. 0.95 g (4.2 mmol) of Pd(OAc)$_2$ and 12.6 ml of a 1 M tri-tert-butylphosphine solution are added to this suspension. The reaction mixture is heated under reflux for 24 h. After cooling, the organic phase is separated off, washed three times with 200 ml of water and evaporated to dryness. The residue is extracted with hot toluene and recrystallised three times from toluene and finally sublimed in a high vacuum, giving 13.1 g (15 mmol), corresponding to 53% of theory. The purity is 99.9%.

Example 54

Step a): (3-Bromo-9H-fluoren-2-yl)diphenylamine

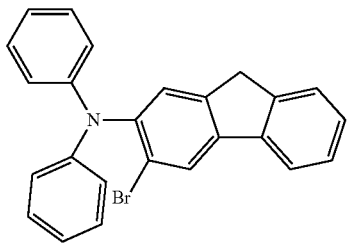 [SMILES: Brc1cc2c(cc1N(c1ccccc1)c1ccccc1)Cc1ccccc1-2]

8.0 g (42.2 mmol) of copper(I) iodide and 11.7 ml (97.5 mmol) of trans-cyclohexanediamine are added to a vigorously stirred suspension of 47.7 g (234 mmol) of iodobenzene, 26 g (100 mmol) of 3-bromo-9H-fluoren-2-ylamine and 416.4 g (1961 mmol) of potassium phosphate in 1170 ml of dioxane, and the mixture is heated under reflux for 16 h. After cooling, the precipitated solid is filtered off with suction, washed three times with 50 ml of toluene, three times with 50 ml of ethanol:water (1:1, v:v) and three times with 100 ml of ethanol. Yield: 33 g (80 mmol), 80%.

Step b): 10-Phenyl-10,12-dihydro-10-azaindeno[2,1-b]fluorene

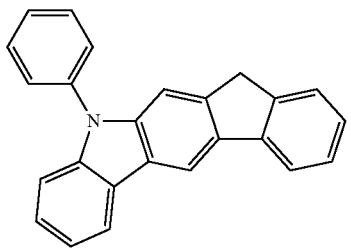 [SMILES: c1ccc(-n2c3ccccc3c3cc4c(cc32)Cc2ccccc2-4)cc1]

35 ml of pivalic acid are added to 14.4 g (35 mmol) of (3-bromo-9H-fluoren-2-yl)diphenylamine, 0.4 g of palladium(II) acetate (1.78 mmol) and 0.5 g of potassium carbonate (3.62 mmol), and the mixture is stirred at 120° C. for 9 h. After this time, 0.4 g of palladium(II) acetate (1.78 mmol) is added, and the mixture is stirred at 120° C. for a further 9 h. 200 ml of dichloromethane and 0.1 M Na$_2$CO$_3$ solution are then added. The mixture is partitioned between water and dichloromethane, the aqueous phase is extracted three times with dichloromethane, the combined organic phases are dried over Na$_2$SO$_4$ and evaporated in a rotary evaporator. The residue is recrystallised from toluene/heptane. The yield is 4.7 g (14 mmol, 42%).

Step c): Reaction with chloro-4,6-diphenyl-1,3,5-triazine

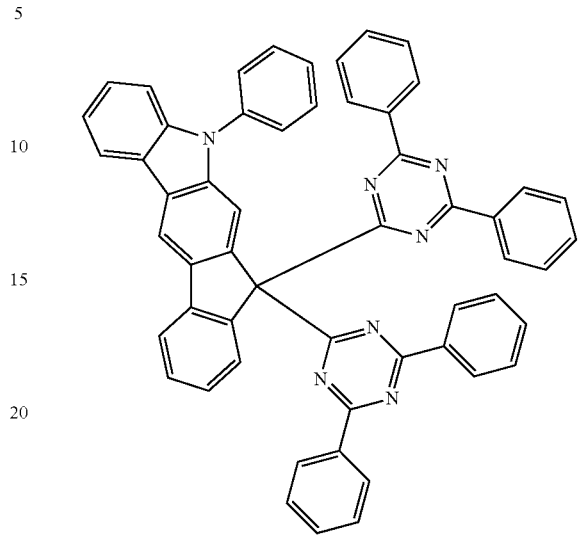

31.4 g (95 mmol) of 10-phenyl-10,12-dihydro-10-azaindeno[2,1-b]fluorene are dissolved in 1500 ml of dry THF, 420 ml (840 mmol) of a 2 M solution of n-butyllithium in cyclohexane are added dropwise at −70° C., after 1 h 63.4 g (237 mmol) of 2-chloro-4,6-diphenyl-1,3,5-triazine, dissolved in 800 ml of dry THF, are added dropwise, the mixture is warmed to room temperature over the course of 1 h, the solvent is removed, the residue is extracted with hot toluene, recrystallised from toluene and finally sublimed in a high vacuum. Yield: 53 g (68 mmol), 72.0%, purity 99.9% (HPLC).

Example 55

Production of Vacuum-Evaporated OLEDs

Vacuum-evaporated OLEDs according to the invention and OLEDs in accordance with the prior art are produced by a general process in accordance with WO 2004/058911, which is adapted to the circumstances described here (layer-thickness variation, materials used).

The data for various OLEDs are presented in Examples C1 to E106 below (see Tables 2 and 3). Glass plates coated with structured ITO (indium tin oxide) in a thickness of 150 nm are coated with 20 nm of PEDOT (poly-(3,4-ethylene-dioxy-2,5-thiophene), spin-coated from water; purchased from H. C. Starck, Goslar, Germany) for improved processing. These coated glass plates form the substrates to which the OLEDs are applied. The OLEDs have in principle the following layer structure: substrate/optional hole-injection layer (HIL)/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 2. The materials required for the production of the OLEDs are shown in Table 4.

The materials are applied by thermal vapour deposition in a vacuum chamber. The emission layer here always consists of at least one matrix material (host material) and an emitting dopant (emitter), which is admixed with the matrix material or materials in a certain proportion by volume by co-evaporation. An expression such as ST1:CBP:TER1 (55%:35%:10%) here means that the material ST1 is present in the layer in a proportion by volume of 55%, CBP is present in a proportion by volume of 35% and TER1 is present in a proportion by volume of 10%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of luminous density, calculated from current-voltage-luminous density characteristic lines (IUL characteristic lines), and the lifetime are determined. The lifetime is defined as the time after which the luminous density has dropped from a certain initial luminous density to a certain proportion. The expression LD50 means that the lifetime given is the time at which the luminous density has dropped to 50% of the initial luminous density, i.e. from, for example, 4000 $cd/m^2$ to 2000 $cd/m^2$. The values for the lifetime can be converted into a figure for other initial luminous densities with the aid of conversion formulae known to the person skilled in the art. The lifetime for an initial luminous density of 1000 $cd/m^2$ is a usual expression here.

The data for the various OLEDs are summarised in Table 3. Examples C1-C22 are comparative examples in accordance with the prior art, Examples E1-E106 show data for OLEDs in which materials according to the invention are employed.

Some of the examples are explained in greater detail below in order to illustrate the advantages of the compounds according to the invention. However, it should be pointed out that this only represents a selection of the results shown in Table 3. As can be seen from the table, significant improvements over the prior art are also achieved on use of the compounds according to the invention that are not described in greater detail, in some cases in all parameters, but in some cases only an improvement in the efficiency or voltage or lifetime is observed. However, even the improvement of one of the said parameters represents a significant advance.

Use of Compounds According to the Invention as Electron-Transport Material

OLEDs C1-C3, C9 are comparative examples in which the materials $Alq_3$, ETM1 and ST1 in accordance with the prior art are employed as electron-transport materials. The emitters used are the blue-emitting material D1 and the green-emitting materials D2 and TEG1, which are doped into matrix materials H1, H2 and H4 respectively.

The blue-emitting OLEDs C1, C2, E1, E3 and E5 exhibit a comparable lifetime of about 150 h at an initial luminance of 6000 $cd/m^2$. This corresponds to about 5500 h at an initial luminance of 1000 $cd/m^2$ if the conversion formulae known to the person skilled in the art are used as the basis. The green-emitting OLEDs C3 and E2 exhibit a comparable lifetime of about 470 h at an initial luminance of 25,000 $cd/m^2$, which corresponds to a lifetime of about 300,000 h at 1000 $cd/m^2$.

OLEDs E1-E3 and E5 comprise the compound H4 or H7 according to the invention as electron-transport material. It can be seen that the use of H4 enables a significant increase in the efficiency and an improvement in the operating voltage to be achieved. If OLEDs C1 and E1 or C3 and E2 are compared, it can be seen that the use of H4 improves the operating voltage by 0.8 V in the case of green emission and by 2.1 V in the case of blue emission. Together with the significant increase in the external quantum efficiency (from 5% to 6.3% in the case of green emission and from 4.2% to 6.7% in the case of blue emission), a considerable improvement in the power efficiency by a factor of 1.5 in the case of green emission and 2.5 in the case of blue emission is obtained.

The use of a mixed H4:LiQ layer in the ratio 50:50% by vol. also gives rise to a significant improvement compared with the prior art. On use of H4 in blue-emitting OLEDs, an operating voltage which is 0.6 V lower, an improved external quantum efficiency (from 6.3% to 7.2%) and thus a significantly improved power efficiency are obtained compared with ETM1. The increase here is about 30% (comparison of Ex. E3 with Ex. C2).

On use of an emission layer comprising the green-emitting phosphorescent dopant TEG1, a significantly improved lifetime at the same time as a slightly reduced power efficiency is obtained through the use of compound H7 according to the invention as electron-transport layer and LiQ as electron-injection layer (Examples C9 and E6).

The use of compounds according to the invention in the electron-transport layer of OLEDs thus enables significant increases to be achieved with respect to operating voltage, external quantum efficiency and thus especially also power efficiency. Furthermore, improved lifetimes are obtained in the case of phosphorescent dopants.

Use of Compounds According to the Invention as Hole-Transport or Electron-Blocking Materials Furthermore, the materials according to the invention can advantageously be employed on the hole-transport side of OLEDs, more precisely as hole-transport or electron-blocking materials. This is shown with reference to examples E4, E7-E15 and E74-77. Comparative Examples C1-C3, C6, C9, C12 und C20 in accordance with the prior art comprise the material HTM1 or SpNPB as hole-transport material and NPB or EBM1 as electron-blocking material.

If Example E4 is compared with Example C3, it can be seen that the operating voltage can be reduced by 0.5 V through the use of material HTM2 according to the invention in the hole-transport layer, which, in combination with the slightly improved quantum efficiency, results in an improvement in the power efficiency from 10.7 lm/W to 12.1 lm/W, i.e. about 15%.

If HTM3 is used as electron-blocking material, a slight improvement in the operating voltage and the power efficiency is likewise achieved compared with NPB (comparison of Ex. E7 with Ex. C2 or Ex. E8 with Ex. V3). However, it is much more important that the lifetime can be increased to about 7400 h at 1000 $cd/m^2$, i.e. by about 40%, through the use of HTM3 compared with NPB in the case of blue emission (Ex. E7). In the case of green emission, the improvement in the lifetime is somewhat less, with an increase of about 25% being obtained, corresponding to a lifetime of about 375,000 h for Example E8, Similar improvements are seen on use of HTM5 as electron-blocking material (E14 and E15).

In phosphorescent OLEDs, the compounds according to the invention exhibit, in particular, a significant improvement in the power efficiency of up to 25%, with the lifetime likewise being improved slightly (Examples C9 and E11 or E15). In particular, it should be mentioned that compound HTM4 can also be used as a single layer, which significantly reduces the processing complexity. In this case, the power efficiency increases by almost 15%, while the lifetime remains approximately the same compared with the prior art (Examples C9 and E12).

The use of compounds according to the invention on the hole-transport side of OLEDs thus produces significant improvements with respect to operating voltage, power efficiency, lifetime and processing complexity.

Use of Compounds According to the Invention as Matrix Materials in Phosphorescent OLEDs The compounds according to the invention can furthermore be employed as matrix materials (host materials) for phosphorescent dopants. Compounds H4-H27, H31-H42 and H44-H48 are used here as individual materials or also in combination with CBP, Compounds ST1 and Ket1 are used as comparison in accordance with the prior art. OLEDs comprising the green-emitting dopant TEG1 and the red-emitting dopants TER1 and TER2 are compared.

The use of the compounds according to the invention gives rise to significant improvements with respect to efficiency, operating voltage and lifetime compared with the use of ST1 or Ket1 in accordance with the prior art (see Table 3). In particular, the increase in the power efficiency at the same time as the improvement in the lifetime should be emphasised, since the energy consumption plays an important role, in particular, in mobile devices. An improvement of just 10% can be regarded as a significant increase here.

Thus, use of the red-phosphorescent dopants TER1 and TER2 in combination with H4 as matrix material produces a reduction in the operating voltage of up to 1.7 V, an increase in the current efficiency of about 5% and thus a significant increase in the power efficiency of about 45%. At the same time, an increase of almost 30% in the lifetime (comparison of Ex. C5 with Ex. E17) is obtained. Also on use of two matrix materials, compound H4 exhibits significant advantages over ST1 in accordance with the prior art (comparison of Ex. C6 with Ex. E18). The improvement in the lifetime here is 20%, while the power efficiency is increased by about 15%.

Even more significantly greater improvements can be achieved through the use of compounds according to the invention in components comprising green-phosphorescent dopants. Although compound ST1 in accordance with the prior art already gives rise to good efficiencies of up to 37 lm/W, 55 cd/A and a lifetime of 27,000 h (Ex. C7 and C8), the use of compound H4 enables the power efficiency to be increased to 50 lm/W (Ex. E20). The best lifetime achieved is 51,000 h on use of H11 with ST1 as hole blocker (Ex. E33) or 47,000 h without a hole blacker (Ex. E34). It should be emphasised that Ex. E33 with the best lifetime has a power efficiency which is more than 40% improved compared with the prior art.

The use of an electron-transport layer consisting of ST1 and an LiQ electron-injection layer with a thickness of 3 nm in combination with material H4 as matrix material (Ex. E26) enables an extremely high power efficiency of 59 lm/W to be achieved, where the lifetime of 30,000 h is still greater than the best value of OLEDs in accordance with the prior art (27,000 h, Ex. C7).

On use as matrix materials in phosphorescent OLEDs, the materials according to the invention thus give rise to significant improvements compared with the prior art in all parameters, especially with respect to lifetime and power efficiency. The large improvement in the power efficiency on use of materials according to the invention is attributable, in particular, to the significant improvement in the operating voltage.

Use of Compounds According to the Invention as Component in Mixed Matrix Systems Mixed matrix systems, i.e. OLEDs having an emission layer consisting of three or more components, in some cases exhibit significant advantages over systems comprising single-matrix materials. The compounds according to the invention can also profitably be employed in systems of this type. Compared with mixed matrix components in accordance with the prior art, significant improvements arise with respect to efficiency, voltage and lifetime. The compounds used in accordance with the prior art are the materials CBP, TCTA and FTPh (see Table 4). The corresponding OLEDs are denoted by C6, C10 and C13-C18. The materials according to the invention employed are compounds H17, H28-H30 and H43 in combination with matrix materials ST1, Ket1 and DAP1. The corresponding OLEDs are denoted by E60-E72 and E78.

Firstly, mixed matrix systems comprising the green-emitting dopant TEG1 are compared. On replacement of CBP or TCTA with compounds H28, H29 and H30 according to the invention (cf. Examples E60-E63 with C10 or C18), an improvement in the operating voltage by 0.9 V, an increase in the power efficiency by about 30% and an increase in the lifetime by 30% are obtained on comparison of the best OLED in accordance with the prior art (C10) with the worst OLED comprising a compound according to the invention (E61). The OLED comprising H30 (E63) even exhibits an improvement by 1.1 V in the operating voltage, about 60% in the power efficiency and 60% in the lifetime. Similar improvements also arise if matrix materials Ket1 and DAP1 are employed instead of ST1 (cf. Examples C13-C17 and E64-E68).

In red-emitting mixed matrix systems, significant improvements are likewise obtained (cf. Example C6 with E69-E72). An example which may be mentioned here is the use of the pyridine-substituted compound H17. On replacement of CBP with H17, an improvement in the voltage by 0.8 V, an increase in the power efficiency by about 30% and an increase in the lifetime by about 60% are obtained (cf, Example C6 with E72).

The use of materials according to the invention in mixed matrix systems thus produces significant improvements with respect to voltage, efficiency and especially also lifetime of the OLEDs. These improvements can be achieved in combination with very different classes of matrix material (ketones Ket1 spiro-triazines ST1, diazaphospholes DAP1). It can thus be assumed that similar improvements can also be achieved by combination of the compounds according to the invention with other classes of material.

| Ex. | HIL thickness | HTL thickness | IL thickness | EBL thickness | EML thickness | HBL thickness | ETL thickness | EIL thickness |
|---|---|---|---|---|---|---|---|---|
| C1 | HIL1 5 nm | HTM1 140 nm | — | NPB 20 nm | H1:D1 (95%:5%) 30 nm | — | Alq$_3$ 20 nm | LiF 1 nm |
| C2 | HIL1 5 nm | HTM1 140 nm | — | NPB 20 nm | H1:D1 (95%:5%) 30 nm | — | ETM1:LiQ (50%:50%) 20 nm | — |

-continued

| Ex. | HIL thickness | HTL thickness | IL thickness | EBL thickness | EML thickness | HBL thickness | ETL thickness | EIL thickness |
|---|---|---|---|---|---|---|---|---|
| C3 | HIL1 5 nm | HTM1 110 nm | — | NPB 20 nm | H2:D2 (90%:10%) 30 nm | — | Alq$_3$ 20 nm | LiF 1 nm |
| C4 | — | HTM1 20 nm | — | NPB 20 nm | ST1:TER1 (85%:15%) 30 nm | — | Alq$_3$ 20 nm | LiF 1 nm |
| C5 | — | HTM1 20 nm | — | NPB 20 nm | ST1:TER2 (85%:15%) 30 nm | — | Alq$_3$ 20 nm | LiF 1 nm |
| C6 | — | HTM1 20 nm | — | NPB 20 nm | ST1:CBP:TER1 (45%:45%:10%) 30 nm | ST1 10 nm | Alq$_3$ 20 nm | LiF 1 nm |
| C7 | — | HTM1 160 nm | — | EBM1 20 nm | ST1:TEG1 (90%:10%) 30 nm | ST1 10 nm | ETM1:LiQ (50%:50%) 30 nm | — |
| C8 | — | HTM1 160 nm | — | EBM1 20 nm | ST1:TEG1 (90%:10%) 30 nm | — | ETM1:LiQ (50%:50%) 40 nm | — |
| C9 | — | HTM1 70 nm | HIL1 5 nm | EBM1 90 nm | H4:TEG1 (85%:15%) 30 nm | — | ST1:LiQ (50%:50%) 40 nm | — |
| C10 | — | HTM1 70 nm | HIL1 5 nm | EBM1 90 nm | ST1:CBP:TEG1 (30%:60%:10%) 30 nm | ST1 10 nm | ST1:LiQ (50%:50%) 30 nm | — |
| C11 | — | HTM1 70 nm | HIL1 5 nm | EBM1 90 nm | ST1:TEG1 (90%:10%) 30 nm | ST1 10 nm | ST1:LiQ (50%:50%) 30 nm | — |
| C12 | — | HTM1 70 nm | HIL1 5 nm | EBM1 90 nm | ST1:TEG1 (90%:10%) 30 nm | — | ST1:LiQ (50%:50%) 40 nm | — |
| C13 | HIL1 20 nm | — | — | EBM1 20 nm | Ket1:FTPh:TEG1 (30%:60%:10%) 30 nm | Ket1 10 nm | ETM2 20 nm | LiF 1 nm |
| C14 | HIL1 20 nm | — | — | EBM1 20 nm | Ket1:FTPh:TEG1 (60%:30%:10%) 30 nm | Ket1 10 nm | ETM2 20 nm | LiF 1 nm |
| C15 | HIL1 20 nm | — | — | EBM1 20 nm | Ket1:TCTA:TEG1 (60%:30%:10%) 30 nm | Ket1 10 nm | ETM2 20 nm | LiF 1 nm |
| C16 | HIL1 20 nm | — | — | EBM1 20 nm | Ket1:CBP:TEG1 (60%:30%:10%) 30 nm | Ket1 10 nm | ETM2 20 nm | LiF 1 nm |
| C17 | — | HTM1 70 nm | HIL1 5 nm | EBM1 90 nm | DAP1:CBP:TEG1 (30%:60%:10%) 30 nm | — | ST1:LiQ (50%:50%) 30 nm | — |
| C18 | — | HTM1 70 nm | HIL1 5 nm | EBM1 90 nm | ST1:TCTA:TEG1 (30%:60%:10%) 30 nm | — | ST1:LiQ (50%:50%) 30 nm | — |
| C19 | — | HTM1 70 nm | HIL1 5 nm | EBM1 90 nm | Ket1:TEG1 (90%:10%) 30 nm | — | ST1:LiQ (50%:50%) 40 nm | — |
| C20 | HIL1 5 nm | SpNBP 40 nm | — | NPB 20 nm | H2:D3 (98.5%:1.5%) 30 nm | — | ST2:LiQ (50%:50%) 20 nm | — |
| C21 | — | HTM1 70 nm | HIL1 5 nm | EBM1 90 nm | ST1:TEG1 (90%:10%) 30 nm | ST1 10 nm | ETM1:LiQ (50%:50%) 30 nm | — |
| C22 | — | HTM1 70 nm | HIL1 5 nm | EBM1 90 nm | ST1:TEG1 (90%:10%) 30 nm | — | ETM1:LiQ (50%:50%) 40 nm | — |
| E1 | HIL1 5 nm | HTM1 140 nm | — | NPB 20 nm | H1:D1 (95%:5%) 30 nm | — | H4 20 nm | LiF 1 nm |
| E2 | HIL1 5 nm | HTM1 110 nm | — | NPB 20 nm | H2:D2 (90%:10%) 30 nm | — | H4 20 nm | LiF 1 nm |
| E3 | HIL1 5 nm | HTM1 140 nm | — | NPB 20 nm | H1:D1 (95%:5%) 30 nm | — | H4:LiQ (50%:50%) 20 nm | — |
| E4 | HIL1 5 nm | HTM2 110 nm | — | NPB 20 nm | H2:D2 (90%:10%) 30 nm | — | Alq3 20 nm | LiF 1 nm |
| E5 | HIL1 5 nm | HTM1 140 nm | — | NPB 20 nm | H1:D1 (95%:5%) 30 nm | — | H7:LiQ (50%:50%) 20 nm | — |
| E6 | — | HTM1 70 nm | HIL1 5 nm | EBM1 90 nm | H4:TEG1 (85%:15%) 30 nm | — | H7 40 nm | LiQ 3 nm |
| E7 | HIL1 5 nm | HTM1 140 nm | — | HTM3 20 nm | H1:D1 (95%:5%) 30 nm | — | ETM1:LiQ (50%:50%) 20 nm | — |
| E8 | HIL1 5 nm | HTM1 110 nm | — | HTM3 20 nm | H2:D2 (90%:10%) 30 nm | — | Alq3 20 nm | LiF 1 nm |
| E9 | HIL1 5 nm | HTM1 140 nm | — | HTM3 20 nm | H1:D1 (95%:5%) 30 nm | — | ETM1:LiQ (50%:50%) 20 nm | — |
| E10 | HIL1 5 nm | HTM1 110 nm | — | HTM4 20 nm | H2:D2 (90%:10%) 30 nm | — | Alq3 20 nm | LiF 1 nm |
| E11 | — | HTM1 70 nm | HIL1 5 nm | HTM4 90 nm | H4:TEG1 (85%:15%) 30 nm | — | ST1:LiQ (50%:50%) 40 nm | — |
| E12 | HIL1 5 nm | — | — | HTM4 200 nm | H4:TEG1 (85%:15%) 30 nm | — | ST1:LiQ (50%:50%) 40 nm | — |
| E13 | HIL1 5 nm | HTM1 140 nm | — | HTM5 20 nm | H1:D1 (95%:5%) 30 nm | — | ETM1:LiQ (50%:50%) 20 nm | — |
| E14 | HIL1 5 nm | HTM1 110 nm | — | HTM5 20 nm | H2:D2 (90%:10%) 30 nm | — | Alq$_3$ 20 nm | LiF 1 nm |
| E15 | — | HTM1 70 nm | HIL1 5 nm | HTM5 90 nm | H4:TEG1 (85%:15%) 30 nm | — | ST1:LiQ (50%:50%) 40 nm | — |
| E16 | — | HTM1 20 nm | — | NPB 20 nm | H4:TER1 (85%:15%) 30 nm | — | Alq$_3$ 20 nm | LiF 1 nm |
| E17 | — | HTM1 20 nm | — | NPB 20 nm | H4:TER2 (85%:15%) 30 nm | — | Alq$_3$ 20 nm | LiF 1 nm |
| E18 | — | HTM1 20 nm | — | NPB 20 nm | H4:CBP:TER1 (45%:45%:10%) 30 nm | ST1 10 nm | Alq$_3$ 20 nm | LiF 1 nm |

-continued

| Ex. | HIL thickness | HTL thickness | IL thickness | EBL thickness | EML thickness | HBL thickness | ETL thickness | EIL thickness |
|---|---|---|---|---|---|---|---|---|
| E19 | — | HTM1 160 nm | — | EBM1 20 nm | H4:TEG1 (90%:10%) 30 nm | ST1 10 nm | ETM1:LiQ (50%:50%) 30 nm | — |
| E20 | — | HTM1 160 nm | — | EBM1 20 nm | H4:TEG1 (90%:10%) 30 nm | — | ETM1:LiQ (50%:50%) 40 nm | — |
| E21 | — | HTM1 160 nm | — | EBM1 20 nm | H5:TEG1 (90%:10%) 30 nm | ST1 10 nm | ETM1:LiQ (50%:50%) 30 nm | — |
| E22 | — | HTM1 160 nm | — | EBM1 20 nm | H5:TEG1 (90%:10%) 30 nm | — | ETM1:LiQ (50%:50%) 40 nm | — |
| E23 | — | HTM1 160 nm | — | EBM1 20 nm | H6:TEG1 (90%:10%) 30 nm | ST1 10 nm | ETM1:LiQ (50%:50%) 30 nm | — |
| E24 | — | HTM1 160 nm | — | EBM1 20 nm | H6:TEG1 (90%:10%) 30 nm | — | ETM1:LiQ (50%:50%) 40 nm | — |
| E25 | — | HTM1 160 nm | — | EBM1 20 nm | H4:TEG1 (90%:10%) 30 nm | H4 10 nm | ETM1:LiQ (50%:50%) 30 nm | — |
| E26 | — | HTM1 160 nm | — | EBM1 20 nm | H4:TEG1 (90%:10%) 30 nm | — | ST1 40 nm | LiQ 3 nm |
| E27 | — | HTM1 20 nm | — | NPB 20 nm | H4:CBP:TER1 (45%:45%:10%) 30 nm | ST1 10 nm | Alq$_3$ 20 nm | LiF 1 nm |
| E28 | — | HTM1 70 nm | HIL 5 nm | EBM1 90 nm | H4:CBP:TEG1 (30%:60%:10%) 30 nm | ST1 10 nm | ST1:LiQ (50%:50%) 30 nm | — |
| E29 | — | HTM1 70 nm | HIL 5 nm | EBM1 90 nm | H9:TEG1 (90%:10%) 30 nm | ST1 10 nm | ETM1:LiQ (50%:50%) 30 nm | — |
| E30 | — | HTM1 70 nm | HIL 5 nm | EBM1 90 nm | H9:TEG1 (90%:10%) 30 nm | — | ETM1:LiQ (50%:50%) 40 nm | — |
| E31 | — | HTM1 70 nm | HIL 5 nm | EBM1 90 nm | H10:TEG1 (90%:10%) 30 nm | ST1 10 nm | ETM1:LiQ (50%:50%) 30 nm | — |
| E32 | — | HTM1 20 nm | — | NPB 20 nm | H10:TER2 (85%:15%) 30 nm | — | Alq$_3$ 20 nm | LiF 1 nm |
| E33 | — | HTM1 70 nm | HIL 5 nm | EBM1 90 nm | H11:TEG1 (90%:10%) 30 nm | ST1 10 nm | ETM1:LiQ (50%:50%) 30 nm | — |
| E34 | — | HTM1 70 nm | HIL 5 nm | EBM1 90 nm | H11:TEG1 (90%:10%) 30 nm | — | ETM1:LiQ (50%:50%) 40 nm | — |
| E35 | — | HTM1 20 nm | — | NPB 20 nm | H11:TER1 (85%:15%) 30 nm | — | Alq$_3$ 20 nm | LiF 1 nm |
| E36 | — | HTM1 20 nm | — | NPB 20 nm | H11:TER2 (85%:15%) 30 nm | — | Alq$_3$ 20 nm | LiF 1 nm |
| E37 | — | HTM1 70 nm | HIL 5 nm | EBM1 90 nm | H12:TEG1 (90%:10%) 30 nm | — | ETM1:LiQ (50%:50%) 40 nm | — |
| E38 | — | HTM1 70 nm | HIL 5 nm | EBM1 90 nm | H13:TEG1 (90%:10%) 30 nm | — | ETM1:LiQ (50%:50%) 40 nm | — |
| E39 | — | HTM1 70 nm | HIL 5 nm | EBM1 90 nm | H14:TEG1 (90%:10%) 30 nm | — | ETM1:LiQ (50%:50%) 40 nm | — |
| E40 | — | HTM1 70 nm | HIL 5 nm | EBM1 90 nm | H15:TEG1 (90%:10%) 30 nm | — | ETM1:LiQ (50%:50%) 40 nm | — |
| E41 | — | HTM1 70 nm | HIL 5 nm | EBM1 90 nm | H16:TEG1 (90%:10%) 30 nm | — | ETM1:LiQ (50%:50%) 40 nm | — |
| E42 | — | HTM1 70 nm | HIL 5 nm | EBM1 90 nm | H17:TEG1 (90%:10%) 30 nm | ST1 10 nm | ETM1:LiQ (50%:50%) 30 nm | — |
| E43 | — | HTM1 70 nm | HIL 5 nm | EBM1 90 nm | H18:TEG1 (90%:10%) 30 nm | — | ETM1:LiQ (50%:50%) 40 nm | — |
| E44 | — | HTM1 20 nm | — | NPB 20 nm | H19:TER1 (85%:15%) 30 nm | — | Alq$_3$ 20 nm | LiF 1 nm |
| E45 | — | HTM1 20 nm | — | NPB 20 nm | H19:TER2 (85%:15%) 30 nm | — | Alq$_3$ 20 nm | LiF 1 nm |
| E46 | — | HTM1 20 nm | — | NPB 20 nm | H19:CBP:TER1 (45%:45%:10%) 30 nm | ST1 10 nm | Alq$_3$ 20 nm | LiF 1 nm |
| E47 | — | HTM1 70 nm | HIL 5 nm | EBM1 90 nm | H20:TEG1 (90%:10%) 30 nm | — | ETM1:LiQ (50%:50%) 40 nm | — |
| E48 | — | HTM1 70 nm | HIL 5 nm | EBM1 90 nm | H21:TEG1 (90%:10%) 30 nm | — | ETM1:LiQ (50%:50%) 40 nm | — |
| E49 | — | HTM1 70 nm | HIL 5 nm | EBM1 90 nm | H21:TEG1 (90%:10%) 30 nm | ST1 10 nm | ETM1:LiQ (50%:50%) 30 nm | — |
| E50 | — | HTM1 70 nm | HIL 5 nm | EBM1 90 nm | H22:TEG1 (90%:10%) 30 nm | — | ETM1:LiQ (50%:50%) 40 nm | — |
| E51 | — | HTM1 70 nm | HIL 5 nm | EBM1 90 nm | H23:TEG1 (90%:10%) 30 nm | — | ETM1:LiQ (50%:50%) 40 nm | — |
| E52 | — | HTM1 70 nm | HIL 5 nm | EBM1 90 nm | H24:TEG1 (90%:10%) 30 nm | — | ETM1:LiQ (50%:50%) 40 nm | — |
| E53 | — | HTM1 70 nm | HIL 5 nm | EBM1 90 nm | H25:TEG1 (90%:10%) 30 nm | — | ETM1:LiQ (50%:50%) 40 nm | — |
| E54 | — | HTM1 70 nm | HIL 5 nm | EBM1 90 nm | H25:TEG1 (90%:10%) 30 nm | ST1 10 nm | ETM1:LiQ (50%:50%) 30 nm | — |
| E55 | — | HTM1 70 nm | HIL 5 nm | EBM1 90 nm | H26:TEG1 (90%:10%) 30 nm | — | ETM1:LiQ (50%:50%) 40 nm | — |
| E56 | — | HTM1 20 nm | — | NPB 20 nm | H26:TER2 (85%:15%) 30 nm | — | Alq$_3$ 20 nm | LiF 1 nm |

-continued

| Ex. | HIL thickness | HTL thickness | IL thickness | EBL thickness | EML thickness | HBL thickness | ETL thickness | EIL thickness |
|---|---|---|---|---|---|---|---|---|
| E57 | — | HTM1 20 nm | — | NPB 20 nm | H26:CBP:TER1 (45%:45%:10%) 30 nm | ST1 10 nm | Alq$_3$ 20 nm | LiF 1 nm |
| E58 | — | HTM1 70 nm | HIL1 5 nm | EBM1 90 nm | H27:TEG1 (90%:10%) 30 nm | — | ETM1:LiQ (50%:50%) 40 nm | — |
| E60 | — | HTM1 70 nm | HIL1 5 nm | EBM1 90 nm | ST1:H28:TEG1 (30%:60%:10%) 30 nm | ST1 10 nm | ST1:LiQ (50%:50%) 30 nm | — |
| E61 | — | HTM1 70 nm | HIL1 5 nm | EBM1 90 nm | ST1:H28:TEG1 (30%:60%:10%) 30 nm | — | ST1:LiQ (50%:50%) 40 nm | — |
| E62 | — | HTM1 70 nm | HIL1 5 nm | EBM1 90 nm | ST1:H29:TEG1 (30%:60%:10%) 30 nm | ST1 10 nm | ST1:LiQ (50%:50%) 30 nm | — |
| E63 | — | HTM1 70 nm | HIL1 5 nm | EBM1 90 nm | ST1:H30:TEG1 (30%:60%:10%) 30 nm | ST1 10 nm | ST1:LiQ (50%:50%) 30 nm | — |
| E64 | HIL1 20 nm | — | — | EBM1 20 nm | Ket1:H28:TEG1 (30%:60%:10%) 30 nm | Ket1 10 nm | ETM2 20 nm | LiF 1 nm |
| E65 | HIL1 20 nm | — | — | EBM1 20 nm | Ket1:H28:TEG1 (60%:30%:10%) 30 nm | Ket1 10 nm | ETM2 20 nm | LiF 1 nm |
| E66 | HIL1 20 nm | — | — | EBM1 20 nm | Ket1:H30:TEG1 (30%:60%:10%) 30 nm | Ket1 10 nm | ETM2 20 nm | LiF 1 nm |
| E67 | — | HTM1 70 nm | HIL1 5 nm | EBM1 90 nm | DAP1:H28:TEG1 (30%:60%:10%) 30 nm | — | ST1:LiQ (50%:50%) 30 nm | — |
| E68 | — | HTM1 70 nm | HIL1 5 nm | EBM1 90 nm | DAP1:H30:TEG1 (30%:60%:10%) 30 nm | — | ST1:LiQ (50%:50%) 30 nm | — |
| E69 | — | HTM1 20 nm | — | NPB 20 nm | ST1:H28:TER1 (45%:45%:10%) 30 nm | ST1 10 nm | Alq$_3$ 20 nm | LiF 1 nm |
| E70 | — | HTM1 20 nm | — | NPB 20 nm | ST1:H29:TER1 (45%:45%:10%) 30 nm | ST1 10 nm | Alq$_3$ 20 nm | LiF 1 nm |
| E71 | — | HTM1 20 nm | — | NPB 20 nm | ST1:H30:TER1 (45%:45%:10%) 30 nm | ST1 10 nm | Alq$_3$ 20 nm | LiF 1 nm |
| E72 | — | HTM1 20 nm | — | NPB 20 nm | ST1:H17:TER1 (45%:45%:10%) 30 nm | ST1 10 nm | Alq$_3$ 20 nm | LiF 1 nm |
| E73 | — | HTM1 70 nm | HIL1 5 nm | EBM1 90 nm | H8:TEG1 (90%:10%) 30 nm | — | ETM1:LiQ (50%:50%) 40 nm | — |
| E74 | HIL1 5 nm | SpNBP 40 nm | — | HTM6 20 nm | H2:D3 (98.5%:1.5%) 30 nm | — | ST2:LiQ (50%:50%) 20 nm | — |
| E75 | HIL1 5 nm | SpNBP 40 nm | — | HTM7 20 nm | H2:D3 (98.5%:1.5%) 30 nm | — | ST2:LiQ (50%:50%) 20 nm | — |
| E76 | — | HTM1 70 nm | HIL1 5 nm | HTM8 90 nm | ST1:TEG1 (90%:10%) 30 nm | — | ST1:LiQ (50%:50%) 40 nm | — |
| E77 | — | HTM1 20 nm | — | HTM8 20 nm | ST1:CBP:TER1 (45%:45%:10%) 30 nm | ST1 10 nm | Alq$_3$ 20 nm | LiF 1 nm |
| E78 | — | HTM1 70 nm | HIL1 5 nm | EBM1 90 nm | ST1:H43:TEG1 (30%:60%:10%) 30 nm | ST1 10 nm | ST1:LiQ (50%:50%) 30 nm | — |
| E79 | — | HTM1 160 nm | — | EBM1 20 nm | H32:TEG1 (90%:10%) 30 nm | ST1 10 nm | ETM1:LiQ (50%:50%) 30 nm | — |
| E80 | — | HTM1 70 nm | HIL1 5 nm | EBM1 90 nm | H32:TEG1 (90%:10%) 30 nm | — | ST1:LiQ (50%:50%) 40 nm | — |
| E81 | — | HTM1 20 nm | — | NPB 20 nm | H32:TER1 (85%:15%) 30 nm | — | Alq$_3$ 20 nm | LiF 1 nm |
| E82 | — | HTM1 70 nm | HIL1 5 nm | EBM1 90 nm | H33:TEG1 (90%:10%) 30 nm | — | ST1:LiQ (50%:50%) 40 nm | — |
| E83 | — | HTM1 70 nm | HIL1 5 nm | EBM1 90 nm | H34:TEG1 (90%:10%) 30 nm | — | ST1:LiQ (50%:50%) 40 nm | — |
| E84 | — | HTM1 70 nm | HIL1 5 nm | EBM1 90 nm | H35:TEG1 (90%:10%) 30 nm | — | ST1:LiQ (50%:50%) 40 nm | — |
| E85 | — | HTM1 70 nm | HIL1 5 nm | EBM1 90 nm | H36:TEG1 (90%:10%) 30 nm | — | ST1:LiQ (50%:50%) 40 nm | — |
| E86 | — | HTM1 70 nm | HIL1 5 nm | EBM1 90 nm | H31:TEG1 (90%:10%) 30 nm | ST1 10 nm | ST1:LiQ (50%:50%) 30 nm | — |
| E87 | — | HTM1 70 nm | HIL1 5 nm | EBM1 90 nm | H31:TEG1 (90%:10%) 30 nm | — | ST1:LiQ (50%:50%) 40 nm | — |
| E88 | — | HTM1 70 nm | HIL1 5 nm | EBM1 90 nm | H37:TEG1 (90%:10%) 30 nm | — | ST1:LiQ (50%:50%) 40 nm | — |
| E89 | — | HTM1 20 nm | — | NPB 20 nm | H37:TER2 (85%:15%) 30 nm | — | Alq$_3$ 20 nm | LiF 1 nm |
| E90 | — | HTM1 70 nm | HIL1 5 nm | EBM1 90 nm | H38:TEG1 (90%:10%) 30 nm | — | ST1:LiQ (50%:50%) 40 nm | — |
| E91 | — | HTM1 70 nm | HIL1 5 nm | EBM1 90 nm | H39:TEG1 (90%:10%) 30 nm | — | ST1:LiQ (50%:50%) 40 nm | — |
| E92 | — | HTM1 70 nm | HIL1 5 nm | EBM1 90 nm | H40:TEG1 (90%:10%) 30 nm | — | ST1:LiQ (50%:50%) 40 nm | — |
| E93 | — | HTM1 70 nm | HIL1 5 nm | EBM1 90 nm | H41:TEG1 (90%:10%) 30 nm | ST1 10 nm | ST1:LiQ (50%:50%) 30 nm | — |
| E94 | — | HTM1 70 nm | HIL1 5 nm | EBM1 90 nm | H41:TEG1 (90%:10%) 30 nm | — | ST1:LiQ (50%:50%) 40 nm | — |
| E95 | — | HTM1 20 nm | — | NPB 20 nm | H41:TER1 (85%:15%) 30 nm | — | Alq$_3$ 20 nm | LiF 1 nm |

| Ex. | HIL thickness | HTL thickness | IL thickness | EBL thickness | EML thickness | HBL thickness | ETL thickness | EIL thickness |
|---|---|---|---|---|---|---|---|---|
| E96 | — | HTM1 70 nm | HIL1 5 nm | EBM1 90 nm | H42:TEG1 (90%:10%) 30 nm | — | ST1:LiQ (50%:50%) 40 nm | — |
| E97 | — | HTM1 70 nm | HIL1 5 nm | EBM1 90 nm | H44:TEG1 (90%:10%) 30 nm | — | ST1:LiQ (50%:50%) 40 nm | — |
| E98 | — | HTM1 70 nm | HIL1 5 nm | EBM1 90 nm | H45:TEG1 (90%:10%) 30 nm | — | ST1:LiQ (50%:50%) 40 nm | — |
| E99 | — | HTM1 70 nm | HIL1 5 nm | EBM1 90 nm | H46:TEG1 (90%:10%) 30 nm | — | ST1:LiQ (50%:50%) 40 nm | — |
| E100 | — | HTM1 20 nm | — | NPB 20 nm | H47:TER1 (85%:15%) 30 nm | — | Alq$_3$ 20 nm | LiF 1 nm |
| E101 | — | HTM1 20 nm | — | NPB 20 nm | H47:TER2 (85%:15%) 30 nm | — | Alq$_3$ 20 nm | LiF 1 nm |
| E102 | — | HTM1 70 nm | HIL1 5 nm | EBM1 90 nm | H48:TEG1 (90%:10%) 30 nm | ST1 10 nm | ST1:LiQ (50%:50%) 30 nm | — |
| E103 | — | HTM1 70 nm | HIL1 5 nm | EBM1 90 nm | H48:TEG1 (90%:10%) 30 nm | — | ST1:LiQ (50%:50%) 40 nm | — |
| E104 | — | HTM1 20 nm | — | NPB 20 nm | H48:TER1 (85%:15%) 30 nm | — | Alq$_3$ 20 nm | LiF 1 nm |
| E105 | — | HTM1 70 nm | HIL1 5 nm | EBM1 90 nm | H7:TEG1 (90%:10%) 30 nm | — | EMT1:LiQ (50%:50%) 40 nm | — |

| Ex. | Voltage for 1000 cd/m$^2$ | Efficiency at 1000 cd/m$^2$ | Efficiency at 1000 cd/m$^2$ | EQE at 1000 cd/m$^2$ | CIE x/y at 1000 cd/m$^2$ | LD50 from 1000 cd/m$^2$ |
|---|---|---|---|---|---|---|
| C1 | 6.4 V | 5.1 cd/A | 2.5 lm/W | 4.2% | 0.142/0.151 | 5500 h |
| C2 | 4.7 V | 8.1 cd/A | 5.4 lm/W | 6.3% | 0.142/0.155 | 5200 h |
| C3 | 5.0 V | 17.1 cd/A | 10.7 lm/W | 5.0% | 0.28/0.61 | 300000 h |
| C4 | 5.0 V | 7.2 cd/A | 4.5 lm/W | 12.0% | 0.69/0.31 | 14000 h |
| C5 | 6.5 V | 9.0 cd/A | 4.3 lm/W | 8.3% | 0.66/0.33 | 18000 h |
| C6 | 5.2 V | 8.1 cd/A | 4.9 lm/W | 11.4% | 0.68/0.32 | 15000 h |
| C7 | 4.7 V | 55 cd/A | 37 lm/W | 15.4% | 0.36/0.61 | 27000 h |
| C8 | 4.6 V | 54 cd/A | 37 lm/W | 15.0% | 0.37/0.60 | 24000 h |
| C9 | 3.6 V | 52 cd/A | 45 lm/W | 14.6% | 0.37/0.60 | 31000 h |
| C10 | 4.4 V | 48 cd/A | 34 lm/W | 13.3% | 0.37/0.60 | 37000 h |
| C11 | 4.2 V | 52 cd/A | 39 lm/W | 14.5% | 0.36/0.61 | 25000 h |
| C12 | 4.1 V | 50 cd/A | 38 lm/W | 13.9% | 0.37/0.61 | 23000 h |
| C13 | 4.3 V | 45 cd/A | 33 lm/W | 12.6% | 0.36/0.61 | 39000 h |
| C14 | 4.0 V | 46 cd/A | 36 lm/W | 12.8% | 0.36/0.61 | 34000 h |
| C15 | 3.9 V | 42 cd/A | 34 lm/W | 11.6% | 0.35/0.61 | 14000 h |
| C16 | 4.1 V | 44 cd/A | 34 lm/W | 12.3% | 0.36/0.61 | 25000 h |
| C17 | 4.6 V | 47 cd/A | 32 lm/W | 13.2% | 0.36/0.60 | 43000 h |
| C18 | 4.2 V | 43 cd/A | 32 lm/W | 12.0% | 0.35/0.60 | 17000 h |
| C19 | 3.9 V | 41 cd/A | 33 lm/W | 11.0% | 0.36/0.61 | 22000 h |
| C20 | 4.3 V | 9.8 cd/A | 7.1 lm/W | 7.6% | 0.14/0.16 | 7600 h |
| C21 | 4.5 V | 53 cd/A | 37 lm/W | 14.9% | 0.36/0.61 | 27000 h |
| C22 | 4.5 V | 53 cd/A | 37 lm/W | 14.7% | 0.37/0.60 | 25000 h |
| E1 | 4.3 V | 8.6 cd/A | 6.3 lm/W | 6.7% | 0.142/0.153 | 5100 h |
| E2 | 4.2 V | 21.5 cd/A | 16.1 lm/W | 6.3% | 0.29/0.60 | 290000 h |
| E3 | 4.1 V | 9.3 cd/A | 7.1 lm/W | 7.2% | 0.142/0.154 | 5400 h |
| E4 | 4.5 V | 17.4 cd/A | 12.1 lm/W | 5.1% | 0.28/0.60 | 375000 h |
| E5 | 4.5 V | 8.8 cd/A | 6.1 lm/W | 7.1% | 0.142/0.153 | 5300 h |
| E6 | 3.7 V | 49 cd/A | 42 lm/W | 13.8% | 0.37/0.60 | 39000 h |
| E7 | 4.6 V | 8.4 cd/A | 5.7 lm/W | 6.5% | 0.142/0.152 | 7400 h |
| E8 | 4.8 V | 17.8 cd/A | 11.6 lm/W | 5.2% | 0.142/0.153 | 375000 h |
| E9 | 4.4 V | 9.3 cd/A | 6.6 lm/W | 7.2% | 0.142/0.155 | 7800 h |
| E10 | 4.9 V | 17.9 cd/A | 11.5 lm/W | 5.1% | 0.28/0.61 | 390000 h |
| E11 | 3.5 V | 59 cd/A | 53 lm/W | 16.4% | 0.36/0.59 | 33000 h |
| E12 | 3.6 V | 58 cd/A | 51 lm/W | 16.2% | 0.37/0.60 | 32000 h |
| E13 | 4.5 V | 9.0 cd/A | 7.0 lm/W | 7.2% | 0.142/0.155 | 6900 h |
| E14 | 4.9 V | 17.3 cd/A | 11.1 lm/W | 5.0% | 0.28/0.61 | 370000 h |
| E15 | 3.4 V | 62 cd/A | 57 lm/W | 17.4% | 0.37/0.60 | 35000 h |
| E16 | 4.7 V | 7.1 cd/A | 4.7 lm/W | 11.8% | 0.69/0.31 | 15000 h |
| E17 | 4.8 V | 9.5 cd/A | 6.2 lm/W | 8.7% | 0.66/0.33 | 23000 h |
| E18 | 4.7 V | 8.6 cd/A | 5.7 lm/W | 12.0% | 0.69/0.32 | 18000 h |
| E19 | 3.8 V | 57 cd/A | 47 lm/W | 15.9% | 0.37/0.61 | 38000 h |
| E20 | 3.4 V | 54 cd/A | 50 lm/W | 15.2% | 0.37/0.61 | 33000 h |
| E21 | 4.0 V | 58 cd/A | 46 lm/W | 16.1% | 0.38/0.59 | 41000 h |
| E22 | 3.7 V | 53 cd/A | 45 lm/W | 14.8% | 0.37/0.60 | 35000 h |
| E23 | 3.9 V | 54 cd/A | 43 lm/W | 15.3% | 0.37/0.61 | 36000 h |
| E24 | 3.5 V | 53 cd/A | 48 lm/W | 14.9% | 0.37/0.60 | 29000 h |
| E25 | 3.6 V | 56 cd/A | 49 lm/W | 15.7% | 0.38/0.60 | 32000 h |
| E26 | 2.9 V | 54 cd/A | 59 lm/W | 15.1% | 0.37/0.60 | 30000 h |
| E27 | 4.7 V | 8.0 cd/A | 5.3 lm/W | 11.3% | 0.68/0.32 | 21000 h |

-continued

| Ex. | Voltage for 1000 cd/m$^2$ | Efficiency at 1000 cd/m$^2$ | Efficiency at 1000 cd/m$^2$ | EQE at 1000 cd/m$^2$ | CIE x/y at 1000 cd/m$^2$ | LD50 from 1000 cd/m$^2$ |
|---|---|---|---|---|---|---|
| E28 | 3.7 V | 52 cd/A | 44 lm/W | 14.4% | 0.37/0.60 | 48000 h |
| E29 | 3.8 V | 59 cd/A | 49 lm/W | 16.5% | 0.37/0.60 | 38000 h |
| E30 | 3.6 V | 56 cd/A | 48 lm/W | 15.5% | 0.36/0.60 | 36000 h |
| E31 | 3.6 V | 46 cd/A | 40 lm/W | 12.6% | 0.36/0.59 | 24000 h |
| E32 | 5.3 V | 9.2 cd/A | 5.5 lm/W | 8.5% | 0.66/0.33 | 23000 h |
| E33 | 3.5 V | 58 cd/A | 52 lm/W | 16.0% | 0.35/0.59 | 51000 h |
| E34 | 3.4 V | 55 cd/A | 51 lm/W | 15.2% | 0.35/0.59 | 47000 h |
| E35 | 4.1 V | 7.5 cd/A | 5.7 lm/W | 12.6% | 0.69/0.31 | 22000 h |
| E36 | 4.3 V | 8.8 cd/A | 6.4 lm/W | 8.1% | 0.66/0.33 | 27000 h |
| E37 | 4.1 V | 47 cd/A | 36 lm/W | 13.0% | 0.36/0.59 | 34000 h |
| E38 | 3.6 V | 45 cd/A | 39 lm/W | 12.4% | 0.36/0.60 | 21000 h |
| E39 | 3.6 V | 53 cd/A | 46 lm/W | 14.9% | 0.36/0.60 | 31000 h |
| E40 | 3.5 V | 58 cd/A | 52 lm/W | 16.2% | 0.36/0.60 | 28000 h |
| E41 | 3.6 V | 42 cd/A | 37 lm/W | 11.7% | 0.37/0.61 | 22000 h |
| E42 | 3.9 V | 46 cd/A | 37 lm/W | 12.9% | 0.36/0.60 | 44000 h |
| E43 | 3.8 V | 43 cd/A | 36 lm/W | 11.9% | 0.35/0.59 | 20000 h |
| E44 | 4.1 V | 8.1 cd/A | 6.2 lm/W | 13.6% | 0.69/0.31 | 22000 h |
| E45 | 4.3 V | 9.9 cd/A | 7.2 lm/W | 9.1% | 0.66/0.33 | 23000 h |
| E46 | 4.0 V | 9.3 cd/A | 7.3 lm/W | 13.1% | 0.68/0.32 | 31000 h |
| E47 | 3.8 V | 47 cd/A | 39 lm/W | 13.0% | 0.36/0.60 | 29000 h |
| E48 | 3.4 V | 45 cd/A | 42 lm/W | 12.7% | 0.36/0.59 | 25000 h |
| E49 | 3.7 V | 49 cd/A | 42 lm/W | 13.5% | 0.36/0.59 | 28000 h |
| E50 | 3.7 V | 55 cd/A | 47 lm/W | 15.3% | 0.37/0.60 | 40000 h |
| E51 | 3.8 V | 44 cd/A | 36 lm/W | 12.4% | 0.36/0.61 | 27000 h |
| E52 | 4.1 V | 59 cd/A | 45 lm/W | 16.4% | 0.36/0.60 | 35000 h |
| E53 | 3.5 V | 55 cd/A | 49 lm/W | 15.7% | 0.37/0.60 | 39000 h |
| E54 | 3.6 V | 61 cd/A | 53 lm/W | 17.0% | 0.36/0.60 | 41000 h |
| E55 | 4.2 V | 46 cd/A | 34 lm/W | 12.9% | 0.37/0.59 | 26000 h |
| E56 | 5.7 V | 9.8 cd/A | 5.4 lm/W | 9.0% | 0.66/0.33 | 26000 h |
| E57 | 4.6 V | 8.5 cd/A | 5.9 lm/W | 12.1% | 0.68/0.32 | 23000 h |
| E58 | 4.0 V | 50 cd/A | 39 lm/W | 13.9% | 0.36/0.61 | 43000 h |
| E60 | 3.5 V | 57 cd/A | 51 lm/W | 15.8% | 0.36/0.61 | 53000 h |
| E61 | 3.5 V | 51 cd/A | 45 lm/W | 14.3% | 0.36/0.61 | 49000 h |
| E62 | 3.6 V | 55 cd/A | 48 lm/W | 15.5% | 0.36/0.60 | 54000 h |
| E63 | 3.3 V | 57 cd/A | 54 lm/W | 16.0% | 0.36/0.61 | 59000 h |
| E64 | 3.2 V | 49 cd/A | 48 lm/W | 13.6% | 0.36/0.61 | 48000 h |
| E65 | 3.7 V | 47 cd/A | 40 lm/W | 13.2% | 0.36/0.61 | 43000 h |
| E66 | 3.1 V | 49 cd/A | 50 lm/W | 13.7% | 0.36/0.61 | 55000 h |
| E67 | 4.1 V | 45 cd/A | 34 lm/W | 12.6% | 0.36/0.60 | 51000 h |
| E68 | 3.9 V | 48 cd/A | 39 lm/W | 13.4% | 0.36/0.60 | 58000 h |
| E69 | 4.3 V | 9.3 cd/A | 6.8 lm/W | 13.0% | 0.68/0.32 | 27000 h |
| E70 | 4.5 V | 8.9 cd/A | 6.2 lm/W | 12.5% | 0.68/0.32 | 24000 h |
| E71 | 4.0 V | 9.4 cd/A | 7.4 lm/W | 13.1% | 0.68/0.32 | 31000 h |
| E72 | 4.4 V | 8.8 cd/A | 6.3 lm/W | 12.2% | 0.68/0.32 | 23000 h |
| E73 | 3.9 V | 47 cd/A | 38 lm/W | 12.9% | 0.36/0.61 | 28000 h |
| E74 | 4.1 V | 10.5 cd/A | 8.1 lm/W | 8.1% | 0.14/0.16 | 11500 h |
| E75 | 4.4 V | 9.3 cd/A | 6.6 lm/W | 7.2% | 0.14/0.16 | 9500 h |
| E76 | 4.2 V | 53 cd/A | 40 lm/W | 14.7% | 0.37/0.61 | 27000 h |
| E77 | 5.1 V | 7.8 cd/A | 4.8 lm/W | 11.1% | 0.68/0.32 | 19000 h |
| E78 | 3.7 V | 54 cd/A | 46 lm/W | 14.9% | 0.36/0.61 | 47000 h |
| E79 | 3.8 V | 57 cd/A | 47 lm/W | 16.1% | 0.36/0.61 | 33000 h |
| E80 | 3.5 V | 53 cd/A | 48 lm/W | 14.8% | 0.37/0.61 | 31000 h |
| E81 | 4.0 V | 7.0 cd/A | 5.5 lm/W | 11.9% | 0.69/0.31 | 21000 h |
| E82 | 4.0 V | 54 cd/A | 42 lm/W | 15.1% | 0.37/0.60 | 29000 h |
| E83 | 3.6 V | 50 cd/A | 44 lm/W | 14.0% | 0.36/0.60 | 29000 h |
| E84 | 3.9 V | 47 cd/A | 38 lm/W | 13.0% | 0.36/0.61 | 27000 h |
| E85 | 3.5 V | 44 cd/A | 40 lm/W | 12.2% | 0.26/0.60 | 23000 h |
| E86 | 3.6 V | 51 cd/A | 44 lm/W | 14.3% | 0.37/0.60 | 39000 h |
| E87 | 3.5 V | 47 cd/A | 42 lm/W | 13.2% | 0.37/0.61 | 35000 h |
| E88 | 3.3 V | 43 cd/A | 41 lm/W | 12.1% | 0.37/0.61 | 43000 h |
| E89 | 5.3 V | 9.5 cd/A | 5.6 lm/W | 8.8% | 0.66/0.33 | 29000 h |
| E90 | 3.8 V | 46 cd/A | 38 lm/W | 12.9% | 0.37/0.60 | 26000 h |
| E91 | 4.1 V | 48 cd/A | 37 lm/W | 13.5% | 0.37/0.61 | 23000 h |
| E92 | 3.4 V | 50 cd/A | 46 lm/W | 13.9% | 0.37/0.61 | 30000 h |
| E93 | 3.5 V | 49 cd/A | 44 lm/W | 13.6% | 0.37/0.61 | 36000 h |
| E94 | 3.4 V | 47 cd/A | 43 lm/W | 13.1% | 0.36/0.61 | 35000 h |
| E95 | 4.5 V | 7.5 cd/A | 5.3 lm/W | 12.6% | 0.69/0.31 | 24000 h |
| E96 | 3.5 V | 47 cd/A | 42 lm/W | 13.1% | 0.37/0.61 | 22000 h |
| E97 | 4.1 V | 51 cd/A | 39 lm/W | 14.2% | 0.36/0.60 | 29000 h |
| E98 | 4.2 V | 53 cd/A | 39 lm/W | 14.7% | 0.36/0.60 | 26000 h |
| E99 | 3.9 V | 46 cd/A | 37 lm/W | 12.7% | 0.37/0.60 | 29000 h |
| E100 | 4.4 V | 7.7 cd/A | 5.5 lm/W | 12.8% | 0.69/0.31 | 29000 h |
| E101 | 5.2 V | 10.5 cd/A | 6.4 lm/W | 9.7% | 0.66/0.33 | 30000 h |
| E102 | 3.4 V | 58 cd/A | 53 lm/W | 16.1% | 0.36/0.61 | 44000 h |

-continued
| Ex. | Voltage for 1000 cd/m² | Efficiency at 1000 cd/m² | Efficiency at 1000 cd/m² | EQE at 1000 cd/m² | CIE x/y at 1000 cd/m² | LD50 from 1000 cd/m² |
|---|---|---|---|---|---|---|
| E103 | 3.4 V | 55 cd/A | 51 lm/W | 15.4% | 0.37/0.61 | 39000 h |
| E104 | 4.3 V | 7.6 cd/A | 5.5 lm/W | 12.6% | 0.69/0.31 | 28000 h |
| E105 | 3.7 V | 52 cd/A | 44 lm/W | 14.5% | 0.37/0.61 | 31000 h |
TABLE 4
Structural formulae of the materials for the OLEDs
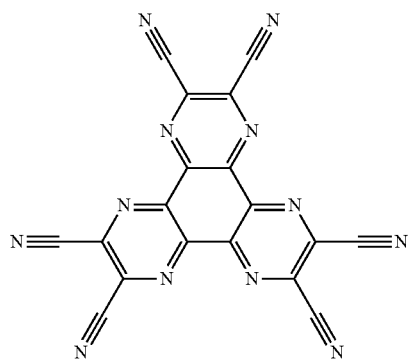
HIL1
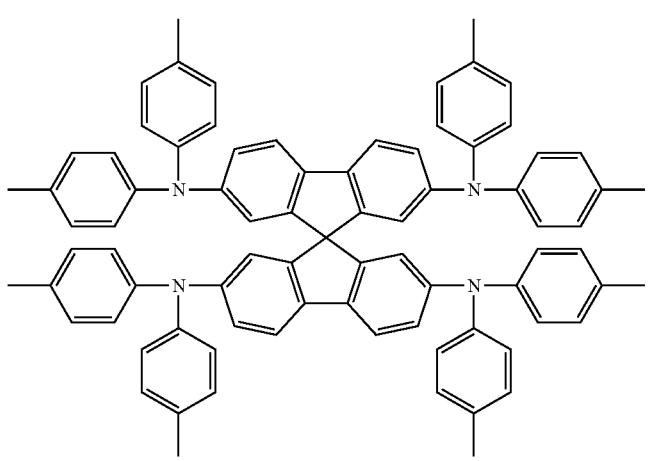
HTM1 (prior art)
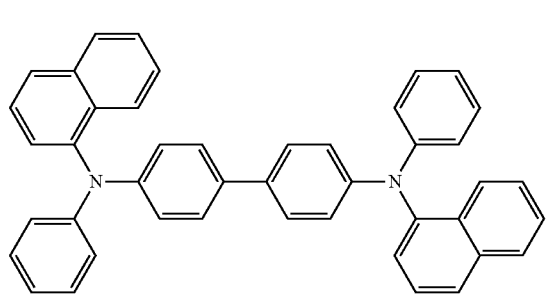
NPB (prior art)

TABLE 4-continued
Structural formulae of the materials for the OLEDs
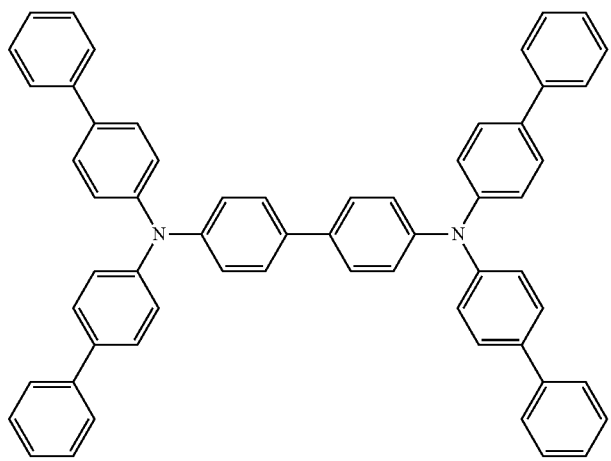
EBM1 (prior art)
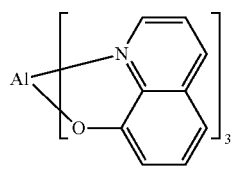
Alq₃ (prior art)
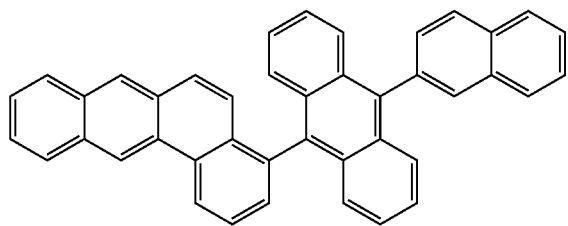
H1
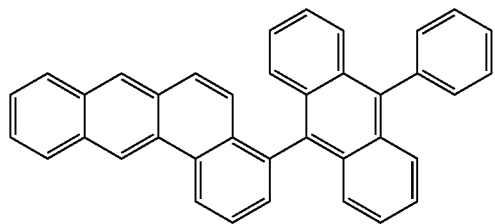
H2
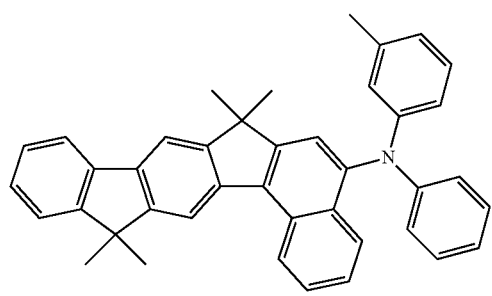
D1

TABLE 4-continued
Structural formulae of the materials for the OLEDs
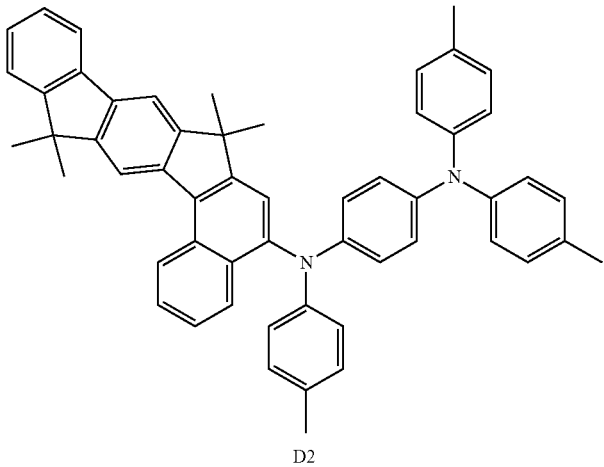
D2
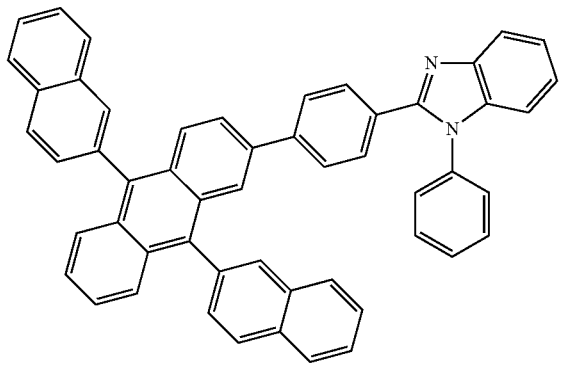
ETM1 (prior art)
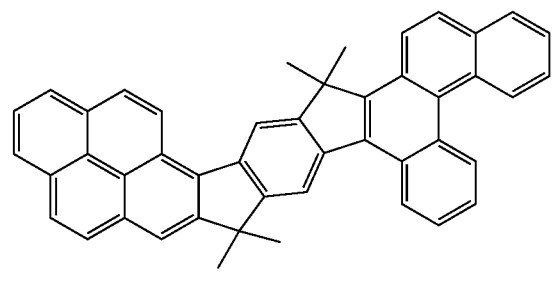
D3
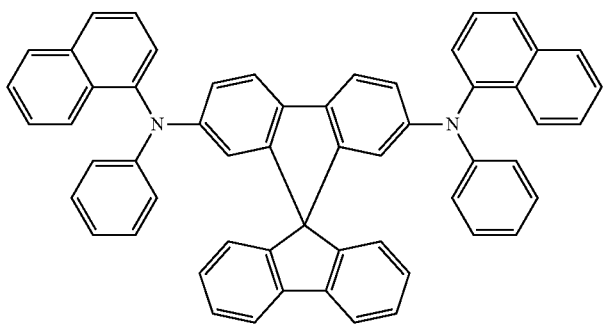
SpNBP TABLE 4-continued
Structural formulae of the materials for the OLEDs
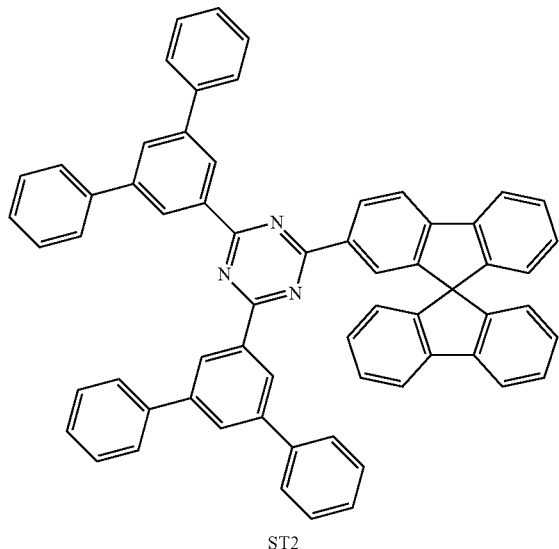 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1 ; "ST2"]
ST2
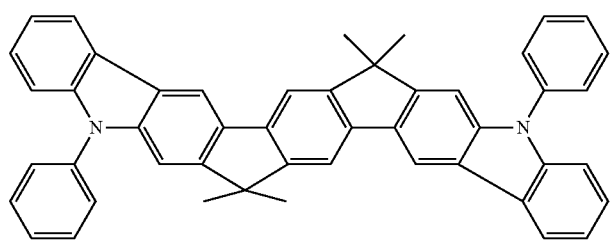
HTM2 (according to the invention)
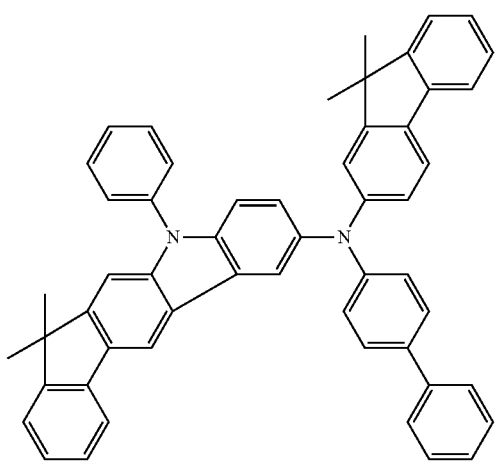
HTM3 (according to the invention)

TABLE 4-continued
Structural formulae of the materials for the OLEDs
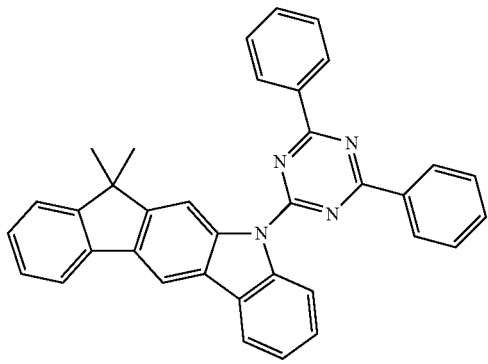
H4 (according to the invention)
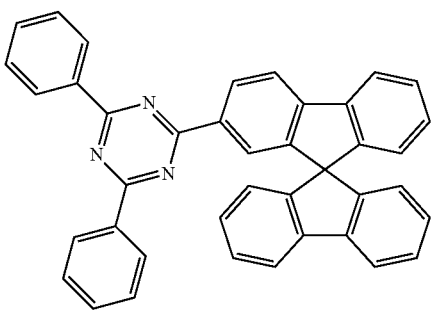
ST1 (prior art)
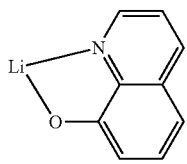
LiQ
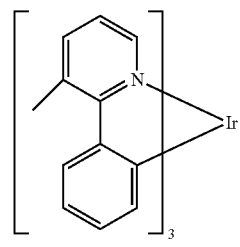
TEG1
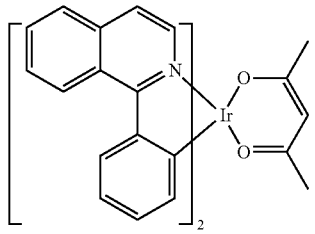
TER1

TABLE 4-continued
Structural formulae of the materials for the OLEDs
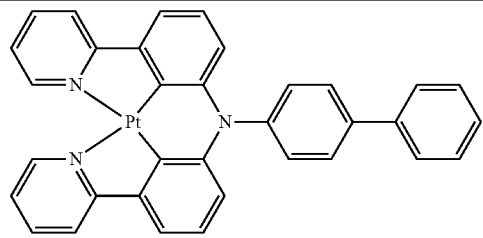
TER2
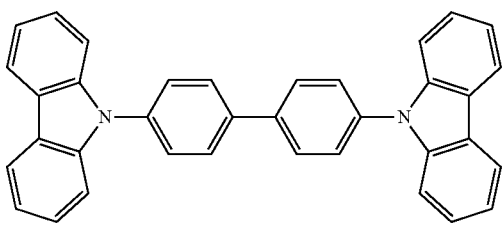
CBP (prior art)
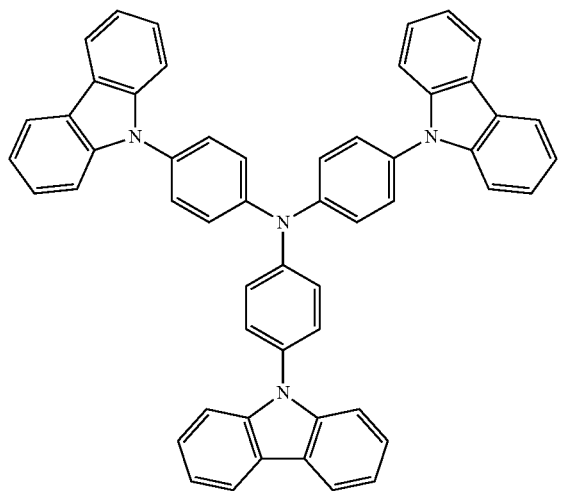
TCTA (prior art)
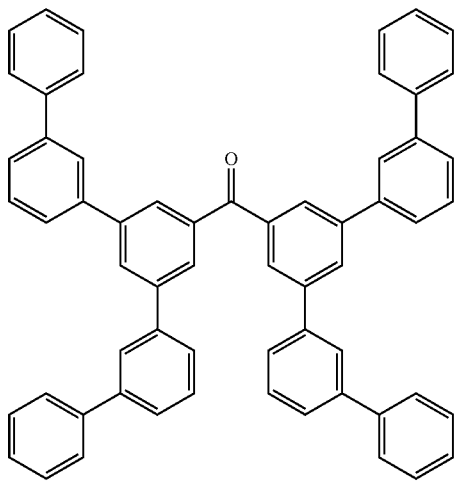
Ket1 (prior art)

TABLE 4-continued
Structural formulae of the materials for the OLEDs
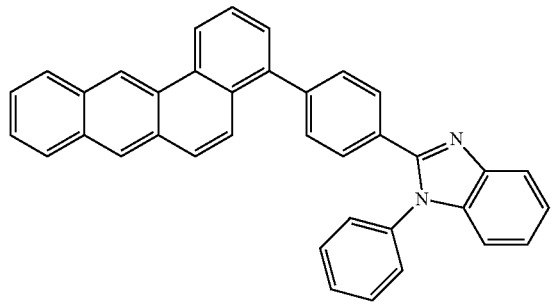
ETM2 (prior art)
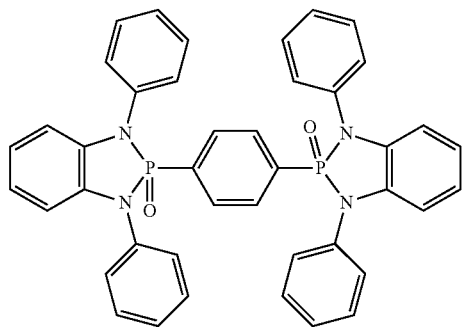
DAP1 (prior art)
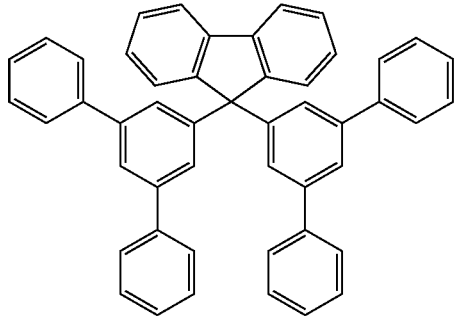
FTPh (prior art)
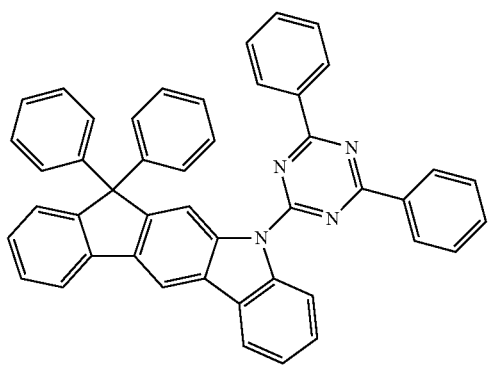
H5 (according to the invention)

TABLE 4-continued
Structural formulae of the materials for the OLEDs
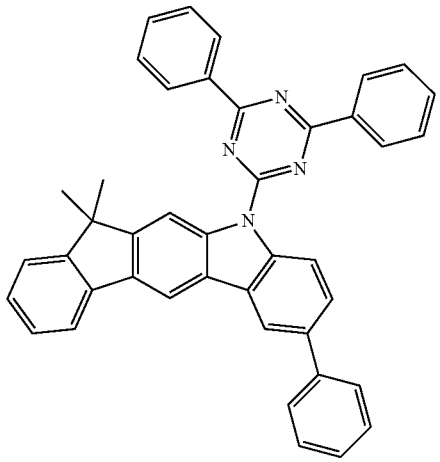
H6 (according to the invention)
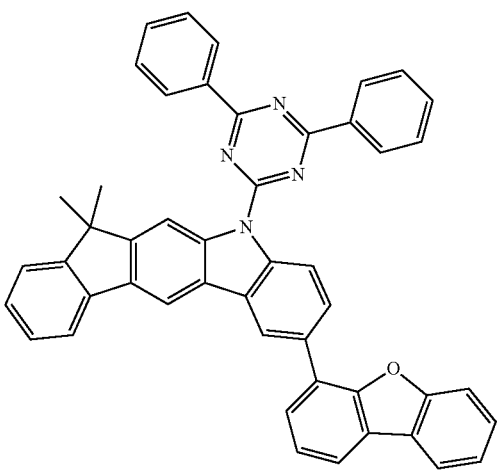
H7 (according to the invention)
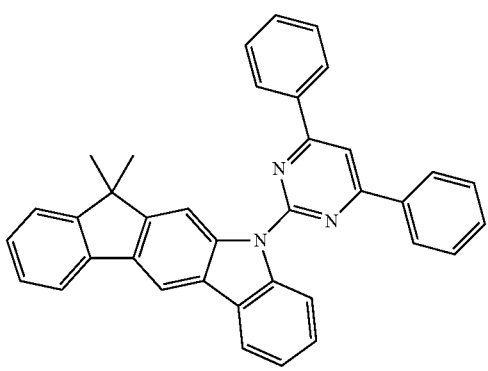
H9 (according to the invention)

TABLE 4-continued
Structural formulae of the materials for the OLEDs
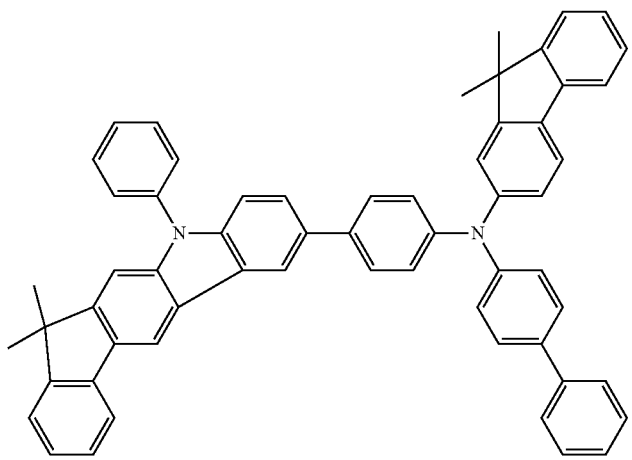
HTM4 (according to the invention)
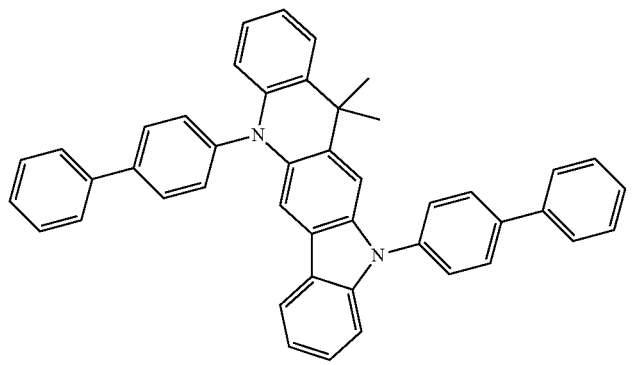
HTM5 (according to the invention)
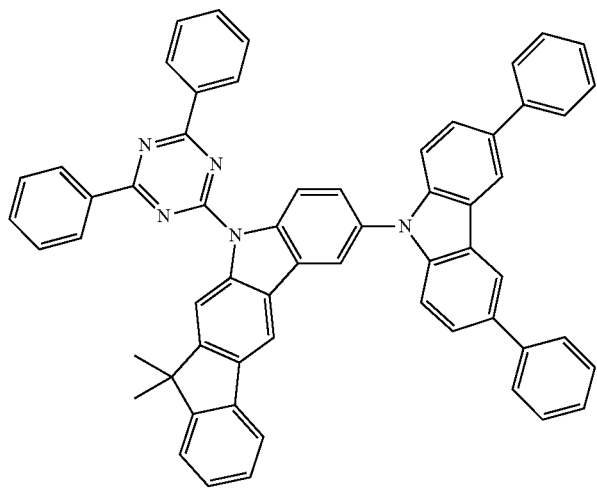
H10 (according to the invention)

TABLE 4-continued
Structural formulae of the materials for the OLEDs
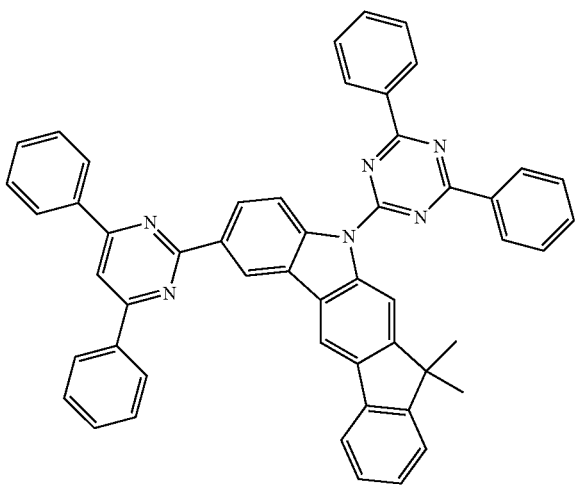
H11 (according to the invention)
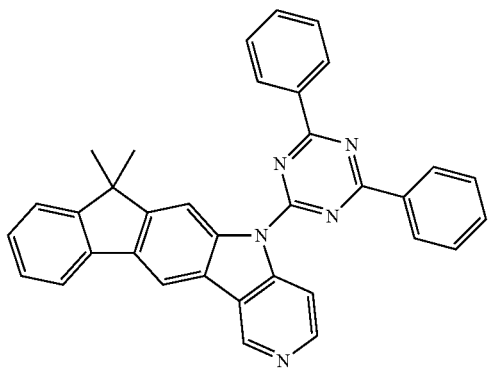
H12 (according to the invention)
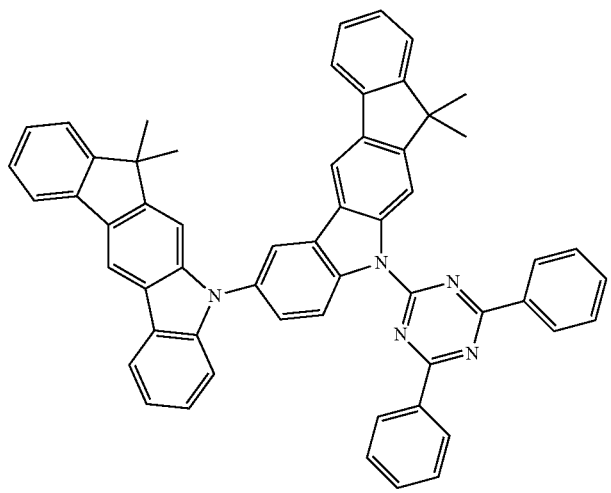
H13 (according to the invention)

TABLE 4-continued
Structural formulae of the materials for the OLEDs
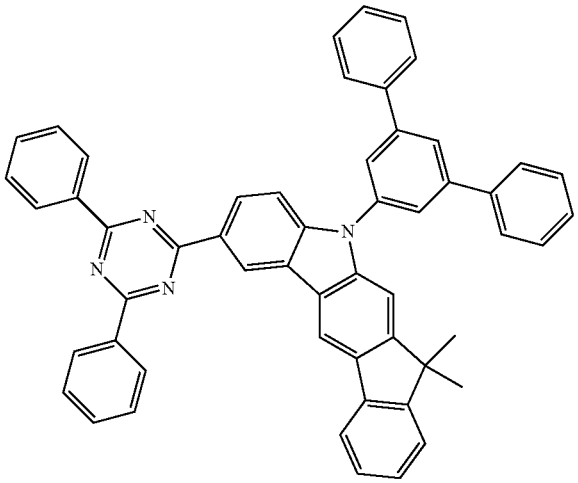
H14 (according to the invention)
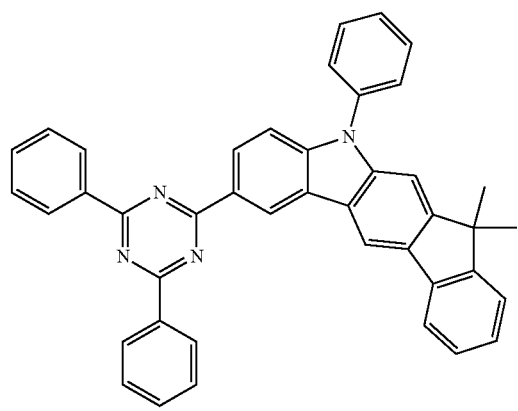
H15 (according to the invention)
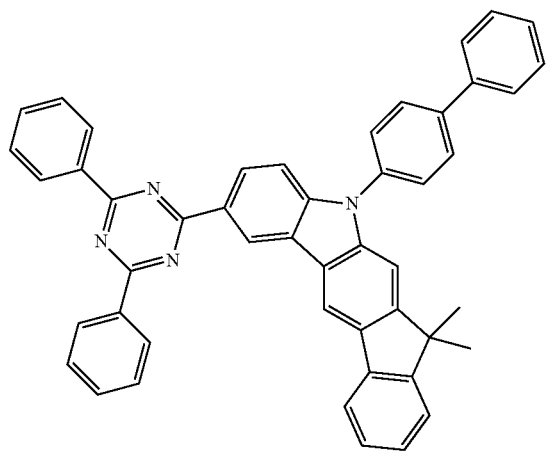
H16 (according to the invention)

TABLE 4-continued
Structural formulae of the materials for the OLEDs
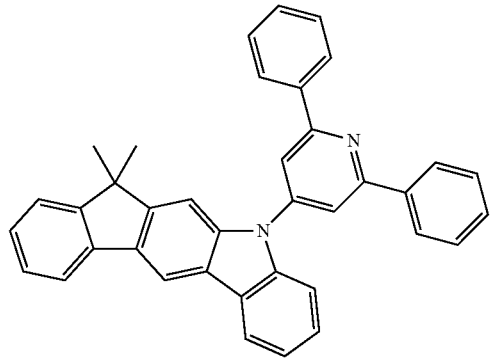
H17 (according to the invention)
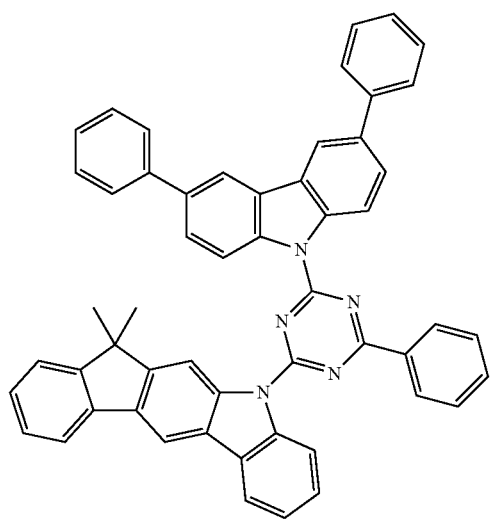
H18 (according to the invention)
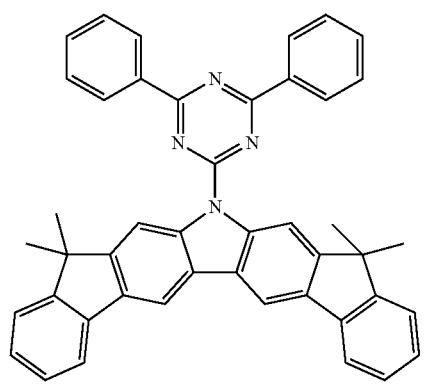
H19 (according to the invention)

TABLE 4-continued
Structural formulae of the materials for the OLEDs
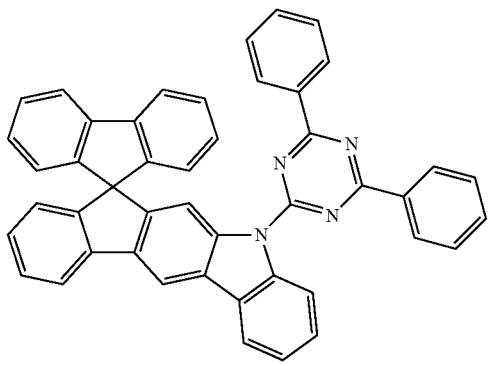
H20 (according to the invention)
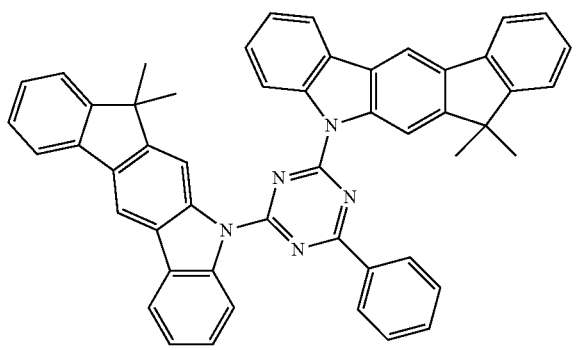
H21 (according to the invention)
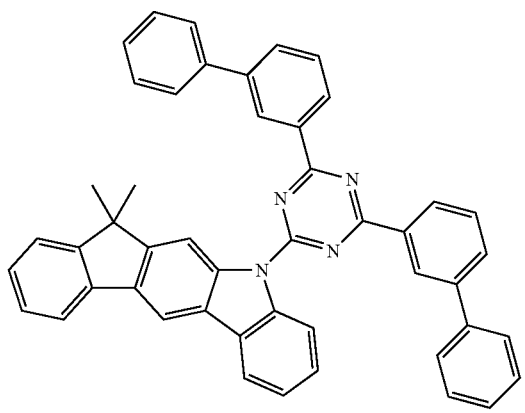
H22 (according to the invention)

TABLE 4-continued
Structural formulae of the materials for the OLEDs
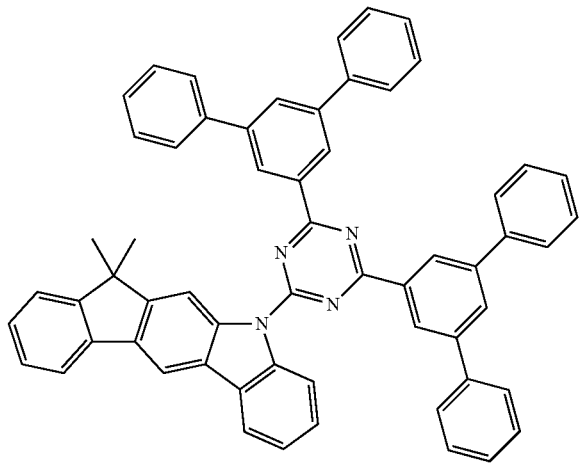
H23 (according to the invention)
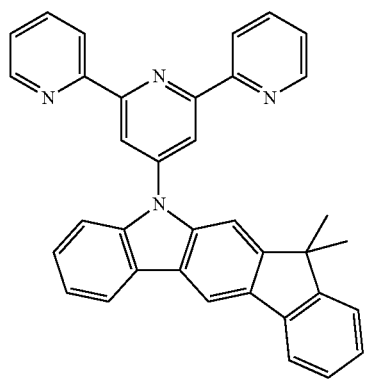
H24 (according to the invention)
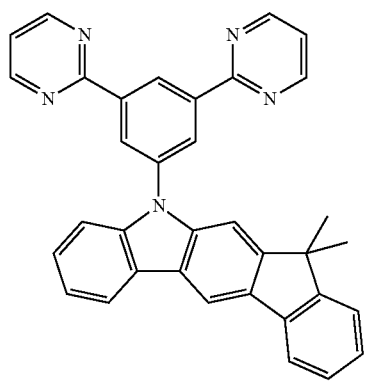
H25 (according to the invention)

TABLE 4-continued
Structural formulae of the materials for the OLEDs
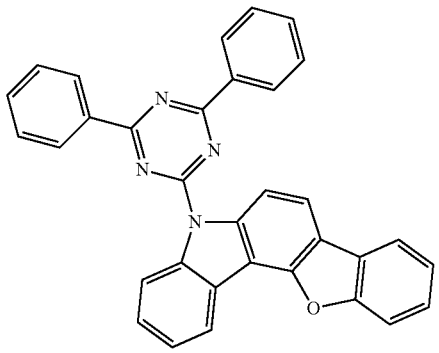
H26 (according to the invention)
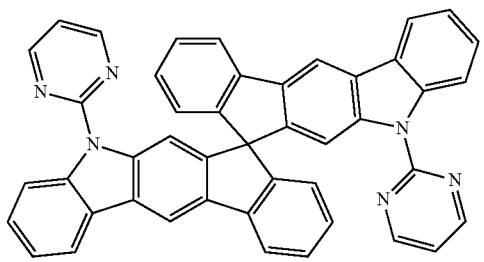
H27 (according to the invention)
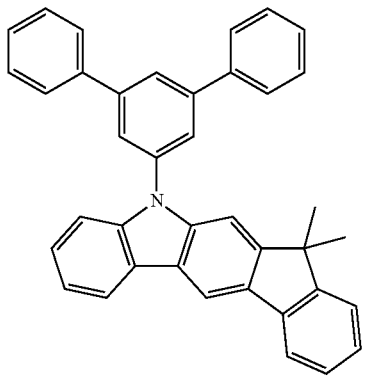
H28 (according to the invention)
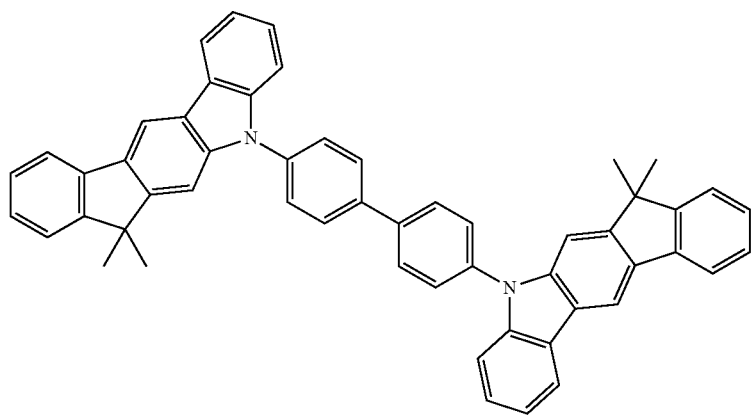
H29 (according to the invention)

TABLE 4-continued
Structural formulae of the materials for the OLEDs
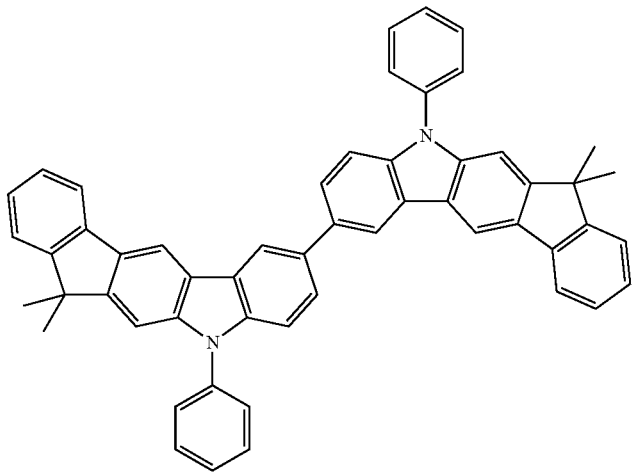
H30 (according to the invention)
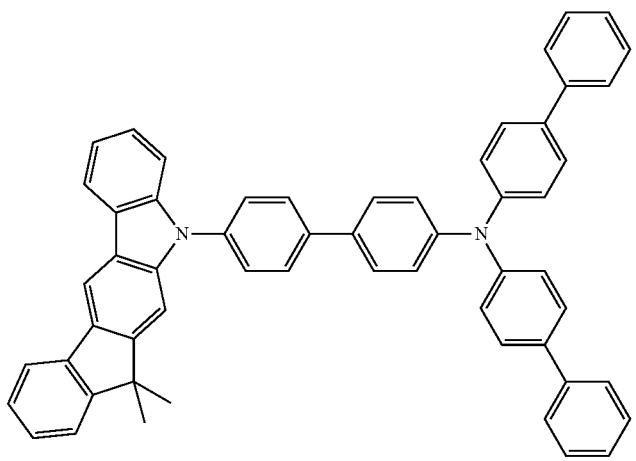
HTM6 (according to the invention)
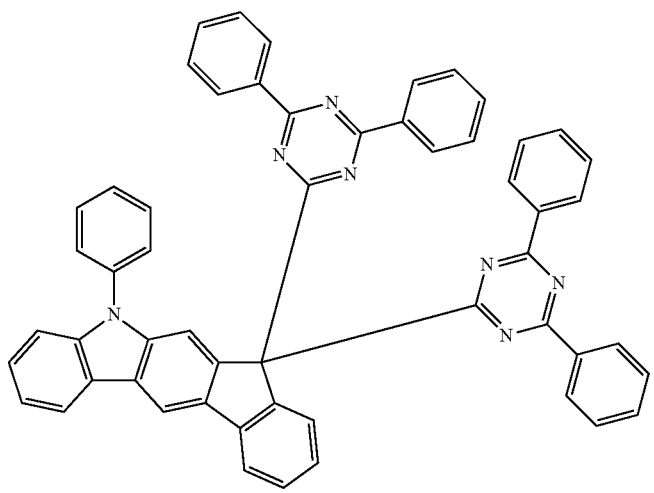
H31 (according to the invention)

TABLE 4-continued
Structural formulae of the materials for the OLEDs
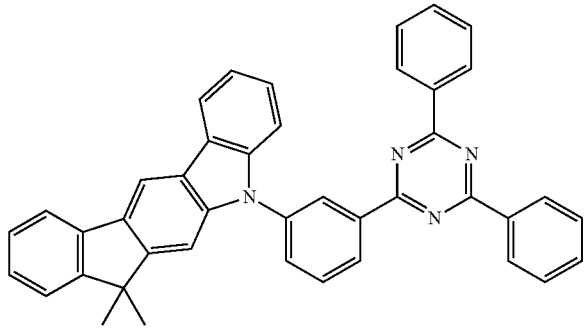
H32 (according to the invention)
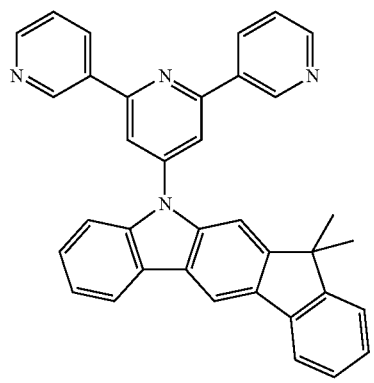
H33 (according to the invention)
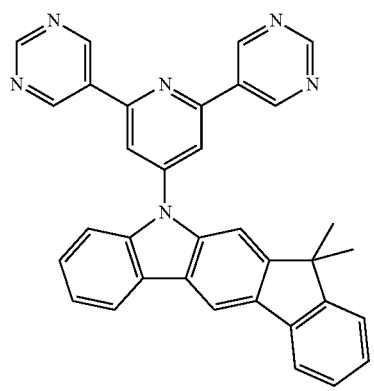
H34 (according to the invention)

TABLE 4-continued
Structural formulae of the materials for the OLEDs
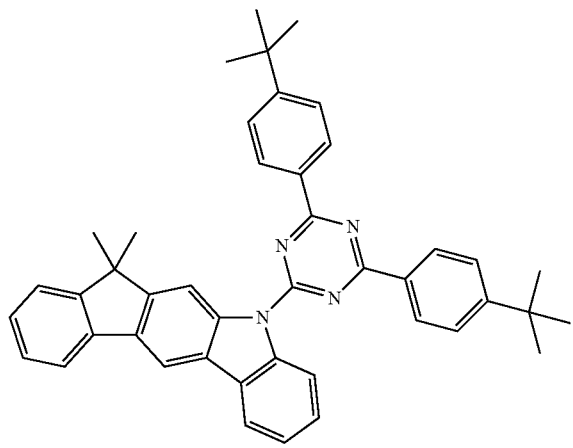
H35 (according to the invention)
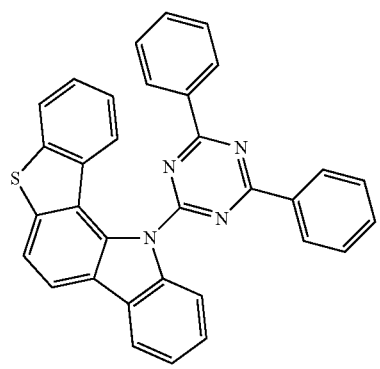
H36 (according to the invention)
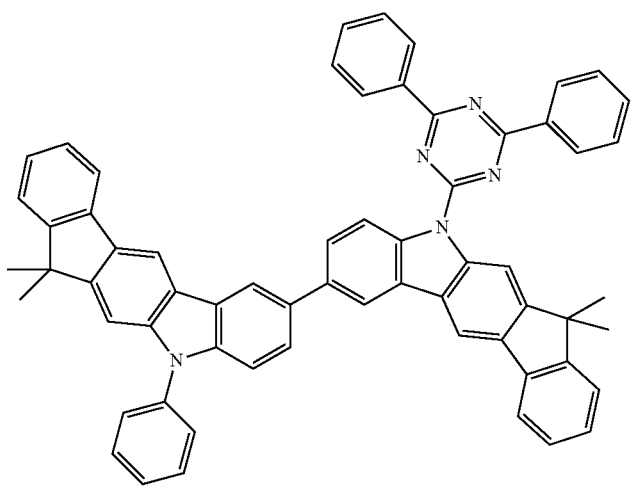
H37 (according to the invention)

TABLE 4-continued
Structural formulae of the materials for the OLEDs
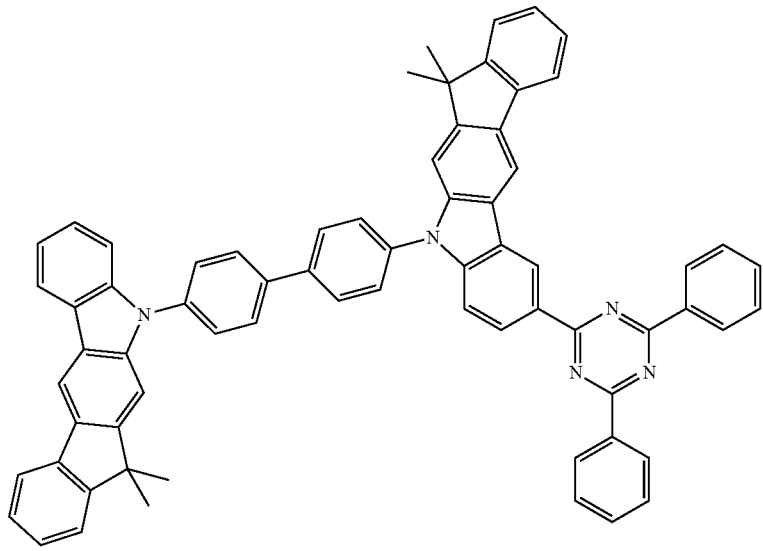
H38 (according to the invention)
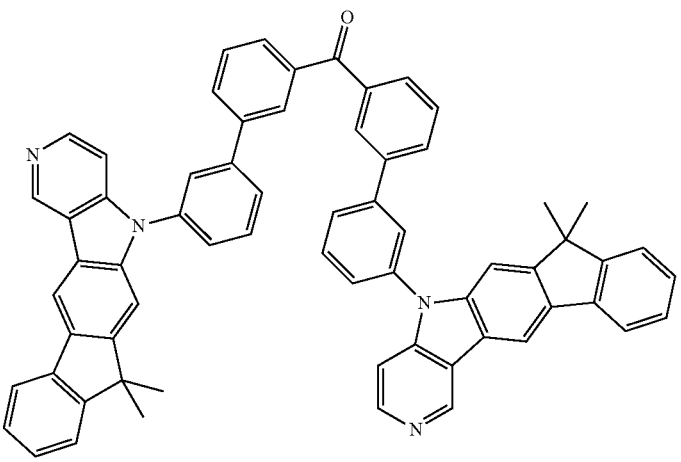
H39 (according to the invention)
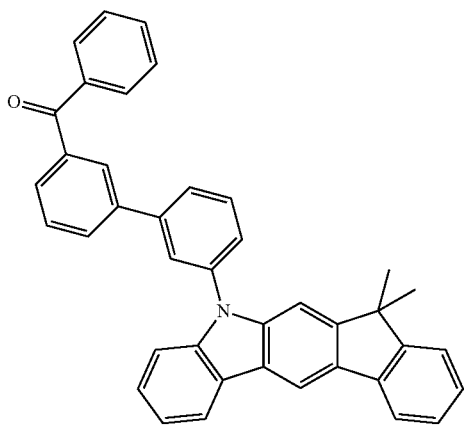
H40 (according to the invention)

TABLE 4-continued
Structural formulae of the materials for the OLEDs
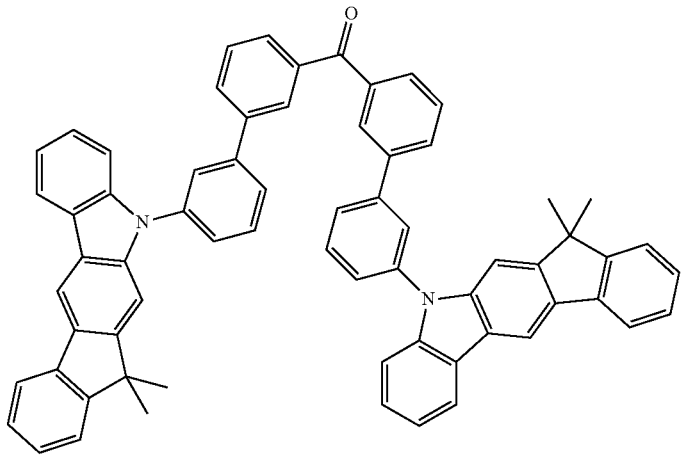
H41 (according to the invention)
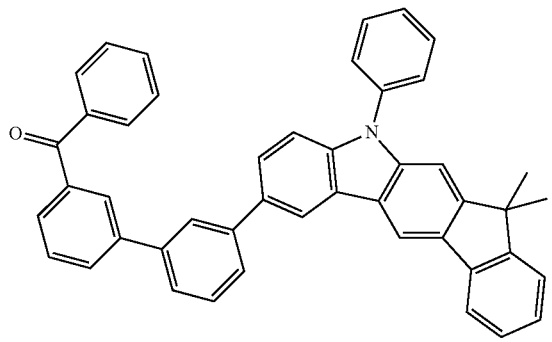
H42 (according to the invention)
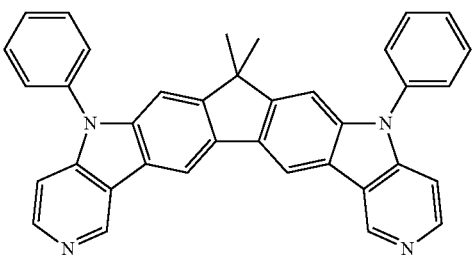
H43 (according to the invention)
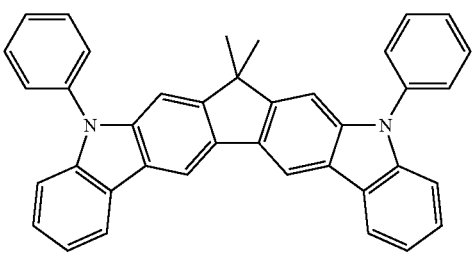
HTM7 (according to the invention)

TABLE 4-continued
Structural formulae of the materials for the OLEDs
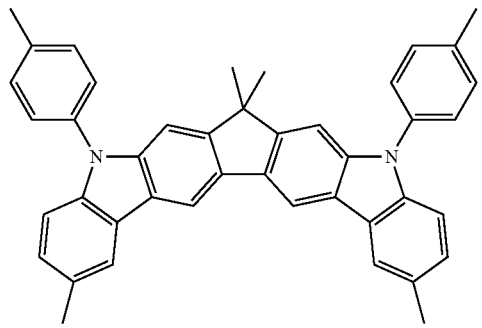
HTM8 (according to the invention)
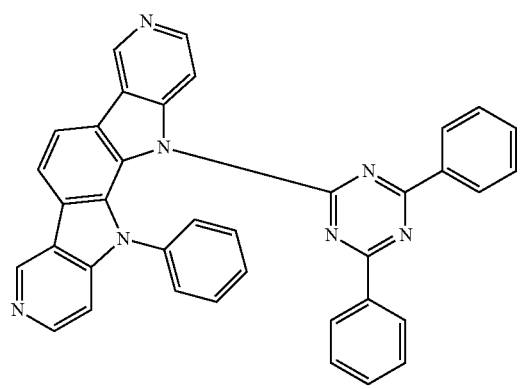
H44 (according to the invention)
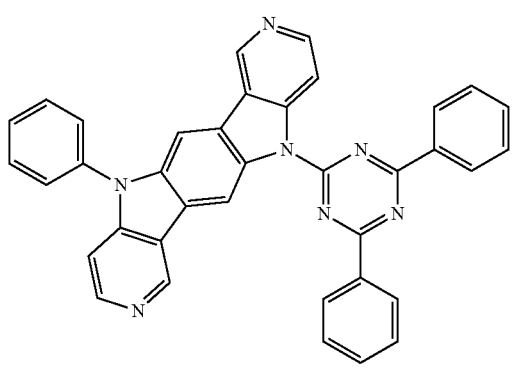
H45 (according to the invention)

TABLE 4-continued
Structural formulae of the materials for the OLEDs
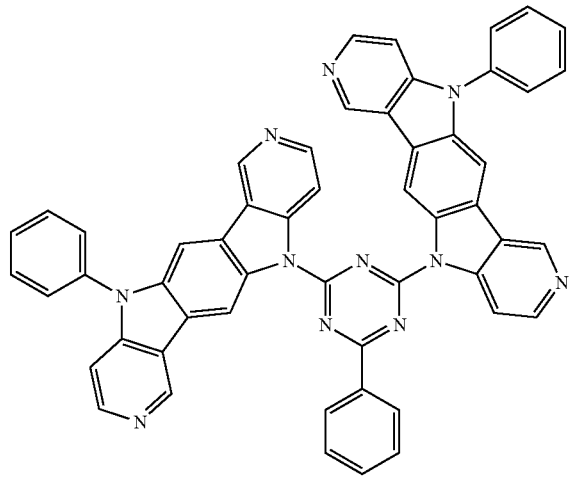
H46 (according to the invention)
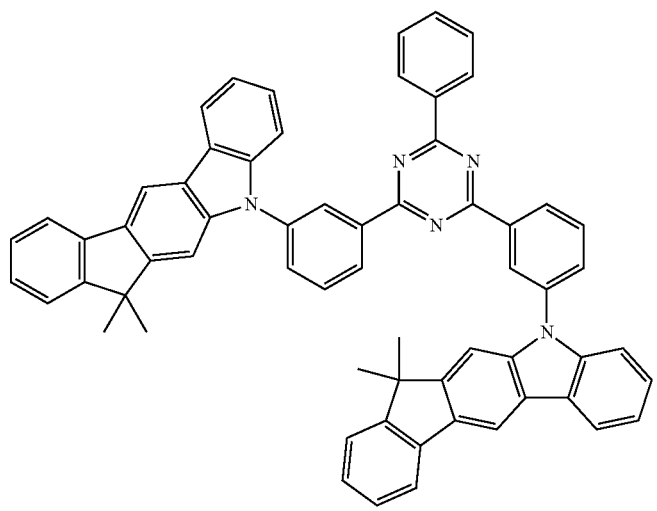
H47 (according to the invention)
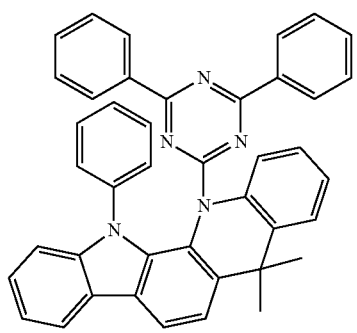
H48 (according to the invention)

Example 56
Production of Solution-Processed OLEDs
The structures of the emitter Ti used in the solution-processed OLEDs, the matrix materials SH1, SH2 according to the invention and the further matrix components C1 and C2 are depicted in Table 5 for clarity.
TABLE 5
Structures of the materials used in the solution-processed OLEDs
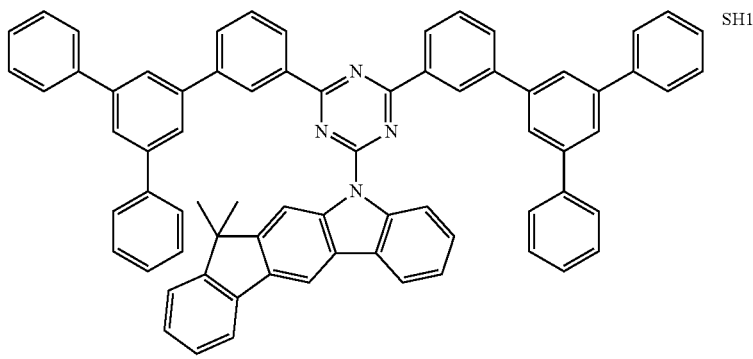
SH1
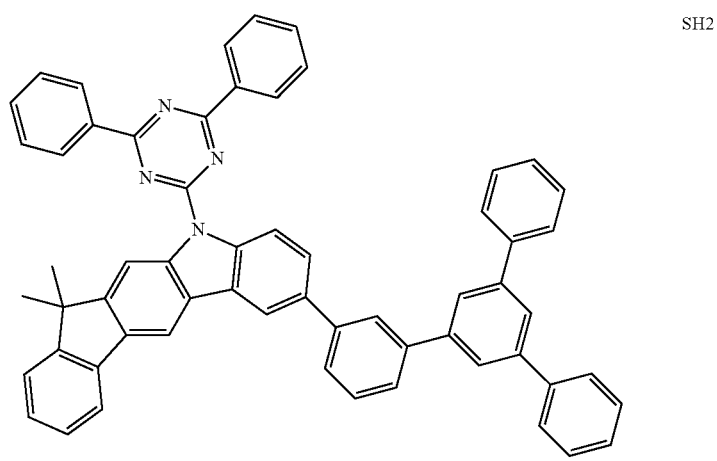
SH2
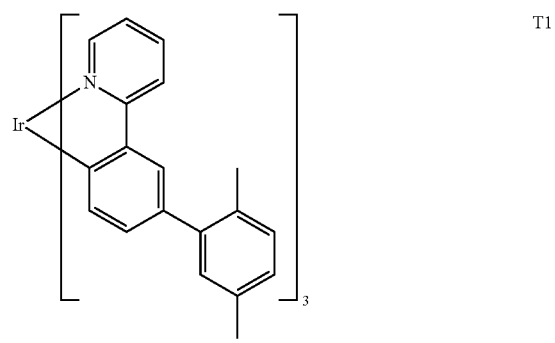
T1

TABLE 5-continued

Structures of the materials used in the solution-processed OLEDs

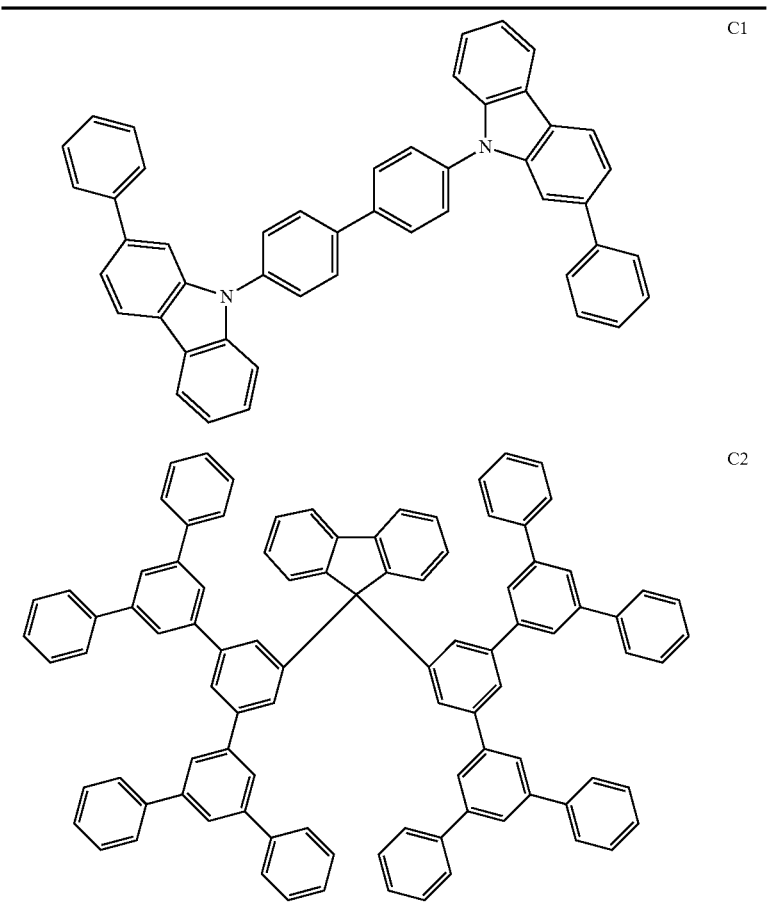

Materials according to the invention can also be used from solution, where they result in significantly simpler devices which nevertheless have good properties. The production of such components is based on the production of polymeric light-emitting diodes (PLEDs), which has already been described many times in the literature (for example in WO 2004/037887 A2). In the present case, the compounds according to the invention are dissolved in toluene or chlorobenzene. The concentration employed in the examples given here is 20% by weight of the emitter and 80% by weight of compounds SH1 and SH2. The typical solids content of such solutions is between 16 and 25 g/l if, as here, the typical layer thickness of 80 nm for a device is to be achieved by means of spin coating. The typical structure of the solution-processed OLED is as follows: ITO anode//80 nm buffer layer (PEDOT)//20 nm interlayer (HIL-012)//80 nm emitting layer (Ti in SH1 or in SH2)//cathode (3 nm of Ba, 150 nm of Al). This structure is also used in the case of the OLEDs mentioned in Table 6. The emission layer (EML) comprises the dissolved matrix materials and the emitter in the form of an amorphous layer. Structured ITO substrates and the material for the so-called buffer layer (PEDOT, actually PEDOT:PSS) are commercially available (ITO from Technoprint and others, PEDOT:PSS as Clevios P aqueous dispersion from H.C. Starck). The interlayer used serves for hole injection; in this case, HIL-012 from Merck is used. The emission layer is applied by spin coating in an inert-gas atmosphere, in the present case argon, and dried by heating for 10 min at 160° C. (SH1) or 180° C. (SH2). Finally, a barium and aluminium cathode is applied by vacuum vapour deposition. The layers HBL and ETL used in the above-mentioned examples can also be applied between the EML and the cathode by vapour deposition, and the interlayer can also be replaced by one or more layers, which merely have to satisfy the condition of not being detached again by the following processing step of EML deposition from solution.

The solution-processed devices are characterised by standard methods and have not been optimised.

The results obtained on use of compounds SH1 and SH2 in solution-processed OLEDs are summarised in Table 6.

TABLE 6

Results in the device configuration indicated above

| Ex. | EML 80 nm | Max. eff. [cd/A] | Voltage [V] at 100 cd/m$^2$ | CIE (x, y) | Lifetime [h], initial luminous density 1000 cd/m$^2$ |
|---|---|---|---|---|---|
| 1 | SH1:T1 | 26 | 4.1 | 0.34/0.62 | 7400 |
| 2 | SH2:T1 | 28 | 4.0 | 0.34/0.62 | 8100 |

Besides the less expensive production, solution-based OLEDs also have the advantage that materials can be combined in a layer easily and in reproducible concentration. Materials SH1 and SH2 according to the invention can therefore also be combined with other matrix materials ("cohosts"). Materials C1 and C2 are used, each in a ratio of 1:1 based on the other matrix component SH1 or SH2 respectively. For the concentrations, this means that 40 mg/ml of SH1 or SH2, 40 mg/ml of co-host and 20 mg/ml of T1 are weighed out. The solvent used is chlorobenzene in the case of C1 and toluene in the case of C2. Otherwise, the OLEDs are produced in the same way as described above for the simple components. The structure of the solution-processed OLED is as follows: ITO anode//80 nm buffer layer (PEDOT)//20 nm interlayer (HIL-012)//80 nm emitting layer (T1 in SH1 or in SH2, in each case+co-host)//cathode (3 nm of Ba, 150 nm of Al). This structure is also used in the case of the OLEDs shown in Table 7.

TABLE 7

Results in the device configuration indicated above

| Ex. | EML 80 nm | Max. eff. [cd/A] | Voltage [V] at 100 cd/m² | CIE (x, y) | Lifetime [h], initial luminous density 1000 cd/m² |
|---|---|---|---|---|---|
| 3 | (SH1 + C1):T1 | 30 | 4.1 | 0.34/0.62 | 27000 |
| 4 | (SH1 + C2):T1 | 32 | 4.4 | 0.33/0.62 | 24000 |
| 5 | (SH2 + C1):T1 | 25 | 3.8 | 0.32/0.63 | 20000 |
| 6 | (SH2 + C2):T1 | 26 | 4.3 | 0.33/0.62 | 20000 |

The invention claimed is:
1. A compound of the formula (4e):

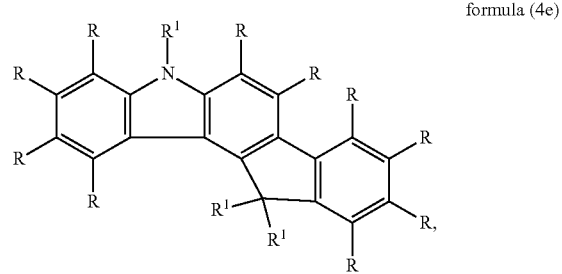

formula (4e)

where the following applies to the symbols and indices used:

R is on each occurrence, identically or differently, H, D, F, Cl, Br, I, $N(Ar)_2$, $C(=O)Ar$, $P(=O)Ar_2$, $S(=O)Ar$, $S(=O)_2Ar$, $CR^2=CR^2Ar$, CN, $NO_2$, $Si(R^2)_3$, $B(OR^2)_2$, $OSO_2R^2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$, where one or more non-adjacent $CH_2$ groups may be replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aryl or heteroaryl group having 6 to 40 ring atoms, which may in each case be substituted by one or more radicals $R^2$, or a heteroaromatic system having 5 to 60 aromatic ring atoms, which may in each case be substituted by one or more radicals $R^2$, or an aryloxy or heteroaryl-oxy group having 5 to 40 aromatic ring atoms, which may be substituted by one or more radicals $R^2$, or an aralkyl or heteroaralkyl group having 5 to 40 aromatic ring atoms, which may be substituted by one or more radicals $R^2$, or a combination of these systems; two or more substituents R here, together with the atoms to which they are bonded, may also form a mono- or polycyclic aliphatic or aromatic ring system with one another;

Ar is on each occurrence, identically or differently, an aromatic or heteroaromatic ring system which may be substituted by one or more radicals $R^1$;

$R^1$ is on each occurrence, identically or differently, H, D, F, Cl, Br, I, CN, $NO_2$, $CF_3$, $B(OR^2)_2$, $Si(R^2)_3$, a straight-chain alkyl, alkoxy or thioalkoxy group having 1 to 40 C atoms or a branched or cyclic alkyl, alkoxy or thioalkoxy group having 3 to 40 C atoms, or an alkenyl or alkynyl group having 2 to 40 C atoms, each of which may be substituted by one or more radicals $R^2$, where one or more non-adjacent $CH_2$ groups may be replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $O$, $S$, $COO$ or $CONR^2$ and where one or more H atoms may be replaced by F, Cl, Br, I, CN or $NO_2$, or arylamines, or substituted or un-substituted carbazoles, which may in each case be substituted by one or more radicals $R^2$, or an aryl or heteroaryl group having 5 to 40 ring atoms, which may be substituted by one or more aromatic, heteroaromatic or non-aromatic radicals $R^2$, or an aromatic or heteroaromatic ring system having 5 to 60 aromatic ring atoms, which may be substituted by one or more non-aromatic radicals $R^2$, or an aryloxy or heteroaryloxy group having 5 to 40 aromatic ring atoms, which may be substituted by one or more radicals $R^2$, or an aralkyl or heteroaralkyl group having 5 to 40 aromatic ring atoms, which may be substituted by one or more radicals $R^2$, or a combination of these systems; two or more substituents $R^1$ here may also form a mono- or poly-cyclic aliphatic or aromatic ring system with one another, together with the atoms to which they are bonded;

$R^2$ is on each occurrence, identically or differently, H, D or an aliphatic hydrocarbon radical having 1 to 20 C atoms or an aryl or heteroaryl group having 5 to 40 ring atoms, or a combination of these groups;

the following compound is furthermore excluded from the invention:

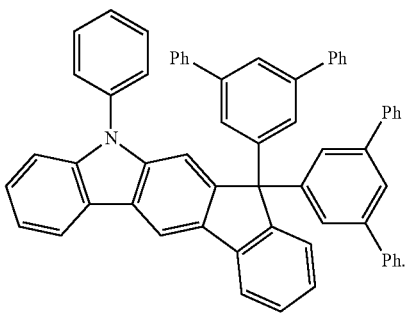

Ph = phenyl

2. The compound according to claim 1, wherein R is selected from H, D, $N(Ar)_2$, a substituted or unsubstituted arylamine, a straight-chain alkyl group having 1 to 20 C atoms, a branched alkyl group having 3 to 20 C atoms, or an aromatic or heteroaromatic ring system having 5 to 40 ring atoms.

3. The compound according to claim 2, wherein the heteroaromatic system is selected from substituted or unsubstituted pyridine, triazine, pyrimidine, benzimidazole, thiophene, triphenylamine or combinations of these groups and/or combinations of these groups with phenyl or naphtyl.

4. The compound according to claim 1, wherein $R^1$ is selected on each occurrence, independently of one another, from alkyl, substituted or unsubstituted triazine, pyridine, pyrimidine, pyrazine, phenyl, biphenyl, terphenyl, naphthyl, anthracenyl and carbazole, and two radicals $R^1$ which are bonded to the same C atom together with the atom(s) to which they are bonded may also form an aliphatic, aromatic or heteroaromatic ring.

5. An electronic device comprising at least one compound according to claim 1.

6. An organic electroluminescent device which comprises the compound according to claim 1 is employed in an emitting layer and/or as electron-transport material and/or as hole-transport material and/or as hole-injection material and/or as hole-blocking material.

7. An electronic device which comprises the compound according to claim 1 is employed as matrix material for phosphorescent emitters in an emitting layer.

8. A mixture comprising at least one compound according to claim 1 and at least one phosphorescent emitter.

9. A formulation comprising at least one compound according to claim 1 and at least one solvent.

10. A founulation comprising the mixture according to claim 8 and at least one solvent.

* * * * *